(12) United States Patent
Taylor et al.

(10) Patent No.: US 7,467,046 B2
(45) Date of Patent: Dec. 16, 2008

(54) GERANYLGERANYL TRANSFERASE TYPE I (GGTASE-I) STRUCTURE AND USES THEREOF

(75) Inventors: Jeffrey S. Taylor, Milford, CT (US); T. Scott Reid, Durham, NC (US); Lorena S. Beese, Durham, NC (US)

(73) Assignee: Duke University, Durham, NC (US)

( * ) Notice: Subject to any disclaimer, the term of this patent is extended or adjusted under 35 U.S.C. 154(b) by 239 days.

(21) Appl. No.: 10/957,517

(22) Filed: Oct. 1, 2004

(65) Prior Publication Data
US 2005/0221459 A1 Oct. 6, 2005

Related U.S. Application Data

(60) Provisional application No. 60/507,685, filed on Oct. 1, 2003.

(51) Int. Cl.
G06G 7/48 (2006.01)
G06G 7/58 (2006.01)
G06F 19/00 (2006.01)
G01N 33/48 (2006.01)

(52) U.S. Cl. .......................... 702/19; 703/11; 530/350

(58) Field of Classification Search ................ 702/19, 702/27; 703/11
See application file for complete search history.

(56) References Cited

OTHER PUBLICATIONS

Qian et al. J. Med. Chem. 1996, 39, 217-223.*
Misutani et al (J. Mol. Biol., 1994, 243, 310-326.*

* cited by examiner

*Primary Examiner*—Michael Borin
(74) *Attorney, Agent, or Firm*—Jenkins, Wilson, Taylor & Hunt, P.A.

(57) ABSTRACT

Protein geranylgeranyl transferase type I (GGTase-I), a $Ca_1a_2X$ prenyltransferase, is an essential enzyme in eukaryotes. GGTase-I catalyzes the carboxyl-terminal lipidation of over one hundred proteins, including many GTP-binding regulatory proteins (G proteins). The presently disclosed subject matter comprises a plurality of crystal structures of mammalian GGTase-I in complex with substrates and products that provide the first structural information for this enzyme, facilitating the elucidation of a generalized method of action for all protein prenyltransferases; the method includes a role in product transport. The structures reveal specificity determinants that allow classification of putative protein prenyltransferase sequences and can facilitate optimization of GGTase-I and FTase modulators.

7 Claims, 31 Drawing Sheets
(20 of 31 Drawing Sheet(s) Filed in Color)

Isoprenoid Diphosphate:

FPP lacks
isoprene 4   isoprene 3   isoprene 2   isoprene 1

FPT-II - FPP analog

3'Azageranylgeranyl diphosphate - GGPP analog

| Name | classification | C | a1 | a2 | X | FT | GGT-I |
|---|---|---|---|---|---|---|---|
| Apolipoprotein L3 (Apolipoprotein L-III) | apolipoprotein L family | C | H | T | H | H | |
| CNL3 (Batten disease protein) | battenin family | C | Q | L | Q | Y | |
| Rod cGMP-specific 3',5'-cyclic phosphodiesterase α-subunit | cyclic nucleotide phosphodiesterase family | C | C | I | Q | Y | |
| Cyclin G2 | cyclin family | C | F | P | S | H | |
| Aspartoacylase (Aminoacylase-2) | deacylase | C | C | L | H | H | |
| Prostacyclin receptor (Prostanoid IP receptor) (PGI receptor) | family 1 of G-protein coupled receptors | C | S | L | C | Y | |
| Heterotrimeric G-protein γ-11 subunit | G protein γ family | C | V | I | S | Y | |
| Heterotrimeric G-protein γ-T2 subunit | G protein γ family | C | L | I | S | H | |
| Transducin γ chain (Guanine nucleotide-binding protein G(T) gamma-T1 subunit) | G protein γ family | C | V | I | S | Y | |
| Interferon-induced guanylate-binding protein 1 | GBP family | C | T | I | S | Y | |
| β-1,4-galactosyltransferase 7 | glycosyltransferase family 7 | C | T | F | S | H | |
| DnaJ homolog subfamily A member 1 (HDJ-2) | heat shock protein | C | Q | T | S | Y | |
| DnaJ homolog subfamily A member 4 | heat shock protein | C | Q | T | A | H | |
| Type 5 inositol-1,4,5-triphosphate 5-phosphatase | inositol-1,4,5-triphosphate 5-phosphatase family | C | S | V | S | H | |
| Type I inositol-1,4,5-triphosphate 5-phosphatase | inositol-1,4,5-triphosphate 5-phosphatase family | C | V | V | Q | Y | |
| Lamin A/C (70 kDa lamin) (prelamin A) | intermediate filament family | C | S | I | M | Y | |
| Lamin B1 | intermediate filament family | C | A | I | M | Y | |
| Lamin B2 | intermediate filament family | C | Y | V | M | H | |
| CENP-E (Centromeric protein E) | kinesin-like protein family | C | K | T | Q | Y | |
| CENP-F (mitosin) | | C | K | V | Q | Y | |
| Paralemmin | paralemmin family | C | S | I | M | Y | |
| Protein phosphatase 1 regulatory inhibitor subunit 16A | phosphatase inhibitor | C | L | L | M | H | |
| Protein phosphatase 1 regulatory inhibitor subunit 16B | phosphatase inhibitor | C | R | I | S | H | |
| Phosphorylase B kinase α regulatory chain, liver isoform | phosphorylase b kinase regulatory chain family | C | Q | M | Q | H | |
| Phosphorylase B kinase α regulatory chain, skeletal muscle isoform | phosphorylase b kinase regulatory chain family | C | A | M | Q | Y | |
| Phosphorylase B kinase β regulatory chain | phosphorylase b kinase regulatory chain family | C | L | I | S | Y | |
| Ubiquitin specific protease 32 | protease | C | V | I | Q | Y | |
| Peroxisomal farnesylated protein | PXF/PEX19 family | C | L | I | M | Y | |
| Rhodopsin kinase | Ser/Thr protein kinase family, GPRK subfamily | C | L | V | S | Y | |
| RRP22 (Ras-related protein on chromosome 22) | small GTPase superfamily | C | S | L | M | H | |
| H-Ras | small GTPase superfamily, Ras family | C | V | L | S | Y | |
| K-Ras 2A (K-Ras) | small GTPase superfamily, Ras family | C | I | I | M | Y | |
| K-Ras 2B (K-Ras) | small GTPase superfamily, Ras family | C | V | I | M | Y | Y* |
| N-Ras | small GTPase superfamily, Ras family | C | V | V | M | Y | Y* |
| Rap-2a | small GTPase superfamily, Ras family | C | N | I | Q | Y | |
| Di-Ras1 (small GTP-binding tumor suppressor 1) | small GTPase superfamily, Ras family, Di-Ras subfamily | C | T | L | M | Y | Y* |
| Di-Ras2 | small GTPase superfamily, Ras family, Di-Ras subfamily | C | V | I | M | H | |
| Dexamethasone-induced Ras-related protein 1 | small GTPase superfamily, RasD family | C | V | I | S | H | |
| Rhes (Ras homolog enriched in striatum) | small GTPase superfamily, RasD family | C | T | I | Q | Y | |
| Rheb (Ras homolog enriched in brain 2) | small GTPase superfamily, Rheb family | C | S | V | M | Y | |
| Rho6 (Rnd1) | small GTPase superfamily, Rho family | C | S | I | M | Y | |
| RhoD | small GTPase superfamily, Rho family | C | V | V | T | H | |
| RhoE (Rho8) (Rnd3) | small GTPase superfamily, Rho family | C | T | V | M | H | |
| RhoI | small GTPase superfamily, Rho family | C | I | I | M | H | |
| RhoN (Rho7) (Rnd2) | small GTPase superfamily, Rho family | C | N | L | M | H | |
| RhoQ (TC10) | small GTPase superfamily, Rho family | C | L | I | T | H | |
| Rho-related BTB domain-containing protein 3 | small GTPase superfamily, Rho family | C | L | V | M | H | |

FIGURE 22

| Protein | Family | | | | | |
|---|---|---|---|---|---|---|
| Stonin 1 (Stoned B-like factor) | Stoned B family | C | I | T | Q | H |
| Tetraspan NET-7 | tetraspanin (TM4SF) family | C | Y | P | N | H |
| Tetraspanin 1 | tetraspanin (TM4SF) family | C | N | L | Q | H |
| Protein tyrosine phosphatase PTPCAAX1 | tyrosine phosphatase | C | C | I | Q | Y |
| Protein tyrosine phosphatase PTPCAAX2 | tyrosine phosphatase | C | C | V | Q | Y |
| Protein tyrosine phosphatase type IVA, member 3 isoform 1 | tyrosine phosphatase | C | C | V | M | H |
| CAAX box protein 1 (Cerebral protein-5) | unknown | C | V | L | A | H |
| LIM-only protein 6 (triple LIM domain protein 6) | unknown | C | I | V | A | H |
| Parkin coregulated gene protein (PARK2 coregulated) | unknown | C | L | L | N | H |
| WD and tetratricopeptide repeats protein 1 | unknown | C | R | P | S | H |
| Zinc finger DHHC domain containing protein 19 | unknown | C | F | P | S | H |
| Hepatitis delta virus large antigen | viral protein | C | R | P | Q | Y |
| B melanoma antigen 1 precursor | BAGE family | C | F | I | F | H | H |
| B melanoma antigen 5 precursor | BAGE family | C | F | I | F | H | H |
| NADH-cytochrome b5 reductase | reductase | C | F | V | F | H | H |
| TC21 (R-Ras2) | small GTPase superfamily, Ras family | C | V | I | F | Y | Y |
| Cdc42 homolog (G25K GTP-binding protein) | small GTPase superfamily, Rho family | C | C | I | F | H | Y |
| Rac3 (Ras-related C3 botulinum toxin substrate 3) | small GTPase superfamily, Rho family | C | T | V | F | H | H |
| RhoB | small GTPase superfamily, Rho family | C | K | V | L | Y | Y |
| RhoH (GTP-binding protein TTF) | small GTPase superfamily, Rho family | C | K | I | F | H | H |
| 2',3'-cyclic nucleotide 3'-phosphodiesterase | 2',3'-cyclic nucleotide 3'-phosphodiesterase | C | T | I | I | Y |
| Aldehyde dehydrogenase 7 | aldehyde dehydrogenase family | C | T | L | L | H |
| Aldehyde dehydrogenase 8 | aldehyde dehydrogenase family | C | T | L | L | H |
| Cone cGMP-specific 3',5'-cyclic phosphodiesterase α-subunit | cyclic nucleotide phosphodiesterase family | C | L | M | L | H |
| Rod cGMP-specific 3',5'-cyclic phosphodiesterase β-subunit | cyclic nucleotide phosphodiesterase family | C | C | I | L | Y |
| Heterotrimeric G-protein γ-10 subunit | G protein γ family | C | A | L | L | Y |
| Heterotrimeric G-protein γ-12 subunit | G protein γ family | C | I | I | L | H |
| Heterotrimeric G-protein γ-13 subunit | G protein γ family | C | T | I | L | H |
| Heterotrimeric G-protein γ-2 subunit | G protein γ family | C | A | I | L | Y |
| Heterotrimeric G-protein γ-3 subunit | G protein γ family | C | A | L | L | Y |
| Heterotrimeric G-protein γ-4 subunit | G protein γ family | C | T | I | L | Y |
| Heterotrimeric G-protein γ-5 like subunit | G protein γ family | C | S | F | L | H |
| Heterotrimeric G-protein γ-5 subunit | G protein γ family | C | S | F | L | Y |
| Heterotrimeric G-protein γ-7 subunit | G protein γ family | C | I | I | L | Y |
| Heterotrimeric G-protein γ-8 subunit | G protein γ family | C | V | L | L | H |
| Interferon-induced guanylate-binding protein 2 | GBP family | C | N | I | L | Y |
| Interferon-induced guanylate-binding protein 5 | GBP family | C | V | L | L | H |
| X-linked retinitis pigmentosa GTPase regulator | guanine-nucleotide releasing factor | C | T | I | L | H |
| Type II inositol-1,4,5-trisphosphate 5-phosphatase precursor | inositol-1,4,5-triphosphate 5-phosphatase type II family | C | N | P | L | Y |
| Mannose-6-phosphate isomerase | mannose-6-phosphate isomerase family 1 | C | C | L | L | H |
| Mitochondrial 28S ribosomal protein S29 (death-associated protein 3) | mitochondrial ribosome | C | A | Y | L | H |
| CASP8 and FADD-like apoptosis regulator precursor (splice isoform 10) | peptidase family C14 | C | S | T | L | H |
| G protein-coupled receptor kinase 7 | Ser/Thr protein kinase family, GPRK subfamily | C | L | L | L | Y |
| M-Ras (R-Ras3) | small GTPase superfamily, Ras family | C | V | I | L | H |
| Ral-A | small GTPase superfamily, Ras family | C | C | I | L | Y |
| Ral-B | small GTPase superfamily, Ras family | C | C | L | L | H |
| Rap-1a | small GTPase superfamily, Ras family | C | L | L | L | Y |
| Rap-1b | small GTPase superfamily, Ras family | C | Q | L | L | Y |
| Rap-2b | small GTPase superfamily, Ras family | C | V | I | L | Y |
| R-Ras | small GTPase superfamily, Ras family | C | V | L | L | H |
| Cdc42 (splice isoform 2) | small GTPase superfamily, Rho family | C | V | L | L | Y |
| Rac1 (Ras-related C3 botulinum toxin substrate 1) | small GTPase superfamily, Rho family | C | L | L | L | Y |

FIGURE 22 (cont.)

| | | | | | | |
|---|---|---|---|---|---|---|
| Rac2 (Ras-related C3 botulinum toxin substrate 2) | small GTPase superfamily, Rho family | C | S | L | L | Y |
| RacX (Ras-related C3 botulinum toxin substrate homolog) | small GTPase superfamily, Rho family | C | L | Q | L | H |
| RhoA | small GTPase superfamily, Rho family | C | L | V | L | Y |
| RhoC | small GTPase superfamily, Rho family | C | P | I | L | Y |
| RhoF (Rif) | small GTPase superfamily, Rho family | C | L | I | L | Y |
| RhoG | small GTPase superfamily, Rho family | C | I | L | L | Y |
| RhoJ (Tc10-like GTP-binding protein TCL) | small GTPase superfamily, Rho family | C | S | I | I | H |
| RhoU (Wrch1) | small GTPase superfamily, Rho family | C | C | F | V | K |
| T-cell surface glycoprotein CD4 precursor | Type I membrane protein | C | P | S | I | H |
| CUB and sushi multiple domains protein 1 precursor | Type I membrane protein (potential) | C | T | V | V | H |
| CUB and sushi multiple domains protein 3 precursor | Type I membrane protein (potential) | C | T | M | V | H |
| Integral membrane protein 2C | Type II membrane protein (potential) | C | G | V | V | H |
| Beta-1,3-galactosyltransferase 5 | Type II membrane protein (potential) | C | P | P | V | H |
| Down syndrome critical region protein 10 | unknown | C | M | P | L | H |
| F-box/LRR-repeat protein 2 | unknown | C | V | I | L | H |
| F-box/LRR-repeat protein 2-like | unknown | C | I | I | L | H |
| Protein C20orf24 (Rab5-interacting protein) | unknown | C | H | P | L | H |
| Protein C21orf80 | unknown | C | L | L | V | H |
| Suppressor of potassium transport defect 3 | unknown | C | N | T | I | H |
| Cohen syndrome protein 1 (isoform 5) | vesicle-mediated sorting and intracellular protein transport (potential) | C | L | Y | L | H |

FIGURE 22 (cont.)

| Name | GI | classification | cellular localization | biological relevance | C et al X | substrate for FT | substrate for GGT4 | PMID |
|---|---|---|---|---|---|---|---|---|
| Apolipoprotein L3 (Apolipoprotein L-III) | 17433260 | apolipoprotein L family | cytoplasmic (probable) | may affect the movement of lipids in the cytoplasm or allow the binding of lipids to organelles | C H T H | H | | |
| CLN3 (Batten disease protein) | 2498243 | battenin family | liposomal membrane-associated | defects result in juvenile-onset ceroid lipofuscinosis neuronal type 3 (CLN3), also known as Batten disease | C Q L Q | Y | | 9151320 |
| Rod cGMP-specific 3',5'-cyclic phosphodiesterase α-subunit | 2851392 | cyclic nucleotide phosphodiesterase family | membrane-associated | Visual signal transduction; defects result in autosomal recessive retinitis pigmentosa (ARRP) | C C I Q | Y | | 1308771 |
| Cyclin G2 | 9087132 | cyclin family | cytoplasmic (by similarity) | may play a role in growth regulation and in negative regulation of cell cycle progression | C F P S | H | | |
| Aspartoacylase (Aminoacylase-2) | 1166340 | deacylase | high concentration in brain | catalyzes the deacylation of N-acetylaspartic acid (NAA) to produce acetate and L-aspartate; defects cause Canavan disease | C C L H | H | | |
| Prostacyclin receptor (Prostanoid IP receptor) (PGI receptor) | 1172500 | family 1 of G-protein coupled receptors | membrane-associated | signal transduction; receptor for prostacyclin | C S L C | Y | | 10446129 |
| Heterotrimeric G-protein γ-11 subunit | 1730223 | G protein γ family | membrane-associated (by similarity); high levels in all tissues tested except brain | signal transduction | C V I S | Y | | 7885598 |
| Heterotrimeric G-protein γ-T2 subunit | 3025844 | G protein γ family | membrane-associated (by similarity); retinal cones | signal transduction | C L I S | H | | |
| Transducin γ chain (Guanine nucleotide-binding protein G(T) gamma-T1 subunit) | 585181 | G protein γ family | membrane-associated; retinal rod outer segment | signal transduction | C V I S | Y | | 2217200 |
| Interferon-induced guanylate-binding protein 1 | 417031 | GBP family | primarily cytosolic (85%) | unknown | C T I S | Y | | 8830800 |
| β-1,4-galactosyltransferase 7 | 13123960 | glycosyltransferase family 7 | membrane-associated (cis cisternae of Golgi stack); high levels in heart, pancreas and liver, medium in placenta and kidney, low in brain, skeletal muscle and lung | role in glycosylation pathway; defects result in progeroid Ehlers-Danlos syndrome (EDS) | C T F S | H | | |
| DnaJ homolog subfamily A member 1 (HDJ-2) | 1708474 | heat shock protein | membrane-associated | may have role in protein import into mitochondria; co-chaperone of Hsc70 | C Q T S | Y | | 10873082 |
| DnaJ homolog subfamily A member 4 | 27805462 | heat shock protein | membrane-associated | unknown | C Q T A | H | | |
| Type 5 Inositol-1,4,5-trisphosphate 5-phosphatase | 8925264 | inositol-1,4,5-trisphosphate 5-phosphatase family | unknown | unknown | C S V S | H | | |
| Type I Inositol-1,4,5-trisphosphate 5-phosphatase | 3122245 | inositol-1,4,5-trisphosphate 5-phosphatase family | membrane-associated; expressed in brain, with high levels in Purkinje cells | signal termination through hydrolysis of calcium-mobilizing second messenger Ins(1,4,5)P3 | C V V Q | Y | | 8626618 |

FIGURE 23

| Name | GI | classification | cellular localization | biological relevance | C | a1 | a2 | X | FT | GGT-I | PMID |
|---|---|---|---|---|---|---|---|---|---|---|---|
| Lamin A/C (70 kDa family) (prelamin A) | 125962 | intermediate filament family | nuclear membrane | component of nuclear lamina, may provide framework for the nuclear envelope and may interact with chromatin; defects cause a variety of diseases including Emery-Dreifuss muscular dystrophy type 2 (EDMD2), dilated cardiomyopathy 1A (CMD1A), Hutchinson-Gilford progeria syndrome (HGPS), and Werner syndrome | C | S | I | M | Y | | 1557405 |
| Lamin B1 | 125953 | intermediate filament family | nucleoplasmic side of the inner nuclear membrane | component of nuclear lamina, may provide framework for the nuclear envelope and may interact with chromatin | C | A | I | M | Y | | 2884978 |
| Lamin B2 | 2393978 | intermediate filament family | nucleoplasmic side of the inner nuclear membrane | component of nuclear lamina, may provide framework for the nuclear envelope and may interact with chromatin | C | Y | V | M | H | | |
| CENP-E (Centromeric protein E) | 390227 | kinesin-like protein family | associated with kinetochores during congression, moves to spindle midzone at anaphase | microtubule motor, probably kinetochore motor | C | K | T | Q | Y | | 10852815 |
| CENP-F (mitosin) | 1345731 | | nuclear matrix; kinetochore/centromere and spindle during mitosis | involved in chromosome segregation during mitosis; interacts with retinoblastoma protein (RB), CENP-E and BUBR1 | C | K | V | Q | Y | | 10852815 |
| Paralemmin | 2253899 | paralemmin family | membrane-associated; widely expressed, with highest levels in brain and testis, intermediate levels in heart and adrenal gland | may help control cell shape | C | S | I | M | Y | | 9813098 |
| Protein phosphatase 1 regulatory inhibitor subunit 16A | 22259876 | phosphatase inhibitor | plasma membrane | inhibits protein phosphatase 1 activity on phosphorylase, myosin light chain and myosin substrates | C | L | L | M | H | | |
| Protein phosphatase 1 regulatory inhibitor subunit 16B | 22259877 | phosphatase inhibitor | plasma membrane; CNS, lung, spleen, kidney, and testis | possible downstream target of TGF-beta1 signaling cascade in endothelial cells | C | R | I | B | H | | |
| Phosphorylase B kinase α regulatory chain, liver isoform | 1170685 | phosphorylase b kinase regulatory chain family | primarily expressed in liver and other non-muscle tissue | involved in glycogen metabolism; defects associated with X-linked muscle glycogenosis | C | Q | M | Q | H | | |
| Phosphorylase B kinase α regulatory chain, skeletal muscle isoform | 1170688 | phosphorylase b kinase regulatory chain family | primarily cytoplasmic, with small pool membrane-associated; expressed in muscle tissue | involved in glycogen metabolism; defects associated with X-linked muscle glycogenosis | C | A | M | Q | Y | | 1409885 |
| Phosphorylase B kinase β regulatory chain | 2499582 | phosphorylase b kinase regulatory chain family | primarily cytoplasmic, with small pool membrane-associated; expressed in muscle tissue | serine phosphorylation; glycogen metabolism | C | L | I | B | Y | | 1409885 |
| Ubiquitin specific protease 32 | 22550104 | protease | unknown | unknown | C | V | I | Q | Y | | 8917711 |
| Peroxisomal farnesylated protein | 729723 | PXF/PEX19 family | outer surface of the peroxisome membrane | may be involved in peroxisomal biogenesis or assembly | C | L | I | M | Y | | 8188701 |
| Rhodopsin kinase | 2833269 | Ser/Thr protein kinase family, GPRK subfamily | membrane-associated; expressed in retina and pineal gland | phosphorylation of rhodopsin, defects result in Oguchi disease 2, autosomal recessive retinitis pigmentosa (ARRP), and autosomal dominant retinitis pigmentosa (ADRP) | C | L | V | S | Y | | 1522899 |
| RRP22 (Ras-related protein on chromosome 22) | 3024572 | small GTPase superfamily | membrane-associated | signal transduction | C | S | L | M | H | | |

FIGURE 23 (cont.)

| Name | GI | classification | cellular localization | biological relevance | C | a1 | a2 | X | FT | GGT-I | PMID |
|---|---|---|---|---|---|---|---|---|---|---|---|
| H-Ras | 131869 | small GTPase superfamily, Ras family | membrane-associated | signal transduction; mutations associated with a variety of human tumor types including bladder cancers and oral squamous cell carcinomas | C | V | L | S | Y | | 1751289 |
| K-Ras 2A (Ki-Ras) | 131875 | small GTPase superfamily, Ras family | membrane-associated | signal transduction; mutations associated with a variety of human tumor types | C | I | I | M | Y | | 1751289 |
| K-Ras 2B (Ki-Ras) | 131879 | small GTPase superfamily, Ras family | membrane-associated | signal transduction; mutations associated with a variety of human tumor types | C | V | I | M | Y | Y | 1751289 |
| N-Ras | 131883 | small GTPase superfamily, Ras family | membrane-associated | signal transduction; mutations associated with a variety of human tumor types | C | V | V | M | Y | Y | 1751289 |
| Rap-2a | 131852 | small GTPase superfamily, Ras family | membrane-associated | signal transduction | C | N | I | Q | Y | | 8424780 |
| Di-Ras1 (small GTP-binding tumor suppressor 1) | 21553323 | small GTPase superfamily, Ras family, Di-Ras subfamily | membrane-associated; expressed in brain and heart | signal transduction; may have role in regulation of membrane transport | C | T | L | M | Y | Y | 12107276 |
| Di-Ras2 | 21703397 | small GTPase superfamily, Ras family, Di-Ras subfamily | membrane-associated; expressed in brain | signal transduction; may have role in regulation of membrane transport | C | V | I | M | H | | 12194967 |
| Dexamethasone-induced Ras-related protein 1 | 38258372 | small GTPase superfamily, RasD family | expressed in heart, brain, placenta, lung, liver, skeletal muscle, kidney, and pancreas; highest levels in heart | may have role in dexamethasone-induced alterations in cell morphology, growth and cell-extracellular matrix interactions | C | V | I | G | H | | |
| Rhes (Ras homolog enriched in striatum) | 21362868 | small GTPase superfamily, RasD family | membrane-associated; expressed in pancreatic endocrine cells (islets of Langerhans) | signal transduction; may be involved in mediating insulin secretory response to afroxan | C | T | L | Q | Y | | 14724534 |
| Rheb (Ras homolog enriched in brain 2) | 6919657 | small GTPase superfamily, Rheb family | membrane-associated; highest levels in skeletal and cardiac muscle | signal transduction | C | S | V | M | Y | | 9099708 |
| RhoB (Rnd1) | 2500182 | small GTPase superfamily, Rho family | membrane-associated; expressed in brain and liver | role in rearrangement of the actin cytoskeleton and formation of some neuritic processes | C | S | I | M | Y | | 9531558 |
| RhoD | 5034539 | small GTPase superfamily, Rho family | membrane-associated; highest levels in heart, placenta, liver, skeletal muscle, and pancreas | may be involved in endosome dynamics; may coordinate membrane transport with function of cytoskeleton and aid in reorganization of actin cytoskeleton | C | V | V | T | H | | |
| RhoE (Rho8) (Rnd3) | 1710230 | small GTPase superfamily, Rho family | membrane-associated; ubiquitous | may have role in actin cytoskeleton organization and biogenesis, and cell adhesion | C | T | V | M | H | | |
| RhoI | 13633745 | small GTPase superfamily, Rho family | membrane-associated (by similarity); expressed in normal breast and ovarian epithelial cells, but not in breast and ovarian cancers | signal transduction | C | I | I | M | H | | |
| RhoN (Rho7) (Rnd2) | 2507301 | small GTPase superfamily, Rho family | membrane-associated (by similarity); high levels in testis | may have role in neuronal and hepatic functions | C | N | L | M | H | | |
| RhoQ (TC10) | 134080 | small GTPase superfamily, Rho family | membrane-associated | signal transduction | C | L | I | T | H | | |
| Rho-related BTB domain-containing protein 3 | 26006843 | small GTPase superfamily, Rho family | membrane-associated (by similarity); high levels in neural and cardiac tissues, pancreas, placenta and testis | signal transduction | C | L | V | M | H | | |
| Storin 1 (Stoned B-like factor) | 33860221 | Stoned B family | cytoplasmic, some fraction is membrane-associated | may be involved in endocytic machinery | C | I | T | Q | H | | |

FIGURE 23 (cont.)

| Name | GI | classification | cellular localization | biological relevance | C | a1 | a2 | X | substrate for FT | substrate for GGT-1 | PMID |
|---|---|---|---|---|---|---|---|---|---|---|---|
| Tetraspan NET-7 | 11135165 | tetraspanin (TM4SF) family | integral membrane protein (probable) | unknown | C | Y | P | N | H | | |
| Tetraspanin 1 | 12643622 | tetraspanin (TM4SF) family | membrane-associated | unknown | C | N | L | Q | H | | |
| Protein tyrosine phosphatase PTPCAAX1 | 1777755 | tyrosine phosphatase | membrane-associated | unknown | C | C | I | Q | Y | | 9016050 |
| Protein tyrosine phosphatase PTPCAAX2 | 1777757 | tyrosine phosphatase | membrane-associated | unknown | C | C | V | Q | Y | | 9016050 |
| Protein tyrosine phosphatase type IVA, member 3 isoform 1 | 14589856 | tyrosine phosphatase | membrane-associated | overexpression inhibits angiotensin-II-induced calcium mobilization and promotes cell growth | C | C | V | M | H | | |
| CAAX box protein 1 (Cervinal protein-5) | 9087144 | unknown | plasma membrane | unknown | C | V | L | A | H | | |
| LIM-only protein 8 (triple LIM domain protein 8) | 22095394 | unknown | widely expressed | unknown | C | I | V | A | H | | |
| Parkin coregulated gene protein (PARK2 coregulated) | 46590403 | unknown | cytoplasmic (probable) | susceptibility to leprosy is associated with PARK2 | C | L | L | N | H | | |
| WD and tetratricopeptide repeats protein 1 | 41010470 | unknown | unknown | unknown | C | R | P | B | H | | |
| Zinc finger DHHC domain containing protein 1B | 37999851 | unknown | integral membrane protein (potential) | unknown | C | F | P | S | H | | |
| Hepatitis delta virus large antigen | 46200328 | viral protein | nuclear membrane | facilitates viral assembly and release | C | R | P | Q | Y | | |
| B melanoma antigen 1 precursor | 5915765 | BAGE family | not expressed in normal tissues, except in testis; high levels in melanomas and other tumors (bladder, head and neck, squamous cell, lung, and breast carcinomas) | unknown | C | F | I | F | H | H | |
| B melanoma antigen 5 precursor | 37537778 | BAGE family | not expressed in normal tissues, except in testis; expressed in melanoma and bladder and lung carcinomas | unknown | C | F | I | F | H | H | |
| NADH-cytochrome b5 reductase | 127848 | reductase | membrane-bound on cytoplasmic side of the ER; soluble in erythrocytes | involved in microsomal electron transport system; desaturation and elongation of fatty acids, cholesterol biosynthesis, drug metabolism, and methemoglobin reduction (in erythrocytes); defects cause hereditary methemoglobinemia (HM) | C | F | V | F | H | H | |
| TC21 (R-Ras2) | 2507282 | small GTPase superfamily, Ras family | inner surface of plasma membrane; high levels in heart, placenta, and skeletal muscle; moderate levels in lung and liver, low levels in brain, kidney, and pancreas | may transduce growth inhibitory signals across the cell membrane; antagonist of Ras proteins | C | V | I | F | Y | Y | 7791052 |
| Cdc42 homolog (G25K GTP-binding protein) | 46397381 | small GTPase superfamily, Rho family | membrane-associated | involved in epithelial cell polarization processes; induces formation of filopodia | C | C | I | F | H | Y | 1868778 |
| Rac3 (Ras-related C3 botulinum toxin substrate 3) | 46397872 | small GTPase superfamily, Rho family | cytoplasmic, membrane-associated when activated; high levels in brain, heart, placenta, and pancreas | signal transduction | C | T | V | F | Y | H | |
| RhoB | 132542 | small GTPase superfamily, Rho family | membrane-associated | regulates signal transduction pathway affecting the assembly of focal adhesions and actin stress fibers | C | K | V | L | Y | Y | 14003319 |
| RhoH (GTP-binding protein TTF) | 2500200 | small GTPase superfamily, Rho family | membrane-associated (by similarity); expressed only in hemopoietic cells | involved in chromosomal translocation with BCL6 | C | K | I | F | H | H | |
| 2',3'-cyclic nucleotide 3'-phosphodiesterase | 1705945 | 2',3'-cyclic nucleotide 3'-phosphodiesterase | membrane-associated in brain white matter | phosphodiesterase | C | T | I | I | Y | Y | 7854518 |
| Aldehyde dehydrogenase 7 | 1169285 | aldehyde dehydrogenase family | high levels in kidney and lung | ethanol metabolism | C | T | L | L | H | H | |

FIGURE 23 (cont.)

| Name | GI | classification | cellular localization | biological relevance | C | a1 | a2 | X | substrate for FT | substrate for GGT-I | PMID |
|---|---|---|---|---|---|---|---|---|---|---|---|
| Aldehyde dehydrogenase 8 | 13522247 | aldehyde dehydrogenase family | high levels in salivary gland | ethanol metabolism | C | T | L | L | | H | |
| Cone cGMP-specific 3',5'-cyclic phosphodiesterase α-subunit | 1705960 | cyclic nucleotide phosphodiesterase family | membrane-associated | visual signal transduction; cGMP-specific phosphodiesterase activity | C | L | M | L | | H | |
| Rod cGMP-specific 3',5'-cyclic phosphodiesterase β-subunit | 544052 | cyclic nucleotide phosphodiesterase family | membrane-associated | visual signal transduction; necessary for the formation of a functional phosphodiesterase holoenzyme; defects result in autosomal recessive/dominant retinitis pigmentosa (ARRP/ADRP) | C | C | I | L | | Y | 1309771 |
| Heterotrimeric G-protein γ-10 subunit | 1730222 | G protein γ family | membrane-associated (by similarity) | signal transduction | C | A | L | L | | Y | 7885596 |
| Heterotrimeric G-protein γ-12 subunit | 12228617 | G protein γ family | membrane-associated (by similarity) | signal transduction | C | I | I | L | | H | |
| Heterotrimeric G-protein γ-13 subunit | 20138402 | G protein γ family | membrane-associated (by similarity) | signal transduction | C | T | I | L | | H | |
| Heterotrimeric G-protein γ-2 subunit | 33689499 | G protein γ family | membrane-associated (by similarity); expressed in fetal tissues, including testis, adrenal gland, brain, white blood cells and brain | signal transduction | C | A | I | L | | Y | 7782251 |
| Heterotrimeric G-protein γ-3 subunit | 232146 | G protein γ family | membrane-associated (by similarity); high levels in brain; low levels in testis | signal transduction; activation of MAPK | C | A | L | L | | Y | 7885596 |
| Heterotrimeric G-protein γ-4 subunit | 1730219 | G protein γ family | membrane-associated (by similarity); expressed in brain, kidney, pancreas, skeletal muscle and faintly in cardiac muscle | signal transduction | C | T | I | L | | Y | 7885596 |
| Heterotrimeric G-protein γ-5 like subunit | 12228649 | G protein γ family | membrane-associated (by similarity) | signal transduction | C | B | F | L | | H | |
| Heterotrimeric G-protein γ-5 subunit | 232147 | G protein γ family | membrane-associated (by similarity); expressed in a variety of tissues | signal transduction | C | B | F | L | | Y | 7885596 |
| Heterotrimeric G-protein γ-7 subunit | 60186106 | G protein γ family | membrane-associated (by similarity); expressed in a variety of tissues; down-regulated in pancreatic cancer | signal transduction | C | I | I | L | | Y | 7885596 |
| Heterotrimeric G-protein γ-8 subunit | 12232629 | G protein γ family | membrane-associated (by similarity) | signal transduction | C | V | L | L | | H | |
| Interferon-induced guanylate-binding protein 2 | 1166868 | GBP family | membrane-associated | binds GTP, GDP, and GMP; induced by interferon gamma during macrophage activation | C | N | I | L | | Y | 8702422 |
| Interferon-induced guanylate-binding protein 6 | 37699787 | GBP family | membrane-associated | signal transduction | C | V | L | L | | H | |
| X-linked retinitis pigmentosa GTPase regulator | 2350309 | guanine-nucleotide releasing factor | Golgi-associated; expressed in heart, brain, placenta, lung, liver, muscle, kidney, retina, pancreas and fetal retinal pigment epithelium | may have role in intracellular transport and visual perception; defects result in X-linked retinitis pigmentosa type 3 (RP3) | C | T | I | L | | H | |
| Type II inositol-1,4,5-triphosphate 5-phosphatase precursor | 1352493 | inositol-1,4,5-triphosphate 5-phosphatase type II family | membrane-associated; expressed in platelets | signal termination by hydrolysis of calcium-mobilizing second messenger Ins(1,4,5)P3 | C | N | P | L | | Y | 7721880 |
| Mannose-6-phosphate isomerase | 462567 | mannose-6-phosphate isomerase family 1 | cytoplasmic (probable); expressed in all tissues, more abundant in heart, brain, and skeletal muscle | glycosylation; defects result in congenital disorder glycosylation type Ib (CDG-Ib) | C | C | L | L | | H | |
| Mitochondrial 28S ribosomal protein S29 (death-associated protein 3) | 1700399 | mitochondrial ribosome | mitochondria | involved in mediating interferon-gamma-induced cell death | C | A | Y | L | | H | |
| CASP8 and FADD-like apoptosis regulator precursor (splice isoform 10) | 12643547 | peptidase family C14 | high levels in skeletal muscle, pancreas, heart, kidney, placenta, and peripheral blood leukocytes | regulator of apoptosis | C | S | T | L | | H | |
| G protein-coupled receptor kinase 7 | 21263559 | Ser/Thr protein kinase family, GPRK subfamily | membrane-associated; expressed in retina (rods and cones) | phosphorylates cone opsins, initiating their deactivation | C | L | L | L | | Y | 11717351 |

FIGURE 23 (cont.)

| Name | GI | classification | cellular localization | biological relevance | C | a1 | a2 | X | substrate for FT | substrate for GGT-I | PMID |
|---|---|---|---|---|---|---|---|---|---|---|---|
| M-Ras (R-Ras3) | 6226045 | small GTPase superfamily, Ras family | membrane-associated (by similarity); expression restricted to brain and heart | may be important in controlling cell proliferation; weakly activates MAPK pathway; role in reorganization of actin cytoskeleton | C | V | I | L | | H | |
| RalA | 131834 | small GTPase superfamily, Ras family | membrane-associated (by similarity) | signal transduction, chemotaxis | C | C | I | L | | Y | 1903399 |
| RalB | 131835 | small GTPase superfamily, Ras family | membrane-associated (by similarity) | signal transduction | C | C | L | L | | H | |
| Rap-1a | 131855 | small GTPase superfamily, Ras family | membrane-associated | signal transduction; partially counteracts the mitogenic function of Ras | C | L | L | L | | Y | 1899909 |
| Rap-1b | 131859 | small GTPase superfamily, Ras family | membrane-associated | signal transduction | C | Q | L | L | | Y | 2123345 |
| Rap-2b | 20981707 | small GTPase superfamily, Ras family | membrane-associated | signal transduction | C | V | I | L | | Y | 8424780 |
| R-Ras | 133456 | small GTPase superfamily, Ras family | inner surface of plasma membrane | signal transduction | C | V | L | L | | H | |
| Cdc42 (splice isoform 2) | 46397351 | small GTPase superfamily, Rho family | plasma membrane | involved in epithelial cell polarization processes; induces formation of filopodia | C | V | L | L | | Y | 10078816 |
| Rac1 (Ras-related C3 botulinum toxin substrate 1) | 131807 | small GTPase superfamily, Rho family | inner surface of plasma membrane | signal transduction; in active state, regulates cellular responses, such as secretory processes, phagocytosis of apoptotic cells, and epithelial cell polarization | C | L | L | L | | Y | 1903399 |
| Rac2 (Ras-related C3 botulinum toxin substrate 2) | 131808 | small GTPase superfamily, Rho family | cytoplasmic; membrane-associated when activated | regulators a variety of cellular responses, including secretory processes, phagocytosis of apoptotic cells, and epithelial cell polarization; possibly involved in regulation of NADPH oxidase | C | S | L | L | | Y | 1903399 |
| RacX (Ras-related C3 botulinum toxin substrate homolog) | 15033367 | small GTPase superfamily, Rho family | inner surface of plasma membrane | may regulate secretory processes | C | L | Q | L | | H | |
| RhoA | 132540 | small GTPase superfamily, Rho family | membrane-associated | regulates signal transduction pathway affecting the assembly of focal adhesions and actin stress fibers; target for yopT cysteine peptidase from Y. pestis (plague vector) and Y. pseudotuberculosis (cause of gastrointestinal disorders) | C | L | V | L | | Y | 1902099 |
| RhoC | 132543 | small GTPase superfamily, Rho family | membrane-associated (by similarity) | regulates signal transduction pathway affecting the assembly of focal adhesions and actin stress fibers | C | P | I | L | | Y | 1400319 |
| RhoF (Rif) | 18533711 | small GTPase superfamily, Rho family | membrane-associated (by similarity) | induces formation of filopodia; functions with CDC42 and Rac to form additional structures | C | L | L | L | | H | |
| RhoG | 404811 | small GTPase superfamily, Rho family | membrane-associated (by similarity) | signal transduction; regulates cell cycle | C | I | L | L | | H | |
| RhoJ (Tc10-like GTP-binding protein TCL) | 24418546 | small GTPase superfamily, Rho family | membrane-associated (by similarity) | signal transduction; induces formation of F-actin-rich structures in fibroblasts and involved in regulation of cell morphology | C | S | I | I | | H | |

FIGURE 23 (cont.)

| Name | GI | classification | cellular localization | biological relevance | C | a1 | a2 | X | FT | OGT4 | PMID |
|---|---|---|---|---|---|---|---|---|---|---|---|
| RhoU (Wrch1) | 28304072 | small GTPase superfamily, Rho family | membrane-associated (by similarity); highest levels in brain, skeletal muscle, and placenta; moderate levels in liver, lung, and heart; low levels in colon, spleen, kidney, and small intestine | regulates actin cytoskeletal organization; induces formation of filopodia and dissolution of stress fibers; Wnt-1-induced | C | C | F | V | | H | |
| T-cell surface glycoprotein CD4 precursor | 115013 | Type I membrane protein | membrane-associated | Involved in immune function; accessory protein for MHC class-II antigen/T-cell receptor interaction; may regulate T-cell activation; involved in HIV infection | C | P | S | I | | H | |
| CUB and sushi multiple domains protein 1 precursor | 38604978 | Type I membrane protein (potential) | membrane-associated (potential) | potential suppressor of squamous cell carcinomas. Defects in CSMD1 may be a cause of oral and oropharyngeal squamous cell carcinomas | C | T | V | V | | H | |
| CUB and sushi multiple domains protein 3 precursor | 38604740 | Type I membrane protein (potential) | membrane-associated (potential) | unknown | C | T | M | V | | H | |
| Integral membrane protein 2C | 12585259 | Type II membrane protein (potential) | membrane-associated (potential) | unknown | C | G | V | V | | H | |
| Beta-1,3-galactosyltransferase 5 | 13123895 | Type II membrane protein (potential) | Golgi membrane (potential) | Involved in glycosylation; catalyzes the transfer of GAL to GLNCNAC-based acceptors with a preference for the Core3 O-linked glycan | C | P | P | V | | H | |
| Down syndrome critical region protein 10 | 23398579 | unknown | unknown | expressed in placenta and testis | C | M | P | L | | H | |
| F-box/LRR-repeat protein 2 | 38502830 | unknown | expressed in brain, heart, kidney, liver, lung, pancreas, and placenta | probably binds phosphorylated proteins and promotes ubiquitination and degradation; part of a SCF protein ligase complex (by similarity) | C | V | I | L | | H | |
| F-box/LRR-repeat protein 2-like | 38503141 | unknown | cytoplasmic (by similarity) | probably binds phosphorylated proteins and promotes ubiquitination and degradation; part of a SCF protein ligase complex (by similarity) | C | I | I | L | | H | |
| Protein C20orf24 (Rab5-interacting protein) | 24211596 | unknown | unknown | membrane trafficking (proposed) | C | H | P | L | | H | |
| Protein C21orf59 | 22261796 | unknown | unknown | unknown | C | L | L | V | | H | |
| Suppressor of potassium transport defect 3 | 25002267 | unknown | unknown | may function as a regulatory ATPase and be related to secretion/protein trafficking process | C | N | T | I | | H | |
| Cohen syndrome protein 1 (isoform 5) | 42558898 | vesicle-mediated sorting and intracellular protein transport (potential) | integral membrane protein (potential) | defects cause Cohen syndrome | C | L | Y | L | | H | |

FIGURE 23 (cont.)

SEQUENCE LISTING

```
<160> NUMBER OF SEQ ID NOS: 27

<210> SEQ ID NO 1
<211> LENGTH: 11
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 1

Lys Lys Lys Ser Lys Thr Lys Cys Val Ile Leu
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 2

Cys Val Ile Leu
1

<210> SEQ ID NO 3
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 3

Cys Val Leu Ser
1
```

```
<210> SEQ ID NO 4
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 4

Cys Val Leu Leu
1

<210> SEQ ID NO 5
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 5

Cys Val Leu Ser
1

<210> SEQ ID NO 6
<211> LENGTH: 5
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 6

Gly Cys Val Leu Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 7

Thr Lys Cys Val Ile Leu
1               5

<210> SEQ ID NO 8
<211> LENGTH: 11
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 8

Lys Lys Lys Ser Lys Thr Lys Cys Val Ile Met
1               5                   10

<210> SEQ ID NO 9
<211> LENGTH: 10
<212> TYPE: PRT
```

```
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 9

Lys Lys Ser Lys Thr Lys Cys Val Ile Phe
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 10

Asp Asp Pro Thr Ala Ser Ala Cys Asn Ile Gln
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 11

Gly Cys Ile Asn Cys Cys Lys Val Leu
1               5

<210> SEQ ID NO 12
<211> LENGTH: 10
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 12

Lys Lys Ser Lys Thr Lys Cys Lys Val Leu
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 13

Phe Arg Glu Lys Lys Phe Phe Cys Ala Ile Leu
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
```

-continued bind to one or more prenyltransferases.

<400> SEQUENCE: 14

Arg Arg Cys Val Leu Leu
1               5

<210> SEQ ID NO 15
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 15

Cys Leu Ile Thr
1

<210> SEQ ID NO 16
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 16

Cys Ser Leu Cys
1

<210> SEQ ID NO 17
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 17

Cys Val Leu Ala
1

<210> SEQ ID NO 18
<211> LENGTH: 7
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 18

Asp Asp Pro Thr Ala Ser Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 19

```
Lys Lys Lys Ser Lys Thr Lys
1               5
```

<210> SEQ ID NO 20
<211> LENGTH: 7
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 20

```
Phe Arg Glu Lys Lys Phe Phe
1               5
```

<210> SEQ ID NO 21
<211> LENGTH: 5
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 21

```
Gly Cys Ile Asn Cys
1               5
```

<210> SEQ ID NO 22
<211> LENGTH: 4
<212> TYPE: PRT
<213> ORGANISM: Artificial
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 22

```
Cys Lys Val Leu
1
```

<210> SEQ ID NO 23
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 23

```
Cys Val Ile Phe
1
```

<210> SEQ ID NO 24
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 24

```
Cys Val Ile Met
1
```

```
<210> SEQ ID NO 25
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 25

Cys Val Phe Leu
1

<210> SEQ ID NO 26
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 26

Cys Asn Ile Gln
1

<210> SEQ ID NO 27
<211> LENGTH: 4
<212> TYPE: PRT
<213> ORGANISM: Artificial Sequence
<220> FEATURE:
<223> OTHER INFORMATION: Synthesized artificial peptide substrate, which
      has a C-terminal C-A1-A2-X sequence, and thus are predicted to
      bind to one or more prenyltransferases.

<400> SEQUENCE: 27

Cys Ala Ile Leu
1
```

GERANYLGERANYL TRANSFERASE TYPE I (GGTASE-I) STRUCTURE AND USES THEREOF

CROSS REFERENCE TO RELATED APPLICATIONS

This application is based on and claims priority to U.S. Provisional Patent application Ser. No. 60/507,685, filed Oct. 1, 2003, herein incorporated by reference in its entirety.

CROSS REFERENCE TO TABLES PROVIDED ON CD-ROM

The atomic coordinate data associated with the instant disclosure have been provided as fourteen (14) ASCII text files on CD-ROM (provided in duplicate). The CD-ROMs are marked in indelible ink to identify the Applicants, Title, Creation Date (Sep. 30, 2004), Computer System (IBM-PC/MS-DOS/MS-Windows), and Ser. No. 10/957,517, . The filenames and sizes of the files on the CD-ROM are as follows: Table A.txt (388 KB); Table B.txt (392 KB); Table C.txt (380 KB); Table D.txt (377 KB); Table E.txt (435 KB); Table F.txt (2241 KB); Table G.txt (2185 KB); Table H.txt (2212 KB); Table I.txt (2226 KB); Table J.txt (2223 KB); Table K.txt (2230 KB); Table L.txt (421 KB); Table M.txt (424 KB); and Table N.txt (446 KB). The atomic coordinate data submitted on CD-ROM is hereby incorporated by reference into the instant disclosure.

TECHNICAL FIELD

The presently disclosed subject matter relates generally to the design of inhibitors of prenyltransferases, more particularly to the design of inhibitors of farnesyl transferase (FTase) and/or geranylgeranyl transferase (GGTase), and even more particularly to the design of inhibitors of FTase and/or geranylgeranyl transferase (GGTase) by taking advantage of differences between the crystalline structures of FTase and geranylgeranyl transferase type I (GGTase-I) in complex with substrates and products.

Abbreviations

Å Angstrom(s)
ANL-APS Argonne National Labs-Advanced Photon Source
BNLNSLS Brookhaven National Labs National Synchrotron Light Source
BPV bovine papilloma virus
$Ca_1a_2X$ a peptide substrate for prenyltransferases, typically characterized by a peptide sequence Cys-aliphatic-aliphatic-X
CaMV cauliflower mosaic virus
CCDB Cambridge Crystallographic Data Bank
cDNA complementary DNA
CVIL a representative $Ca_1a_2X$ peptide having the amino acid sequence Cys-Val-Ile-Leu (SEQ ID NO: 2)
DNA deoxyribonucleic acid
DTT dithiothreitol
EBV Epstein-Barr virus
$EC_{50}$ a concentration of modulator that produces 50% of the maximum response for the modulator
EDTA ethylenediaminetetraacetic acid
ER endoplasmic reticulum
FPP farnesyl diphosphate
FTase farnesyl transferase
FTI(s) farnesyl transferase inhibitor(s)
GGPP geranylgeranyl diphosphate
GGTase-I geranylgeranyl transferase type I
GST tag a glutathione S-transferase tag
GTI(s) GGTase-I inhibitor(s)
His a histidine tag, typically a sequence of 5 or 6 consecutive histidine residues
HPLC high performance liquid chromatography
$K_d$ dissociation constant
kDa kilodalton(s)
MAD multiwavelength anomalous diffraction
MIR multiple isomorphous replacement
MPD methyl pentanediol
NCS non-crystallographic symmetry
nt nucleotide
PAGE polyacrylamide gel electrophoresis
PCR polymerase chain reaction
PEG polyethylene glycol
pI isoelectricpoint
PTI(s) prenyltransferasae inhibitor(s)
RabGGTase protein geranylgeranyl transferase type-II
REP RabGGTase escort protein
RMSD root-mean-square deviation
RNA ribonucleic acid
RUBISCO ribulose-1,5-bisphosphate carboxylase/oxygenase
SDS sodium dodecyl sulfate
SDS-PAGE sodium dodecyl sulfate polyacrylamide gel electrophoresis
SIRAS single isomorphous replacement anomalous scattering
SV40 simian virus 40
TCEP tris(2-carboxyethyl)phosphine-HCl
$T_d$ dissociation temperature
$T_m$ thermal melting point
TMV tobacco mosaic virus
WT wild type

| Amino Acid Abbreviations, Codes, and Functionally Equivalent Codons | | | |
|---|---|---|---|
| Amino Acid | 3-Letter | 1-Letter | Codons |
| Alanine | Ala | A | GCA; GCC; GCG; GCU |
| Arginine | Arg | R | AGA; AGG; CGA; CGC; CGG; CGU |
| Asparagine | Asn | N | AAC; AAU |
| Aspartic Acid | Asp | D | GAC; GAU |
| Cysteine | Cys | C | UGC; UGU |
| Glutamic acid | Glu | E | GAA; GAG |
| Glutamine | Gln | Q | CAA; CAG |
| Glycine | Gly | G | GGA; GGC; GGG; GGU |
| Histidine | His | H | CAC; CAU |
| Isoleucine | Ile | I | AUA; AUC; AUU |
| Leucine | Leu | L | UUA; UUG; CUA; CUC; CUG; CUU |
| Lysine | Lys | K | AAA; AAG |
| Methionine | Met | M | AUG |
| Phenylalanine | Phe | F | UUC; UUU |
| Proline | Pro | P | CCA; CCC; CCG; CCU |
| Serine | Ser | S | ACG; AGU; UCA; UCC; UCG; UCU |
| Threonine | Thr | T | ACA; ACC; ACG; ACU |
| Tryptophan | Trp | W | UGG |
| Tyrosine | Tyr | Y | UAC; UAU |
| Valine | Val | V | GUA; GUC; GUG; GUU |

BACKGROUND

Over one hundred proteins important for cell growth, differentiation, and morphology, including many GTP-binding regulatory proteins (G proteins), require posttranslational modification by covalent attachment of an isoprenoid lipid (prenylation) for proper function (Tamanoi & Sigman, 2001). The three known enzymes that catalyze protein prenylation are the two $Ca_1a_2X$ prenyltransferases, protein geranylgeranyltransferase type-I (GGTase-I) and protein farnesyltransferase (FTase), and a third enzyme, protein geranylgeranyltransferase type-II (RabGGTase; Casey & Seabra, 1996). GGTase-I modifies most monomeric G proteins in the Rho, Rac, and Rap subfamilies, and nine of the twelve heterotrimeric G protein γ subunits. Loss of GGTase-I function has dramatic biological effects, blocking the cell cycle at the G1 to S phase transition and promoting apoptosis (Li et al., 2002; Vogt et al., 1996). Since the demonstration that inhibition of FTase causes tumor regression in mice (Kohl et al., 1995), the prenyltransferase enzyme family has been studied in increasing detail. Drug design efforts have produced a number of $Ca_1a_2X$ prenyltransferase inhibitors (PTIs) that are now in advanced clinical trials as anti-cancer treatments (Johnston, 2001).

Although the majority of these drug discovery efforts have focused on FTase inhibition, GGTase-I is increasingly of interest as a drug target. GGTase-I inhibitors (GTIs) have demonstrated efficacy in pre-clinical models of tumor progression (Sebti & Hamilton, 2000) and show promise in the treatment of smooth muscle hyperplasia (Stark et al., 1998). Recently, GGTase-I inhibitors were shown to attenuate clinical signs of disease in animal models of multiple sclerosis (Walters et al., 2002). GGTase-I has also been proposed as a target for countering parasitic infections such as malaria by selective inhibition of the parasite enzyme (Chakrabarti et al., 1998).

The use of prenyltransferasae inhibitors (PTIs) as human therapeutics has not been universally successful, however. Ongoing study has made clear that the use of protein prenyltransferase inhibitors (PTIs) as human therapeutics requires carefully calibrated levels of FTase or GGTase-I inhibition to avoid toxicity and unwanted side effects. The statin family of drugs blocks the committed step of cholesterol synthesis, in turn reducing farnesyl diphosphate (FPP) and geranylgeranyl diphosphate (GGPP) synthesis and ultimately reducing the protein prenylation levels in the cell. This chronic, low-level inhibition of protein prenylation has anti-cancer effects (Wong et al., 2002), but outright inhibition of all protein prenylation activity is toxic (deSolms et al., 2003). GTIs show anti-tumor activity (Sebti & Hamilton, 2000), and show promise in pre-clinical studies for the treatment of heart disease (Stark et al., 1998) and multiple-sclerosis (Walters et al., 2002). Reports of GTIs toxicity, however, are wide ranging, with side-effects ranging from benign (Sun et al., 1998) to lethal (Lobell et al., 2001). Overall, the clinical application of protein prenyltransferase to human disease would greatly benefit from a better understanding of inhibitor potency and selectivity.

Accordingly, it is an object of the presently disclosed subject matter to provide methods and compositions that can be used to identify new inhibitors of protein prenyltransferases. This object is achieved in whole or in part by the presently disclosed subject matter.

An object of the presently disclosed subject matter having been stated hereinabove, other objects will be evident as the description proceeds, when taken in connection with the accompanying Drawings and Examples as best described hereinbelow.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for designing an ligand for a farnesyl transferase (FTase). In some embodiments the method comprises (a) providing a molecule that binds to a geranylgeranyl transferase type I (GGTase-I) $a_2$ site; (b) determining a moiety of the molecule that interacts with the $a_2$ site; (c) modifying the moiety to produce a modified molecule; (d) modeling an interaction between the modified molecule and the GGTase-I $a_2$ site; and (e) selecting the modified molecule as a ligand for FTase if the interaction is predicted to be disrupted. In some embodiments, the ligand comprises an inhibitor. In some embodiments, the determining comprises identifying a moiety of the molecule that interacts with residues Thr 49β, Phe 106β, and Leu 361β of a human GGTase-I polypeptide. In some embodiments, the modifying comprises substituting the moiety with a group comprising an aromatic ring. In some embodiments, the selecting further comprises (a) modeling a first interaction between the modified molecule with the GGTase-I $a_2$ site; (b) modeling a second interaction between the modified molecule with an FTase $a_2$ site; and (c) identifying a modified molecule that is predicted to be unable to bind to the GGTase-I $a_2$ site but able to bind to the FTase $a_2$ site. In some embodiments, the selecting further comprises modeling an interaction between the modified molecule identified in step (b) with a farnesyl transferase (FTase) to identify a modified molecule that is predicted to interact with an FTase $a_2$ site. In some embodiments of the instant method, the molecule is a peptide or a small molecule. In some embodiments, the modified molecule comprises a change in an amino acid that interacts with the $a_2$ site of the GGTase from an amino acid with a non-aromatic side chain to an amino acid comprising an aromatic side chain. In some embodiments, the modifying comprises modifying a moiety that interacts with one or more of residues Thr 49β, Phe 106β, and Leu 361β of a human GGTase-I polypeptide.

The presently disclosed subject matter also provides methods of designing a modulator that selectively modulates the activity of an FTase. In some embodiments, the method comprises (a) evaluating a three-dimensional structure of a crystallized GGTase-I complex; and (b) synthesizing a potential modulator based on the three-dimensional structure of the crystallized GGTase-I polypeptide complex, whereby a modulator that selectively modulates the activity of FTase is designed. In some embodiments, the evaluating comprises comparing the GGTase-I structure to a structure of FTase. In some embodiments, the complex comprises a ligand selected from the group consisting of GGPP, a GGPP analog, a $Ca_1a_2X$ peptide, a prenyl peptide product, and combinations thereof. In some embodiments, the method further comprises contacting a FTase polypeptide with the potential modulator and a ligand; and assaying the FTase for binding of the potential modulator, for a change in activity of the a FTase, or both.

The presently disclosed subject matter also provides methods of designing a modulator of a prenyltransferase. In some embodiments, the method comprises (a) designing a potential modulator of a prenyltransferase that will make interactions with amino acids in a binding site of the prenyltransferase, based upon a crystalline structure selected from the group consisting of a GGTase-I in complex with a product, a GGTase-I in complex with a substrate, and a GGTase-I in complex with a substrate and a product; (b) synthesizing the modulator; and (c) determining whether the potential modulator modulates the activity of the prenyltransferase, whereby a modulator of a prenyltransferase is designed. In some embodiments, the prenyltransferase is selected from the group consisting of GGTase-I, FTase and RabGGTase. In some embodiments, the substrate is selected from the group consisting of GGPP, a GGPP analog, a $Ca_1a_2X$ peptide. In some embodiments, the product is a prenyl peptide product. In some embodiments, the ligand binding site comprises GGTase-I residues selected from the group consisting of His 201α, Glu 169β, Arg 173β, Gln 167α, Phe 174β, His 121β, Asp 269β, Cys 271β, His 321β, Leu 320β, Phe 52β, Phe 53β, Thr 49β, Met 124β, Tyr 166α, Phe 324β, Ala 123β, and combinations thereof.

The presently disclosed subject matter also provides methods of designing a modulator that selectively modulates the activity of GGTase-I or FTase to the exclusion of other prenyltransferases. In some embodiments, the method comprises (a) evaluating a three-dimensional structure of a crystallized GGTase-I polypeptide complex; and (b) synthesizing a potential modulator based on the three-dimensional structure of the crystallized GGTase-I polypeptide complex, whereby a modulator that selectively modulates the activity of GGTase-I or FTase to the exclusion of other prenyltransferases is designed. In some embodiments, the complex comprises a ligand selected from the group consisting of GGPP, a GGPP analog, a $Ca_1a_2X$ peptide, a prenyl peptide product, and combinations thereof. In some embodiments, the method further comprises contacting a GGTase-I polypeptide with the potential modulator and a ligand; and assaying the GGTase-I for binding of the potential modulator, for a change in activity of the GGTase-I, or both. In some embodiments, the ligand is selected from the group consisting of GGPP, a GGPP analog, a $Ca_1a_2X$ peptide, a prenyl peptide product, and combinations thereof. In some embodiments, the evaluating comprises comparing a GGTase-I structure to a structure of a prenylation enzyme other than GGTase-I.

The presently disclosed subject matter also provides methods of screening a plurality of compounds for a modulator of a prenyltransferase. In some embodiments, the method comprises (a) providing a library of test samples; (b) contacting a crystalline form comprising a prenyltransferase in complex with a ligand with each test sample; (c) detecting an interaction between a test sample and the crystalline prenyltransferase in complex with a ligand; (d) identifying a test sample that interacts with the crystalline prenyltransferase in complex with a ligand; and (e) isolating a test sample that interacts with the crystalline prenyltransferase in complex with a ligand, whereby a plurality of compounds is screened for a modulator of a prenyltransferase. In some embodiments, the prenyltransferase is selected from the group consisting of GGTase-I, FTase and RabGGTase. In some embodiments, the library of test samples are bound to a support. In some embodiments, the library of test samples are synthesized directly on a support. In some embodiments, the ligand is selected from the group consisting of GGPP, a GGPP analog, a $Ca_1a_2X$ peptide, a prenyl peptide product, and combinations thereof.

The presently disclosed subject matter also provides methods for identifying a prenyltransferase modulator. In some embodiments, the method comprises (a) providing atomic coordinates of a GGTase-I in complex with a ligand to a computerized modeling system; and (b) modeling a ligand that fits spatially into an active site of the GGTase-I to thereby identify a prenyltransferase modulator. In some embodiments, the active site of the GGTase-I comprises His 201α, Glu 169β, Arg 173β, Gln 167α, Phe 174β, His 121β, Asp 269β, Cys 271β, His 321β, Leu 320β, Phe 52β, Phe 53β, Thr 49β, Met 124β, Tyr 166α, Phe 324β, Ala 123β, and combinations thereof. In some embodiments, the method further comprises identifying in an assay for prenyltransferase-mediated activity a modeled ligand that increases or decreases the activity of the prenyltransferase. In some embodiments, the ligand is selected from the group consisting of GGPP, a GGPP analog, a $Ca_1a_2X$ peptide, a prenyl peptide product, and combinations thereof.

The presently disclosed subject matter also provides methods of designing a modulator of a prenyltransferase. In some embodiments, the method comprises (a) selecting a candidate prenyltransferase ligand; (b) determining which amino acid or amino acids of the prenyltransferase interact with the ligand using a three-dimensional model of a crystallized protein, the model comprising a GGTase-I complex; (c) identifying in a biological assay for prenyltransferase activity a degree to which the ligand modulates the activity of the prenyltransferase; (d) selecting a chemical modification of the ligand wherein the interaction between the amino acids of the prenyltransferase and the ligand is predicted to be modulated by the chemical modification; (e) synthesizing a ligand having the chemical modified to form a modified ligand; (f) contacting the modified ligand with the prenyltransferase; (g) identifying in a biological assay for prenyltransferase activity a degree to which the modified ligand modulates the biological activity of the prenyltransferase; and (h) comparing the biological activity of the prenyltransferase in the presence of modified ligand with the biological activity of the prenyltransferase in the presence of the unmodified ligand, whereby a modulator of a prenyltransferase is designed. In some embodiments, the prenyltransferase is selected from the group consisting of GGTase-I, FTase and RabGGTase. In some embodiments, the complex comprises a ligand selected from the group consisting of GGPP, a GGPP analog, a $Ca_1a_2X$ peptide, a prenyl peptide product, and combinations thereof. In some embodiments, the method further comprises repeating steps (a) through (f), if the biological activity of the prenyltransferase in the presence of the modified ligand varies from the biological activity of the prenyltransferase in the presence of the unmodified ligand.

The presently disclosed subject matter also provides methods of modeling a three-dimensional structure of a target prenyltransferase in complex with a ligand from a template comprising the X-ray structure of a GGTase-I in complex with a ligand. In some embodiments, the method comprises (a) selecting an X-ray structure of a target prenyltransferase as a starting model for the target prenyltransferase; (b) manipulating the starting model for the target prenyltransferase as a rigid body to superimpose its backbone atoms onto corresponding backbone atoms of a three-dimensional template structure comprising a GGTase-I in complex with a ligand to form a manipulated model; (c) making a copy of the ligand from the template structure to form a model of a ligand bound to a template prenyltransferase; (d) merging the model of the ligand into the manipulated model to form a modified model; (e) removing one or more amino acids from the modified model; and (f) optimizing side-chain conformations, whereby a three-dimensional structure of a target prenyltransferase in complex with a ligand is modeled from a template comprising the X-ray structure of a prenyltransferase in complex with a ligand. In some embodiments, the X-ray structure of a target prenyltransferase is a structure built by homology modeling. In some embodiments, the ligand in complex with the GGTase-I is selected from the group consisting of GGPP, a GGPP analog, a $Ca_1a_2X$ peptide, a prenyl peptide product, and combinations thereof. In some embodiments, the three-dimensional template structure is a structure characterized by coordinates are represented by a table selected from the group consisting of Tables A-N. In some embodiments, the optimizing comprises varying distance constraints.

Accordingly, it is an object of the presently disclosed subject matter to provide a method of designing a modulator of a prenyltransferase. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description of the presently disclosed subject matter and non-limiting Examples.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

FIG. 7A is a stick model depicting a GGTase-I transition state model. New hydrogen bonds during the transition state are shown in red, while those unchanged from what is observed in Complexes 1, 2, and 3, as described herein under the section heading "General Considerations," are colored blue.

FIG. 7B is a stereoview of of two substrates, GGPP and the CVIL peptide (gray; SEQ ID NO: 2) superimposed on the prenylated peptide product (yellow). Before catalysis, the zinc-coordinated cysteine thiolate of the CVIL peptide (SEQ ID NO: 2) and the $C_1$ of the GGPP are separated by 8.2 Å (dotted line). Rotation of the first two isoprene units brings the substrate into the product conformation (black arrow).

FIG. 10A is a ribbon diagram of FTase Complex 5 with bound L-778,123 (black) and FPP (purple). FIG. 10B is a stereoview of omit electron density of L-778,123 and a sulfate anion bound in the GGTase-I active site. Electron density is shown at a +5δ level and was calculated using Fourier coefficients $(F_{obs}-F_{calc})\alpha_{calc}$, with the L-778,123 and sulfate atoms omitted from the final model.

The Figures depict stereopairs illustrating the FTase/FPP/ L-778,123 ternary Complex 5 (FIG. 11A), the GGTase-I/ SO4/L-778,123 anion Complex 6 (FIG. 11C), and the GGTase-I/GGPP/L-778,123 Complex 7 (FIG. 11E). Only active-site residues involved in ligand coordination are shown. FIG. 11B depicts a superposition of FTase Complex 5 (only FPP and L-778,123 are shown) with a previously determined structure of FTase complexed with a K-Ras peptide substrate and an FPP analogue (PDB 1D8D, only the peptide CVIM (SEQ ID NO: 24) $Ca_1a_2X$ motif is shown). FIG. 11D depicts a superposition of GGTase-I Complex 5, a previously determined structure of a GGTase-I binary complex with GGPP (PDB 1 N4P, only GGPP is shown), and a GGTase-I ternary complex with a GGPP analogue and a Rap2A substrate peptide (PDB 1N4Q, only the $Ca_1a_2X$ motif CVIL (SEQ ID NO: 2) is shown). FIG. 11F depicts a superposition of GGTase-I Complex 7 (only GGPP and L-778,123 are shown), with the two GGTase-I. structures described in FIG. 11D.

FIG. 12A depicts a stereopair of a superposition of the FTase Complex 5 (blue) and GGTase-I Complex 6 (red). Only the residues that contact the $a_2$ residue of the $Ca_1a_2X$ substrate peptide, the "$a_2$-binding site", and a conserved Arg residue are shown. Aromatic stacking interactions between L-778,123 and the $a_2$-binding site govern the formation of a peptide-competitive-binding mode in FTase. These stacking interactions are not possible between L-778,123 and the GGTase-I $a_2$-binding site, encouraging L-778,123 to adopt a lipid-competitive-binding mode that permits formation of a hydrogen bond. FIG. 12B depicts a stereopair of a superposition of GGTase-I Complex 6 (red) and GGTase-I Complex 7 (green). In Complex 7, an additional GGPP molecule binds with L-778,123 in the peptide-binding site; the lipid moiety of the second GGPP molecule occupies the $a_2$-binding site and provides a complementary surface for stacking interactions with L-778,123. FIG. 12C depicts a superposition of Complex 5 (only L-778,123 is shown, green) with a structure of FTase complexed with FPP and the tetrapeptide inhibitor CVFL (SEQ ID NO: 25; PDB 1JCR, only the peptide is shown). This comparison illustrates that the binding of the aromatic ring in the $a_2$-binding site is a conserved motif in FTase inhibition.

FIGS. 16A and 16B depict only the substrate peptide $Ca_1a_2X$ motif, the lipid analog, the catalytic zinc ion, and protein residues involved in ligand coordination. FIG. 16C depcits FTase complexed with FPT-II (gray) and H-Ras (CVLS; SEQ ID NO: 3), Rap2a (CNIQ; SEQ ID NO: 26), and TC21 (CVIF; SEQ ID NO: 23), respectively. FIG. 16D depicts a superposition of GGTase-I complexed with 3'azaG-GPP (gray) and RhoB (CKVL; SEQ ID NO: 22, blue), K-Ras4B (CVIM; SEQ ID NO: 24, red) and TC21 (CVIF; SEQ ID NO: 23, purple). In all structures, the $Ca_1a_2X$ peptide adopts an extended conformation with the cysteine thiolate coordinated by the zinc ion (magenta). Carbonyl oxygens and the C-terminus of the $Ca_1a_2X$ sequence make water-mediated and direct hydrogen bonds with conserved side-chains in both the α (red) and β (blue) subunits.

FIG. 17A depicts a superposition of four FTase substrate complexes (left panel) and three GGTase-I substrate complexes (right panel), shown in approximately the same orientation as FIG. 16, illustrating that cognate and crossreactive peptides adopt a common binding mode. In FTase, however, the C-terminal Phe residue of TC21 binds in a different pocket than the C-terminal Met, Gln, and Ser residues. FIG. 17B depicts a stereo pair of three FTase peptide complexes (K-Ras4B, H-Ras, Rap2a, and the corresponding van der Waals surfaces; red) and three GGTase-I peptide complexes (RhoB, K-Ras4B, TC21, and the corresponding van der Waals surfaces; blue). In all six structures the $Ca_1a_2$ portion of the $Ca_1a_2X$ motif and carboxyl terminus bind isosterically. The X residues, however, have enzyme-specific binding pockets. Differences between the X residue binding pockets are created primarily by a shift in helix 4β and a Trp/Thr difference between the two enzymes.

FIGS. 20A-20C are charts depicting $Ca_1a_2X$ motif $a_1$, $a_2$, and X residue identity, respectively, for all proteins demonstrated to be prenylated by FTase (red) and GGTase (blue).

FIG. 21A depicts the overall structure of FTase complexed with Rap2a (DDPTASACNIQ; SEQ ID NOL 10) and a FPP analog (purple), shown as a surface representation with the α subunit colored red and the β subunit colored blue. FIG. 21B depicts a close-up of the Rap2a structure, shown as a stereo pair in the same orientation as in FIG. 21A. The Rap2a upstream sequence binds along the rim of the active site, stabilized by hydrogen bonds and van der Waals contacts with the enzyme. Lys 164α was omitted for clarity (side chain atoms). FIG. 21C depicts a superposition of the FTase Rap2a (yellow) and K-Ras4B (KKKSKTKCVIM; SEQ ID NO: 8, gray) structures. Only the substrate peptide and FPP analog (purple) are shown. Although the conformation upstream of the $Ca_1a_2X$ motif differs, both $Ca_1a_2X$ motifs adopt the same "extended" conformation.

FIG. 22 presents a list of potential human $Ca_1a_2X$ prenyltransferase substrates. The list of known and hypothetical FTase and GGTase protein substrates within the human genome was compiled using the rules of substrate specificity disclosed herein. Columns 7 and 8 mark the proposed modifying enzyme, FTase or GGTase-I, respectively (substrates with published evidence of modification by that enzyme are marked with a Y, those hypothesized to be substrates are marked with an H; a * indicates prenylation by GGTase-I when FTase activity is compromised).

FIG. 23 presented a more extensive annotation, including references, of the potential human $Ca_1a_2X$ prenyltransferase substrates presented in FIG. 22. Columns 1, 2, 3, 4, and 5 show the protein name, associated genInfo identifier (GI) number, functional classification, cellular localization, and biological relevance, respectively. Column 6 shows the associated C-terminal $Ca_1a_2X$ motif. Columns 7 and 8 mark the proposed modifying enzyme, FTase or GGTase-I, respectively. Substrates with published evidence of modification by that enzyme are marked with a Y, those hypothesized to be substrates are marked with an H; a * indicates prenylation by GGTase-I when FTase activity is compromised. Publication references for evidence of modification are shown in column 9 in the form of PubMed ID numbers (PMID).

BRIEF DESCRIPTION OF THE SEQUENCE LISTING

Figure 1:
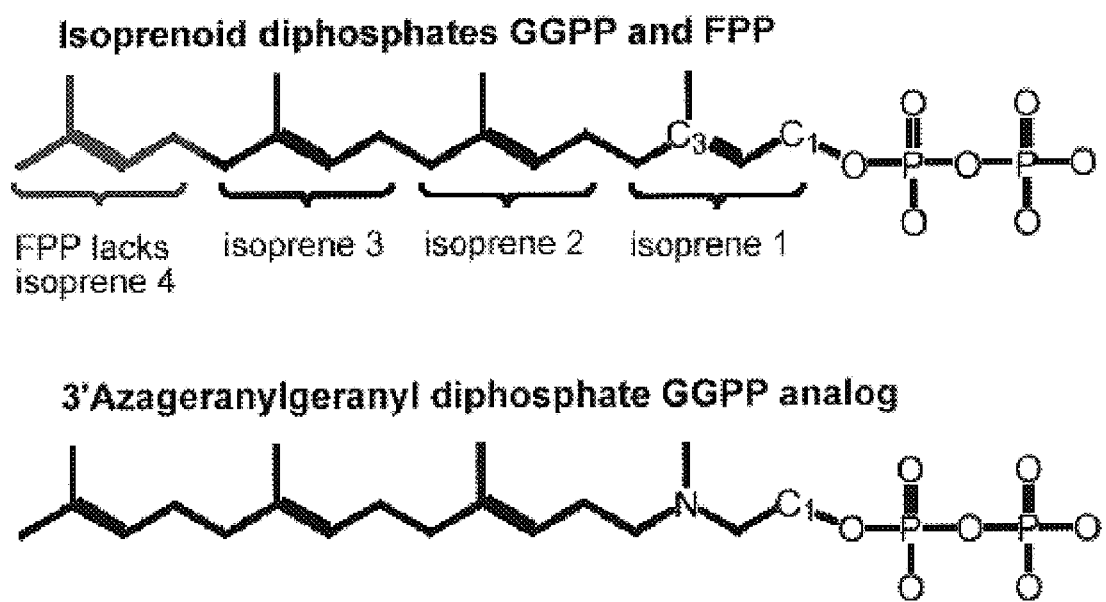
FIG. 1 depicts chemical structures depicting geranylgeranyl diphosphate (upper structure) (GGPP) and farnesyl diphosphate (FPP); the fourth isoprenoid unit, which is underlined, is present in GGPP but absent in FPP. The GGPP analog 3'-asageranylgeranyl diphosphate is depicted in the lower structure.

SEQ ID NOs: 1-27 disclose the amino acid sequences of various peptides tested for their abilities to act as substrates for the prenyltransferases disclosed herein. SEQ ID NOs: 1-17 and 21-27 all have a C-terminal $Ca_1a_2X$ sequence, and thus are predicted to bind to one or more prenyltransferases.

DETAILED DESCRIPTION

GGTase-I and FTase catalyze the transfer of a 20-carbon and a 15-carbon isoprenoid respectively from geranylgeranyl diphosphate (GGPP) or farnesyl diphosphate (FPP) to a protein, or short peptide, with a C-terminal $Ca_1a_2X$ sequence recognition motif. The $Ca_1a_2X$ box is defined by the cysteine (C), two typically aliphatic residues (aa), and the C-terminal residue (X) that contributes to substrate specificity (Casey et al., 1991; Moores et al., 1991; Reiss et al., 1990; Yokoyama et al., 1991). The steady-state kinetic parameters of GGTase-I are similar to those of FTase, although the GGTase-I reaction has not been characterized in as much detail, and indicate that the enzyme binds substrates by an ordered mechanism (Stirtan & Poulter, 1997; Yokoyama et al., 1995). For both GGTase-I and FTase, product release is the slow step in the reaction. In FTase this step is accelerated by the binding of additional substrate (Tschantz et al., 1997). Despite these similarities, the two enzymes differ in co-factor requirements: unlike FTase, GGTase-I does not require magnesium for activity (Zhang & Casey, 1996).

Three-dimensional structures of mammalian FTase with substrates, products, and inhibitors have been determined (Dunten et al., 1998; Long et al., 1998; Long et al., 2000; Long et al., 2002; Long et al., 2001; Park et al., 1997; Strickland et al., 1998). Structural information is available only for the apo RabGGTase (Zhang et al., 2000); RabGGTase is more specialized than the $Ca_1a_2X$ enzymes, exclusively modifying members of the Rab subfamily of G proteins (Seabra, 1998). RabGGTase processively transfers geranylgeranyl groups to both cysteine residues of CC- or CxC-containing Rab proteins (Farnsworth et al., 1994; Thoma et al., 2001). RabGGTase also requires an escort protein (REP) to present the Rab substrate for modification (Andres et al., 1993). Unlike the $Ca_1a_2X$ enzymes, short peptides are not substrates for RabGGTase (Seabra et al., 1992).

Disclosed herein is the first structural information for a GGTase-I, including a series of structures that represent the major steps along the reaction coordinate, from binding of substrates to product formation and release. The main mechanistic features of the catalytic cycle appear to be common to all three protein prenyltransferases. Comparative analysis of the structures exposes features unique to GGTase-I. In particular, determinants within the protein prenyltransferase family that dominate substrate specificity are revealed. The importance of these features has been confirmed by mutagenesis as disclosed herein. The GGTase-I structures also provide further insight into the double prenylation mechanism of RabGGTase and its substrate selection. The structures of the GGTase-I complexes are likely to facilitate design of inhibitors that are selective for one type of prenyltransferase over another. Furthermore, the product complexes suggest a mechanism for the transportation of newly prenylated proteins within the cell. Thus, what is needed is detailed structural information for prenyltransferases in general and a GGTase-I in particular; such information could take the form of, for example, a series of structures that trace binding of substrates through product formation and release. The presently disclosed subject matter addresses this and other problems, and also provides a generalized method of action for all protein prenyltransferases.

Disclosed herein are crystal structures of GGTase-I complexed with substrates, products, and substrates and products that were determined to a resolution of about 3.5 Å or better. Insight provided by the structures of the presently disclosed subject matter is useful for the design of GGTase-I-selective modulators, and for the design of FTase-selective modulators (e.g., by designing modulators that do not interact with GGTase-I). The general similarity of GGTase-I with other prenyltransferases (e.g., FTase and RabGGTase) exposes patterns in their function and highlights the unique features of GGTase-I. The GGTase-I structures of the presently disclosed subject matter (e.g., GGTase-I in the presence of substrates or substrate analogs, GGTase-I in the presence of substrates/ substrate analogs and a prenylated product, and GGTase-I in the presence of a prenylated product) are also useful in answering the critical questions regarding how substrates are bound by RabGGTase and regarding the mechanism of the double prenylation reaction this enzyme catalyzes. The GGTase-I substrate and product complexes can be employed in prenyltransferase modulator design efforts, and the product complexes provide insight into the question of how newly prenylated proteins are transported within the cell.

Until disclosure of the presently disclosed subject matter presented herein, the ability to obtain crystalline forms of GGTase-I in complex with substrates, substrate analogs, a prenylated product and combinations thereof has not been realized. And until disclosure of the presently disclosed subject matter presented herein, a detailed three-dimensional crystal structure of a GGTase-I polypeptide in complex with substrates and/or products has not been solved.

In addition to providing structural information, crystalline polypeptides provide other advantages. For example, the crystallization process itself further purifies the polypeptide, and satisfies one of the classical criteria for homogeneity. In fact, crystallization frequently provides unparalleled purification quality, removing impurities that are not removed by other purification methods such as high performance liquid chromatography (HPLC), dialysis, conventional column chromatography, etc. Moreover, crystalline polypeptides are often stable at ambient temperatures and free of protease contamination and other degradation associated with solution storage. Crystalline polypeptides can also be useful as pharmaceutical preparations. Finally, crystallization techniques in general are largely free of problems, such as denaturation, associated with other stabilization methods (e.g., lyophilization). Once crystallization has been accomplished, crystallographic data provides useful structural information that can assist the design of compounds that can serve as agonists or antagonists, as described herein below.

I. Definitions

For convenience, certain terms employed in the specification, examples, and appended claims are collected here. Unless defined otherwise, all technical and scientific terms used herein have the same meaning as commonly understood by one of ordinary skill in the art to which the presently disclosed subject matter belongs.

Following long-standing patent law convention, the terms "a" and "an" refer to "one or more" when used in this application, including the claims. Thus, the articles "a" and "an" are used herein to refer to one or to more than one (i.e., to at least one) of the grammatical object of the article. By way of example, "an element" refers to one element or more than one element.

As used herein, the term "about", when referring to a value or to an amount of mass, weight, time, volume, concentration, or percentage, is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed method.

As used herein, the terms "agonist" and "activator" are synonymous and refer to an agent that supplements or potentiates the bioactivity of a functional GGTase-I gene or protein, or that supplements or potentiates the bioactivity of a naturally occurring or engineered non-functional GGTase-I gene or protein.

As used herein, the terms "α-helix" and "alpha-helix" refer to the conformation of a polypeptide chain wherein the polypeptide backbone is wound around the long axis of the molecule in a left-handed or right-handed direction, and the R groups of the amino acids protrude outward from the helical backbone, wherein the repeating unit of the structure is a single turnoff the helix, which extends about 0.56 nm along the long axis.

As used herein, the terms "amino acid" and "amino acid residue" are used interchangeably and refer to any of the twenty naturally occurring amino acids. An amino acid is formed upon chemical digestion (hydrolysis) of a polypeptide at its peptide linkages. The amino acid residues described herein are in some embodiments in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature abbreviations for amino acid residues are shown in tabular form presented herein-above. Thus, the term "amino acid" is intended to embrace all molecules, whether natural or synthetic, which include both an amino functionality and an acid functionality and capable of being included in a polymer of naturally occurring amino acids. Exemplary amino acids include naturally occurring amino acids; analogs, derivatives and congeners thereof; amino acid analogs having variant side chains; and all stereoisomers of any of any of the foregoing.

It is noted that all amino acid residue sequences represented herein by formulae have a left-to-right orientation in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

As used herein, the term "antagonist" and "inhibitor" are synonymous and refer to an agent that decreases or inhibits the bioactivity of a functional GGTase-I gene or protein, or that decreases or inhibits the bioactivity of a naturally occurring or engineered non-functional GGTase-I gene or protein.

As used herein, the terms "β-sheet" and "beta-sheet" refer to the conformation of a polypeptide chain stretched into an extended zigzag conformation. Portions of polypeptide chains that run "parallel" all run in the same direction. Portions of polypeptide chains that run "antiparallel" run in the opposite direction from each other.

The term "binding" refers to an association, which can be a stable association, between two molecules, e.g., between a polypeptide of the presently disclosed subject matter and a binding partner, due to, for example, electrostatic, hydrophobic, ionic, and/or hydrogen-bond interactions under particular conditions.

As used herein, the term "biological activity" refers to any observable effect flowing from interaction between a prenyltransferase (e.g. a GGTase-I) polypeptide and a ligand (e.g., a substrate or a product). Representative, but non-limiting, examples of biological activities in the context of the presently disclosed subject matter include binding an isoprenoid-comprising compound, binding a peptide comprising the $Ca_1a_2X$ box, binding a prenylated product and catalyzing a prenylation reaction.

As used herein, the term "$Ca_1a_2X$ prenyltransferase" refers to an enzyme adapted to catalyze the transfer of a chemical moiety from an isoprenoid-comprising compound to a substrate comprising the $Ca_1a_2X$ box. Examples of $Ca_1a_2X$ prenyltransferases include GGTase-I, FTase, and RabGGTase.

As used herein, the terms "candidate substance" and "candidate compound" are used interchangeably and refer to a substance that is believed to interact with another moiety, for example a given ligand that is believed to interact with a complete GGTase-I polypeptide or a fragment thereof, and which can be subsequently evaluated for such an interaction. Representative candidate substances or compounds include "xenobiotics", such as drugs and other therapeutic agents, carcinogens and environmental pollutants, natural products and extracts, as well as "endobiotics", such as steroids, fatty acids, and prostaglandins. Other examples of candidate compounds that can be investigated using the methods of the presently disclosed subject matter include, but are not restricted to, agonists and antagonists of a GGTase-I polypeptide, toxins and venoms, viral epitopes, hormones (e.g., opioid peptides, steroids, etc.), hormone receptors, peptides, enzymes, enzyme substrates, co-factors, lectins, sugars, oligonucleotides or nucleic acids, oligosaccharides, proteins, small molecules, and monoclonal antibodies.

A "comparison window," as used herein, refers to a conceptual segment of at least 20 contiguous amino acid positions wherein a protein sequence can be compared to a reference sequence of at least 20 contiguous amino acids and wherein the portion of the protein sequence in the comparison window can comprise additions or deletions (i.e., gaps) of 20 percent or less as compared to the reference sequence (which does not comprise additions or deletions) for optimal alignment of the two sequences. Optimal alignment of sequences for aligning a comparison window can be conducted by the local homology algorithm of Smith & Waterman, 1981, by the homology alignment algorithm of Needleman & Wunsch, 1970, by the search for similarity method of Pearson & Lipman, 1988, by computerized implementations of these algorithms (GAP, BESTFIT, FASTA, and TFASTA in the GCG® WISCONSIN PACKAGE® available from Accelrys Inc., San Diego, Calif., United States of America), or by inspection, and the best alignment (i.e., resulting in the highest percentage of homology over the comparison window) generated by the various methods can be identified. See also discussion below in Section IX.D.1.

As used herein, the term "complementary DNA (cDNA)" refers to a single-stranded DNA molecule that is formed from an mRNA template by the enzyme reverse transcriptase. Typically, a primer complementary to portions of mRNA is employed for the initiation of reverse transcription. Those of ordinary skill in the art also use the term "cDNA" to refer to a double-stranded DNA molecule consisting of such a single-stranded DNA molecule and its complementary DNA strand.

The term "complex" refers to an association between at least two moieties (e.g. chemical or biochemical) that have an affinity for one another. Examples of complexes include associations between antigen/antibodies, lectin/avidin, target polynucleotide/probe oligonucleotide, antibody/anti-antibody, receptor/ligand, enzyme/ligand, polypeptide/polypeptide, polypeptide/polynucleotide, polypeptide/co-factor, polypeptide/substrate, polypeptide/inhibitor, polypeptide/small molecule, and the like. "Member of a complex" refers to one moiety of the complex, such as an antigen or ligand. "Protein complex" or "polypeptide complex" refers to a complex comprising at least one polypeptide.

As used herein, the terms "cells", "host cells", and "recombinant host cells" are used interchangeably and refer not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the terms "chimeric protein" and "fusion protein" are used interchangeably and refer to a fusion of a first amino acid sequence encoding a prenyltransferase (e.g. GGTase-I) polypeptide with a second amino acid sequence defining a polypeptide domain foreign to, and not homologous with, any domain or sequence of a prenyltransferase (e.g. GGTase-I) polypeptide. A chimeric protein can present a foreign domain that is found in an organism that also expresses the first protein, or it can be an "interspecies" or "intergenic" fusion of protein structures expressed by different kinds of organisms. In some embodiments, a chimeric protein or a fusion protein can be represented by the general formula X-GGTase-I-Y, wherein GGTase-I represents a portion of the protein which is derived from a GGTase-I polypeptide, and X and Y are independently absent or represent amino acid sequences which are not related to a GGTase-I sequence in an organism, including naturally occurring mutants. For example, a fusion protein can comprise amino acid sequences of a transit peptide joined with an amino acid sequence of at least part of a GGTase-I polypeptide. As another example, a fusion protein can comprise at least part of a GGTase-I amino acid sequence fused with a polypeptide that binds an affinity matrix. Such fusion proteins can be useful for isolating large quantities of GGTase-I protein with affinity chromatography. The term "chimeric gene" refers to a nucleic acid construct that encodes a "chimeric protein" or "fusion protein" as defined herein.

Thus, in many examples of fusion proteins, there are two different polypeptide sequences, and in certain cases, there can be more. The sequences can be linked in frame. A fusion protein can include a domain that is found (albeit in a different protein) in an organism that also expresses the first protein, or it can be an "interspecies", "intergenic", etc. fusion expressed by different species of organisms. In various embodiments, the fusion polypeptide can comprise one or more amino acid sequences linked to a first polypeptide. In the case where more than one amino acid sequence is fused to a first polypeptide, the fusion sequences can be multiple copies of the same sequence, or alternatively, can be different amino acid sequences. The fusion polypeptides can be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain, or an immunoglobulin binding domain.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz & Schirmer, 1979). According to such analyses, groups of amino acids can be defined where amino acids within a group exchange preferentially with each other, and therefore resemble each other most in their impact on the overall protein structure (Schulz & Schirmer, 1979). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and lie, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

As used herein, the term "crystal lattice" refers to the array of points defined by the vertices of packed unit cells.

As used herein, the term "detecting" refers to confirming the presence of a target entity by observing the occurrence of a detectable signal, such as a radiologic or spectroscopic signal that will appear exclusively in the presence of the target entity.

The term "domain", when used in connection with a polypeptide, refers to a specific region within such polypeptide that comprises a particular structure or mediates a particular function. In the typical case, a domain of a polypeptide of the presently disclosed subject matter is a fragment of the polypeptide. In certain instances, a domain is a structurally stable domain, as evidenced, for example, by mass spectroscopy, or by the fact that a modulator can bind to a druggable region of the domain.

As used herein, the term "DNA segment" refers to a DNA molecule that has been isolated free of total genomic DNA of a particular species. In some embodiments, a DNA segment encoding a GGTase-I polypeptide refers to a DNA segment that comprises a full length polypeptide, but can optionally comprise fewer or additional nucleic acids, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

As used herein, the term "DNA sequence encoding a GGTase-I polypeptide" can refer to one or more coding sequences within a particular individual. Moreover, certain differences in nucleotide sequences can exist between individual organisms, which are called alleles. It is possible that such allelic differences might or might not result in differences in the amino acid sequence of the encoded polypeptide yet still encode a protein with the same biological activity. As is well known, genes for a particular polypeptide can exist in single or multiple copies within the genome of an individual. Such duplicate genes can be identical or can have certain modifications, including nucleotide substitutions, additions, or deletions, all of which still code for polypeptides having substantially the same activity.

The term "druggable region", when used in reference to a polypeptide, nucleic acid, complex and the like, refers to a region of the molecule that is a target or is a likely target for binding a modulator. For a polypeptide, a druggable region generally refers to a region wherein several amino acids of a polypeptide would be capable of interacting with a modulator or other molecule. For a polypeptide or complex thereof, exemplary druggable regions including binding pockets and sites, enzymatic active sites, interfaces between domains of a polypeptide or complex, surface grooves or contours or surfaces of a polypeptide or complex which are capable of participating in interactions with another molecule. In certain instances, the interacting molecule is another polypeptide, which can be naturally occurring. In other instances, the druggable region is on the surface of the molecule. In some embodiments, a druggable region is a prenyltransferase binding pocket.

Druggable regions can be described and characterized in a number of ways. For example, a druggable region can be characterized by some or all of the amino acids that make up the region, or the backbone atoms thereof, or the side chain atoms thereof (optionally with or without the Cα atoms). Alternatively, in certain instances, the volume of a druggable region corresponds to that of a carbon based molecule of at least about 200 amu and often up to about 800 amu. In other instances, it will be appreciated that the volume of such region can correspond to a molecule of at least about 600 amu and often up to about 1600 amu or more.

Alternatively, a druggable region can be characterized by comparison to other regions on the same or other molecules. For example, the term "affinity region" refers to a druggable region on a molecule (such as a polypeptide of the presently disclosed subject matter) that is present in several other molecules, in so much as the structures of the same affinity regions are sufficiently the same so that they are expected to bind the same or related structural analogs. An example of an affinity region is an ATP-binding site of a protein kinase that is found in several protein kinases (whether or not of the same origin). The term "selectivity region" refers to a druggable region of a molecule that can not be found on other molecules, in so much as the structures of different selectivity regions are sufficiently different so that they are not expected to bind the same or related structural analogs. An exemplary selectivity region is a catalytic domain of a protein kinase that exhibits specificity for one substrate. In certain instances, a single modulator can bind to the same affinity region across a number of proteins that have a substantially similar biological function, whereas the same modulator can bind to only one selectivity region of one of those proteins.

Continuing with examples of different druggable regions, the term "undesired region" refers to a druggable region of a molecule that upon interacting with another molecule results in an undesirable affect. For example, a binding site that oxidizes the interacting molecule (such as cytochrome P450 activity) and thereby results in increased toxicity for the oxidized molecule can be deemed an "undesired region". Other examples of potential undesired regions include regions that upon interaction with a drug decrease the membrane permeability of the drug, increase the excretion of the drug, or increase the blood brain transport of the drug. It can be the case that, in certain circumstances, an undesired region will no longer be deemed an undesired region because the affect of the region will be favorable, i.e., a drug intended to treat a brain condition would benefit from interacting with a region that resulted in increased blood brain transport, whereas the same region could be deemed undesirable for drugs that were not intended to be delivered to the brain.

When used in reference to a druggable region, the "selectivity" or "specificity" of a molecule such as a modulator to a druggable region can be used to describe the binding between the molecule and a druggable region. For example, the selectivity of a modulator with respect to a druggable region can be expressed by comparison to another modulator, using the respective values of $K_d$ (i.e., the dissociation constants for each modulator-druggable region complex) or, in cases where a biological effect is observed below the $K_d$, the ratio of the respective $EC_{50}$'s (i.e., the concentrations that produce 50% of the maximum response for the modulator interacting with each druggable region).

As used herein, the phrase "enhancer-promoter" refers to a composite unit that contains both enhancer and promoter elements. An enhancer-promoter is operatively linked to a coding sequence that encodes at least one gene product.

As used herein, the term "expression" generally refers to the cellular processes by which a polypeptide is produced from RNA.

As used herein, the term "gene" is used for simplicity to refer to a functional protein, polypeptide, or peptide encoding unit. As will be understood by those of ordinary skill in the art, this functional term encompasses both genomic sequences and cDNA sequences. Exemplary embodiments of genomic and cDNA sequences are disclosed herein.

As used herein, the term "GGTase-I" refers to nucleic acids encoding a geranylgeranyl transferase I (GGTase-I) polypeptide that can bind one or more ligands. The term "GGTase-I" includes invertebrate homologs; however, GGTase-I nucleic acids and polypeptides can also be isolated from vertebrate sources. "GGTase-I" further includes vertebrate homologs of GGTase-I family members, including, but not limited to, mammalian, and avian homologs. Representative mammalian homologs of GGTase-I family members include, but are not limited to, murine, and human homologs. The term "GGTase-I" can also be employed to refer to a polypeptide, which will be apparent to those of ordinary skill in the art upon reflection of the context in which the term is employed herein.

As used herein, the terms "GGTase-I gene" and "recombinant GGTase-I gene" refer to a nucleic acid molecule comprising an open reading frame encoding a GGTase-I polypeptide of the presently disclosed subject matter, including both exon and (optionally) intron sequences.

As used herein, the terms "GGTase-I gene product", "GGTase-I protein", "GGTase-I polypeptide", and "GGTase-I peptide" are used interchangeably and refer to peptides having amino acid sequences which are substantially identical to native amino acid sequences from an organism of interest and which are biologically active in that they comprise all or a part of the amino acid sequence of a GGTase-I polypeptide, or cross-react with antibodies raised against a GGTase-I polypeptide, or retain all or some of the biological activity (e.g., ligand binding ability) of the native amino acid sequence or protein. Such biological activity can include immunogenicity.

As used herein, the terms "GGTase-I gene product", "GGTase-I protein", "GGTase-I polypeptide", and "GGTase-I peptide" also include analogs of a GGTase-I polypeptide. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct GGTase-I analogs. There is no need for a "GGTase-I gene product", "GGTase-I protein", "GGTase-I polypeptide", or "GGTase-I peptide" to comprise all or substantially all of the amino acid sequence of a GGTase-I polypeptide gene product. Shorter or longer sequences are anticipated to be of use in the presently disclosed subject matter; shorter sequences are herein referred to as "segments". Thus, the terms "GGTase-I gene product", "GGTase-I protein", "GGTase-I polypeptide", and "GGTase-I peptide" also include fusion, chimeric or recombinant GGTase-I polypeptides and proteins comprising sequences of the presently disclosed subject matter. Methods of preparing such proteins are disclosed herein and are known in the art.

The term "having substantially similar biological activity", when used in reference to two polypeptides, refers to a biological activity of a first polypeptide which is substantially similar to at least one of the biological activities of a second polypeptide. A substantially similar biological activity refers to that the polypeptides carry out a similar function, e.g., a similar enzymatic reaction or a similar physiological process, etc. For example, two homologous proteins can have a substantially similar biological activity if they are involved in a similar enzymatic reaction, e.g., they are both kinases which catalyze phosphorylation of a substrate polypeptide, however, they can phosphorylate different regions on the same protein substrate or different substrate proteins altogether. Alternatively, two homologous proteins can also have a substantially similar biological activity if they are both involved in a similar physiological process, e.g., transcription. For example, two proteins can be transcription factors, however, they can bind to different DNA sequences or bind to different polypeptide interactors. Substantially similar biological activities can also be associated with proteins carrying out a similar structural role, for example, two membrane proteins.

As used herein, the term "hybridization" refers to the binding of a probe molecule, a molecule to which a detectable moiety has been bound, to a target sample. Hybridization can include the pairing of substantially complementary nucleotide sequences (strands of nucleic acid) to form a duplex or heteroduplex by the establishment of hydrogen bonds between complementary base pairs. Hybridization is a specific, i.e. non-random, interaction between two complementary polynucleotides.

As used herein, the term "interact" refers to detectable interactions between molecules, such as can be detected using, for example, a yeast two hybrid assay. The term "interact" is also meant to include "binding" interactions and "associations" between molecules. Interactions can, for example, be protein-protein or protein-nucleic acid in nature.

As used herein, the term "intron" refers to a DNA sequence present in a given gene that is not translated into protein.

As used herein, the term "isolated" refers to a molecule substantially free of other nucleic acids, proteins, lipids, carbohydrates, and/or other materials with which it is normally associated, such association being either in cellular material or in a synthesis medium. Thus, the term "isolated nucleic acid" refers to a polynucleotide of genomic, cDNA, or synthetic origin or some combination thereof, which (1) is not associated with the cell in which the "isolated nucleic acid" is found in nature, or (2) is operatively linked to a polynucleotide to which it is not linked in nature. Similarly, the term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

As used herein, the term "isomorphous replacement" refers to a method of using heavy atom derivative crystals to obtain the phase information necessary to elucidate the three-dimensional structure of a native crystal (Blundell & Johnson, 1976; Otwinowski, 1991). The phrase "heavy-atom derivatization" is synonymous with the term "isomorphous replacement".

As used herein, the terms "label" and "labeled" refer to the attachment of a moiety, capable of detection by spectroscopic, radiologic, or other methods, to a probe molecule. Thus, the terms "label" or "labeled" refer to incorporation or attachment, optionally covalently or non-covalently, of a detectable marker into a molecule, such as a polypeptide. Various methods of labeling polypeptides are known in the art and can be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

As used herein, the term "ligand" refers to any compound having the ability to associate with a given target (e.g., a polypeptide). By way of particular example, a polypeptide can be an enzyme (e.g., GGTase-I) and a ligand can be either a substrate (e.g., GGPP) or a product (e.g., a prenylated product). Thus, the term "ligand" encompasses both substrates and products, as well as moieties that can serve as agonists and antagonists; the term also includes moieties that can associate with a site on the polypeptide spatially distant from an active site. Thus, the term "ligand" refers to any molecule that is known or suspected to associate with another molecule. The term "ligand" encompasses inhibitors, activators, natural substrates, and analogs of natural substrates.

The term "mammal" is known in the art, and exemplary mammals include humans, primates, bovines, porcines, canines, felines, and rodents (e.g., mice and rats).

As used herein, the term "modified" refers to an alteration from an entity's normally occurring state. An entity can be modified by removing discrete chemical units or by adding discrete chemical units. The term "modified" encompasses detectable labels as well as those entities added as aids in purification.

As used herein, the term "modulate" refers to an increase, decrease, or other alteration of any, or all, chemical and biological activities or properties of a biochemical entity, e.g., a wild-type or mutant GGTase-I polypeptide. The term "modulation" as used herein refers to both upregulation (i.e., activation or stimulation) and downregulation (i.e., inhibition or suppression) of a response. Thus, the term "modulation", when used in reference to a functional property or biological activity or process (e.g., enzyme activity or receptor binding), refers to the capacity to upregulate (e.g., activate or stimulate), downregulate (e.g., inhibit or suppress), or otherwise change a quality of such property, activity, or process. In certain instances, such regulation can be contingent on the occurrence of a specific event, such as activation of a signal transduction pathway, and/or can be manifest only in particular cell types.

The term "modulator" refers to a polypeptide, nucleic acid, macromolecule, complex, molecule, small molecule, compound, species or the like (naturally occurring or non-naturally occurring), or an extract made from biological materials such as bacteria, plants, fungi, or animal cells or tissues, that can be capable of causing modulation. Modulators can be evaluated for potential activity as inhibitors or activators (directly or indirectly) of a functional property, biological activity or process, or combination of them, (e.g., agonist, partial antagonist, partial agonist, inverse agonist, antagonist, antimicrobial agents, inhibitors of microbial infection or proliferation, and the like) by inclusion in assays. In such assays, many modulators can be screened at one time. The activity of a modulator can be known, unknown or partially known.

As used herein, the term "molecular replacement" refers to a method of solving the three-dimensional structure of a compound (e.g., a protein) that involves generating a preliminary model of a crystal (e.g., a wild-type GGTase-I, or a GGTase-I mutant crystal) whose structure coordinates are unknown, by orienting and positioning a molecule whose structure coordinates are known within the unit cell of the unknown crystal so as best to account for the observed diffraction pattern of the unknown crystal. Molecular replacement operations can be conveniently carried out on a computer running a suitable software package, such as AmoRe (Navaza & Saludjian, 1997). Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. See e.g., Lattman, 1985; Rossmann, 1972. For example, using the structure coordinates of the GGTase-I provided by the presently disclosed subject matter, molecular replacement can be used to determine the structure coordinates of a crystalline mutant or homolog of a GGTase-I, or of a different crystal form of the GGTase-I.

As used herein, the term "monoclinic unit cell" refers to a unit cell wherein $a \neq b \neq c$ and $\alpha = \gamma = 90°$. The vectors a, b, and c describe the unit cell edges and the angles $\alpha$, $\beta$, and $\gamma$ describe the unit cell angles.

The term "motif" refers to an amino acid sequence that is commonly found in a protein of a particular structure or function. Typically, a consensus sequence is defined to represent a particular motif. The consensus sequence need not be strictly defined and can contain positions of variability, degeneracy, variability of length, etc. The consensus sequence can be used to search a database to identify other proteins that can have a similar structure or function due to the presence of the motif in its amino acid sequence. For example, on-line databases can be searched with a consensus sequence in order to identify other proteins containing a particular motif. Various search algorithms and/or programs can be used, including FASTA, BLAST, or ENTREZ. FASTA and BLAST are available as a part of the GCG® WISCONSIN PACKAGE® (Accelrys Inc., San Diego, Calif., United States of America). ENTREZ is available through the National Center for Biotechnology Information, National Library of Medicine, National Institutes of Health, Bethesda, Md., United States of America.

As used herein, the term "mutation" carries its traditional connotation and refers to a change, inherited, naturally occurring or introduced, in a nucleic acid or polypeptide sequence, and is used in its sense as generally known to those of skill in the art.

The term "naturally occurring", as applied to an object, refers to the fact that an object can be found in nature. For example, a polypeptide or polynucleotide sequence that is present in an organism (including bacteria) that can be isolated from a source in nature and which has not been intentionally modified by man in the laboratory is naturally occurring.

As used herein, the terms "nucleic acid" and "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., $\alpha$-enantiomeric forms of naturally occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids", which comprise naturally occurring or modified nucleic acid bases attached to a polyamide backbone. Nucleic acids can be either single stranded or double stranded.

The term "operatively linked", when describing the relationship between two nucleic acid regions, refers to a juxtaposition wherein the regions are in a relationship permitting them to function in their intended manner. For example, a control sequence "operatively linked" to a coding sequence is ligated in such a way that expression of the coding sequence is achieved under conditions compatible with the control sequences, such as when the appropriate molecules (e.g., inducers and polymerases) are bound to the control or regulatory sequence(s). Thus, in some embodiments, the phrase "operatively linked" refers to that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

As used herein, the term "orthorhombic unit cell" refers to a unit cell wherein a≠b≠c; and a α=γ=γ=90°. The vectors a, b, and c describe the unit cell edges and the angles α, β, and γ describe the unit cell angles.

The term "phenotype" refers to the entire physical, biochemical, and physiological makeup of a cell, e.g., having any one trait or any group of traits.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment can comprise a druggable region, and optionally additional amino acids on one or both sides of the druggable region, which additional amino acids can number from 5, 10, 15, 20, 30, 40, 50, or up to 100 or more residues. Further, fragments can include a sub-fragment of a specific region, which sub-fragment retains a function of the region from which it is derived. In some embodiments, a fragment can have immunogenic properties.

As used herein, the term "prenyltransferase" refers to any polypeptide having the ability to catalyze the transfer of a prenyl group from a first moiety to a second moiety. Thus, GGTase-I, FTase, and RabGGTase-I are all examples of prenyltransferases.

As used herein, the term "primer" refers to a sequence comprising in some embodiments two or more deoxyribonucleotides or ribonucleotides, in some embodiments more than three, in some embodiments more than eight, and in some embodiments at least about 20 nucleotides of an exonic or intronic region. Such oligonucleotides are in some embodiments between ten and thirty bases in length.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species can be purified to essential homogeneity (contaminant species cannot be detected in the composition by conventional detection methods) wherein the composition consists essentially of a single species. A skilled artisan can purify a polypeptide of the presently disclosed subject matter using standard techniques for protein purification in light of the teachings herein. Purity of a polypeptide can be determined by a number of methods known to those of skill in the art, including for example, amino-terminal amino acid sequence analysis, gel electrophoresis, mass-spectrometry analysis and the methods described in the Exemplification section herein.

The terms "recombinant protein" or "recombinant polypeptide" refer to a polypeptide that is produced by recombinant DNA techniques. An example of such techniques includes the case when DNA encoding the expressed protein is inserted into a suitable expression vector that is in turn used to transform a host cell to produce the protein or polypeptide encoded by the DNA.

A "reference sequence" is a defined sequence used as a basis for a sequence comparison. A reference sequence can be a subset of a larger sequence, for example, as a segment of a full-length nucleotide or amino acid sequence, or can comprise a complete sequence. Generally, when used to refer to a nucleotide sequence, a reference sequence is at least 200, 300 or 400 nucleotides in length, frequently at least 600 nucleotides in length, and often at least 800 nucleotides in length. Because two proteins can each (1) comprise a sequence (i.e., a portion of the complete protein sequence) that is similar between the two proteins, and (2) can further comprise a sequence that is divergent between the two proteins, sequence comparisons between two (or more) proteins are typically performed by comparing sequences of the two proteins over a "comparison window" (defined hereinabove) to identify and compare local regions of sequence similarity.

The term "regulatory sequence" is a generic term used throughout the specification to refer to polynucleotide sequences, such as initiation signals, enhancers, regulators and promoters, which are necessary or desirable to affect the expression of coding and non-coding sequences to which they are operably linked. Exemplary regulatory sequences are described in Goeddel, 1990, and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. The nature and use of such control sequences can differ depending upon the host organism. In prokaryotes, such regulatory sequences generally include promoter, ribosomal binding site, and transcription termination sequences. The term "regulatory sequence" is intended to include, at a minimum, components whose presence can influence expression, and can also include additional components whose presence is advantageous, for example, leader sequences, and fusion partner sequences. In certain embodiments, transcription of a polynucleotide sequence is under the control of a promoter sequence (or other regulatory sequence) that controls the expression of the polynucleotide in a cell-type in which expression is intended. It will also be understood that the polynucleotide can be under the control of regulatory sequences that are the same or different from those sequences which control expression of the naturally occurring form of the polynucleotide.

The term "reporter gene" refers to a nucleic acid comprising a nucleotide sequence encoding a protein that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters. Generally, a reporter gene encodes a polypeptide not otherwise produced by the host cell, which is detectable by analysis of the cell(s), e.g., by the direct fluorometric, radioisotopic or spectrophotometric analysis of the cell(s) and typically without the need to kill the cells for signal analysis. In certain instances, a reporter gene encodes an enzyme, which produces a change in fluorometric properties of the host cell, which is detectable by qualitative, quantitative, or semiquantitative function or transcriptional activation. Exemplary enzymes include esterases, β-lactamase, phosphatases, peroxidases, proteases (tissue plasminogen activator or urokinase) and other enzymes whose function can be detected by appropriate chromogenic or fluorogenic substrates known to those skilled in the art or developed in the future.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" refers to that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

As used herein, the term "sequencing" refers to determining the ordered linear sequence of nucleic acids or amino acids of a DNA or protein target sample, using conventional manual or automated laboratory techniques.

The term "small molecule" refers to a compound, which has a molecular weight of less than about 5 kilodaltons (kDa), less than about 2.5 kDa, less than about 1.5 kDa, or less than about 0.9 kDa. Small molecules can be, for example, nucleic acids, peptides, polypeptides, peptide nucleic acids, peptidomimetics, carbohydrates, lipids, or other organic (carbon containing) or inorganic molecules. Many pharmaceutical companies have extensive libraries of chemical and/or biological mixtures, often fungal, bacterial, or algal extracts, which can be screened with any of the assays of the presently disclosed subject matter. The term "small organic molecule" refers to a small molecule that is often identified as being an organic or medicinal compound, and does not include molecules that are exclusively nucleic acids, peptides, or polypeptides.

The term "soluble" as used herein with reference to a polypeptide of the presently disclosed subject matter or other protein, refers to that upon expression in cell culture, at least some portion of the polypeptide or protein expressed remains in the cytoplasmic fraction of the cell and does not fractionate with the cellular debris upon lysis and centrifugation of the lysate. Solubility of a polypeptide can be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups). The solubility of polypeptides can be measured using a variety of art recognized techniques, including, dynamic light scattering to determine aggregation state, UV absorption, centrifugation to separate aggregated from non-aggregated material, and sodium dodecyl sulfate (SDS) gel electrophoresis (e.g., the amount of protein in the soluble fraction is compared to the amount of protein in the soluble and insoluble fractions combined). When expressed in a host cell, the polypeptides of the presently disclosed subject matter can be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the presently disclosed subject matter will produce at least about 0.1, 0.2, 0.5, 1, 2, 5, 10, 20, 30, 40, 50 milligrams or more of soluble protein. In an exemplary embodiment, a polypeptide of the presently disclosed subject matter is at least about 10% soluble and will produce at least about 1 milligram of protein from a one liter cell culture.

The term "specifically hybridizes" refers to detectable and specific nucleic acid binding. Polynucleotides, oligonucleotides, and nucleic acids of the presently disclosed subject matter selectively hybridize to nucleic acid strands under hybridization and wash conditions that minimize appreciable amounts of detectable binding to nonspecific nucleic acids. Stringent conditions can be used to achieve selective hybridization conditions as known in the art and discussed herein. Generally, the nucleic acid sequence homology between the polynucleotides, oligonucleotides, and nucleic acids of the presently disclosed subject matter and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions under which a test nucleic acid molecule will hybridize to a target reference nucleotide sequence, to a detectably greater degree than other sequences (e.g., at least two-fold over background). Stringent conditions are sequence-dependent and will differ in experimental contexts. For example, longer sequences hybridize specifically at higher temperatures. In some embodiments, stringent conditions are selected to be about 5° C. to about 20° C. lower, and in some embodiments 5° C. lower, than the thermal melting point ($T_m$) for the specific target sequence at a defined ionic strength and pH. The $T_m$ is the temperature (under defined ionic strength and pH) at which 50% of a complementary target sequence hybridizes to a perfectly matched probe. Typically, stringent conditions are those in which the salt concentration is less than about 1.0 M sodium ion concentration (or other salts), typically about 0.01 to 1.0 M Na ion concentration (or other salts), at pH 7.0 to 8.3, and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include 6×SSC, 0.2% polyvinylpyrrolidone, 0.2% Ficoll, 0.2% bovine serum albumin, 0.1% sodium dodecyl sulfate, 100 μg/ml salmon sperm DNA and 15% formamide at 60° C.

A variety of techniques for estimating the $T_m$ are available. Typically, G-C base pairs in a duplex are estimated to contribute about 3° C. to the $T_m$, while A-T base pairs are estimated to contribute about 2° C., up to a theoretical maximum of about 80-100° C. However, more sophisticated models of $T_m$ are available in which G-C stacking interactions, solvent effects, the desired assay temperature, and the like are taken into account. For example, probes can be designed to have a dissociation temperature ($T_d$) of approximately 60° C., using the formula: $T_d=(((((3\times\#GC)+(2\times\#AT))\times37)-562)/\#bp)-5$; where #GC, #AT, and #bp are the number of guanine-cytosine base pairs, the number of adenine-thymine base pairs, and the number of total base pairs, respectively, involved in the formation of the duplex.

Hybridization can be carried out in 5×SSC, 4×SSC, 3×SSC, 2×SSC, 1×SSC, or 0.2×SSC for at least about 1 hour, 2 hours, 5 hours, 12 hours, or 24 hours. The temperature of the hybridization can be increased to adjust the stringency of the reaction, for example, from about 25° C. (room temperature), to about 45° C., 50° C., 55° C., 60° C., or 65° C. The hybridization reaction can also include another agent affecting the stringency; for example, hybridization conducted in the presence of 50% formamide increases the stringency of hybridization at a defined temperature.

The hybridization reaction can be followed by a single wash step, or two or more wash steps, which can be at the same or a different salinity and temperature. For example, the temperature of the wash can be increased to adjust the stringency from about 25° C. (room temperature), to about 45° C., 50° C., 55° C., 60° C., 65° C., or higher. The wash step can be conducted in the presence of a detergent, e.g., 0.1% or 0.2% SDS. For example, hybridization can be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 42° C. in a solution comprising, or consisting of, 50% formamide, 10× Denhardt's (0.2% Ficoll, 0.2% Polyvinylpyrrolidone, 0.2% bovine serum albumin) and 100 μg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization can consist of hybridizing two nucleic acids in solution, or a nucleic acid in solution to a nucleic acid attached to a solid support, e.g., a filter. When one nucleic acid is on a solid support, a prehybridization step can be conducted prior to hybridization. Prehybridization can be carried out for at least about 1 hour, 3 hours or 10 hours in the same solution and at the same temperature as the hybridization solution (without the complementary polynucleotide strand).

Appropriate stringency conditions are known to those skilled in the art or can be determined experimentally by the skilled artisan. See e.g., Ausubel et al., 1989 at 6.3.1-12.3.6; Sambrook & Russell, 2001; Agrawal, 1993; Tijssen, 1993; Tibanyenda et al., 1984; and Ebel et al., 1992.

As applied to proteins or nucleic acids, the term "substantial identity" refers to that two protein or nucleic acid sequences, when optimally aligned, such as by the programs GAP or BESTFIT using default gap weights, typically share at least about 70% sequence identity, alternatively at least about 80%, 85%, 90%, 95%, 97%, or 99% percent sequence identity or more. With respect to amino acid sequences, in certain instances residue positions that are not identical differ by conservative amino acid substitutions, which are described above.

As used herein, the term "space group" refers to the arrangement of symmetry elements of a crystal.

As used herein, the terms "structure coordinates", "structural coordinates" and "atomic coordinates" are used interchangeably and refer to mathematical coordinates derived from mathematical equations related to the patterns obtained on diffraction of a monochromatic beam of X-rays by the atoms (scattering centers) of a molecule in crystal form. The diffraction data are used to calculate an electron density map of the repeating unit of the crystal. The electron density maps are used to establish the positions of the individual atoms within the unit cell of the crystal.

Those of skill in the art understand that a set of structure coordinates determined by X-ray crystallography is not without standard error. For the purpose of the presently disclosed subject matter, any set of structure coordinates for GGTase-I or a GGTase-I mutant that have a root mean square deviation (RMSD) from ideal of in some embodiments no more than 1.5 Å, in some embodiments no more than 1.0 Å, and in some embodiments no more than 0.5 Å when superimposed, using the polypeptide backbone atoms, on the structure coordinates listed in Tables A-N shall be considered identical.

As used herein, the term "substantially pure" refers to that the polynucleotide or polypeptide is substantially free of the sequences and molecules with which it is associated in its natural state, and those molecules used in the isolation procedure. The term "substantially free" refers to that the sample is in some embodiments at least 50%, in some embodiments at least 70%, in some embodiments 80%, in some embodiments 90%, in some embodiments 95%, and in some embodiments 99% free of the materials and compounds with which is it associated in nature.

The term "structural motif", when used in reference to a polypeptide, refers to a polypeptide that, although it can have different amino acid sequences, can result in a similar structure, wherein by structure is meant that the motif forms generally the same tertiary structure, or that certain amino acid residues within the motif, or alternatively their backbone or side chains (which can or can not include the Cα atoms of the side chains) are positioned in a like relationship with respect to one another in the motif.

As used herein, the term "target cell" refers to a cell, into which it is desired to insert a nucleic acid sequence or polypeptide, or to otherwise effect a modification from conditions known to be standard in the unmodified cell. A nucleic acid sequence introduced into a target cell can be of variable length. Additionally, a nucleic acid sequence can enter a target cell as a component of a plasmid or other vector or as a naked sequence.

The term "test compound" refers to a molecule to be tested by one or more screening method(s) as a putative modulator of a polypeptide of the presently disclosed subject matter or other biological entity or process. A test compound is usually not known to bind to a target of interest. The term "control test compound" refers to a compound known to bind to the target (e.g., a known agonist, antagonist, partial agonist or inverse agonist). The term "test compound" does not include a chemical added as a control condition that alters the function of the target to determine signal specificity in an assay. Such control chemicals or conditions include chemicals that (1) nonspecifically or substantially disrupt protein structure (e.g., denaturing agents (e.g., urea or guanidinium), chaotropic agents, sulfhydryl reagents (e.g., dithiothreitol and β-mercaptoethanol), and proteases); (2) generally inhibit cell metabolism (e.g., mitochondrial uncouplers); and (3) non-specifically disrupt electrostatic or hydrophobic interactions of a protein (e.g., high salt concentrations, or detergents at concentrations sufficient to non-specifically disrupt hydrophobic interactions). Further, the term "test compound" also does not include compounds known to be unsuitable for a therapeutic use for a particular indication due to toxicity of the subject. In certain embodiments, various predetermined concentrations of test compounds are used for screening such as 0.01 μM, 0.1 μM, 1.0 μM, and 10.0 μM. Examples of test compounds include, but are not limited to, peptides, nucleic acids, carbohydrates, and small molecules. The term "novel test compound" refers to a test compound that is not in existence as of the filing date of this application. In certain assays using novel test compounds, the novel test compounds comprise at least about 50%, 75%, 85%, 90%, 95%, 97%, 99%, or more of the test compounds used in the assay or in any particular trial of the assay.

As used herein, the term "therapeutic agent" is a chemical entity intended to effectuate a change in an organism. In one example, the organism is a human being. It is not necessary that a therapeutic agent be known to effectuate a change in an organism; chemical entities that are suspected, predicted, or designed to effectuate a change in an organism are therefore encompassed by the term "therapeutic agent". The effectuated change can be of any kind, observable or unobservable, and can include, for example, a change in the biological activity of a protein.

Representative therapeutic compounds include small molecules, proteins and peptides, oligonucleotides of any length, "xenobiotics", such as drugs and other therapeutic agents, carcinogens and environmental pollutants, natural products and extracts, as well as "endobiotics", such as epoxycholesterols. Other examples of therapeutic agents can include, but are not restricted to, agonists and antagonists of a prenyltransferase (e.g., a GGTase-I polypeptide), toxins and venoms, viral epitopes, hormones (e.g., opioid peptides, steroids, etc.), hormone receptors, enzymes, enzyme substrates, co-factors, lectins, sugars, nucleic acids, oligosaccharides, and monoclonal antibodies.

The term "therapeutically effective amount" refers to that amount of a modulator, drug, or other molecule that is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

As used herein, the term "transcription" refers to a cellular process involving the interaction of an RNA polymerase with a gene that directs the expression as RNA of the structural information present in the coding sequences of the gene. The process includes, but is not limited to, the following steps: (a) the transcription initiation; (b) transcript elongation; (c) transcript splicing; (d) transcript capping; (e) transcript termination; (f) transcript polyadenylation; (g) nuclear export of the transcript; (h) transcript editing; and (i) stabilizing the transcript.

As used herein, the term "transcription factor" refers to a cytoplasmic or nuclear protein which binds to a gene, or binds to an RNA transcript of a gene, or binds to another protein which binds to a gene or an RNA transcript or another protein which in turn binds to a gene or an RNA transcript, so as to thereby modulate expression of the gene. Such modulation can additionally be achieved by other mechanisms; the essence of a "transcription factor for a gene" pertains to a factor that alters the level of transcription of the gene in some way.

The term "transfection" refers to the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell can express a recombinant form of a polypeptide of the presently disclosed subject matter or antisense expression can occur from the transferred gene so that the expression of a naturally occurring form of the gene is disrupted.

As used herein, the term "unit cell" refers to a basic parallelepiped shaped block. The entire volume of a crystal can be constructed by regular assembly of such blocks. Each unit cell comprises a complete representation of the unit of pattern, the repetition of which builds up the crystal. Thus, the term "unit cell" refers to the fundamental portion of a crystal structure that is repeated infinitely by translation in three dimensions. A unit cell is characterized by three vectors a, b, and c, not located in one plane, which form the edges of a parallelepiped. Angles α, β, and γ define the angles between the vectors: angle α is the angle between vectors b and c; angle β is the angle between vectors a and c; and angle γ is the angle between vectors a and b. The entire volume of a crystal can be constructed by regular assembly of unit cells; each unit cell comprises a complete representation of the unit of pattern, the repetition of which builds up the crystal.

The term "vector" refers to a nucleic acid capable of transporting another nucleic acid to which it has been linked. One type of vector that can be used in accord with the presently disclosed subject matter is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules that, in their vector form are not bound to the chromosome. In the present specification, "plasmid" and "vector" are used interchangeably as the plasmid is the most commonly used form of vector. However, the presently disclosed subject matter is intended to include such other forms of expression vectors which serve equivalent functions and which become known in the art subsequently hereto.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

II. General Considerations

The structural "snapshots" of the GGTase-I reaction cycle disclosed herein provide a reaction pathway and generalize the mechanism of action to the family of protein prenyltransferases. Detailed structural comparisons of the active sites of $Ca_1a_2X$ prenyltransferases reveal common modes of substrate and product recognition, along with the subtle structural differences between these enzymes that account for their distinct substrate specificities. Protein prenyltransferases with reengineered specificity can provide a tool for further in vivo investigation of the cellular roles of protein prenyltransferases.

Protein prenyltransferases are promising targets for chemotherapeutics. Exploitation of these proteins as drug targets can involve the production of pharmaceuticals that are highly specific for one enzyme. The presently disclosed subject matter provides for calibration of drug specificity to take advantage of the observed differences between the active sites in the various prenyltransferases. One difference between GGTase-I and other prenyltransferases, such as FTase, is the tryptophan-for-threonine substitution at 49β that is in contact with both bound isoprenoid and peptide. Additionally, the altered binding surface (near Phe 53β and Leu 320β) in contact with the $a_2$ residue of the $Ca_1a_2X$ box, the aspartic acid-for lysine substitution at 311β, and possibly the arginine-for-proline substitution at 317β in the exit groove are all structural differences between GGTase-I and other prenyltransferases that can be exploited to create specific inhibitors for GGTase-1 (i.e. GTIs), FTase (i.e. FTIs), and other prenyltransferases (i.e. PTIs).

Seven ligand complexes were solved in various aspects of the presently disclosed subject matter. They have been numbered 1 to 7 as follows: Complex 1 comprises a binary complex comprising GGTase-I and GGPP; Complex 2 comprises a ternary complex comprising GGTase-I, a non-hydrolyzable GGPP analog and a $Ca_1a_2X$ peptide; Complex 3 comprises a binary complex comprising GGTase-I and a prenyl-peptide product; Complex 4 comprises a ternary complex comprising a GGTase-I, a prenylated product and GGPP; Complex 5 comprises a ternary complex comprising FTase, FPP, and L-778,123; Complex 6 comprises a complex of GGTase-I, L-778,123, and a sulfate anion; and Complex 7 comprises a complex of GGTase-I, GGPP, and L-778,123.

III. Production of GGTase-I Polypeptides

The native and mutated GGTase-I polypeptides, and fragments thereof, of the presently disclosed subject matter can be chemically synthesized in whole or part using techniques that are known in the art (see e.g., Creighton, 1983, incorporated herein in its entirety). Alternatively, methods that are known to those skilled in the art can be used to construct expression vectors containing a partial or the entire native or mutated GGTase-I polypeptide coding sequence and appropriate transcriptional/translational control signals. These methods include in vitro recombinant DNA techniques, synthetic techniques, and in vivo recombination/genetic recombination. See e.g., the techniques described in Sambrook & Russell, 2001, and Ausubel et al., 1989, both incorporated herein in their entirety.

A variety of host-expression vector systems can be utilized to express a GGTase-I coding sequence. These include but are not limited to microorganisms such as bacteria transformed with recombinant bacteriophage DNA, plasmid DNA or cosmid DNA expression vectors containing GGTase-I coding sequence; yeast transformed with recombinant yeast expression vectors containing a GGTase-I coding sequence; insect cell systems infected with recombinant virus expression vectors (e.g., baculovirus) containing a GGTase-I coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a GGTase-I coding sequence; or animal cell systems. The expression elements of these systems vary in their strength and specificities.

Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrp-lac hybrid promoter) and the like can be used. When cloning in insect cell systems, promoters such as the baculovirus polyhedrin promoter can be used. When cloning in plant cell systems, promoters derived from the genome of plant cells, such as heat shock promoters; the promoter for the small subunit of RUBISCO (ribulose-1,5-bisphosphate carboxylase/oxygenase); the promoter for the chlorophyll a/b binding protein) or from plant viruses (e.g., the 35S RNA promoter of CaMV; the coat protein promoter of TMV) can be used. When cloning in mammalian cell systems, promoters derived from the genome of mammalian cells (e.g., metallothionein promoter) or from mammalian viruses (e.g., the adenovirus late promoter; the vaccinia virus 7.5K promoter) can be used. When generating cell lines that contain multiple copies of the tyrosine kinase domain DNA, SV40-, BPV- and EBV-based vectors can be used with an appropriate selectable marker. Representative methods of producing GGTase-I polypeptides are also disclosed in the Examples.

IV. Formation of GGTase-I Crystals

Exemplary methods for obtaining the three dimensional structure of the crystalline form of a molecule or complex are described herein and, in view of this specification, variations on these methods will be apparent to those skilled in the art (see Ducruix & Geige 1992).

A variety of methods involving X-ray crystallography are contemplated by the presently disclosed subject matter. For example, contemplated is producing a crystallized polypeptide of the presently disclosed subject matter, or a fragment thereof, by: (a) introducing into a host cell an expression vector comprising a nucleic acid encoding for a polypeptide of the presently disclosed subject matter, or a fragment thereof; (b) culturing the host cell in a cell culture medium to express the polypeptide or fragment; (c) isolating the polypeptide or fragment from the cell culture; and (d) crystallizing the polypeptide or fragment thereof. Alternatively, contemplated is determining the three dimensional structure of a crystallized polypeptide of the presently disclosed subject matter, or a fragment thereof, by: (a) crystallizing a polypeptide of the presently disclosed subject matter, or a fragment thereof, such that the crystals will diffract X-rays to a resolution of 3.5 Å or better; and (b) analyzing the polypeptide or fragment by X-ray diffraction to determine the three-dimensional structure of the crystallized polypeptide.

X-ray crystallography techniques generally require that the protein molecules be available in the form of a crystal. Crystals can be grown from a solution containing a purified polypeptide of the presently disclosed subject matter, or a fragment thereof (e.g., a stable domain), by a variety of conventional processes. These processes include, for example, batch, liquid, bridge, dialysis, vapor diffusion (e.g., hanging drop or sitting drop methods). See e.g., McPherson, 1982; McPherson, 1990; Weber, 1991.

In certain embodiments, native crystals of the presently disclosed subject matter can be grown by adding precipitants to the concentrated solution of the polypeptide. The precipitants are added at a concentration just below that necessary to precipitate the protein. Water can be removed by controlled evaporation to produce precipitating conditions, which are maintained until crystal growth ceases.

The formation of crystals is dependent on a number of different parameters, including pH, temperature, protein concentration, the nature of the solvent and precipitant, as well as the presence of added ions or ligands to the protein. In addition, the sequence of the polypeptide being crystallized will have a significant affect on the success of obtaining crystals. Many routine crystallization experiments can be needed to screen all these parameters for the few combinations that might give crystal suitable for X-ray diffraction analysis (see e.g., Jancarik & Kim, 1991).

Crystallization robots can automate and speed up the work of reproducibly setting up large number of crystallization experiments. Once some suitable set of conditions for growing the crystal are found, variations of the condition can be systematically screened in order to find the set of conditions which allows the growth of sufficiently large, single, well ordered crystals. In certain instances, a polypeptide of the presently disclosed subject matter is co-crystallized with a compound that stabilizes the polypeptide.

A number of methods are available to produce suitable radiation for X-ray diffraction. For example, X-ray beams can be produced by synchrotron rings where electrons (or positrons) are accelerated through an electromagnetic field while traveling at close to the speed of light. Because the admitted wavelength can also be controlled, synchrotrons can be used as a tunable X-ray source (Hendrickson, 2000). For less conventional Laue diffraction studies, polychromatic X-rays covering a broad wavelength window are used to observe many diffraction intensities simultaneously (Stoddard, 1998). Neutrons can also be used for solving protein crystal structures (Gutberlet et al., 2001).

Before data collection commences, a protein crystal can be frozen to protect it from radiation damage. A number of different cryo-protectants can be used to assist in freezing the crystal, such as methyl pentanediol (MPD), isopropanol, ethylene glycol, glycerol, formate, citrate, mineral oil, or a low-molecular-weight polyethylene glycol (PEG). Contemplated is a composition comprising a polypeptide of the presently disclosed subject matter and a cryo-protectant. As an alternative to freezing the crystal, the crystal can also be used for diffraction experiments performed at temperatures above the freezing point of the solution. In these instances, the crystal can be protected from drying out by placing it in a narrow capillary of a suitable material (generally glass or quartz) with some of the crystal growth solution included in order to maintain vapor pressure.

X-ray diffraction results can be recorded by a number of ways know to one of skill in the art. Examples of area electronic detectors include charge coupled device detectors, multi-wire area detectors and phosphoimager detectors (Amemiya, 1997; Westbrook & Naday, 1997; Kahn & Fourme, 1997).

A suitable system for laboratory data collection might include a Bruker AXS Proteum R system, equipped with a copper rotating anode source, Confocal Max-Flux™ optics and a SMART 6000 charge coupled device detector. Collection of X-ray diffraction patterns is well documented by those skilled in the art (see e.g., Ducruix & Geige, 1992).

The theory behind diffraction by a crystal upon exposure to X-rays is well known. Because phase information is not directly measured in the diffraction experiment, and is needed to reconstruct the electron density map, methods that can recover this missing information are required. One method of solving structures ab initio are the real/reciprocal space cycling techniques. Suitable real/reciprocal space cycling search programs include SHAKE-AND-BAKE (Weeks et al., 1994).

Other methods for deriving phases can also be needed. These techniques generally rely on the idea that if two or more measurements of the same reflection are made where strong, measurable, differences are attributable to the characteristics of a small subset of the atoms alone, then the contributions of other atoms can be, to a first approximation, ignored, and positions of these atoms can be determined from the difference in scattering by one of the above techniques. Knowing the position and scattering characteristics of those atoms, one can calculate what phase the overall scattering must have had to produce the observed differences.

One version of this technique is isomorphous replacement technique, which requires the introduction of new, well ordered, X-ray scatterers into the crystal. These additions are usually heavy metal atoms, (so that they make a significant difference in the diffraction pattern); and if the additions do not change the structure of the molecule or of the crystal cell, the resulting crystals should be isomorphous. Isomorphous replacement experiments are usually performed by diffusing different heavy-metal metals into the channels of a pre-existing protein crystal. Growing the crystal from protein that has been soaked in the heavy atom is also possible (Petsko, 1985). Alternatively, the heavy atom can also be reactive and attached covalently to exposed amino acid side chains (such as the sulfur atom of cysteine) or it can be associated through non-covalent interactions. It is sometimes possible to replace endogenous light metals in metallo-proteins with heavier ones, e.g., zinc by mercury, or calcium by samarium (Petsko, 1985). Exemplary sources for such heavy compounds include, without limitation, sodium bromide, sodium selenate, trimethyl lead acetate, mercuric chloride, methyl mercury acetate, platinum tetracyanide, platinum tetrachloride, nickel chloride, and europium chloride.

A second technique for generating differences in scattering involves the phenomenon of anomalous scattering. X-rays that cause the displacement of an electron in an inner shell to a higher shell are subsequently rescattered, but there is a time lag that shows up as a phase delay. This phase delay is observed as a (generally quite small) difference in intensity between reflections known as Friedel mates that would be identical if no anomalous scattering were present. A second effect related to this phenomenon is that differences in the intensity of scattering of a given atom will vary in a wavelength dependent manner, given rise to what are known as dispersive differences. In principle anomalous scattering occurs with all atoms, but the effect is strongest in heavy atoms, and can be maximized by using X-rays at a wavelength where the energy is equal to the difference in energy between shells. The technique therefore requires the incorporation of some heavy atom much as is needed for isomorphous replacement, although for anomalous scattering a wider variety of atoms are suitable, including lighter metal atoms (copper, zinc, iron) in metallo-proteins. One method for preparing a protein for anomalous scattering involves replacing the methionine residues in whole or in part with selenium containing seleno-methionine. Soaks with halide salts such as bromides and other non-reactive ions can also be effective (Dauter et al., 2001).

In another process, known as multiple anomalous scattering or MAD, two to four suitable wavelengths of data are collected (Hendrickson & Ogata, 1997). Phasing by various combinations of single and multiple isomorphous and anomalous scattering are possible too. For example, SIRAS (single isomorphous replacement with anomalous scattering) utilizes both the isomorphous and anomalous differences for one derivative to derive phases. More traditionally, several different heavy atoms are soaked into different crystals to get sufficient phase information from isomorphous differences while ignoring anomalous scattering, in the technique known as multiple isomorphous replacement (MIR; Petsko, 1985).

Additional restraints on the phases can be derived from density modification techniques. These techniques use either generally known features of electron density distribution or known facts about that particular crystal to improve the phases. For example, because protein regions of the crystal scatter more strongly than solvent regions, solvent flattening/flipping can be used to adjust phases to make solvent density a uniform flat value (Zhang K Y J et al., 1997). If more than one molecule of the protein is present in the asymmetric unit, the fact that the different molecules should be virtually identical can be exploited to further reduce phase error using non-crystallographic symmetry averaging (Villieux & Read, 1997). Suitable programs for performing these processes include DM and other programs of the CCP4 suite (Collaborative Computational Project, 1994) and CNX.

The unit cell dimensions, symmetry, vector amplitude and derived phase information can be used in a Fourier transform function to calculate the electron density in the unit cell, i.e., to generate an experimental electron density map. This can be accomplished using programs of the CNX or CCP4 packages. The resolution is measured in Ångstrom (Å) units, and is closely related to how far apart two objects need to be before they can be reliably distinguished. The smaller this number is, the higher the resolution and therefore the greater the amount of detail that can be seen. In representative embodiments, crystals of the presently disclosed subject matter diffract X-rays to a resolution of better than about 4.0, 3.5, 3.0, 2.5, 2.0, 1.5, 1.0, 0.5 Å, or better.

In some embodiments, the presently disclosed subject matter provides crystals of GGTase. In some embodiments, the presently disclosed subject matter provides crystals of GGTase-I. The crystals were obtained using the methodology disclosed in the Examples. The GGTase-I crystals, which can be native crystals, derivative crystals or co-crystals, can comprise, for example, (a) orthogonal unit cells (an orthogonal unit cell is a unit cell wherein a≠b≠c, and wherein $\alpha=\beta=\gamma=90°$) and space group symmetry of I222 or (b) monoclinic unit cells (a monoclinic unit cell is a unit cell wherein a≠b≠c, and wherein a $\alpha=\gamma=90°$). In some embodiments, there are either three GGTase-I molecules in the asymmetric unit cell (orthorhombic unit cell). In some embodiments, there are six GGTase-I molecules in the asymmetric unit cell (monoclinic unit cell) related by a non-crystallographic dyad. Unit cell dimensions for the various GGTase-I are presented in Tables A-N.

IV.A. Preparation of GGTase-I Crystals

The native and derivative co-crystals, and fragments thereof, disclosed in the presently disclosed subject matter can be obtained by a variety of techniques, including batch, liquid bridge, dialysis, vapor diffusion, sitting drop and hanging drop methods (see e.g., McPherson, 1982; McPherson, 1990; Weber, 1991). In some embodiments, the vapor diffusion and hanging drop methods are used for the crystallization of GGTase-I polypeptides and fragments thereof.

In general, native crystals of the presently disclosed subject matter are grown by dissolving substantially pure GGTase-I polypeptide or a fragment thereof in an aqueous buffer comprising a precipitant at a concentration just below that necessary to precipitate the protein. Water is removed by controlled evaporation to produce precipitating conditions, which are maintained until crystal growth ceases.

In some embodiments of the presently disclosed subject matter, native crystals are grown by the hanging drop method (see e.g., McPherson, 1982; McPherson, 1990). In this method, the polypeptide/precipitant solution is allowed to equilibrate in a closed container with a larger aqueous reservoir having a precipitant concentration optimal for producing crystals. Generally, less than about 25 μL of GGTase-I polypeptide solution is mixed with an equal volume of reservoir solution, giving a precipitant concentration about half that required for crystallization. This solution is suspended as a droplet underneath a coverslip, which is sealed onto the top of the reservoir. The sealed container is allowed to stand, until crystals grow. Crystals generally form within two to six weeks, and are suitable for data collection within approximately seven to ten weeks. Of course, those of ordinary skill in the art will recognize that the above-described crystallization procedures and conditions can be varied.

IV.B. Preparation of Derivative Crystals

Derivative crystals of the presently disclosed subject matter, e.g., heavy atom derivative crystals, can be obtained by soaking native crystals in mother liquor containing salts of heavy metal atoms. Alternatively, a ligand comprising a heavy atom can be associated with a protein, and subsequently co-crystallized. Such derivative crystals are useful for phase analysis in the solution of crystals of the presently disclosed subject matter. This mechanism provides derivative crystals suitable for use as isomorphous replacements in determining the X-ray crystal structure of a GGTase-I polypeptide. Additional reagents useful for the preparation of the derivative crystals of the presently disclosed subject matter will be apparent to those of ordinary skill in the art upon review of the disclosure of the presently disclosed subject matter presented herein.

The structure of a heavy atom derivatized form of a GGTase-I-ligand structure can be solved using single isomorphous replacement anomalous scattering (SIRAS) techniques and/or multiwavelength anomalous diffraction (MAD) techniques. In the SIRAS method of solving protein crystals, a derivative crystal is prepared that contains an atom that is heavier than the other atoms of the sample. Heavy atom derivative crystals are commonly prepared by soaking a crystal in a solution containing a selected heavy atom salt. For example, some heavy atom derivative crystals have been prepared by soaking a crystalline form of the protein of interest in a solution of methyl mercury chloride (MeHgCl). Another representative heavy atom that can be incorporated into a derivative crystal is iodine. Heavy atoms can associate with the protein of interest, or can be localized in a ligand that associates with a protein of interest.

Analysis of derivative crystals takes advantage of differences in the reflections from the derivative crystal as compared to the underivatized crystal. Symmetry-related reflections in the X-ray diffraction pattern, which are usually identical, are altered by the anomalous scattering contribution of the heavy atoms. The measured differences in symmetry-related reflections are used to determine the position of the heavy atoms, leading to an initial estimation of the diffraction phases, and subsequently, an electron density map is prepared. The prepared electron density map is then used to identify the position of the other atoms in the sample.

IV.C. Preparation of Co-Crystals

Co-crystals of the presently disclosed subject matter can be obtained by soaking a native crystal in mother liquor comprising compounds known or predicted to bind the a GGTase-I, or a fragment thereof (e.g., a GGTase-I α subunit or a GGTase-I β subunit). Alternatively, co-crystals can be obtained by co-crystallizing a GGTase-I polypeptide or a fragment thereof (e.g., a GGTase-I α subunit or a GGTase-I β subunit) in the presence of one or more compounds known or predicted to bind the polypeptide. In some embodiments of the presently disclosed subject matter, for example, the one or more substrates and/or products is/are co-crystallized with GGTase-I.

IV.D. Solving a Crystal Structure

Crystal structures of the presently disclosed subject matter can be solved using a variety of techniques including, but not limited to, isomorphous replacement anomalous scattering or molecular replacement methods. Computer software packages are also helpful in solving a crystal structure of the presently disclosed subject matter. Applicable software packages include but are not limited to AmoRe (Navaza & Saludjian, 1997; AmoRe is available on the internet at various sites on the World Wide Web), X-PLOR™ program (Brünger, 1992; X-PLOR is available from Molecular Simulations, Inc., now Accelrys Inc., San Diego, Calif., United States of America), Xtal View (McRee, 1992; X-tal View is available from the San Diego Supercomputer Center, University of California at San Diego, San Diego, Calif., United States of America), SHELXS 97 (Sheldrick, 1990; SHELX 97 is available from the Institute of Inorganic Chemistry, Georg-August-Universität, Göttingen, Germany), HEAVY (Terwilliger, Los Alamos National Laboratory, Los Alamos, N. Mex., United States of America) can be used and SHAKE-AND-BAKE (Hauptman, 1997; Weeks et al., 1994; available from the Hauptman-Woodward Medical Research Institute, Buffalo, N.Y., United States of America). See also Ducruix & Geige, 1992, and references cited therein.

IV.E. Generation of Easily-Solved GGTase-I Crystals

The presently disclosed subject matter discloses a substantially pure GGTase-I polypeptide in crystalline form. In some embodiments, exemplified in the Figures and Examples, GGTase-I is crystallized with bound substrates and/or products. Crystals are sometimes formed from prenyltransferases (e.g., GGTase-I) that are expressed by a cell culture, such as *E. Coli*. Bromo-, iodo-, and other substitutions can be included during the preparation of crystal forms and can act as heavy atom substitutions in GGTase-I ligands and in crystals of GGTase-I. This method can be advantageous for the phasing of the crystal, which is a crucial, and sometimes limiting, step in solving the three-dimensional structure of a crystallized entity. Thus, the need for generating the heavy metal derivatives traditionally employed in crystallography can be eliminated. After the three-dimensional structure of a GGTase-I polypeptide with or without a ligand bound is determined, the resultant three-dimensional structure can be used in computational methods to design synthetic ligands for a GGTase-I polypeptide and fragments thereof. Further activity structure relationships can be determined through routine testing, using assays disclosed herein and known those of ordinary skill in the art.

V. Prenyltransferase Ligands

Various prenyltransferase ligands can be employed in the presently disclosed subject matter. For example, GGPP, a natural substrate of the prenyltransferase GGTase-I, can be employed. Other isoprenoid-comprising compounds can also be employed, such as FPP. FPP is a natural substrate for the prenyltransferase FTase, however as noted herein, FPP can also act as a substrate for at least GGTase-I.

Various isoprenoid-comprising substrate analogs can also be employed as prenyltransferase ligands in the presently disclosed subject matter. For example, a non-hydrolyzable analog of a natural substrate (e.g., GGPP or FPP) can be employed.

A prenyltransferase ligand can also comprise a peptide or polypeptide. As described herein, peptide substrates comprising the $Ca_1a_2X$ box are natural substrates for prenyltransferases. Thus, peptides comprising this sequence can be employed as prenyltransferase ligands in the presently disclosed subject matter. Similarly, analogs of such peptides, such as those comprising functionalized moieties, can also be employed.

VI. The Structure of GGTase-I

In one aspect of the presently disclosed subject matter, the three dimensional structure of GGTase-I was solved. In another aspect of the presently disclosed subject matter, the structure of GGTase-I in complex with substrates and products was solved. A description of the various GGTase-I structures that form aspects of the presently disclosed subject matter follows. In these embodiments of the presently disclosed subject matter, rat GGTase-I was crystallized, although the disclosed methods and approaches can be employed to crystallize and solve prenyltransferases from all types of organisms, including humans, mice, rabbits and other species.

VI.A. Overview of GGTase-I Structure

Figure 2:
FIG. 2 is a ribbon diagram depicting protein geranylgeranyl transferase type I substrate Complex 2, as described herein under the section heading "General Considerations", and comprising a ternary complex comprising GGTase-I, a non-hydrolyzable GGPP analog and a $Ca_1a_2X$ peptide. Protein geranylgeranyl transferase type-I comprises a heterodimer consisting of a 48 kilodalton (kDa) alpha subunit (red) and a 43 kDa beta subunit (blue). In this ternary complex the non-reactive isoprenoid analog 3'AzaGGPP (cyan) is bound in the active site pocket. The $Ca_1a_2X$ peptide substrate (yellow) binds against the isoprenoid with the cysteine sulfur near to the catalytic zinc ion (magenta).
Figure 3:
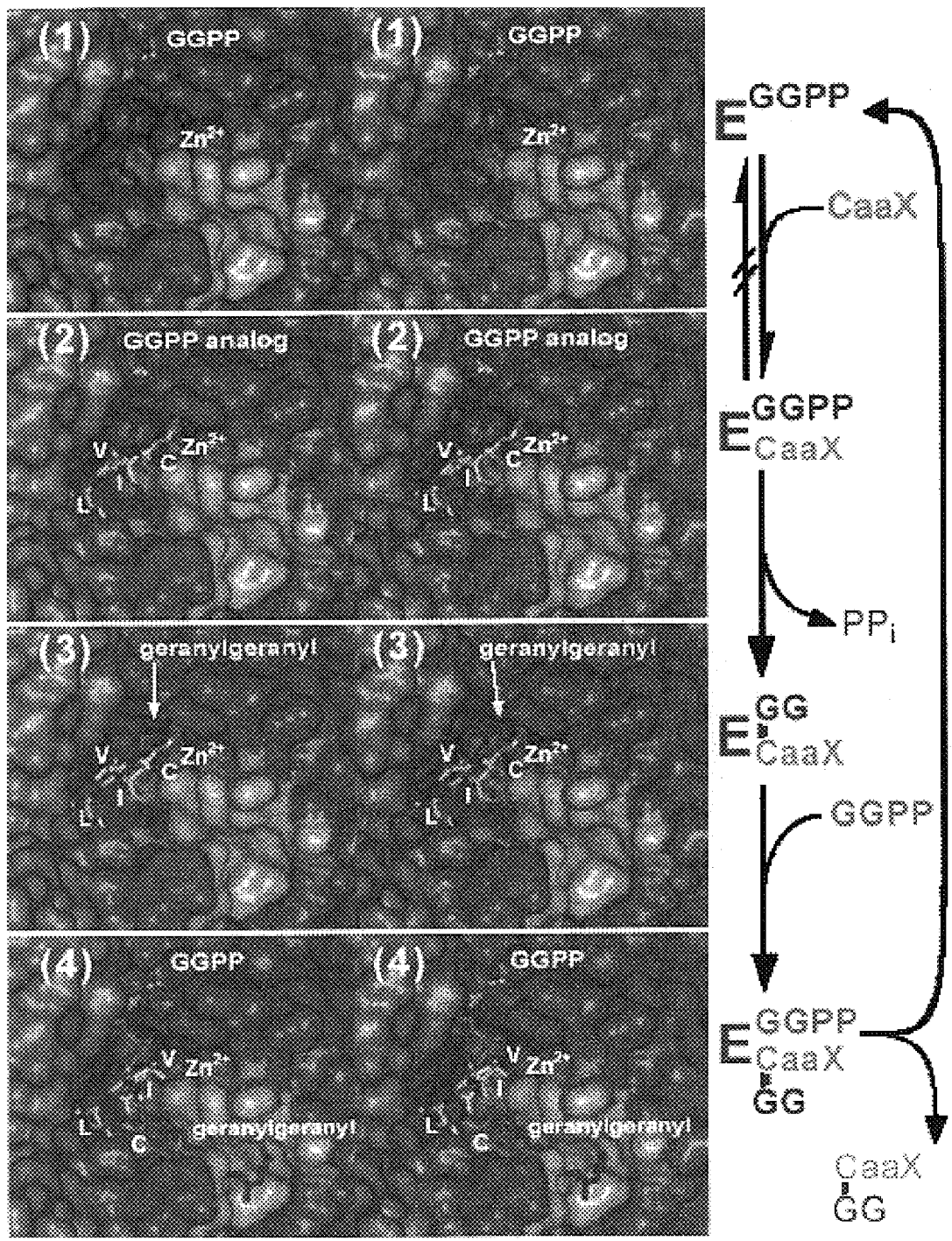
FIG. 3 is a series of stereo diagrams depicting the structures of the GGTase-I reaction cycle. Panel 1 depicts the enzyme with bound GGPP; Panel 2 depicts the ternary complex with 3'AzaGGPP analog and peptide substrate; Panel 3 depicts the product complex; and Panel 4 depicts the displaced product with GGPP. The GGTase-I active site is shown as a molecular surface, with the a subunit colored red, the β subunit blue, and the exit groove highlighted in cyan.

The overall structure of GGTase-I is shown in FIG. 2. In FIG. 3, four ligand complexes are presented: Complex 1, depicted in Panel 1, comprises a binary complex with GGPP; Complex 2, depicted in Panel 2, comprises a ternary complex with a non-hydrolyzable GGPP analog and $Ca_1a_2X$ peptide; Complex 3, depicted in Panel 3, comprises a binary complex with prenyl-peptide product; and Complex 4, depicted in Panel 4, comprises a ternary complex with prenylated product and GGPP. All have backbone RMSD values of about 0.2 Å, and the differences between the structures can be traced, in part, to the identity of the ligands themselves.

In some embodiments, GGTase-I crystals have space group I222, and comprise three complete 91 kDa heterodimers in the asymmetric unit (see Table 2). Phases were determined by single isomorphous replacement with anomalous scattering (SIRAS). In some embodiments, a second crystal form was obtained that diffracted to higher resolution. The molecular packing of the two crystal forms was similar, but a slight shift reduced the symmetry of the later crystals to space group C2, with six heterodimers in the asymmetric unit. In both crystal forms, the individual heterodimers within the crystallographic asymmetric units are similar, except for a few side chains in crystal contacts, and thus only one molecule from the asymmetric unit is considered in the following exemplary discussion.

The helices of the GGTase-I α subunit are arranged in α-helical hairpin pairs, forming a crescent that wraps around the β subunit. The GGTase-I α subunit is identical in sequence with the FTase α subunit, but because the rat GGTase-I β subunit is smaller than the rat FTase β subunit (377 residues versus 437) the curvature of the crescent-shaped α subunit is slightly different (1.5 Å RMSD). The interface between the α and β subunits is extensive, over 3300 Å². The β subunit forms a compact, globular, alpha-alpha barrel domain with a central cavity. The substrates binding site begins at the α-β subunit interface and extends into the central funnel shaped cavity of the β subunit, which is lined with hydrophobic residues. A zinc ion is bound at the top of this active site funnel. The zinc ion is required for catalytic activity (Zhang & Casey, 1996); it can be removed using chelating agents, however, without significantly altering the structure. Because the α subunit is common with FTase, functional differences are the result of differences in the β subunits where sequence identity is just 25%.

Figure 4:
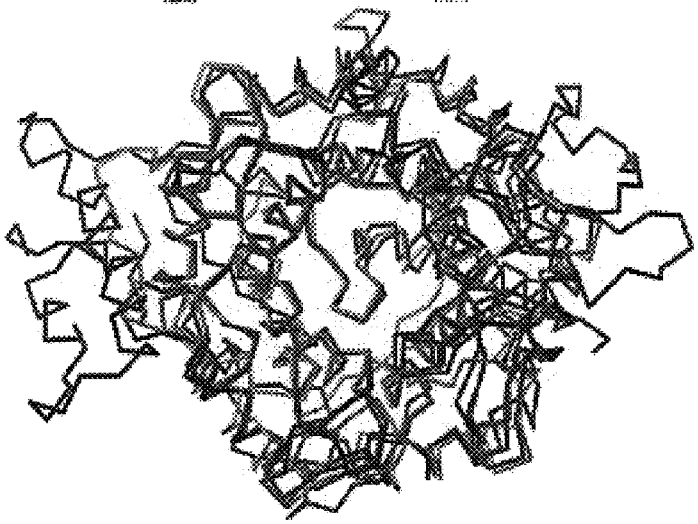
FIG. 4A is a wireframe diagram depicting a beta subunit alignment. The beta subunits from the three protein prenyltransferases are shown as superimposed C-alpha traces. FTase (blue) and GGTase-II (green) were aligned with GGTase-I (yellow) using the Cα positions.
FIG. 4B depicts a structure-based sequence alignment highlighting residues that contact the zinc (blue), peptide substrate (red), or isoprenoid (green). The alignment depicts the amino acid sequences of: human GGTase-I (GEN-BANK® Accession No. NP_005014.1), human FTase (GENBANK® Accession No. B49274), and RabGGTase (GENBANK® Accession No. Q08603).

The GGTase-I structure facilitates a structure-based sequence alignment of the β subunits of all three protein prenyltransferases, which shows that there is only 32% sequence similarity with FTase and RabGGTase, despite nearly identical topology (FIG. 4). The solvent accessible surfaces of the GGTase-I and FTase β subunits differ not only in side chain identities, but also in the lengths of several loops. The FTase β subunit has an additional 53 residues at the N-terminus and two insertions near the C-terminus of 13 and 16 residues. In GGTase-I, residues 79β-121β form a loop connecting helix 3β and helix 4β that has an insertion of 26 residues relative to FTase and RabGGTase (see FIGS. 4A and 4B). This loop terminates at helix 4β, which makes up part of the $Ca_1a_2X$ binding site, and thus a shift in its position can influence the enzyme's $Ca_1a_2X$ specificity. These loops are located primarily on the surface of the molecule and the altered molecular surface can be important for specifying protein-protein interactions.

TABLE 2

Data Collection and Refinement Statistics

| | Derivative λ1 | Derivative λ2 | Native (ternary) | Binary (1) | Ternary (2) | Product (3) | Displaced Product (4) |
|---|---|---|---|---|---|---|---|
| Data collection (all data) | | | | | | | |
| Beamline | NSLS X12B | NSLS X12B | APS 14BMC | APS 14BMC | APS 14BMC | NSLS X12B | NSLS X25 |
| Wavelength, Å | 1.071416 | 1.070676 | 1.00000 | 0.900000 | 1.00000 | 1.00008 | 1.00000 |
| Resolution, Å | 40-3.5 | 40-3.5 | 50-2.7 | 30-2.65 | 30-2.4 | 30.0-2.8 | 40-2.6 |
| Outer shell, Å | 3.63-3.5 | 3.63-3.5 | 2.8-2.7 | 2.74-2.65 | 2.49-2.4 | 2.9-2.8 | 2.69-2.6 |
| No. reflections | | | | | | | |
| Unique | 125,705 | 126,788 | 139,616 | 286,863 | 355,317 | 240,519 | 300,000 |
| Total | 393,410 | 337,591 | 745,344 | 1,038,571 | 997,257 | 785,048 | 1,011,902 |
| Mean I/σ$_I$[a] | 8.6 (1.7) | 9.2 (2.0) | 18.8 (2.4) | 14.0 (2.2) | 15.1 (2.1) | 13.0 (2.3) | 13.6 (2.6) |
| Completeness % | 98.0 (97.1) | 98.8 (97.4) | 99.6 (99.6) | 98.7 (91.5) | 93.0 (87.1) | 99.4 (98.0) | 99.7 (100) |
| $R_{sym}$ %[a] | 9.2 (58.0) | 8.5 (65.4) | 7.8 (66.3) | 7.7 (50.0) | 5.6 (35.2) | 7.4 (43.2) | 6.9 (43.5) |
| $R_{iso}/R_{anom}$ % | 22.1/7.9 | 22.2/8.3 | | | | | |
| Space group | I222 | I222 | I222 | C2 | C2 | C2 | C2 |
| Unit cell Dimensions, Å | | | | | | | |
| a, Å | 185.25 | 185.25 | 185.05 | 272.34 | 271.05 | 272.07 | 271.12 |
| b, Å | 204.34 | 204.34 | 204.31 | 271.57 | 268.03 | 268.80 | 268.43 |
| c, Å | 273.01 | 273.01 | 269.22 | 185.42 | 184.97 | 185.31 | 184.82 |
| β, ° | 90° | 90° | 90° | 131.56° | 131.72° | 131.55° | 131.68° |
| Refinement (F ≥ σ$_F$) | | | | | | | |
| Completeness, %[a] | | | 98.2 (97.3) | 98.2 (90.5) | 92.8 (86.8) | 99.1 (97.4) | 99.2 (97.3) |
| $R_{cryst}$, %[a] | | | 20.7 (31.5) | 20.4 (34.4) | 21.4 (33.4) | 19.8 (31.4) | 19.4 (29.3) |
| $R_{free}$, %[a] | | | 23.0 (33.3) | 22.8 (36.9) | 23.4 (35.6) | 21.7 (32.9) | 21.4 (31.5) |
| Non-hydrogen atoms | | | | | | | |
| Total | | | 16,344 | 33,444 | 33,546 | 33,247 | 33,926 |
| Solvent | | | 260 | 1024 | 1117 | 708 | 1298 |
| Ramachandran plot | | | | | | | |
| Most favored regions, % | | | 88.8 | 89.0 | 89.2 | 88.0 | 89.0 |
| Allowed regions | | | 11.2 | 11.0 | 10.8 | 12.0 | 11.0 |
| RMSD from ideal geometry | | | | | | | |
| Bond lengths, Å | | | 0.01 | 0.007 | 0.006 | 0.007 | 0.006 |
| Bond angles, ° | | | 1.45 | 1.18 | 1.19 | 1.18 | 1.17 |
| Average isotropic B-value, Å² | | | 59.5 | 53.7 | 58.3 | 54.2 | 54.0 |

$R_{sym} = \Sigma|(I \pm <I>)|)/(\Sigma I)$, where <I> is the average intensity of multiple measurements.
$R_{cryst}$ and $R_{free} = (\Sigma|F_{obs} \pm F_{calc}|)/(\Sigma|F_{obs}|)$. $R_{free}$ was calculated over 5% of the amplitudes not used in refinement.
[a]Values in parentheses correspond to those in the outer resolution shell.

VI.B. Determinants of Isoprenoid Specificity

One of the functional differences between the three protein prenyltransferases (i.e., GGTase-I, FTase, RabGGTase) is the selective binding of either GGPP or FPP. Specific lipidation of protein substrates affects functions, such as communication with other regulatory proteins (Myung et al., 1999). A stereochemical feature that distinguishes GGPP and FPP is the length of the lipid (see FIG. 1). The complex of GGTase-I with the isoprenoid diphosphate substrate GGPP (depicted in FIG. 2 and in Panel 1 of FIG. 3) indicates how lipid length is used to selectively bind the cognate substrate. The GGPP binds with its diphosphate moiety placed at the α-β subunit interface and the lipid inserted into the central cavity of the β subunit (see FIG. 5). The first three isoprene units are arranged in a straight line. The fourth isoprene unit is turned about 90° relative to this axis. This geometry of the bound lipid is quite different from the other known structures with bound isoprenoids (e.g., FTase (Long et al., 1998); RhoGDI (Hoffman et al., 2000); and the phosducin-$G_t\beta\gamma$ complex (Loew et al., 1998)) in which the isoprenoid is completely extended. Alignment of the active sites of the GGTase-I and FTase complexes by Cα atom superposition of the heterodimers shows a slight divergence in the position of first isoprene unit, shifting the diphosphate moiety of GGPP about 1.0 Å toward Asn 199α, while the second and third isoprene units are in essentially identical positions. The position of the fourth isoprene unit of the GGPP shows that a particular β subunit residue, Thr 49β, is a primary determinant of lipid length discrimination. In FTase, this residue is tryptophan, which fills the space where the fourth isoprene unit binds in GGTase-I (see FIG. 6), accounting for the inability of FTase to bind GGPP productively.

In GGTase-I, Phe 324β is also positioned near the fourth isoprene unit. The equivalent residue is tyrosine in FTase, which places a hydroxyl group near the fourth isoprene's binding site, and thus this residue can also impact isoprenoid binding. In a sequence alignment, the identity of these two residues provides a strong indication whether an unknown sequence is a GGTase or an FTase. Across many species, residue 49β is always a small amino acid such as Thr, Ser, Val, or Ala in GGTase-I and RabGGTase, whereas in FTase it is always tryptophan. Residue 324β, which is always tyrosine in FTase, is usually phenylalanine in GGTase-I. These altered residues would prevent FTase from binding the longer GGPP in a productive manner; however, there are no obvious structural features to prevent GGTase-I from binding the shorter FPP molecule in precisely the same geometry as GGPP. Indeed, FPP has been shown to be a substrate for GGTase-I (Yokoyama et al., 1995).

VI.C. Determinants of Protein Substrate Specificity

Figure 5:
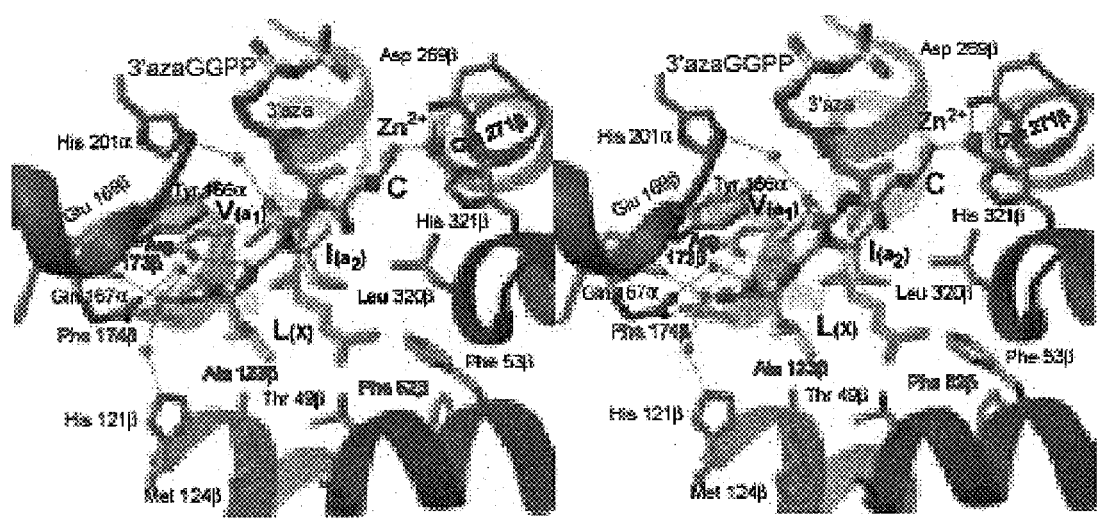
FIG. 5 is a stereoview of the active site in approximately the same orientation as depicted in Panels 1-4 of FIG. 3 showing the $Ca_1a_2X$ portion of the KKKSKTKCVIL (SEQ ID NO: 1) peptide (yellow) and 3'AzaGGPP (purple). The $Ca_1a_2X$ motif is bound in an extended conformation with the cysteine thiolate coordinated by the zinc ion (magenta). Carbonyl oxygens and the C-terminus of the $Ca_1a_2X$ sequence make water-mediated (cyan) and direct hydrogen bonds with conserved hydrophilic side-chains (orange) in both the α (red) and β (blue) subunits of the protein.
Figure 6:
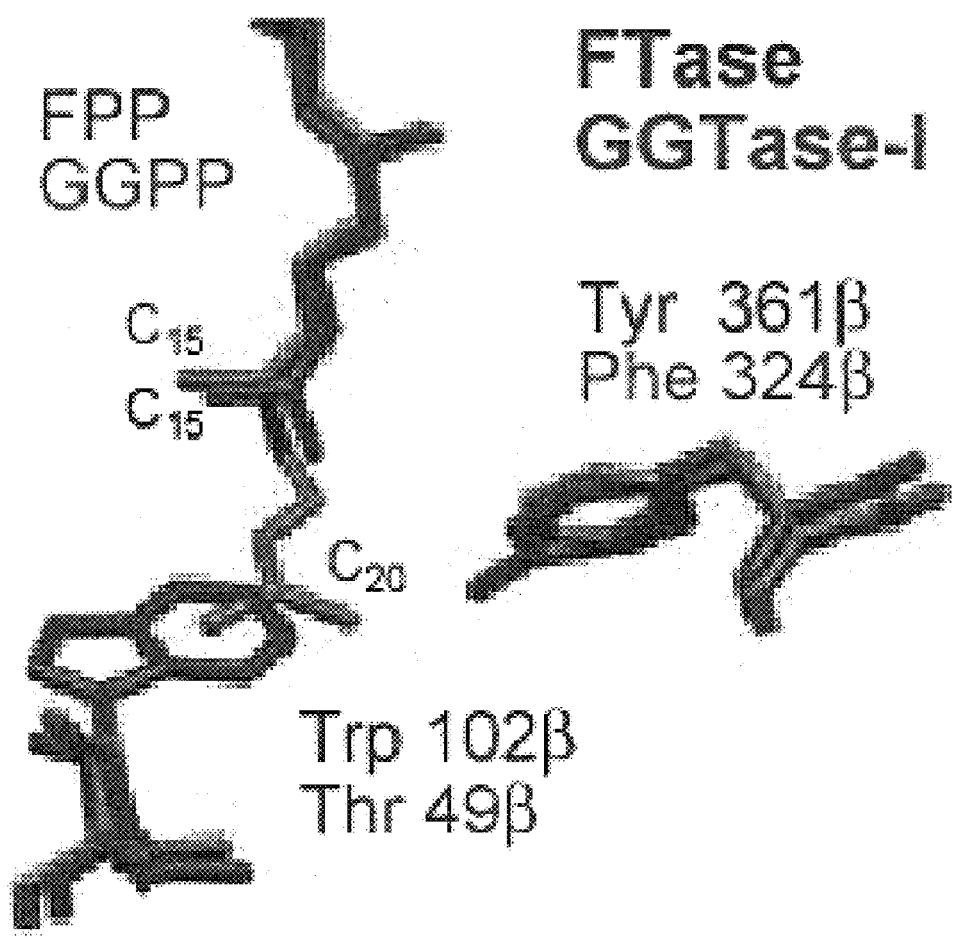
FIG. 6 is a stick model depicting residues involved in the discrimination between FPP and GGPP, shown in red for FTase and blue for GGTase-I.

The GGTase-I ternary Complex 2 shows the 3'AzaGGPP (Steiger et al., 1992) bound at the same location as the GGPP in Complex 1, and a peptide substrate with the terminal sequence -CVIL (SEQ ID NO: 2), the sequence of GTPase Rap2B, bound adjacently in an extended conformation (see FIGS. 3B and 5). The $Ca_1a_2X$ peptide shields a total of 140 Å$^2$ of the isoprenoid from the solvent. This large contact area between the two substrates is likely responsible for the reaction's observed ordered substrate binding. Without the isoprenoid in place, the peptide binding site has a different shape and, if peptide binds first, it adopts a non-productive conformation and must dissociate before the reaction can proceed (Stirtan & Poulter, 1997; Yokoyama et al., 1995).

The $Ca_1a_2X$ cysteine coordinates the catalytic zinc ion located at the top of the funnel-shaped central cavity. The specificity determining X residue is anchored at the bottom of the funnel-shaped active site by hydrogen bonds from the $Ca_1a_2X$ terminal carboxyl group to Gln 167α, and via water-mediated hydrogen bonds to to His 121β, Glu 169β, and Arg 173β. One additional hydrogen bond is present between the carbonyl oxygen of the $a_2$ residue (isoleucine) and Arg 173β. All four of these protein residues, as well as the position of the water molecule, are conserved in FTase (Long et al., 2000). GGTase-I prefers $Ca_1a_2X$ protein substrates with leucine in the X position, whereas FTase accepts substrates with methionine, serine, alanine, or glutamine in the X position (Casey et al., 1991; Yokoyama et al., 1991).

A comparison of the GGTase-I and FTase ternary complexes reveals the structural determinants for this selectivity. Specificity at the X position is determined by surface complementarity between the X residue and the "specificity pocket: in which the X side chain binds (see FIG. 5A). The hydrophobic specificity pocket discriminates against polar side chains; the shape and volume further restrict the identity of the X residue, which for GGTase-I must be leucine. Other amino acids with van der Waals volumes similar to leucine are either polar (histidine and glutamine) or are actually weak substrates for GGTase-I (phenylalanine and methionine). $Ca_1a_2X$ sequences ending in glycine or alanine are worse GGTase-I substrates (Moores et al., 1991) than would be expected from simply not filling the pocket, indicating that these sequences may bind in an alternative and unproductive conformation. Some of the same structural features in GGTase-I that allow it to bind the longer GGPP isoprenoid also shape the pocket to fit leucine. A threonine at residue 49β (tryptophan in FTase) provides space for the $C\delta_1$ atom of the leucine side chain. Additionally, a steric clash between the leucine $C\delta_2$ atom and Ala 123β (Ala 151β in FTase) is avoided through a small shift in the backbone of helix 4β. There is little or no sequence constraint on the $a_1$ residue, as its side chain projects into the solvent and makes no direct contact with the protein. In GGTase-I, the $a_2$ side chain makes extensive hydrophobic contacts with Phe 53β and Leu 320β as well as the fourth isoprene unit. All three of these $a_2$ contacts are different in FTase: Phe 53β is tryptophan, Leu 320β is tyrosine, and the isoprenoid contact is replaced in FTase by tryptophan 102β. These changes might result in altered sequence preference at the $a_2$ position and provide additional steric differences that can be taken advantage of in the design of specific inhibitors.

A specificity mechanism general to both GGTase-I and FTase might be important in allowing for selected cross-specificity. The $Ca_1a_2X$ prenyltransferases are usually very selective for their protein substrates, but cross-specificity has been observed in some cases (Armstrong et al., 1995; James et al., 1995; Moores et al., 1991). For example, RhoB and TC21 can be modified by either FTase or GGTase-I (Kato et al., 1992). Cross-specificity can also be a rescue mechanism as has been shown with K-Ras, where in the absence of FTase activity GGTase-I will modify the FTase substrate K-Ras (Zhang F L et al., 1997).

Thus, in one example, if it is desired to design a modulator that is specific for GGTase-I, to the exclusion of FTase, the modulator can be designed so as to facilitate interactions between the modulator and the structural features of GGTase-I that are not found in FTase. For example, GGTase-I has a threonine at residue 49β, while FTase has a tryptophan at this position; a potential GGTase-I modulator could incorporate a moiety that would interact with the threonine at this position in GGTase-I. Similarly, an FTase modulator could incorporate a moiety that would interact with a tryptophan at this position, but not a threonine.

In some embodiments, a modulator can be designed that takes advantage of the observation that in GGTase-I, the residues Phe 53β and Leu 320β all make contact with the substrate. Thus, a candidate modulator can comprise moieties that are adapted to interact with these residues, which are present in GGTase-I but absent from FTase and other prenyltransferases.

VI.D. Product Complexes

Structures of GGTase-I product complexes reveal a change in the isoprenoid conformation and a secondary product-binding site, thus generalizing for the family of protein prenyltransferases recent observations for FTase (Long et al., 2002). Crystals of the GGTase-I product complexes show that the product remains bound in the active site at full occupancy many weeks after crystallization (FIG. 3, Panel (3)). In this complex, the active site is occupied by the prenylated peptide, and the characteristic electron density of the diphosphate leaving group is no longer present. The peptide portion of the product is in the identical position as seen in the substrate Complex 2, with the sulfur atom, now part of a thioether, still coordinating the catalytic zinc. However, the GGPP markedly changes conformation during the reaction. The third and fourth isoprene units are in the same location as in Complex 2, but atoms $C_1$ through $C_{10}$ are in a new conformation with the $C_1$ atom now covalently bonded to the cysteine of the $Ca_1a_2X$ peptide. The conformational change includes an about 160° rotation about the $C_8$-$C_9$ bond in the second isoprene unit and additional rotations in the first isoprene unit. There is no evidence to support any conformational change in the protein backbone during the reaction.

A fourth complex in which the product is displaced to a secondary binding site was created when crystals of Complex 3 were soaked in a solution containing additional GGPP (Panel (4) of FIG. 3). The new GGPP binds in the identical location as in Complex 1 but the product is not completely released. To make space for the new GGPP, the isoprenoid moiety of the prenylated product is displaced to a solvent accessible groove that in Complexes 1-3 is solvated and runs from the active site to the rim of the β subunit alpha-alpha barrel, the "exit groove". In this displaced product Complex 4, the first three isoprene units of the prenyl product lie in the exit groove in an extended conformation while the fourth unit is turned about 90° towards the solvent. As a result of the rearrangement, the $Ca_1a_2X$ cysteine of the prenylated product no longer interacts with the zinc ion. The product's $a_2$ and X residues (Ile and Leu) are displaced by about 0.9 Å but are otherwise in a similar conformation to that seen in Complex 2 and Complex 3. The $a_1$ valine residue is rotated 120° about its ψ Ramachandran backbone angle, which reorients the side chain and brings the prenyl-cysteine residue to a position where its carbonyl oxygen can hydrogen bond with the backbone nitrogen of the $a_2$ residue (isoleucine), forming a type-1β turn. A type-1β turn can accommodate any residue including proline at the $a_1$ position, but precludes proline from the $a_2$ position. A $Ca_1a_2X$ peptide with proline in the $a_2$ position can adopt the conformation required to be a substrate, but there are no known prenylated proteins ending in CaPX suggesting that the formation of the type-1β turn in the exit complex is important.

Upon moving to the exit groove, the product can be fully displaced from the enzyme by soaking new peptide substrate into the crystals or simply by waiting several days. In vivo, product release might require an interaction with a membrane or other protein, or could be triggered by binding of a new $Ca_1a_2X$ substrate. Similar complexes with a product in the exit groove have been observed in FTase (Long et al., 2002), and the RabGGTase also has an exit groove at the same location. The GGTase-I structures confirm that the exit groove region is a functionally conserved structural feature, despite little sequence conservation between the three enzymes.

Repeated attempts to displace the product in a similar manner by soaking with FPP failed. This indicates that the stability of the enzyme-product complex contributes to selectivity GGPP over FPP, as the shorter FPP molecule cannot readily displace the product. After moving to the exit site, the product can be fully displaced from the enzyme by soaking new peptide substrate into the crystals or simply by waiting several days. In vivo product release might require an interaction with a membrane or other protein, or could be triggered by binding of a new $Ca_1a_2X$ substrate. There is little sequence conservation between the three enzymes in the exit groove region, but the GGTase-I structures prove that it is a functionally conserved structural feature.

VI.E. Metal Co-factors

Figure 7:
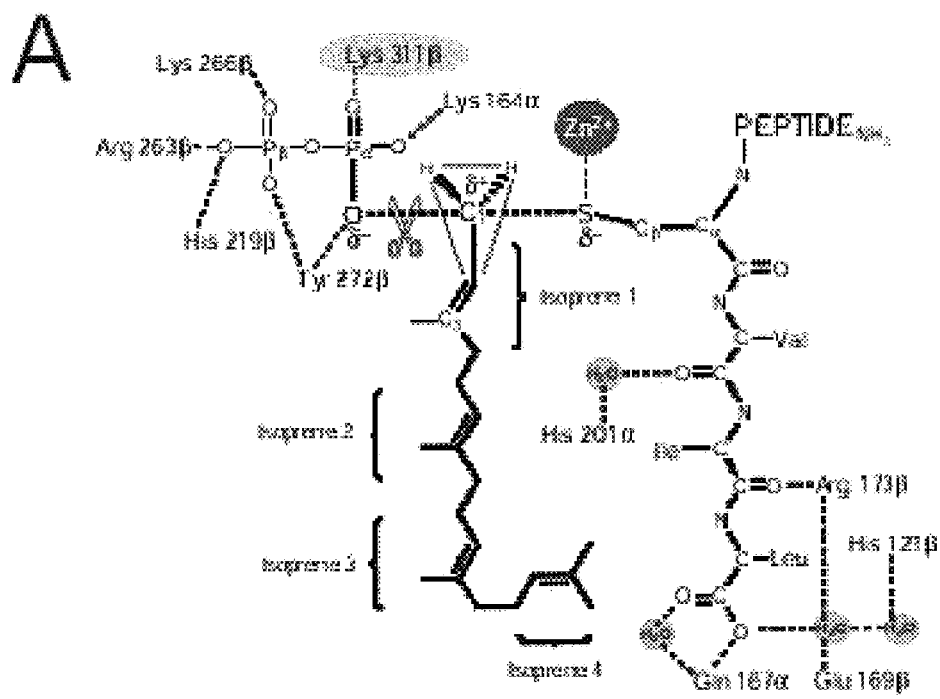
FIGS. 7A and 7B depict a model for the transition state of the prenylation reaction.
Figure 7:
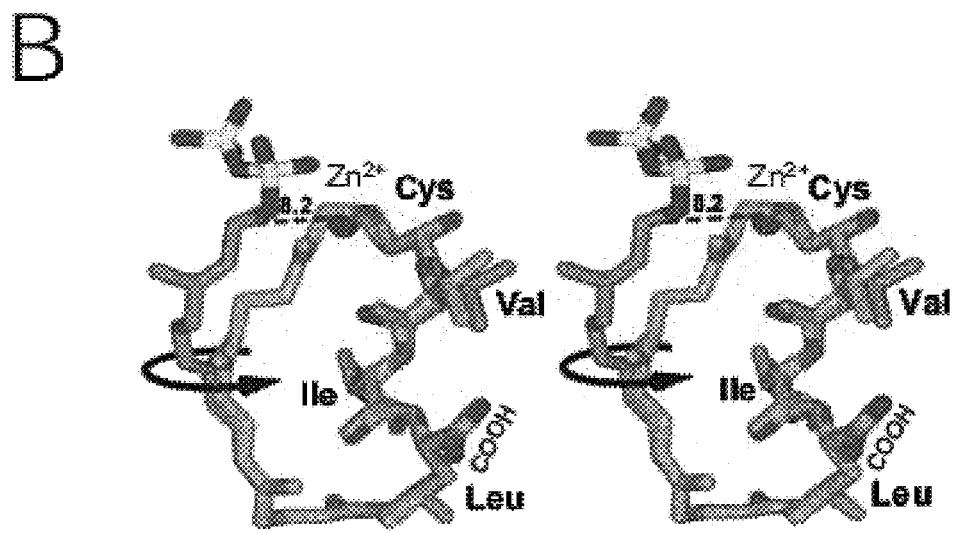

All of the GGTase-I complexes contain a zinc ion bound at full occupancy with a B-factor comparable with the surrounding protein residues. The zinc ion is coordinated by three residues, Asp 269β, Cys 271β, His 321β, that are strictly conserved across all the protein prenyltransferases. In the ternary complex, Complex 2, and product complex, Complex 3, the zinc ion is also coordinated by the $Ca_1a_2X$ cysteine. Spectroscopic observations suggest that the $Ca_1a_2X$ cysteine sulfur is in the deprotonated thiolate form when coordinated by the zinc ion and is directly involved in the chemical step (Hightower et al., 1998). GGTase-I requires only the enzyme-bound zinc, whereas FTase requires the zinc and millimolar levels of magnesium for optimal activity (Zhang & Casey, 1996). The GGTase-I structure suggests an explanation for this difference. Residue 311β is lysine in GGTase-I, whereas it is aspartic acid in FTase and RabGGTase. In the GGTase-I structures the amine group of lysine 311β is observed near to the $Mg^{2+}$ in the FTase transition state model. It might be the case that the amine group substitutes for the positively charged magnesium ion, permitting magnesium independent catalysis by GGTase-I (see FIG. 7A).

VII. The Protein Prenyltransferase Reaction Cycle

Figure 8:
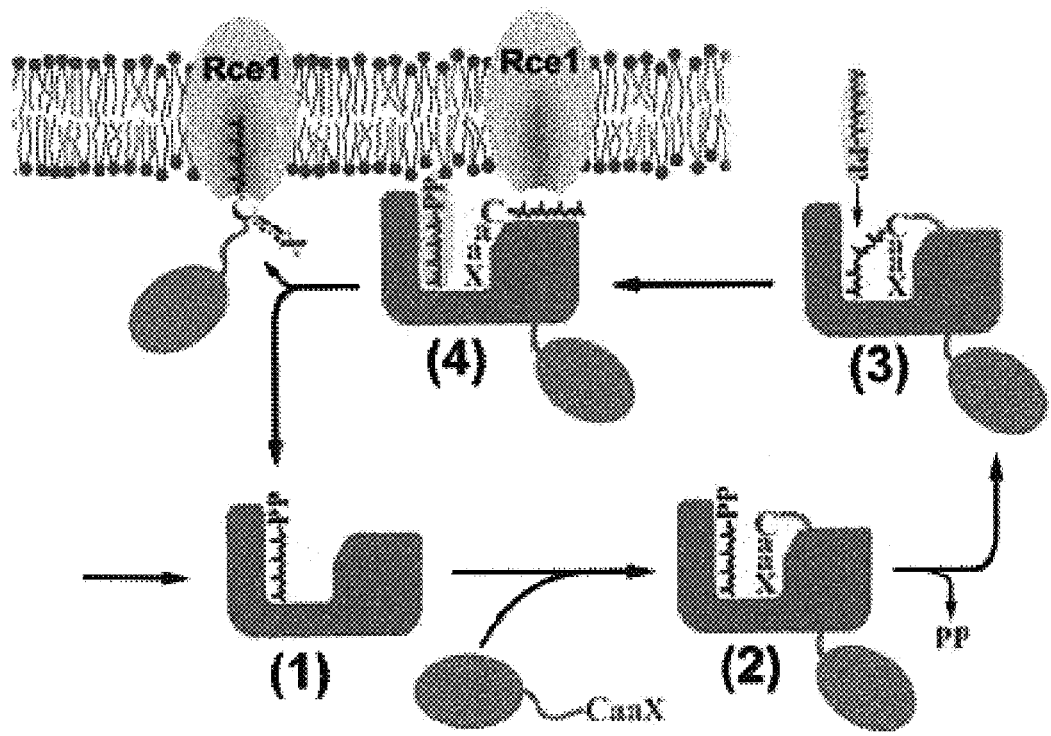
FIG. 8 is a schematic diagram depicting a GGTase-I reaction cycle and product escort. The diagram depicts how GGTase-I can function as an escort.

A reaction cycle was proposed for FTase, (Long et al., 2002). However, the presently disclosed subject matter discloses some aspects of the cycle for GGTase-I. The GGTase-I structures represent four different states in a reaction cycle that begins with the binding of GGPP, as depicted in FIG. 8. Once charged with GGPP in Complex 1, the enzyme binds a protein with a C-terminal $Ca_1a_2X$ motif in Complex 2. The observed ordered substrate binding is consistent with the $Ca_1a_2X$ binding mode seen in Complex 2, where the isoprenoid in Complex 1 forms much of the $Ca_1a_2X$ binding site in Complex 2. These two steps are identical to those seen in FTase, with the exception of the substrate specificity differences discussed above. The formation of Complex 2 is followed by a conformational change in the isoprenoid diphosphate substrate to reposition it for catalysis, maintaining the conformation of the peptide substrate position, and keeping the protein rigid (see FIG. 7B).

The conformational change in the GGPP reorients the diphosphate moiety and the first two isoprene units from their observed positions in Complex 2. The β-phosphate of the leaving diphosphate group stays in roughly the same position, but the α-phosphate is repositioned to interact with Lys 164α, Lys 311β, and Tyr 272β, bringing the $C_1$ atom close to the cysteine thiolate. The $Ca_1a_2X$ peptide substrate remains in place, with the zinc and the Cβ-Sγ bond of the cysteine thiolate orienting a free pair of electrons for nucleophilic attack on $C_1$.

Synthesis of all available data on the mechanism, including the comparison of the structures of Complexes 2 and 3, allows a model of the transition state to be constructed (FIG. 7A), as was done for FTase (Long et al., 2002). The proposed structure retains elements of both the postulated electrophilic and nucleophilic components of the reaction mechanism (Clausen et al., 2001; Yokoyama et al., 1997). In this model, Lys 311β in GGTase-I fulfills the role of $Mg^{2+}$ in FTase discussed hereinabove. The enzyme then releases pyrophosphate and creates Complex 3, a stable product complex. Binding a new GGPP molecule then shifts the product to the exit site (Complex 4), where binding the next protein substrate or an interaction with the next enzyme in the pathway facilitates its release. These product complexes again confirm observations of the FTase reaction cycle in all critical aspects, including that changes in substrate conformation during the reaction are not correlated with conformational changes in the enzyme. Indeed, the structures of these four GGTase-I complexes, determined using two crystal forms, have the same protein conformations. Thus, the ability to provide a general reaction scheme for a prenyltransferase is disclosed for this first time herein.

The nature of the GGTase-I reaction cycle suggests that lipid substrate specificity can be coupled to product release, resolving the apparent paradox of how GGTase-I selects GGPP over FPP. The four structures presented here indicate that the GGTase-I lipid-binding site is always occupied, either by GGPP or the geranylgeranyl moiety of the prenyl-peptide product. Reaction cycle progression requires the binding of fresh isoprenoid diphosphate to displace the product from the active site. FPP cannot displace GGPP from the active site, and it has been found that only GGPP can displace the prenyl-peptide product. Thus, there is no opportunity for FPP to bind to GGTase-I during the reaction cycle. Repeated attempts to displace a geranylgeranyl-peptide product from GGTase-I by soaking product crystals with FPP failed (soak times of up to 1 week, results not shown), suggesting that the stability of the enzyme-product complex contributes towards selectivity of GGPP over FPP. RabGGTase-I likely shares the same mechanism. Thus, the protein prenyltransferase enzymes are unique in that they appear to couple product release to lipid substrate specificity.

After lipidation, the prenyl-protein product is further processed first by Rce1, a protease that cleaves the 'aaX' portion from the $Ca_1a_2X$ motif, followed by lcmt, which methylates the C-terminus (Tamanoi & Sigman, 2001). The $Ca_1a_2X$ motif is the main determinant for directing proteins to this next processing step (Choy et al., 1999). The unusual substrate-mediated product release might provide a mechanism for the regulated handover of the prenyl-protein product to the next step in this processing pathway (see FIG. 8). In the $Ca_1a_2X$ prenyltransferases, the prenylated product remains tightly bound and is therefore shielded from the cytoplasm, preventing aggregation or association with an incorrect membrane compartment. Only upon binding of an additional GGPP molecule is the product isoprenoid displaced into the exit groove, presenting the product for delivery to the next processing step. The product can then be either directly delivered to the membrane bilayer or passed to another protein such as the Rce1 protease, the next enzyme in the prenylation pathway. The mechanism for this handover is analogous to one of the roles of REP, which escorts RabGGTase products to their final destination (Alexandrov et al., 1994), and similar to that of the GDI proteins, which extract prenylated G proteins such as Rho from membranes by binding the isoprenoid moiety in a hydrophobic pocket and transporting them throughout the cell (Hoffman et al., 2000). Consistent with this hypothesis of a role for $Ca_1a_2X$ prenyltransferases in product delivery, in vivo studies of Rce1 knock-out fibroblasts have shown that Ras, although prenylated normally, becomes mislocalized (Bergo et al., 2000; Kim et al., 1999).

VII.A. An Additional Cellular Role for $Ca_1a_2X$ Prenyltransferases

After prenylation, it might be difficult or impossible for the lipid-modified protein to simply diffuse through the cytoplasm to its next destination, which for most is the endoplasmic reticulum (ER), for further processing by the Rce1 $Ca_1a_2X$ protease and the lcmt methyl transferase. For RabGGTase this apparent problem is solved by REP, which presents the substrate protein to RabGGTase for prenylation and then escorts the modified protein to its destination following catalysis (Alexandrov et al., 1994).

This function appears to be an inherent property of the $Ca_1a_2X$ prenyltransferases themselves. The unusual product release mechanism and the conserved structural features of these enzymes suggest that they can serve as the escort of their own prenyl-protein product. The mechanism for this transport could be similar to that utilized by GDIs, proteins capable of extracting prenylated G proteins, such as Rho, from membranes and transporting them throughout the various cellular membranes by burying the isoprenoid moiety in a hydrophobic pocket (Hoffman et al., 2000). The exit groove of the $Ca_1a_2X$ prenyltransferases could serve a similar function, sequestering the prenylated product from the cytosol until it reaches its destination. This would explain why Rab1B (a RabGGTase substrate) was still targeted to the ER even when altered to not interact with either GDI or REP, so long as the C-terminus was modified to be a substrate for GGTase-I (Overmeyer et al., 2001). At the proper location, the prenylated product could be directly delivered to the membrane bilayer, or passed to another protein such as the Rce1 protease, the next enzyme in the prenylation pathway. Consistent with this mechanism, in vivo studies of Rce1 knockout fibroblasts have shown that Ras, although prenylated normally, becomes mislocalized (Bergo et al., 2000; Kim et al., 1999). Another possible benefit of this unusual mechanism could be to uncouple product release from substrate binding, permitting product delivery to locations other than where GGPP is encountered.

VII.B. Molecular Mechanisms of RabGGTase

Much of the insight gained from the GGTase-I and FTase structures can be applied to understand the function of RabGGTase. A comparison of GGTase-I and the unliganded RabGGTase structure reveals the strong similarity in the GGPP binding site and allows GGPP binding by RabGGTase to be modeled. Although RabGGTase adds two isoprenoids to its target Rab proteins, the comparison supports biochemical studies showing that RabGGTase binds only a single GGPP at a time (Desnoyers & Seabra, 1998). The GGPP binding site of GGTase-I, defined as all residues within 4.5 Å of the GGPP, is made up of eighteen residues in the center of the β subunit barrel and six residues contributed by the loops connecting αsubunit helices 4 to 5, and 6 to 7. These residues include His 201α, Glu 169β, Arg 173β, Gln 167α, Phe 174β, His 121β, Asp 269β, Cys 271β, His 321β, Leu 320β, Phe 52β, Phe 53β, Thr 49β, Met 124β, Tyr 166α, Phe 324β, and Ala 123β. The six α subunit residues are identical in all three enzymes, except for a phenylalanine for tyrosine substitution in RabGGTase. Of the eighteen β subunit residues, nine are identical in all three enzymes. The others are structurally conservative substitutions. The specificity-determining residues Thr 49β and Phe 324β are identical in both GGTase-I and RabGGTase (see FIG. 4B). A single GGPP can be modeled into the apo structure of RabGGTase in the same conformation as seen in GGTase-I, with rotamer changes in only a few side chains. These results indicate that a general mechanism is used for isoprenoid selection by all of the protein prenyltransferases, with RabGGTase selecting its two isoprenoids sequentially.

RabGGTase modifies both cysteines of -CC or -CXC motifs and does not have selectivity mechanisms similar to the $Ca_1a_2X$ enzymes. As the -CC and -CXC motifs do not uniquely identify RabGGTase targets, it is might be that some or all of the selectivity is provided by the REP. Indeed, evolution necessarily avoided a $Ca_1a_2X$-like binding site, because RabGGTase must allow for variation in the substrate peptide length. This requires that the C-terminus not be anchored, as in the $Ca_1a_2X$ enzymes. In RabGGTase, an aspartic acid replaces Ala 129α, thus placing a negatively charged group at the location where the $Ca_1a_2X$ C-terminal carboxyl group binds in GGTase-I. Gln167α, which forms a water-mediated hydrogen bond to the $Ca_1a_2X$ C-terminus in GGTase-I, is replaced by glycine in RabGGTase. In addition, substitutions of leucine and tyrosine in RabGGTase for Ala 123β and Met 124β, respectively, fill much of the space where the $Ca_1a_2X$ peptide's terminal residue side chain binds in GGTase-I.

RabGGTase has an exit groove at the same location as the $Ca_1a_2X$ prenyltransferases. However in RabGGTase, a 7.5 Å diameter tunnel branches from the floor of the exit groove and extends through the β subunit. The tunnel is lined with primarily hydrophobic residues (Tyr 30β, Tyr 39β, Arg 46β, Gly 49β, and Pro 288β). This tunnel could accommodate an isoprenoid lipid and might be part of the double prenylation mechanism. Multiple binding sites for product molecules have been observed previously in processive enzyme systems in which substrate binding is involved in product release or translocation (e.g., the P and E sites of the ribosome), and the prenyltransferase exit groove/tunnel might have evolved to assist the processive RabGGTase reaction. After the first GG is attached it could slide into the tunnel moving the second cysteine into position to add the next GG. The depth to which it enters the tunnel could accommodate different spacing of the cysteines (i.e., CC or CXC).

VIII. Uses of GGTase-I Crystals

The GGTase-I crystals, three-dimensional structures, and homology modules that form aspects of the presently disclosed subject matter can be employed in a variety of applications. A brief discussion of several of these applications is presented hereinbelow. Additional uses for GGTase-I crystals, three-dimensional structures, and homology modules disclosed herein will be apparent to those of skill in the art upon consideration of the present disclosure.

VIII.A. Design and Development of a Prenyltransferase Polypeptide (e.g. FTase or GGTase-I) Modulator The knowledge of the structure of the GGTase-I in complex with substrates and/or products, an aspect of the presently disclosed subject matter, provides a tool for investigating the mechanism of action of GGTase-I and other prenyltransferases in a subject. For example, modulators of GGTase-I are known to be useful in treatment regimes. Such modulators can be designed and/or their mechanisms investigated using a structure of GGTase-I as a guide. In another example, various computer models, as described herein, can predict the binding of various substrate molecules to GGTase-I. Upon discovering that such binding in fact takes place, knowledge of the protein structure then allows design and synthesis of small molecules that mimic the functional binding of the substrate to GGTase-I. This is the method of "rational" drug design, further described hereinbelow.

Use of the GGTase-I crystalline structures of the presently disclosed subject matter in rational drug design is thus provided in accordance with the presently disclosed subject matter. Additional rational drug design techniques are described in U.S. Pat. No. 5,834,228 to Becker et al. and U.S. Pat. No. 5,872,011 to Burley et al., incorporated herein in their entirety.

Thus, in addition to the compounds described herein, other sterically similar compounds can be formulated to mimic the key structural regions of prenyltransferases in general, or of GGTase-I in particular. The generation of a structural functional equivalent can be achieved by the techniques of modeling and chemical design known to those of skill in the art and described herein. It will be understood that all such sterically similar constructs fall within the scope of the presently disclosed subject matter.

VIII.A.1. Rational Drug Design

A number of techniques can be used to screen, identify, select and design chemical entities capable of associating with polypeptides of the presently disclosed subject matter, structurally homologous molecules, and other molecules. Knowledge of the structure for a polypeptide of the presently disclosed subject matter, determined in accordance with the methods described herein, permits the design and/or identification of molecules and/or other modulators which have a shape complementary to the conformation of a polypeptide of the presently disclosed subject matter, or more particularly, a druggable region thereof. It is understood that such techniques and methods can use, in addition to the exact structural coordinates and other information for a polypeptide of the presently disclosed subject matter, structural equivalents thereof described above (including, for example, those structural coordinates that are derived from the structural coordinates of amino acids contained in a druggable region as described above).

Modulators to polypeptides of the presently disclosed subject matter and other structurally related molecules, and complexes containing the same, can be identified and developed as set forth below and otherwise using techniques and methods known to those of skill in the art.

The presently disclosed subject matter contemplates making any molecule that is shown to modulate the activity of a polypeptide of the presently disclosed subject matter.

In some embodiments, inhibitors, modulators of the subject polypeptides, or biological complexes containing them, can be used in the manufacture of a medicament for any number of uses, including, for example, treating any disease or other treatable condition of a patient (including humans and animals), and particularly a disease caused by aberrant GGTase-I regulation or activity.

A number of techniques can be used to screen, identify, select, and design chemical entities capable of associating with polypeptides of the presently disclosed subject matter, structurally homologous molecules, and other molecules. Knowledge of the structure for a polypeptide of the presently disclosed subject matter, determined in accordance with the methods described herein, permits the design and/or identification of molecules and/or other modulators which have a shape complementary to the conformation of a polypeptide of the presently disclosed subject matter, or more particularly, a druggable region thereof. It is understood that such techniques and methods can use, in addition to the exact structural coordinates and other information for a polypeptide of the presently disclosed subject matter, structural equivalents thereof described above (including, for example, those structural coordinates that are derived from the structural coordinates of amino acids contained in a druggable region as described above).

In another aspect, methods for identifying a druggable region of a polypeptide of the presently disclosed subject matter are provided. For example, one such method includes: (a) obtaining crystals of a polypeptide of the presently disclosed subject matter or a fragment thereof such that the three dimensional structure of the crystallized protein can be determined to a resolution of 3.5 Å or better; (b) determining the three dimensional structure of the crystallized polypeptide or fragment using X-ray diffraction; and (c) identifying a druggable region of a polypeptide of the presently disclosed subject matter based on the three-dimensional structure of the polypeptide or fragment.

A three dimensional structure of a molecule or complex can be described by the set of atoms that best predict the observed diffraction data (that is, which possesses a minimal R value). Files can be created for the structure that defines each atom by its chemical identity, spatial coordinates in three dimensions, root mean squared deviation from the mean to observed position and fractional occupancy of the observed position.

Those of skill in the art understand that a set of structure coordinates for a protein, complex, or a portion thereof, is a relative set of points that define a shape in three dimensions. Thus, it is possible that an entirely different set of coordinates could define a similar or identical shape. Moreover, slight variations in the individual coordinates can have little affect on overall shape. Such variations in coordinates can be generated because of mathematical manipulations of the structure coordinates. For example, structure coordinates could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little affect on overall shape. If such variations are within an acceptable standard error as compared to the original coordinates, the resulting three-dimensional shape is considered to be structurally equivalent. It should be noted that slight variations in individual structure coordinates of a polypeptide of the presently disclosed subject matter or a complex thereof would not be expected to significantly alter the nature of modulators that could associate with a druggable region thereof. Thus, for example, a modulator that bound to the active site of a polypeptide of the presently disclosed subject matter would also be expected to bind to or interfere with another active site whose structure coordinates define a shape that falls within the acceptable error.

A crystal structure of the presently disclosed subject matter can be used to make a structural or computer model of the polypeptide, complex or portion thereof. A model can represent the secondary, tertiary, and/or quaternary structure of the polypeptide, complex, or portion. The configurations of points in space derived from structure coordinates according to the presently disclosed subject matter can be visualized as, for example, a holographic image, a stereodiagram, a model or a computer-displayed image, and the presently disclosed subject matter thus includes such images, diagrams or models.

The term "chemical entity", as used herein, refers to chemical compounds, complexes of two or more chemical compounds, and fragments of such compounds or complexes. In certain instances, it is desirable to use chemical entities exhibiting a wide range of structural and functional diversity, such as compounds exhibiting different shapes (i.e., flat aromatic rings(s), puckered aliphatic rings(s), straight and branched chain aliphatics with single, double, or triple bonds) and diverse functional groups (i.e., carboxylic acids, esters, ethers, amines, aldehydes, ketones, and various heterocyclic rings).

In one aspect, the method of drug design generally includes computationally evaluating the potential of a selected chemical entity to associate with any of the molecules or complexes of the presently disclosed subject matter (or portions thereof). For example, this method can include the steps of (a) employing computational means to perform a fitting operation between the selected chemical entity and a druggable region of the molecule or complex; and (b) analyzing the results of said fitting operation to quantify the association between the chemical entity and the druggable region.

A chemical entity can be examined either through visual inspection or through the use of computer modeling using a docking program such as GRAM, DOCK, or AUTODOCK (Dunbrack et al., 1997). This procedure can include computer fitting of chemical entities to a target to ascertain how well the shape and the chemical structure of each chemical entity will complement or interfere with the structure of the subject polypeptide (Bugg et al., 1993; West & Fairlie, 1995). Computer programs can also be employed to estimate the attraction, repulsion, and steric hindrance of the chemical entity to a druggable region, for example. Generally, the tighter the fit (i.e., the lower the steric hindrance, and/or the greater the attractive force) the more potent the chemical entity will be because these properties are consistent with a tighter binding constant. Furthermore, the more specificity in the design of a chemical entity the more likely that the chemical entity will not interfere with related proteins, which can minimize potential side-effects due to unwanted interactions.

A variety of computational methods for molecular design, in which the steric and electronic properties of druggable regions are used to guide the design of chemical entities, are known (see e.g., Cohen et al., 1990; Kuntz et al., 1982; DesJarlais et al., 1988; Bartlett et al., 1989; Goodford, 1985; DesJarlais et al., 1986). Directed methods generally fall into two categories: (1) design by analogy in which 3-D structures of known chemical entities (such as from a crystallographic database) are docked to the druggable region and scored for goodness-of-fit; and (2) de novo design, in which the chemical entity is constructed piece-wise in the druggable region. The chemical entity can be screened as part of a library or a database of molecules. Databases which can be used include ACD (MDL Systems Inc., San Leandro, Calif., United States of America), NCI (National Cancer Institute, Bethesda, Md., United States of America), CCDC (Cambridge Crystallographic Data Center, Cambridge, England, United Kingdom), CAST (Chemical Abstract Service), Derwent (Derwent Information Limited, London, England, United Kingdom), Canbridge (Canbridge Chemical Company Ltd., Cornwall, England, United Kingdom), Aldrich (Aldrich Chemical Company, St. Louis, Mo., United States of America), DOCK (University of California in San Francisco, San Francisco, Calif., United States of America), and the Directory of Natural Products (Chapman & Hall). Computer programs such as CONCORD (Tripos Inc., St. Louis, Mo., United States of America) or DB-Converter (Molecular Simulations Limited, Cambridge, England, United Kingdom) can be used to convert a data set represented in two dimensions to one represented in three dimensions.

Chemical entities can be tested for their capacity to fit spatially with a druggable region or other portion of a target protein. As used herein, the term "fits spatially" refers to that the three-dimensional structure of the chemical entity is accommodated geometrically by a druggable region. A favorable geometric fit occurs when the surface area of the chemical entity is in close proximity with the surface area of the druggable region without forming unfavorable interactions. A favorable complementary interaction occurs where the chemical entity interacts by hydrophobic, aromatic, ionic, dipolar, or hydrogen donating and accepting forces. Unfavorable interactions can be steric hindrance between atoms in the chemical entity and atoms in the druggable region.

If a model of the presently disclosed subject matter is a computer model, the chemical entities can be positioned in a druggable region through computational docking. If, on the other hand, the model of the presently disclosed subject matter is a structural model, the chemical entities can be positioned in the druggable region by, for example, manual docking. As used herein the term "docking" refers to a process of placing a chemical entity in close proximity with a druggable region, or a process of finding low energy conformations of a chemical entity/druggable region complex.

In an illustrative embodiment, the design of potential modulator begins from the general perspective of shape complimentary for the druggable region of a polypeptide of the presently disclosed subject matter, and a search algorithm is employed which is capable of scanning a database of small molecules of known three-dimensional structure for chemical entities which fit geometrically with the target druggable region. Most algorithms of this type provide a method for finding a wide assortment of chemical entities that are complementary to the shape of a druggable region of the subject polypeptide. Each of a set of chemical entities from a particular data-base, such as the Cambridge Crystallographic Data Bank (CCDB; Allen et al., 1991), is individually docked to the druggable region of a polypeptide of the presently disclosed subject matter in a number of geometrically permissible orientations with use of a docking algorithm. In certain embodiments, a set of computer algorithms called DOCK, can be used to characterize the shape of invaginations and grooves that form the active sites and recognition surfaces of the druggable region (Kuntz et al., 1982). The program can also search a database of small molecules for templates whose shapes are complementary to particular binding sites of a polypeptide of the presently disclosed subject matter (DesJarlais et al., 1988).

The orientations are evaluated for goodness-of-fit and the best are kept for further examination using molecular mechanics programs, such as AMBER or CHARMM. Such algorithms have previously proven successful in finding a variety of chemical entities that are complementary in shape to a druggable region.

Goodford, 1985 and Boobbyer et al., 1989 describe a computer program (GRID) that seeks to determine regions of high affinity for different chemical groups (termed probes) of the druggable region. GRID hence provides a tool for suggesting modifications to known chemical entities that might enhance binding. It can be anticipated that some of the sites discerned by GRID as regions of high affinity correspond to "pharmacophoric patterns" determined inferentially from a series of known ligands. As used herein, a "pharmacophoric pattern" is a geometric arrangement of features of chemical entities that is believed to be important for binding. Attempts have been made to use pharmacophoric patterns as a search screen for novel ligands' (Jakes et al., 1987; Brint & Willett, 1987; Jakes & Willett, 1986).

Yet a further embodiment of the presently disclosed subject matter utilizes a computer algorithm such as CLIX which searches such databases as CCDB for chemical entities which can be oriented with the druggable region in a way that is both sterically acceptable and has a high likelihood of achieving favorable chemical interactions between the chemical entity and the surrounding amino acid residues. The method is based on characterizing the region in terms of an ensemble of favorable binding positions for different chemical groups and then searching for orientations of the chemical entities that cause maximum spatial coincidence of individual candidate chemical groups with members of the ensemble. The algorithmic details of CLIX are described in Lawrence & Davis, 1992.

In this way, the efficiency with which a chemical entity can bind to or interfere with a druggable region can be tested and optimized by computational evaluation. In some embodiments, for a favorable association with a druggable region, a chemical entity demonstrates a relatively small difference in energy between its bound and free states (i.e., a small deformation energy of binding). Thus, certain, more desirable chemical entities will be designed with a deformation energy of binding of in some embodiments not greater than about 10 kcal/mole, and in some embodiments, not greater than 7 kcal/mole. Chemical entities can interact with a druggable region in more than one conformation that is similar in overall binding energy. In those cases, the deformation energy of binding is taken to be the difference between the energy of the free entity and the average energy of the conformations observed when the chemical entity binds to the target.

In this way, the presently disclosed subject matter provides computer-assisted methods for identifying or designing a potential modulator of the activity of a polypeptide of the presently disclosed subject matter including: supplying a computer modeling application with a set of structure coordinates of a molecule or complex, the molecule or complex including at least a portion of a druggable region from a polypeptide of the presently disclosed subject matter; supplying the computer modeling application with a set of structure coordinates of a chemical entity; and determining whether the chemical entity is expected to bind to the molecule or complex, wherein binding to the molecule or complex is indicative of potential modulation of the activity of a polypeptide of the presently disclosed subject matter.

In another aspect, provided is a computer-assisted method for identifying or designing a potential modulator to a polypeptide of the presently disclosed subject matter, supplying a computer modeling application with a set of structure coordinates of a molecule or complex, the molecule or complex including at least a portion of a druggable region of a polypeptide of the presently disclosed subject matter; supplying the computer modeling application with a set of structure coordinates for a chemical entity; evaluating the potential binding interactions between the chemical entity and active site of the molecule or molecular complex; structurally modifying the chemical entity to yield a set of structure coordinates for a modified chemical entity, and determining whether the modified chemical entity is expected to bind to the molecule or complex, wherein binding to the molecule or complex is indicative of potential modulation of the polypeptide of the presently disclosed subject matter.

In some embodiments, a potential modulator can be obtained by screening a peptide library (Scott & Smith, 1990; Cwirla et al., 1990; Devlin et al., 1990). A potential modulator selected in this manner could then be systematically modified by computer modeling programs until one or more promising potential drugs are identified. Such analysis has been shown to be effective in the development of HIV protease inhibitors (Lam et al., 1994; Wlodawer & Erickson, 1993; Appelt, 1993; Erickson, 1993). Alternatively a potential modulator can be selected from a library of chemicals such as those that can be licensed from third parties, such as chemical and pharmaceutical companies. A third alternative is to synthesize the potential modulator de novo.

For example, in certain embodiments, a method for making a potential modulator for a polypeptide of the presently disclosed subject matter is provided, the method including synthesizing a chemical entity or a molecule containing the chemical entity to yield a potential modulator of a polypeptide of the presently disclosed subject matter, the chemical entity having been identified during a computer-assisted process including supplying a computer modeling application with a set of structure coordinates of a molecule or complex, the molecule or complex including at least one druggable region from a polypeptide of the presently disclosed subject matter; supplying the computer modeling application with a set of structure coordinates of a chemical entity; and determining whether the chemical entity is expected to bind to the molecule or complex at the active site, wherein binding to the molecule or complex is indicative of potential modulation. This method can further include the steps of evaluating the potential binding interactions between the chemical entity and the active site of the molecule or molecular complex and structurally modifying the chemical entity to yield a set of structure coordinates for a modified chemical entity, which steps can be repeated one or more times.

Once a potential modulator is identified, it can then be tested in any standard assay for the macromolecule depending of course on the macromolecule, including in high throughput assays. Further refinements to the structure of the modulator will generally be necessary and can be made by the successive iterations of any and/or all of the steps provided by the particular screening assay, in particular further structural analysis by i.e., 15N NMR relaxation rate determinations or X-ray crystallography with the modulator bound to the subject polypeptide. These studies can be performed in conjunction with biochemical assays.

Once identified, a potential modulator can be used as a model structure, and analogs to the compound can be obtained. The analogs are then screened for their ability to bind the subject polypeptide. An analog of the potential modulator might be chosen as a modulator when it binds to the subject polypeptide with a higher binding affinity than the predecessor modulator.

In a related approach, iterative drug design is used to identify modulators of a target protein. Iterative drug design is a method for optimizing associations between a protein and a modulator by determining and evaluating the three dimensional structures of successive sets of protein/modulator complexes. In iterative drug design, crystals of a series of protein/modulator complexes are obtained and then the three-dimensional structures of each complex are solved. Such an approach provides insight into the association between the proteins and modulators of each complex. For example, this approach can be accomplished by selecting modulators with inhibitory activity, obtaining crystals of this new protein/modulator complex, solving the three dimensional structure of the complex, and comparing the associations between the new protein/modulator complex and previously solved protein/modulator complexes. By observing how changes in the modulator affected the protein/modulator associations, these associations can be optimized.

In addition to designing and/or identifying a chemical entity to associate with a druggable region, as described above, the same techniques and methods can be used to design and/or identify chemical entities that either associate, or do not associate, with affinity regions, selectivity regions or undesired regions of protein targets. By such methods, selectivity for one or a few targets, or alternatively for multiple targets, from the same species or from multiple species, can be achieved.

For example, a chemical entity can be designed and/or identified for which the binding energy for one druggable region, ie., an affinity region or selectivity region, is more favorable than that for another region, i.e., an undesired region, by about 20%, 30%, 50% to about 60% or more. It can be the case that the difference is observed between (a) more than two regions, (b) between different regions (selectivity, affinity or undesirable) from the same target, (c) between regions of different targets, (d) between regions of homologs from different species, or (e) between other combinations. Alternatively, the comparison can be made by reference to the $K_d$, usually the apparent $K_d$, of said chemical entity with the two or more regions in question.

In another aspect, prospective modulators are screened for binding to two nearby druggable regions on a target protein. For example, a modulator that binds a first region of a target polypeptide does not bind a second nearby region. Binding to the second region can be determined by monitoring changes in a different set of amide chemical shifts in either the original screen or a second screen conducted in the presence of a modulator (or potential modulator) for the first region. From an analysis of the chemical shift changes, the approximate location of a potential modulator for the second region is identified. Optimization of the second modulator for binding to the region is then carried out by screening structurally related compounds (i.e., analogs as described above). When modulators for the first region and the second region are identified, their location and orientation in the ternary complex can be determined experimentally. On the basis of this structural information, a linked compound, i.e., a consolidated modulator, is synthesized in which the modulator for the first region and the modulator for the second region are linked. In certain embodiments, the two modulators are covalently linked to form a consolidated modulator. This consolidated modulator can be tested to determine if it has a higher binding affinity for the target than either of the two individual modulators. A consolidated modulator is selected as a modulator when it has a higher binding affinity for the target than either of the two modulators. Larger consolidated modulators can be constructed in an analogous manner, i.e., linking three modulators which bind to three nearby regions on the target to form a multilinked consolidated modulator that has an even higher affinity for the target than the linked modulator. In this example, it is assumed that is desirable to have the modulator bind to all the druggable regions. However, it can be the case that binding to certain of the druggable regions is not desirable, so that the same techniques can be used to identify modulators and consolidated modulators that show increased specificity based on binding to at least one but not all druggable regions of a target.

The presently disclosed subject matter provides a number of methods that use drug design as described above. For example, in one aspect, a method for designing a candidate compound for screening for inhibitors of a polypeptide of the presently disclosed subject matter is contemplated, the method comprising: (a) determining the three dimensional structure of a crystallized polypeptide of the presently disclosed subject matter or a fragment thereof; and (b) designing a candidate inhibitor based on the three dimensional structure of the crystallized polypeptide or fragment.

In another aspect, a method for identifying a potential inhibitor of a polypeptide of the presently disclosed subject matter is contemplated, the method comprising: (a) providing the three-dimensional coordinates of a polypeptide of the presently disclosed subject matter or a fragment thereof; (b) identifying a druggable region of the polypeptide or fragment; and (c) selecting from a database at least one compound that comprises three dimensional coordinates which indicate that the compound can bind the druggable region; (d) wherein the selected compound is a potential inhibitor of a polypeptide of the presently disclosed subject matter.

In another aspect, the presently disclosed subject matter contemplates a method for identifying a potential modulator of a molecule comprising a druggable region of a prenyltransferase (e.g., FTase or GGTase-1), the method comprising: (a) using the atomic coordinates of GGTase-1, or a fragment thereof, ± a root mean square deviation from the backbone atoms of the amino acids of not more than 1.5 Å, to generate a three-dimensional structure of a molecule comprising a druggable region that is a portion of a prenyltransferase (e.g., FTase or GGTase-1); (b) employing the three dimensional structure to design or select the potential modulator; (c) synthesizing the modulator; and (d) contacting the modulator with the molecule to determine the ability of the modulator to interact with the molecule.

In another aspect, the presently disclosed subject matter contemplates an apparatus for determining whether a compound is a potential inhibitor of a prenyltransferase polypeptide (e.g., FTase or GGTase-1), the apparatus comprising: (a) a memory that comprises: (i) the three dimensional coordinates and identities of the atoms of a polypeptide of the presently disclosed subject matter or a fragment thereof that form a druggable site; and (ii) executable instructions; and (b) a processor that is capable of executing instructions to: (i) receive three-dimensional structural information for a candidate compound; (ii) determine if the three-dimensional structure of the candidate compound is complementary to the structure of the interior of the druggable site; and (iii) output the results of the determination.

In another aspect, the presently disclosed subject matter contemplates a method for designing a potential compound for the prevention or treatment of a disease or disorder, the method comprising: (a) providing the three dimensional structure of a crystallized polypeptide of the presently disclosed subject matter, or a fragment thereof; (b) synthesizing a potential compound for the prevention or treatment of a disease or disorder based on the three dimensional structure of the crystallized polypeptide or fragment; (c) contacting a polypeptide of the presently disclosed subject matter with the potential compound; and (d) assaying the activity of a polypeptide of the presently disclosed subject matter, wherein a change in the activity of the polypeptide indicates that the compound can be useful for prevention or treatment of a disease or disorder.

In another aspect, the presently disclosed subject matter contemplates a method for designing a potential compound for the prevention or treatment of a disease or disorder, the method comprising: (a) providing structural information of a druggable region derived from NMR spectroscopy of a polypeptide of the presently disclosed subject matter, or a fragment thereof; (b) synthesizing a potential compound for the prevention or treatment of a disease or disorder based on the structural information; (c) contacting a polypeptide of the presently disclosed subject matter with the potential compound; and (d) assaying the activity of a polypeptide of the presently disclosed subject matter, wherein a change in the activity of the polypeptide indicates that the compound can be useful for prevention or treatment of a disease or disorder.

The three-dimensional structures of substrates and/or products in complex with GGTase-I are unprecedented and will greatly aid in the development of new synthetic ligands for prenyltransferases, such as agonists and antagonists, including those that bind exclusively to a given prenyltransferase (e.g., GGTase-I or FTase). In addition, GGTase-I is well suited to modern methods, including three-dimensional structure elucidation and combinatorial chemistry, such as those disclosed in U.S. Pat. No. 5,463,564 to Agragiotis et al., incorporated herein by reference. Structure determination using X-ray crystallography is possible, in part, because of the solubility properties of GGTase-I. Computer programs that employ crystallography data when practicing the presently disclosed subject matter will enable the rational design of substrates for GGTase-I and other enzymes. Programs such as RASMOL (Biomolecular Structures Group, Glaxo Wellcome Research & Development Stevenage, Hertfordshire, United Kingdom, Version 2.6, August 1995, Version 2.6.4, December 1998, Copyright © Roger Sayle 1992-1999) can be employed using the atomic structural coordinates from crystals of the presently disclosed subject matter, crystals generated by practicing the presently disclosed subject matter or crystals used to practice the presently disclosed subject matter by generating three-dimensional models and/or determining the structures involved in ligand binding. Computer programs such as those sold under the registered trademark INSIGHT II® (available from Accelrys Inc., San Diego, Calif., United States of America) and such as GRASP (Nicholls et al., 1991) allow for further manipulations and the ability to introduce new structures. In addition, high throughput binding and bioactivity assays can be devised using purified recombinant protein and modern reporter gene transcription assays known to those of skill in the art in order to refine the activity of a designed ligand.

A method of identifying modulators of the activity of a prenyltransferase using rational drug design is thus provided in accordance with the presently disclosed subject matter. The method comprises designing a potential modulator for a prenyltransferase (e.g., a GGTase-I polypeptide) of the presently disclosed subject matter that will form non-covalent bonds (e.g., hydrogen bonds, Van der Waals interactions, and hydrophobic interactions) with amino acids in a ligand binding pocket (e.g., an active site) based upon the crystalline structure of a GGTase-I polypeptide; synthesizing the modulator; and determining whether the potential modulator modulates the activity of the prenyltransferase polypeptide. In some embodiments, the modulator is designed for a GGTase-I polypeptide. The determination of whether the modulator modulates the biological activity of a prenyltransferase is made in accordance with the screening methods disclosed herein, or by other screening methods known to those of skill in the art. Modulators can be synthesized using techniques known to those of ordinary skill in the art.

Modulators can be designed to take advantage of various interactions between the enzyme and the modulator. For example, in one aspect of the presently disclosed subject matter, the active site of GGTase-I is disclosed. The active site can comprise the residues His 201α, Glu 169β, Arg 173β, Gln 167α, Phe 174β, His 121β, Asp 269β, Cys 271β, His 321β, Leu 320β, Phe 52β, Phe 53β, Thr 49β, Met 124β, Tyr 166α, Phe 324β, Ala 123β and combinations thereof. Thus, a modulator can be designed such that the moieties of the modulator can form interactions (e.g., hydrophobic interactions, van der Waals interactions, etc.) with the residues of the active site, such as those disclosed.

In an alternative embodiment, a method of designing a modulator of a prenyltransferase in accordance with the presently disclosed subject matter comprises: (a) selecting a candidate prenyltransferase ligand; (b) determining which amino acid or amino acids of a prenyltransferase interact with the ligand using a three-dimensional model of a crystallized GGTase-I (c) identifying in a biological assay for prenyltransferase activity a degree to which the ligand modulates the activity of the prenyltransferase; (d) selecting a chemical modification of the ligand wherein the interaction between the amino acids of the prenyltransferase and the ligand is predicted to be modulated by the chemical modification; (e) performing the chemical modification on the ligand to form a modified ligand; (f) contacting the modified ligand with the prenyltransferase; (g) identifying in a biological assay for prenyltransferase activity a degree to which the modified ligand modulates the biological activity of the prenyltransferase; and (h) comparing the biological activity of the prenyltransferase in the presence of modified ligand with the biological activity of the prenyltransferase in the presence of the unmodified ligand, whereby a modulator of a prenyltransferase is designed.

VIII.A.2. Methods for Using the GGTase-I Structural Coordinates for Molecular Design For the first time, the presently disclosed subject matter permits the use of molecular design techniques to design, select and synthesize chemical entities and compounds, including modulatory compounds, capable of binding to a ligand binding pocket (e.g., an active site) or an accessory binding site of a prenyltransferase, in whole or in part. Correspondingly, the presently disclosed subject matter also provides for the application of similar techniques in the design of modulators of any prenyltransferase.

In accordance with some embodiments of the presently disclosed subject matter, the structure coordinates of a crystalline GGTase-I can be used to design compounds that bind to a prenyltransferase (for example a GGTase-I or FTase) and alter the properties of a prenyltransferase (for example, ligand binding ability or catalytic efficiency) in different ways. One aspect of the presently disclosed subject matter provides for the design of compounds that act as competitive inhibitors of a prenyltransferase by binding to all, or a portion of, the binding sites on a prenyltransferase. The presently disclosed subject matter also provides for the design of compounds that can act as uncompetitive inhibitors of a prenyltransferase. These compounds can bind to all, or a portion of, an accessory binding site of a prenyltransferase that is already binding its ligand and can, therefore, be more potent and less non-specific than known competitive inhibitors that compete only for a prenylation ligand binding pocket (e.g., active site). Similarly, non-competitive inhibitors that bind to and inhibit prenyltransferase activity, whether or not it is bound to another chemical entity, can be designed using the GGTase-I structure coordinates of the presently disclosed subject matter.

A second design approach is to probe a prenyltransferase (for example, a GGTase-I) crystal with molecules comprising a variety of different chemical entities to determine optimal sites for interaction between candidate modulators and the prenyltransferase. For example, high resolution X-ray diffraction data collected from crystals saturated with solvent allows the determination of the site where each type of solvent molecule adheres. Small molecules that bind tightly to those sites can then be designed, synthesized and tested for their prenyltransferase modulator activity.

Once a computationally-designed ligand is synthesized using the methods of the presently disclosed subject matter or other methods known to those of skill in the art, assays can be used to establish its efficacy of the ligand as a modulator of prenyltransferase (e.g., GGTase-I) activity. After such assays, the ligands can be further refined by generating intact prenyltransferase, crystals with a ligand bound to the enzyme. The structure of the ligand can then be further refined using the chemical modification methods described herein and known to those of skill in the art, in order to improve the modulation activity or the binding affinity of the ligand. This process can lead to second generation ligands with improved properties.

VIII.A.3. Methods of Designing Prenyltransferase Modulator Compounds

The design of candidate substances, also referred to as "compounds," "candidate therapeutics" and "candidate compounds", that bind a prenyltransferase or that inhibit prenyltransferase-mediated activity according to the presently disclosed subject matter generally involves consideration of two factors. First, the compound must be capable of physically and structurally associating with a prenyltransferase. Non-covalent molecular interactions implicated in the association of a prenyltransferase with its substrate include hydrogen bonding, van der Waals interactions, and hydrophobic interactions.

Second, the compound must be able to assume a conformation that allows it to associate with a prenyltransferase. Although certain portions of the compound might not directly participate in this association with a prenyltransferase, those portions can still influence the overall conformation of the molecule. This, in turn, can have a significant impact on potency. Such conformational requirements include the overall three-dimensional structure and orientation of the chemical entity or compound in relation to all or a portion of the binding site, e.g., a ligand binding pocket (e.g., active site), an accessory binding site of a prenyltransferase, and/or the spacing between functional groups of a compound comprising several chemical entities that directly interact with a prenyltransferase.

The potential modulatory or binding effect of a chemical compound on a prenyltransferase can be analyzed prior to its actual synthesis and testing by the use of computer modeling techniques that employ the coordinates of a crystalline GGTase-I polypeptide of the presently disclosed subject matter. If the theoretical structure of the given compound suggests insufficient interaction and association between it and a prenyltransferase, synthesis and testing of the compound is generally obviated. However, if computer modeling indicates a strong interaction, the molecule can then be synthesized and tested for its ability to bind and modulate the activity of a prenyltransferase. In this manner, synthesis of unproductive or inoperative compounds can be avoided.

A modulatory or other binding compound of a prenyltransferase polypeptide (for example a GGTase-I or a FTase) can be computationally evaluated and designed via a series of steps in which chemical entities or fragments are screened and selected for their ability to associate with the individual binding sites or other areas of a crystalline GGTase-I polypeptide of the presently disclosed subject matter.

One of several methods can be used to screen chemical entities or fragments for their ability to associate with a prenyltransferase and, more particularly, with the individual binding sites of a prenyltransferase, such as a ligand binding pocket (e.g., active site) or an accessory binding site. This process can begin by visual inspection of, for example, a ligand binding pocket (e.g., active site) on a computer screen based on the GGTase-I atomic coordinates presented in Tables A-N. Selected fragments or chemical entities can then be positioned in a variety of orientations, or docked, within an individual binding site of a prenyltransferase as defined herein. Docking can be accomplished using software programs such as those available under the trade names QUANTA™ (Molecular Simulations Inc., San Diego, Calif.) and SYBYL™ (Tripos, Inc., St. Louis, Mo.), followed by energy minimization and molecular dynamics with standard molecular mechanics force fields, such as CHARM (Brooks et al., 1983) and AMBER 5 (Case et al., 1997; Pearlman et al., 1995).

Specialized computer programs can also assist in the process of selecting fragments or chemical entities. These include:

1. GRID™ program, version 17 (Goodford, 1985), which is available from Molecular Discovery Ltd., Oxford, United Kingdom;

2. MCSS™ program (Miranker & Karplus, 1991), which is available from Accelrys, San Diego, Calif., United States of America;

3. AUTODOCK™ 3.0 program (Goodsell & Olsen, 1990), which is available from the Scripps Research Institute, La Jolla, Calif., United States of America;

4. DOCK™ 4.0 program (Kuntz et al., 1992), which is available from the University of California, San Francisco, Calif., United States of America;

5. FLEX-X™ program (see Rarey et al., 1996), which is available from Tripos, Inc., St. Louis, Mo., United States of America;

6. MVP program (Lambert, 1997);

7. LUDI™ program (Bohm, 1992), which is available from Accelrys, San Diego, Calif., United States of America.

8. GOLD program (Jones et al., 1995; Jones et al., 1997; Jones et al., 1999), which is available from CCDC of Cambridge, United Kingdom.

9. CATALYST® program (Hahn, 1997), which is available from Accelrys, San Diego, Calif., United States of America.

Once suitable chemical entities or fragments have been selected, they can be assembled into a single compound or modulator. Assembly can proceed by visual inspection of the relationship of the fragments to each other on the three-dimensional image displayed on a computer screen in relation to the structure coordinates of a prenyltransferase (such as GGTase-I, as described herein). Manual model building using software such as QUANTA™ or SYBYL™ typically follows.

Useful programs to aid one of ordinary skill in the art in connecting the individual chemical entities or fragments include:

1. CAVEAT™ program (Bartlett et al., 1989), which is available from the University of California, Berkeley, Calif., United States of America;

2. 3D database systems, such as MACCS-3D™ system program, which is available from MDL Information Systems, San Leandro, Calif., United States of America. This area is reviewed in Martin, 1992; and 3. HOOK™ program (Eisen et al., 1994), which is available from Accelrys Inc., San Diego, Calif., United States of America.

Instead of proceeding to build a prenyltransferase modulator (e.g., a GGTase-I modulator) in a step-wise fashion one fragment or chemical entity at a time as described above, modulatory or other binding compounds can be designed as a whole or de novo using the structural coordinates of a crystalline GGTase-I polypeptide of the presently disclosed subject matter and either an empty binding site or optionally including some portion(s) of a known modulator(s). Applicable methods can employ the following software programs:

1. LUDI™ program (Bohm, 1992), which is available from Accelrys Inc., San Diego, Calif., United States of America;

2. LEGEND™ program (Nishibata & Itai, 1991); and

3. LEAPFROG™, which is available from Tripos Associates, St. Louis, Mo., United States of America.

Other molecular modeling techniques can also be employed in accordance with the presently disclosed subject matter. See e.g., Cohen et al., 1990. See also, Navia & Murcko, 1992; U.S. Pat. No. 6,008,033 to Abdel-Meguid et al., incorporated herein by reference.

Once a compound has been designed or selected by the above methods, the efficiency with which that compound can bind to a prenyltransferase can be tested and optimized by computational evaluation. By way of particular example, a compound that has been designed or selected to function as a GGTase-I modulator can also traverse a volume not overlapping that occupied by the binding site when it is bound to its native ligand. Additionally, an effective prenyltransferase modulator can demonstrate a relatively small difference in energy between its bound and free states (i.e., a small deformation energy of binding). Thus, the most efficient prenyltransferase modulators can be designed with a deformation energy of binding of in some embodiments not greater than about 10 kcal/mole, and in some embodiments not greater than 7 kcal/mole. It is possible for prenyltransferase modulators to interact with the polypeptide in more than one conformation that is similar in overall binding energy. In those cases, the deformation energy of binding is taken to be the difference between the energy of the free compound and the average energy of the conformations observed when the modulator binds to the polypeptide.

A compound designed or selected as binding to a prenyltransferase polypeptide (e.g., a GGTase-I polypeptide) can be further computationally optimized so that in its bound state it would lack repulsive electrostatic interaction with the target polypeptide. Such non-complementary (e.g., electrostatic) interactions include repulsive charge-charge, dipole-dipole and charge-dipole interactions. Specifically, the sum of all electrostatic interactions between the modulator and the polypeptide when the modulator is bound to a prenyltransferase can make a neutral or favorable contribution to the enthalpy of binding.

Specific computer software is available in the art to evaluate compound deformation energy and electrostatic interaction. Examples of programs designed for such uses include:

1. Gaussian 98™, which is available from Gaussian, Inc., Pittsburgh, Pa., United States of America;

2. AMBER™ program, version 6.0, which is available from the University of California at San Francisco, San Francisco, Calif., United States of America;

3. QUANTA™ program, which is available from Accelrys Inc., San Diego, Calif., United States of America;

4. CHARMM® program, which is available from Accelrys Inc., San Diego, Calif., United States of America; and 5. INSIGHT II® program, which is available from Accelrys Inc., San Diego, Calif., United States of America.

These programs can be implemented using a suitable computer system. Other hardware systems and software packages will be apparent to those skilled in the art after review of the disclosure of the presently disclosed subject matter presented herein.

Once a prenyltransferase modulating compound has been optimally selected or designed, as described above, substitutions can then be made in some of its atoms or side groups in order to improve or modify its binding properties. Generally, initial substitutions are conservative, i.e., the replacement group will have approximately the same size, shape, hydrophobicity and charge as the original group. Table 1 discloses some representative, but non-limiting properties that can be used as a guide when selecting a conservative mutation follows:

TABLE 1

Representative Conservative Amino Acid Substitutions

| Amino Acid Property | Amino Acid |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |
| Small: | glycine |
|  | alanine |
|  | serine |
|  | threonine |
|  | methionine |

It should, of course, be understood that components known in the art to alter conformation should be avoided, unless such an alteration is desired. Such substituted chemical compounds can then be analyzed for efficiency of fit to a prenyltransferase binding site using the same computer-based approaches described in detail above.

VIII.B. Method of Screening for Chemical and Biological Modulators of the Biological Activity of a Prenyltransferase A candidate substance identified according to a screening assay of presently disclosed subject matter has an ability to modulate the biological activity of a prenyltransferase. In some embodiments, such a candidate compound can have utility in the treatment of disorders and conditions associated with the biological activity of a prenyltransferase, including, but not limited to cancers, multiple sclerosis, smooth muscle hyperplasia, and parasitic infections. In a cell-free system, a method of screening a candidate compound for biological activity can optimally comprise the steps of establishing a control system comprising a prenyltransferase (e.g., a GGTase-I polypeptide) and a ligand which is capable of binding to the polypeptide; establishing a test system comprising a prenyltransferase, the ligand, and a candidate compound; and determining whether the candidate compound modulates the activity of the polypeptide by comparison of the test and control systems. A representative ligand comprises a small molecule, such as GGPP or a $Ca_1a_2X$ peptide, and in this embodiment the biological activity or property screened includes binding affinity.

In some embodiments of the presently disclosed subject matter, a form of a prenyltransferase (e.g., a GGTase-I polypeptide) or a catalytic or immunogenic fragment or oligopeptide thereof, can be employed when screening libraries of compounds in any of a variety of drug screening techniques. The fragment employed in such a screening can be affixed to a solid support. The formation of binding complexes, between a prenyltransferase and the agent being tested, will be detected.

Another technique for drug screening that can be used provides for high throughput screening of compounds having suitable binding affinity to the protein of interest as described in published PCT application WO 84/03564, herein incorporated by reference. In this method, as applied to a polypeptide of the presently disclosed subject matter, large numbers of different small test compounds are synthesized on a solid substrate, such as plastic pins or some other surface. The test compounds are reacted with the polypeptide, or fragments thereof. Bound polypeptide is then detected by methods well known to those of skill in the art. The polypeptide can also be placed directly onto plates for use in the aforementioned drug screening techniques.

In some embodiments, a method of screening for a modulator of a prenyltransferase (e.g., a GGTase-I or FTase polypeptide) comprises: providing a library of test samples; contacting a prenyltransferase with each test sample; detecting an interaction between a test sample and a prenyltransferase; identifying a test sample that interacts with a prenyltransferase; and isolating a test sample that interacts with a prenyltransferase.

In each of the foregoing embodiments, an interaction can be detected spectrophotometrically, radiologically, or immunologically. An interaction between a prenyltransferase and a test sample can also be quantified using methodology known to those of ordinary skill in the art. In some embodiments, the prenyltransferase is in crystalline form.

In accordance with the presently disclosed subject matter there is also provided a rapid and high throughput screening method that relies on the methods described above. This screening method comprises separately contacting each of a plurality of substantially identical samples with a prenyltransferase and detecting a resulting binding complex. In such a screening method, the plurality of samples comprises in some embodiments more than about $10^4$ samples, and in some embodiments more than about $5 \times 10^4$ samples.

VIII.C. Method of Identifying Compounds Which Inhibit Ligand Binding

Using the crystal structures and ligand orientations, disclosed for the first time in the presently disclosed subject matter, it is possible to design test compounds that inhibit binding of ligands normally bound by a prenyltransferase.

In one aspect of the presently disclosed subject matter, an assay method for identifying a compound that inhibits binding of a ligand to a prenyltransferase is disclosed. A known ligand of a prenyltransferase can be used in the assay method as the ligand against which the inhibition by a test compound is gauged. GGPP and/or a $Ca_1a_2X$ peptide can be employed as a ligand in the assay method. The method comprises (a) incubating a prenyltransferase with a ligand in the presence of a test inhibitor compound; (b) determining an amount of ligand that is bound to the prenyltransferase, wherein decreased binding of ligand to the prenyltransferase in the presence of the test inhibitor compound relative to binding in the absence of the test inhibitor compound is indicative of inhibition; and (c) identifying the test compound as an inhibitor of ligand binding if decreased ligand binding is observed.

In another aspect of the presently disclosed subject matter, the disclosed assay method can be employed in the structural refinement of candidate prenyltransferase inhibitors. For example, multiple rounds of optimization can be followed by gradual structural changes in a strategy of inhibitor design. A strategy such as this is made possible by the disclosure of the coordinates of the GGTase-I polypeptide and the disclosure of the orientation and position of GGTase-I ligands, namely GGPP, a $Ca_1a_2X$ peptide, and a prenylated product.

VIII.D. Design of Prenyltransferase Isoform and Ortholog Modulators

The GGTase-I crystal structures of the presently disclosed subject matter can be used to generate modulators of other prenyltransferase isoforms or orthologs. Analysis of the disclosed crystal structure can provide a guide for designing modulators of prenyltransferase isoforms or orthologs. Purely for purposes of explanation, the development of a human prenyltransferase modulator will be considered herein below. It will be apparent to those of skill in the art, and explicitly noted here, that the following discussion will be applicable mutatis mutandis to prenyltransferase isoforms and other prenyltransferase orthologs.

Absent the crystal structure of the presently disclosed subject matter, researchers would be required to design human prenyltransferase modulators de novo. The presently disclosed subject matter, however, addresses this problem by providing insights into a ligand binding pocket (e.g., active site) of rat GGTase-I, which can be extended, due to significant structural similarity with other prenyltransferase isoforms and orthologs, to a binding pocket (e.g., active site) of, for example, human prenyltransferase (e.g., GGTase-I or FTase). An evaluation of a ligand binding pocket (e.g., active site) of rat GGTase-I indicates that a potential human prenyltransferase modulator would meet a broad set of general criteria. Broadly, it can be stated that, based on the crystal structure of GGTase-I, a potent human prenyltransferase ligand would require several general features including: (a) a hydrophobic binding pocket (e.g., an active site); and (b) the ability to adopt a conformation that is complementary to the shape of the binding pocket.

Using the discerned structural similarities and differences between prenyltransferase isoforms and orthologs, as represented and predicted based on the crystal structure of the presently disclosed subject matter and homology models, a human prenyltransferase modulator can be designed. For example, based on an evaluation of a homology model of a human prenyltransferase, which is derived from the GGTase-I crystal structure, it is expected that a potent ligand would need similar characteristics as listed above for a compound recognized by a prenyltransferase. Additional modifications can be included, based on the disclosed structure, which are predicted to further define a modulator specific for a human prenyltransferase over other orthologs. Thus, the disclosed crystal structure of GGTase-I can be useful when designing modulators of a human prenyltransferase and other prenyltransferase orthologs and isoforms.

VIII.E. Method of Forming a Homology Model

As used herein, the term "modeling" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry and other structure-based constraint models.

Model building can be accomplished by either the crystallographer using a computer graphics program such as TURBO or O (Jones et al., 1991) or, under suitable circumstances, by using a fully automated model building program, such as wARP (Perrakis et al., 1999) or MAID (Levitt, 2001). This structure can be used to calculate model-derived diffraction amplitudes and phases. The model-derived and experimental diffraction amplitudes can be compared and the agreement between them can be described by a parameter referred to as R-factor. A high degree of correlation in the amplitudes corresponds to a low R-factor value, with 0.0 representing exact agreement and 0.59 representing a completely random structure. Because the R-factor can be lowered by introducing more free parameters into the model, an unbiased, cross-correlated version of the R-factor known as the R-free gives a more objective measure of model quality. For the calculation of this parameter a subset of reflections (generally around 10%) are set aside at the beginning of the refinement and not used as part of the refinement target. These reflections are then compared to those predicted by the model (Kleywegt & Brünger, 1996).

The model can be improved using computer programs that maximize the probability that the observed data was produced from the predicted model, while simultaneously optimizing the model geometry. For example, the CNX program can be used for model refinement, as can the XPLOR program (BrUnger, 1992; Murshudov et al., 1997). In order to maximize the convergence radius of refinement, simulated annealing refinement using torsion angle dynamics can be employed in order to reduce the degrees of freedom of motion of the model (Adams et al., 1997). Where experimental phase information is available (e.g. where MAD data was collected) Hendrickson-Lattman phase probability targets can be employed. Isotropic or anisotropic domain, group or individual temperature factor refinement, can be used to model variance of the atomic position from its mean. Well defined peaks of electron density not attributable to protein atoms are generally modeled as water molecules. Water molecules can be found by manual inspection of electron density maps, or with automatic water picking routines. Additional small molecules, including ions, cofactors, buffer molecules, or substrates can be included in the model if sufficiently unambiguous electron density is observed in a map.

In general, the R-free is rarely as low as 0.15 and can be as high as 0.35 or greater for a reasonably well-determined protein structure. The residual difference is a consequence of approximations in the model (inadequate modeling of residual structure in the solvent, modeling atoms as isotropic Gaussian spheres, assuming all molecules are identical rather than having a set of discrete conformers, etc.) and errors in the data (Lattman, 1996). In refined structures at high resolution, there are usually no major errors in the orientation of individual residues, and the estimated errors in atomic positions are usually around 0.1-0.2 up to 0.3 Å.

The three dimensional structure of a new crystal can be modeled using molecular replacement. The term "molecular replacement" refers to a method that involves generating a preliminary model of a molecule or complex whose structure coordinates are unknown, by orienting and positioning a molecule whose structure coordinates are known within the unit cell of the unknown crystal, so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. Lattman, 1985; Rossmann, 1972.

Commonly used computer software packages for molecular replacement are CNX, X-PLOR (Brünger, 1992), AMoRE (Navaza, 1994), the CCP4 package, the MERLOT package (Fitzgerald, 1988), and XTALVIEW (McRee et al., 1992). The quality of the model can be analyzed using a program such as PROCHECK or 3D-Profiler (Laskowski et al., 1993; Luthy et al., 1992; and Bowie et al., 1991).

Homology modeling (also known as comparative modeling or knowledge-based modeling) methods can also be used to develop a three dimensional model from a polypeptide sequence based on the structures of known proteins. The method utilizes a computer model of a known protein, a computer representation of the amino acid sequence of the polypeptide with an unknown structure, and standard computer representations of the structures of amino acids. This method is well known to those skilled in the art (Greer, 1985; Bundell et al., 1988; Knighton et al., 1992). Computer programs that can be used in homology modeling are QUANTA, the INSIGHT II® package, and the MODELLER homology module in the Discovery Studio Modeling 1.1 modeling package, the latter two distributed by Accelrys Inc. (San Diego, Calif., United States of America).

Once a homology model has been generated it is analyzed to determine its correctness. A computer program available to assist in this analysis is the Protein Health module in QUANTA that provides a variety of tests. Other programs that provide structure analysis along with output include PROCHECK and 3D-Profiler (Luthy et al., 1992; and Bowie et al., 1991). Once any irregularities have been resolved, the entire structure can be further refined.

Other molecular modeling techniques can also be employed in accordance with the presently disclosed subject matter. See e.g., Cohen et al., 1990. See also Navia & Murcko, 1992.

Under suitable circumstances, the entire process of solving a crystal structure can be accomplished in an automated fashion by a system such as ELVES (Holton & Alber T, 2004) with little or no user intervention.

Homology models can be valuable in the design of modulators. For example, a homology model of one prenyltransferase can be of assistance in the design of modulators for other prenyltransferases. Thus, in one aspect of the presently disclosed subject matter, a method of forming a homology model of a prenyltransferase is disclosed. In some embodiments, the method comprises: providing a template amino acid sequence comprising GGTase-I wherein the GGTase-I is in complex with a ligand selected from the group consisting of GGPP, a GGPP analog, a $Ca_1a_2X$ peptide, a prenyl peptide product, and combinations thereof. Such sequences (e.g., sequences and structures of Complexes 1-4) form aspects of the presently disclosed subject matter.

Next, a target prenyltransferase amino acid sequence is provided. A target prenyltransferase can be, for example, RabGGTase or FTase. The target sequence and the template sequence are then aligned to form a homology model. A homology model so generated can be employed in modulator design of the target prenyltransferase.

As noted, in some embodiments, the template amino acid sequence can comprise one of (a) atomic coordinates represented by the atomic coordinates of Tables A-N and (b) a subset of the coordinates of Tables A-N. In this and other embodiments, the template amino acid sequence can comprise spatial coordinates characterizing a GGTase-I, and wherein the spatial coordinates further characterize atoms in one or more residues selected from the group consisting of His 201α, Glu 169β, Arg 173β, Gln 167α, Phe 174β, His 121β, Asp 269β, Cys 271β, His 321β, Leu 320β, Phe 52β, Phe 53β, Thr 49β, Met 124β, Tyr 166α, Phe 324β, and Ala 123β that have shifted from their positions in a structure comprising a GGTase-I and a ligand, characterized by the atomic structural coordinates of one of Tables A-N, by one of a heavy-atom RMS deviation of at least about 0.50 angstroms and by a backbone heavy-atom RMS deviation of at least about 0.35 angstroms.

VIII.F. Method of Modeling a Target Prenyltransferase Structure

The structures of the presently disclosed subject matter can also be employed to model a three-dimensional structure of a target prenyltransferase in complex with a ligand from a template comprising the X-ray structure of a prenyltransferase in complex with a ligand. In some embodiments, the method comprises selecting an X-ray structure of a target prenyltransferase as a starting model for the target prenyltransferase. For example, a GGTase-I structure disclosed in the presently disclosed subject matter and comprising some or all of the coordinates of Tables A-N can be employed as a starting model of a prenyltransferase.

The starting model for the target prenyltransferase can then be manipulated as a rigid body to superimpose its backbone atoms onto corresponding backbone atoms of a three-dimensional template structure comprising a GGTase-I in complex with a ligand to form a manipulated model. A manipulated model can comprise, then, a starting model of a target prenyltransferase, the backbone atoms of which have been superimposed onto the backbone atoms of a template structure. A starting model can comprise a GGTase-I structure disclosed in the presently disclosed subject matter.

Next, a copy of the ligand from the template structure is made to form a model of a ligand bound to a template prenyltransferase. Generally, this step of the method comprises employing an observed conformation of a ligand (e.g., GGPP or a $Ca_1a_2X$ peptide) from a starting model in a subsequent model. Before the disclosure of the presently disclosed subject matter, no structure of a ligand bound form of prenyltransferase was available, and thus, this step of the method was not possible.

The model of the ligand is then merged into the manipulated model to form a modified model. One or more amino acids are removed from the modified model. Finally, side-chain conformations are optimized.

The above-presented method can be performed using a computer system and/or software package that is optimized for this type of operation. Representative hardware and software packages are disclosed hereinabove, and include the INSIGHT II® package running on a Silicon Graphics workstation (available from Silicon Graphics of Mountain View, Calif., USA).

IX. Design, Preparation, and Structural Analysis of Prenyltransferases, Prenyltransferase Mutants, and Structural Equivalents The presently disclosed subject matter provides for the generation of prenyltransferases and prenyltransferase mutants (e.g., GGTase-I or FTase and mutants thereof), and the ability to solve the crystal structures of those that crystallize. More particularly, through the provision of the three-dimensional structure of a GGTase-I, desirable sites for mutation can be identified, based on analysis of the three-dimensional GGTase-I structure provided herein.

The structure coordinates of a GGTase-I provided in accordance with the presently disclosed subject matter also facilitate the identification of related proteins or enzymes analogous to GGTase-I in function, structure or both, (for example, a human GGTase-I or FTase), which can lead to novel therapeutic modes for treating or preventing a range of disease states, such as cancer, parasitic infections, multiple sclerosis and smooth muscle hyperplasia.

IX.A. Sterically Similar Compounds

A further aspect of the presently disclosed subject matter is that sterically similar compounds can be formulated to mimic the key portions of a prenyltransferase structure. Such compounds are functional equivalents. The generation of a structural functional equivalent can be achieved by the techniques of modeling and chemical design known to those of skill in the art and described herein. Modeling and chemical design of prenyltransferase structural equivalents can be based on the structure coordinates of a crystalline GGTase-I polypeptide of the presently disclosed subject matter. It will be understood that all such sterically similar constructs fall within the scope of the presently disclosed subject matter.

IX.B. Prenyltransferase Polypeptides

The generation of chimeric prenyltransferase polypeptides (e.g., GGTase-I and FTase) is also an aspect of the presently disclosed subject matter. Such a chimeric polypeptide can comprise a prenyltransferase polypeptide or a portion of a prenyltransferase that is fused to a candidate polypeptide or a suitable region of the candidate polypeptide, for example a prenyltransferase expressed in human or other species. Throughout the present disclosure it is intended that the term "mutant" encompass not only mutants of a prenyltransferase but chimeric proteins generated using a prenyltransferase as well. It is thus intended that the following discussion of mutant prenyltransferases apply mutatis mutandis to chimeric prenyltransferases and to structural equivalents thereof.

In accordance with the presently disclosed subject matter, a mutation can be directed to a particular site or combination of sites of a wild-type prenyltransferase. For example, an accessory binding site or a binding pocket (e.g., an active site) can be chosen for mutagenesis. Similarly, a residue having a location on, at or near the surface of the polypeptide can be replaced, resulting in an altered surface charge of one or more charge units, as compared to the wild-type prenyltransferase. Alternatively, an amino acid residue in a prenyltransferase can be chosen for replacement based on its hydrophilic or hydrophobic characteristics.

Such mutants can be characterized by any one of several different properties as compared with the wild-type prenyltransferase. For example, such mutants can have an altered surface charge of one or more charge units, or can have an increase in overall stability. Other mutants can have altered substrate specificity in comparison with, or a higher specific activity than, a wild-type prenyltransferase.

Prenyltransferase mutants of the presently disclosed subject matter can be generated in a number of ways. For example, the wild-type sequence of a prenyltransferase can be mutated at those sites identified using the presently disclosed subject matter as desirable for mutation, by oligonucleotide-directed mutagenesis or other conventional methods, such as deletion. Alternatively, mutants of a prenyltransferase can be generated by the site-specific replacement of a particular amino acid with an unnaturally occurring amino acid. In addition, prenyltransferase mutants can be generated through replacement of an amino acid residue, for example, a particular cysteine or methionine residue, with selenocysteine or selenomethionine. This can be achieved by growing a host organism capable of expressing either the wild type or mutant polypeptide on a growth medium depleted of either natural cysteine or methionine (or both) but enriched in selenocysteine or selenomethionine (or both).

Mutations can be introduced into a DNA sequence coding for a prenyltransferase using synthetic oligonucleotides. These oligonucleotides contain nucleotide sequences flanking the desired mutation sites. Mutations can be generated in the full-length DNA sequence of a prenyltransferase or in any sequence coding for polypeptide fragments of a prenyltransferase.

According to the presently disclosed subject matter, a mutated prenyltransferase DNA sequence produced by the methods described above, or any alternative methods known in the art, can be expressed using an expression vector. An expression vector, as is well known to those of skill in the art, typically includes elements that permit autonomous replication in a host cell independent of the host genome, and one or more phenotypic markers for selection purposes. Either prior to or after insertion of the DNA sequences surrounding the desired prenyltransferase mutant coding sequence, an expression vector also will include control sequences encoding a promoter, operator, ribosome binding site, translation initiation signal, and, optionally, a repressor gene or various activator genes and a signal for termination. In some embodiments, where secretion of the produced mutant is desired, nucleotides encoding a "signal sequence" can be inserted prior to a prenyltransferase mutant coding sequence. For expression under the direction of the control sequences, a desired DNA sequence must be operatively linked to the control sequences; that is, the sequence must have an appropriate start signal in front of the DNA sequence encoding the prenyltransferase mutant, and the correct reading frame to permit expression of that sequence under the control of the control sequences and production of the desired product encoded by that prenyltransferase sequence must be maintained.

Any of a wide variety of well-known available expression vectors can be useful to express prenyltransferase coding sequences of the presently disclosed subject matter. These expression vectors can be used, for example, in the techniques disclosed in Examples 1-2. Representative vectors comprise segments of chromosomal, non-chromosomal and synthetic DNA sequences, such as various known derivatives of SV40, known bacterial plasmids, e.g., plasmids from *E. coli* including colE1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single stranded DNA phages, yeast plasmids and vectors derived from combinations of plasmids and phage DNAs, such as plasmids which have been modified to employ phage DNA or other expression control sequences. In some embodiments of presently disclosed subject matter, an Sf9 insect cell expression system is employed.

In addition, any of a wide variety of expression control sequences (sequences that control the expression of a DNA sequence when operatively linked to it) can be used in these vectors to express the mutated DNA sequences according to presently disclosed subject matter. Such useful expression control sequences, include, for example, the early and late promoters of SV40 for animal cells, the lac system, the trp system the TAC or TRC system, the major operator and promoter regions of phage λ, the control regions of fd coat protein, all for *E. coli*, the promoter for 3-phosphoglycerate kinase or other glycolytic enzymes, the promoters of acid phosphatase, e.g., Pho5, the promoters of the yeast α-mating factors for yeast, and other sequences known to control the expression of genes of prokaryotic or eukaryotic cells or their viruses, and various combinations thereof.

A wide variety of hosts are also useful for producing mutated prenyltransferases (e.g., GGTase-I and FTase enzymes) according to presently disclosed subject matter. These hosts include, for example, bacteria, such as *E. coli, Bacillus,* and *Streptomyces*; fungi, such as yeasts; animal cells, such as CHO and COS-1 cells; plant cells, insect cells, such as Sf9 cells (as noted herein); and transgenic host cells.

It should be understood that not all expression vectors and expression systems function in the same way to express mutated DNA sequences of presently disclosed subject matter, and/or to produce modified prenyltransferases or prenyltransferase mutants. Neither do all hosts function equally well with the same expression system. One of skill in the art can, however, make a selection among these vectors, expression control sequences and hosts without undue experimentation and without departing from the scope of presently disclosed subject matter. For example, an important consideration in selecting a vector will be the ability of the vector to replicate in a given host. The copy number of the vector, the ability to control that copy number, and the expression of any other proteins encoded by the vector, such as antibiotic markers, should also be considered.

In selecting an expression control sequence, a variety of factors should also be considered. These include, for example, the relative strength of the system, its controllability and its compatibility with the DNA sequence encoding a modified prenyltransferase of presently disclosed subject matter, with particular regard to the formation of potential secondary and tertiary structures.

Hosts can be selected by considering their compatibility with the chosen vector, the toxicity of a modified prenyltransferase to them, their ability to express mature products, their ability to fold proteins correctly, their fermentation requirements (if any), the ease of purification of a modified prenyltransferase and safety. Within these parameters, one of ordinary skill in the art can select various vector/expression control system/host combinations that will produce useful amounts of a mutant prenyltransferase. A mutant prenyltransferase produced in these systems can be purified by a variety of conventional steps and strategies, including those used to purify the wild-type prenyltransferase.

Once a prenyltransferase mutation(s) has been generated in the desired location, such as a ligand binding site, the mutants can be tested for any one of several properties of interest. For example, mutants can be screened for an altered charge at physiological pH. This can be determined by measuring the mutant prenyltransferase isoelectric point (pI) and comparing the observed value with that of the wild-type parent. Isoelectric point can be measured by gel-electrophoresis according to the method of Wellner, 1971. A mutant prenyltransferase containing a replacement amino acid located at the surface of the enzyme, as provided by the structural information of presently disclosed subject matter, can lead to an altered surface charge and an altered pI.

IX.C. Generation of a Prenyltransferase Mutant

In another aspect of the presently disclosed subject matter, a unique prenyltransferase can be generated. Such a mutant can facilitate purification and can facilitate the study of the ligand binding abilities of a prenyltransferase.

As used in the following discussion, the term "prenyltransferase mutant" refers to prenyltransferases having amino acid sequences that contain at least one mutation in the wild-type sequence, which can be a mutation at a selected point in the amino acid sequence of a prenyltransferase or a mutation introduced at a random point in the amino acid sequence of a prenyltransferase. The term also refers to prenyltransferases which are capable of exerting a biological effect in that they comprise all or a part of the amino acid sequence of a prenyltransferase mutant of the presently disclosed subject matter, or cross-react with antibodies raised against a prenyltransferase mutant, or retain all or some or an enhanced degree of the biological activity of the prenyltransferase mutant amino acid sequence or protein. Such biological activity can include ligand (e.g., GGPP or a $Ca_1a_2X$ peptide) binding, as well as association of a cofactor with a prenyltransferase.

The term "prenyltransferase mutant" also includes analogs of a prenyltransferase mutant. By "analog" is meant that a DNA or polypeptide sequence can contain alterations relative to the sequences disclosed herein, yet retain all or some or an enhanced degree of the biological activity of those sequences. Analogs can be derived from genomic nucleotide sequences or from other organisms, or can be created synthetically. Those of skill in the art will appreciate that other analogs, as yet undisclosed or undiscovered, can be used to design and/or construct prenyltransferase mutant analogs. There is no need for a prenyltransferase mutant to comprise all or substantially all of a full length amino acid sequence. Shorter or longer sequences are anticipated to be of use in the presently disclosed subject matter; shorter sequences are herein referred to as "segments". Thus, the term "prenyltransferase mutant" also includes fusion, chimeric or recombinant prenyltransferase mutants, and proteins comprising sequences of the presently disclosed subject matter. Methods of preparing such proteins are disclosed herein above and are known in the art.

Figure 9:
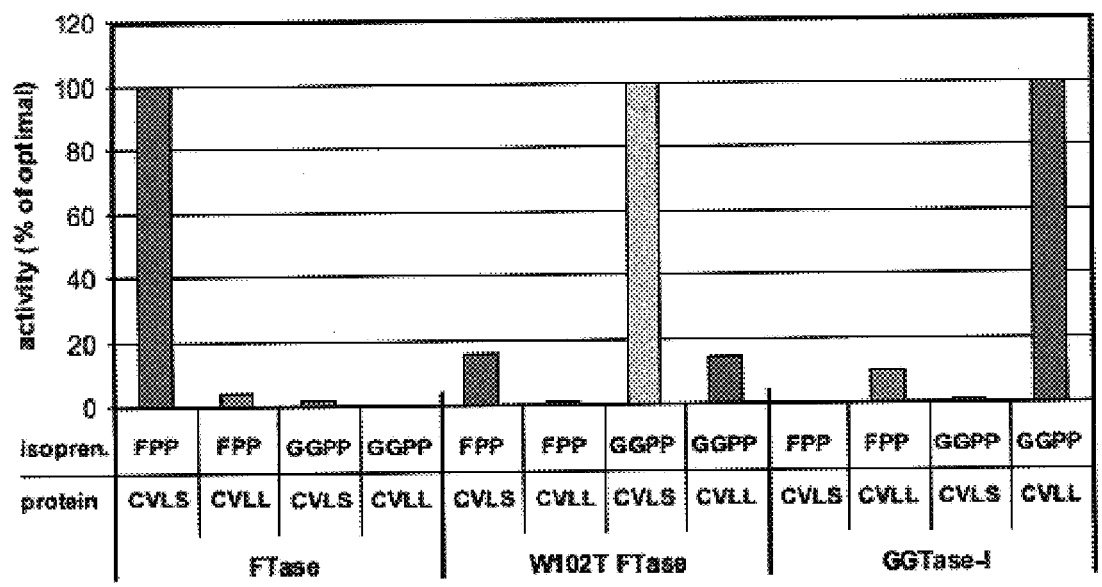
FIG. 9 is a bar graph depicting altered substrate specificity of a protein prenyltransferase. Prenylation reactions assayed the activity of human wild-type FTase, wild-type GGTase-I, and the W102T FTase mutant with four substrate combinations: FPP+Ras-CVLS (blue; SEQ ID NO: 3), FPP+Ras-CVLL (green; SEQ ID NO: 4), GGPP+Ras-CVLS (yellow; SEQ ID NO: 5) and GGPP+Ras-CVLL (red; SEQ ID NO: 4). The activities are shown as percentages of activity with optimal isoprenoid and protein substrates for each of the enzymes tested (FPP and Ras-CVLS (SEQ ID NO: 3), FTase; GGPP and Ras-CVLS (SEQ ID NO: 3), W102T FTase; GGPP and Ras-CVLL (SEQ ID NO: 4), GGTase-I). Turnover numbers under the optimal substrate concentrations were 1.0, 0.59, and 0.65/min for FTase, W102T FTase, and GGTase-I, respectively.

An example of the generation of a prenyltransferase mutant is provided in Example 3. As disclosed therein, a mutant was created to directly test the importance of the Thr/Trp identity in the determination of isoprenoid substrate specificity. Residue W102β of human FTase (corresponding to T49β in GGTase-I) was mutated to a threonine. The mutant was cloned, overexpressed in E. coli, purified (Long et al., 2001), and its substrate specificity characterized by enzymatic assays (Zhang et al., 1994b). As predicted, the resulting mutant FTase acquired the substrate specificity of a GGTase, creating an FTase enzyme greatly preferring GGPP over FPP as its isoprenoid substrate without significantly altering $Ca_1a_2X$ sequence specificity (see FIG. 9).

Steric hindrance plays a dominant role in FTase in selecting the 15-C farnesyl in preference to the 20-C geranylgeranyl substrate. A different mechanism must operate in GGTase to prevent the shorter farnesyl group from functioning as a substrate because there is no steric block to prevent GGTase-I from binding FPP in a productive conformation. Indeed, FPP is a weak substrate for GGTase-I (Yokoyama et al., 1995). As described below, the product release step in the GGTase-I reaction cycle is the dominant mechanism by which GGTase-I selects for GGPP over FPP.

IX.D. Sequence Similarity and Identity

As used herein, the term "substantially similar" refers to that a particular sequence varies from a given nucleic acid sequence, or a given amino acid sequences by one or more deletions, substitutions, or additions, the net effect of which is to retain at least some of biological activity of the natural gene, gene product, or sequence. Such sequences include "mutant" or "polymorphic" sequences, or sequences in which the biological activity and/or the physical properties are altered to some degree but retains at least some or an enhanced degree of the original biological activity and/or physical properties. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

IX.D.1. Sequences that are Substantially Identical to a Prenyltransferase Mutant Sequence of the Presently Disclosed Subject Matter Nucleic acids that are substantially identical to a nucleic acid sequence of a prenyltransferase mutant of the presently disclosed subject matter, e.g., allelic variants, genetically altered versions of the gene, etc., bind to a prenyltransferase mutant sequence under stringent hybridization conditions. By using probes, particularly labeled probes of DNA sequences, one can isolate homologous or related genes. The source of homologous genes can be any species, e.g., primate species; rodents, such as rats and mice, canines, felines, bovines, equines, yeast, nematodes, etc.

Between mammalian species, e.g., human and mouse, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nucleotides (nt) long, more usually at least about 30 nt long, and can extend to the complete sequence that is being compared. Algorithms for sequence analysis are known in the art, such as BLAST, described in Altschul et al., 1990.

Percent identity or percent similarity of a DNA or peptide sequence can be determined, for example, by comparing sequence information using the GAP computer program, available from Accelrys Inc. (San Diego, Calif., United States of America) as part of the GCG® WISCONSIN PACKAGE®. The GAP program utilizes the alignment method of Needleman & Wunsch, 1970, as revised by Smith & Waterman, 1981. Briefly, the GAP program defines similarity as the number of aligned symbols (i.e., nucleotides or amino acids) that are similar, divided by the total number of symbols in the shorter of the two sequences. Exemplary parameters for the GAP program are the default parameters, which do not impose a penalty for end gaps. See e.g., Schwartz & Dayhoff, 1979, and Gribskov & Burgess, 1986.

The term "similarity" is contrasted with the term "identity". Similarity is defined as above; "identity", however, refers to a nucleic acid or amino acid sequence having the same amino acid at the same relative position in a given family member of a gene family. Homology and similarity are generally viewed as broader terms than the term identity. Biochemically similar amino acids, for example leucine/isoleucine or glutamate/aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

As used herein, DNA analog sequences are "substantially identical" to specific DNA sequences disclosed herein if: (a) the DNA analog sequence is capable of hybridization with given DNA sequences under stringent conditions and which encode a biologically active prenyltransferase gene product; or (b) the DNA sequences are degenerate as a result of alternative genetic code to the DNA analog sequences defined in (a). Substantially identical analog proteins and nucleic acids will have in some embodiments between about 70% and 80%, in some embodiments between about 81% to about 90%, and in some embodiments between about 91% and 99% sequence identity with the corresponding sequence of the native protein or nucleic acid. Sequences having lesser degrees of identity but comparable biological activity are considered to be equivalents.

As used herein, "stringent conditions" refers to conditions of high stringency, for example 6×SSC, 0.2% polyvinylpyrrolidone, 0.2% Ficoll, 0.2% bovine serum albumin, 0.1% sodium dodecyl sulfate, 100 µg/ml salmon sperm DNA, and 15% formamide at 60° C. For the purposes of specifying additional conditions of high stringency, exemplary conditions are salt concentration of about 200 mM and temperature of about 45° C. One example of such stringent conditions is hybridization in 4×SSC at 65° C., followed by a washing in 0.1×SSC at 65° C. for one hour. Another exemplary stringent hybridization scheme uses 50% formamide and 4×SSC at 42° C.

In contrast, nucleic acids having sequence similarity are detected by hybridization under lower stringency conditions. Thus, sequence identity can be determined by hybridization under lower stringency conditions, for example, at 50° C. or higher and 0.1×SSC (15 mM NaCl/1.5 mM sodium citrate) and the sequences will remain bound when subjected to washing at 55° C. in 1×SSC.

IX.D.2. Complementarity and Hybridization to a Prenyltransferase Mutant Sequence As used herein, the term "complementary sequences" refers to nucleic acid sequences that are base-paired according to the standard Watson-Crick complementarity rules. The presently disclosed subject matter also encompasses the use of nucleotide segments that are complementary to the sequences of the presently disclosed subject matter.

Hybridization can also be used for assessing complementary sequences and/or isolating complementary nucleotide sequences. As discussed herein, nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions include temperatures in some embodiments in excess of about 30° C., in some embodiments in excess of about 37° C., and in some embodiments in excess of about 45° C. Stringent salt conditions are in some embodiments less than about 1,000 mM, in some embodiments less than about 500 mM, and in some embodiments less than about 200 mM. However, the combination of parameters is much more important than the measure of any single parameter. See e.g., Wetmur & Davidson, 1968. Determining appropriate hybridization conditions to identify and/or isolate sequences containing high levels of homology is well known in the art. See e.g., Sambrook & Russell, 2001.

IX.D.3. Functional Equivalents of a Prenyltransferase Mutant Nucleic Acid Sequence As used herein, the term "functionally equivalent codon" is used to refer to codons that encode the same amino acid, such as the ACG and AGU codons for serine. Thus, when referring to given sequence examples applicants contemplate substitution of functionally equivalent codons into the sequence examples. Thus, applicants are in possession of amino acid and nucleic acids sequences which include such substitutions but which are not set forth herein in their entirety for convenience.

It will also be understood by those of skill in the art that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains biological protein activity where polypeptide expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

IX.D.4. Biological Equivalents

The presently disclosed subject matter envisions and includes biological equivalents of a prenyltransferase mutant of the presently disclosed subject matter. The term "biological equivalent" refers to proteins having amino acid sequences which are substantially identical to the amino acid sequence of a prenyltransferase mutant of the presently disclosed subject matter and which are capable of exerting a biological effect in that they are capable of binding GGPP or a $Ca_1a_2X$ peptide or cross-reacting with anti-prenyltransferase mutant antibodies raised against a mutant prenyltransferase of the presently disclosed subject matter.

For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the protein, but this need not be the case, and the biological activity of the presently disclosed subject matter is not limited to a particular mechanism of action. It is thus in accordance with the presently disclosed subject matter that various changes can be made in the amino acid sequence of a prenyltransferase mutant polypeptide of the presently disclosed subject matter or its underlying nucleic acid sequence without appreciable loss of biological utility or activity.

Biologically equivalent polypeptides, as used herein, are polypeptides in which certain, but not most or all, of the amino acids can be substituted. Thus, when referring to given sequence examples, applicants envision substitution of codons that encode biologically equivalent amino acids, as described herein, into the sequence examples. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged, e.g., substitution of Ile for Leu. Changes designed by man can be introduced through the application of site-directed mutagenesis techniques, e.g., to introduce improvements to the antigenicity of the protein or to test a prenyltransferase mutant polypeptide of the presently disclosed subject matter for its ability to modulate ligand-binding or other activity, at the molecular level.

Amino acid substitutions, such as those that might be employed in modifying a prenyltransferase mutant of the presently disclosed subject matter are generally, but not necessarily, based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. See also the Table of Conservative Amino Acid Substitutions presented herein. Those of ordinary skill in the art will appreciate other biologically functionally equivalent changes. It is implicit in the above discussion, however, that one of ordinary skill in the art can appreciate that a radical, rather than a conservative substitution is warranted in a given situation. Non-conservative substitutions in mutant prenyltransferases of the presently disclosed subject matter are also an aspect of the presently disclosed subject matter.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids can be substituted for other amino acids having a similar hydropathic index or score and still retain a similar biological activity. Changes based upon the hydropathic index can include the substitution of amino acids whose hydropathic indices are in some embodiments within ±2 of the original value, in some embodiments within ±1 of the original value, and in some embodiments within ±0.5 of the original value.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

Changes based upon similar hydrophilicity values can include the substitution of amino acids whose hydrophilicity values are in some embodiments within ±2 of the original value, in some embodiments within ±1 of the original value, and in some embodiments within ±0.5 of the original value.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that presently disclosed subject matter is not limited to particular amino acid and nucleic acid sequences. Recombinant vectors and isolated DNA segments can therefore variously include a mutant prenyltransferase-encoding region itself, include coding regions bearing selected alterations or modifications in the basic coding region, or include larger polypeptides which nevertheless comprise a mutant prenyltransferase-encoding regions or can encode biologically functional equivalent proteins or polypeptides which have variant amino acid sequences. Biological activity of a mutant prenyltransferase can be determined, for example, by ligand binding assays known to those of skill in the art.

The nucleic acid segments of the presently disclosed subject matter, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length being limited in some embodiments by the ease of preparation and use in the intended recombinant DNA protocol. For example, nucleic acid fragments can be prepared which include a short stretch complementary to a given nucleic acid sequence, such as about 10 nucleotides, and which are up to 10,000 or 5,000 base pairs in length. DNA segments with total lengths of about 4,000, 3,000, 2,000, 1,000, 500, 200, 100, and about 50 base pairs in length are also useful.

IX.D.5. Structural Equivalents

Various computational analyses can be used to determine whether a molecule or the active site portion thereof is structurally equivalent with respect to its three-dimensional structure, to all or part of a structure of a polypeptide of the presently disclosed subject matter or a portion thereof.

For the purpose of the presently disclosed subject matter, any molecule or complex or portion thereof, that has a root mean square deviation of conserved residue backbone atoms (N, C$\alpha$, C, O) of less than about 1.75 Å, when superimposed on the relevant backbone atoms described by the reference structure coordinates of a polypeptide of the presently disclosed subject matter, is considered "structurally equivalent" to the reference molecule. That is to say, the crystal structures of those portions of the two molecules are substantially identical, within acceptable error. Alternatively, the root mean square deviation can be is less than about 1.50, 1.40, 1.25, 1.0, 0.75, 0.5 or 0.35 Å.

The term "root mean square deviation" is understood in the art and refers to the square root of the arithmetic mean of the squares of the deviations. It is a way to express the deviation or variation from a trend or object.

In another aspect, the presently disclosed subject matter provides a scalable three-dimensional configuration of points, at least a portion of said points, and in some embodiments all of said points, derived from structural coordinates of at least a portion of a polypeptide of the presently disclosed subject matter and having a root mean square deviation from the structure coordinates of the polypeptide of the presently disclosed subject matter of less than 1.50, 1.40, 1.25, 1.0, 0.75, 0.5 or 0.35 Å. In certain embodiments, the portion of a polypeptide of the presently disclosed subject matter is 25%, 33%, 50%, 66%, 75%, 85%, 90%, 95%, 97%, 99%, or more of the amino acid residues contained in the polypeptide.

In another aspect, a molecule or complex including a druggable region of a polypeptide of the presently disclosed subject matter is provided, the druggable region being defined by a set of points having a root mean square deviation of less than about 1.75 Å from the structural coordinates for points representing (a) the backbone atoms of the amino acids contained in a druggable region of a polypeptide of the presently disclosed subject matter, (b) the side chain atoms (and optionally the C$\alpha$ atoms) of the amino acids contained in such druggable region, or (c) all the atoms of the amino acids contained in such druggable region. In certain embodiments, only a portion of the amino acids of a druggable region can be included in the set of points, such as 25%, 33%, 50%, 66%, 75%, 85%, 90%, 95%, 97%, or 99% or more of the amino acid residues contained in the druggable region. In certain embodiments, the root mean square deviation can be less than 1.50, 1.40, 1.25, 1.0, 0.75, 0.5, or 0.35 Å. In still other embodiments, instead of a druggable region, a stable domain, fragment or structural motif is used in place of a druggable region.

IX.E. Uses of Prenyltransferase Mutants

The prenyltransferase mutants disclosed herein have a variety of applications, including in the screening of components for prenyltransferase ligand binding using the cell-free reporter gene assay methods disclosed herein above, and using whole animal models. The prenyltransferase mutants can also be used in cell-free, cell-based and whole animal assay methods for bioavailability of compounds and for toxicology analysis. Additionally, prenyltransferase mutants can be employed in crystallizations, screening for changes in ligand activation, screening for species-specific changes in ligand activation and screening for changes in oligomerization state both with and without ligand.

X. The Role of the Three-Dimensional Structure of the GGTase-I in Solving Additional Prenyltransferase Crystals Because polypeptides can crystallize in more than one crystal form, the structural coordinates of a GGTase-I, or portions thereof, as provided by the presently disclosed subject matter, are particularly useful in solving the structure of other crystal forms of GGTase-I and the crystalline forms of other prenyltransferases. The coordinates provided in the presently disclosed subject matter can also be used to solve the structure of prenyltransferase mutants (such as those described above), prenyltransferase co-complexes, or of the crystalline form of any other protein with significant amino acid sequence homology to any functional domain of GGTase-I.

One method that can be employed for the purpose of solving additional prenyltransferase crystal structures is molecular replacement. See generally, Rossmann, 1972. In the molecular replacement method, the unknown crystal structure, whether it is another crystal form of a prenyltransferase, (e.g., a GGTase-I or a GGTase-I mutant), or a prenyltransferase complexed with another compound (a "co-complex"), or the crystal of some other protein with significant amino acid sequence homology to any functional region of a GGTase-I, can be determined using the GGTase-I structure coordinates provided in Tables A-N. This method provides an accurate structural form for the unknown crystal more quickly and efficiently than attempting to determine such information ab initio.

In addition, in accordance with presently disclosed subject matter, prenyltransferase mutants (e.g., GGTase-I mutants) can be crystallized in complex with known modulators. The crystal structures of a series of such complexes can then be solved by molecular replacement and compared with that of wild-type prenyltransferase (e.g., GGTase-I). Potential sites for modification within the various binding sites of the enzyme can thus be identified. This information provides an additional tool for determining the most efficient binding interactions, for example, increased hydrophobic interactions, between the prenyltransferase and a chemical entity or compound.

All of the complexes referred to in the present disclosure can be studied using X-ray diffraction techniques (see e.g., Blundell & Johnson, 1985) and can be refined using computer software, such as the X-PLOR™ program (Brünger, 1992; X-PLOR is available from Molecular Simulations, Inc., San Diego, Calif.). This information can thus be used to optimize known classes of prenyltransferase modulators, and equally importantly, to design and synthesize novel classes of prenyltransferase modulators.

XI. Machine Displays and Machine Readable Storage Media

The presently disclosed subject matter provides a machine-readable storage medium including a data storage material encoded with machine readable data which, when using a machine programmed with instructions for using said data, displays a graphical three-dimensional representation of any of the molecules or complexes, or portions thereof, of presently disclosed subject matter. In another embodiment, the graphical three-dimensional representation of such molecule, complex, or portion thereof includes the root mean square deviation of certain atoms of such molecule by a specified amount, such as the backbone atoms by less than 0.8 Å. In another embodiment, a structural equivalent of such molecule, complex, or portion thereof, may be displayed. In another embodiment, the portion may include a druggable region of the polypeptide of the presently disclosed subject matter.

According to one embodiment, the presently disclosed subject matter provides a computer for determining at least a portion of the structure coordinates corresponding to x-ray diffraction data obtained from a molecule or complex, wherein said computer includes: (a) a machine-readable data storage medium comprising a data storage material encoded with machine-readable data, wherein said data comprises at least a portion of the structural coordinates of a polypeptide of the presently disclosed subject matter; (b) a machine-readable data storage medium comprising a data storage material encoded with machine-readable data, wherein said data comprises x-ray diffraction data from said molecule or complex; (c) a working memory for storing instructions for processing said machine-readable data of (a) and (b); (d) a central-processing unit coupled to said working memory and to said machine-readable data storage medium of (a) and (b) for performing a Fourier transform of the machine readable data of (a) and for processing said machine readable data of (b) into structure coordinates; and (e) a display coupled to said central-processing unit for displaying said structure coordinates of said molecule or complex. In certain embodiments, the structural coordinates displayed are structurally equivalent to the structural coordinates of a polypeptide of the presently disclosed subject matter.

In an alternative embodiment, the machine-readable data storage medium includes a data storage material encoded with a first set of machine readable data which includes the Fourier transform of the structure coordinates of a polypeptide of the presently disclosed subject matter or a portion thereof, and which, when using a machine programmed with instructions for using said data, can be combined with a second set of machine readable data including the x-ray diffraction pattern of a molecule or complex to determine at least a portion of the structure coordinates corresponding to the second set of machine readable data.

For example, a system for reading a data storage medium may include a computer including a central processing unit (CPU), a working memory which can be, i.e., random access memory (RAM) or "core" memory, mass storage memory (such as one or more disk drives or CD-ROM drives), one or more display devices (i.e., cathode-ray tube ("CRT") displays, light emitting diode (LED) displays, liquid crystal displays (LCDs), electroluminescent displays, vacuum fluorescent displays, field emission displays (FEDs), plasma displays, projection panels, etc.), one or more user input devices (i.e., keyboards, microphones, mice, touch screens, etc.), one or more input lines, and one or more output lines, all of which are interconnected by a conventional bidirectional system bus. The system may be a stand-alone computer, or may be networked (i.e., through local area networks, wide area networks, intranets, extranets, or the internet) to other systems (i.e., computers, hosts, servers, etc.). The system may also include additional computer controlled devices such as consumer electronics and appliances.

Input hardware may be coupled to the computer by input lines and may be implemented in a variety of ways. Machine-readable data of presently disclosed subject matter may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of presently disclosed subject matter using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of presently disclosed subject matter. Such programs are discussed in reference to the computational methods of drug discovery as described herein. References to components of the hardware system are included as appropriate throughout the following description of the data storage medium.

Machine-readable storage devices useful in the presently disclosed subject matter include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (i.e., drives, controllers, power supplies, etc.) as well as any necessary media (i.e., disks, flash cards, etc.) to enable the storage of data.

In one embodiment, the presently disclosed subject matter contemplates a computer readable storage medium comprising structural data, wherein the data include the identity and three-dimensional coordinates of a polypeptide of the presently disclosed subject matter or portion thereof. In another aspect, the presently disclosed subject matter contemplates a database comprising the identity and three-dimensional coordinates of a polypeptide of the presently disclosed subject matter or a portion thereof. Alternatively, the presently disclosed subject matter contemplates a database comprising a portion or all of the atomic coordinates of a polypeptide of the presently disclosed subject matter or portion thereof.

XII. Conclusions

To aid further drug discovery efforts, the interactions involved in the binding profile of GGTase-I and other prenyltransferases have been identified. In one aspect, the presently disclosed subject matter discloses the atomic structures of the complexes of GGTase-I in complex with products and/or substrates. This structure demonstrates several unique structural features that, prior to the present disclosure, have not been disclosed or observed. In another aspect of the presently disclosed subject matter, residues of GGTase-I that are involved in ligand binding are identified. Some of these interactions are presented in the associated figures.

Although these insights have been gleaned from a structure of GGTase-I, due to the sequence homology between GGTase-I and other prenyltransferases, this structure is valuable as a tool to investigate and understand the modes of ligand binding in other prenyltransferases as well. Thus, the presently disclosed subject matter can be employed to generate modulators of GGTase-I and other prenyltransferases as well.

EXAMPLES

The following Examples have been included to illustrate representative modes of the presently disclosed subject matter. Certain aspects of the following Examples are described in terms of techniques and procedures found or contemplated by the present co-inventors to work well in the practice of the presently disclosed subject matter. These Examples are exemplified through the use of standard laboratory practices of the co-inventors. In light of the present disclosure and the general level of skill in the art, those of skill will appreciate that the following Examples are intended to be exemplary only and that numerous changes, modifications and alterations can be employed without departing from the spirit and scope of the presently disclosed subject matter.

Example 1

Expression, Purification, Crystallization, and Data Collection

Rat GGTase-I was expressed in Sf9 insect cells and purified as previously described (Zhang et al., 1994a) with two additions. The purified enzyme was incubated with GGPP (Sigma Chemical Co., St. Louis, Mo., United States of America) before application to a 26/10 phenyl sepharose FPLC column (Pharmacia, Peapack, N.J., United States of America) followed by a 16/60 SUPERDEX® 200 FPLC column (Pharmacia). GGTase-I was concentrated to about 15 mg/ml and stored at −80° C.

GGTase-I crystals were grown at 17° C. in hanging drops using equal volumes of protein and reservoir solution (1.3 M $NH_4SO_4$, 175 mM $Na_3$ citrate pH 6.5, 20 mM DTT and 100 mM MES, pH 6.3). Micro-seeds were added after equilibration to control nucleation. Seeding solution was produced by crushing GGTase-I crystals in stabilizing solution (1.5 M $NH_4SO_4$, 175 mM $Na_3$ citrate pH 6.5, 5 mM $ZnCl_2$, 20 mM DTT and 100 mM MES, pH 6.3). Initial protein batches produced orthorhombic crystals (I222, 3 molecules per asymmetric unit), but subsequent protein preparations yielded monoclinic crystals (C2, 6 molecules per asymmetric unit). Complex 2 was formed prior to crystallization by equilibrating GGTase-I first with 3'AzaGGPP followed by $Ca_1a_2X$ peptide (KKKSKTKCVIL (SEQ ID NO: 1; Sigma-Genosys, The Woodlands, Tex., United States of America; >95% purity) at a molar ratio of 1:2:2. Product Complex 3 was formed similarly, with GGPP instead of 3'AzaGGPP, at a molar ratio of 1:1:2. The peptide poly-lysine motif, KKKSKTKCVIL (SEQ ID NO: 1; >95% purity), was used for crystallization and is derived from the K-Ras4B protein. Displaced product Complex 4 was obtained by soaking product crystals comprising Complex 3 in stabilizing solution containing 0.1 mM GGPP for 18 hours. Binary Complex 1 was obtained by extending the soak time to 1 week. For data collection crystals were transferred stepwise into cryosolvent (30% (w:v) sucrose, 1.8 M $NH_4SO_4$, 5 mM $ZnCl_2$, 10 mM TCEP, and 100 mM MES, pH 6.3) before flash-freezing in liquid nitrogen. Derivative crystals were soaked 18 hours in cryosolvent containing 1 mM Di-m-iodobis (ethylenediamine) diplatinum (II) nitrate (PIP) and no TCEP.

Diffraction data were collected at 100° K using beamlines X12B and X25 at NSLS, Brookhaven National Laboratories (BNL), Upton, N.Y., United States of America, and beamline BM14C at Advanced Photon Source (APS), Argonne National Laboratories (ANL), Argonne, Ill., United States of America. Data were integrated and scaled using DENZO and SCALEPACK (Otwinowski & Minor, 1997).

Example 2

Phasing, Model Building and Refinement

Phases for the I222 diffraction data were determined using single isomorphous replacement with anomalous scattering (SIRAS). SOLVE (Terwilliger & Berendzen, 1999) was used to locate eighteen diplatinum sites and to make phase calculations. At 3.7 Å resolution, the isomorphous phasing power was 1.45/1.01 (acentric/centric), anomalous phasing power was 0.45 and the mean figure of merit was 0.52. Initial maps revealed three molecules in the asymmetric unit and a 73% solvent content. Experimental phases were improved using maximum-likelihood density modification in RESOLVE (Terwilliger, 1999; Terwilliger, 2000).

An initial model was constructed using the experimental phases and as refinement progressed these were combined with partial model phases using the sigmaA weighting scheme in CNS v1.0 (Brünger et al., 1998). Iterative cycles of manual building using O (Jones et al., 1991) followed by simulated annealing, minimization, B-factor refinement and phase extension techniques in CNS v1.0 continued until the $R_{free}$ converged at the full resolution limit (2.7 Å). Strict non-crystallographic symmetry (NCS) was enforced until the R-factors dropped below 25%. Ambiguous side-chain positions were resolved using REDUCE and PROBE (Word et al., 1999a; Word et al., 1999b). All included waters had a 3σ peak in omit $F_o$-$F_c$ maps, with density recapitulated in $2F_o$-$F_c$ maps.

Phases for the C2 diffraction data were determined by molecular replacement using all three molecules in the I222 structure as the probe. Structure refinement was carried out as described above. The larger size of the C2 model required NCS restraints in order to minimize $R_{free}$. Restraints were chosen empirically by monitoring refinement statistics: moderate restraints (150 Kcal/mol/Å$^2$) were applied to the protein backbone and internal residues, while solvent accessible residues in the N and C-termini were given weak restraints (20 Kcal/mol/Å$^2$).

In the C2 and I222 structures, the first 54 and last 9 amino acids of the α subunit, the first 17 and last 15 amino acids of the β subunit, and the 5 C-terminal residues of the KKKSK- TKCVIL (SEQ ID NO: 1) peptide were not seen in the electron density. The first 54 residues in the a-subunit, which include 14 proline residues, are disordered in the FTase and GGTase-I structures described herein.

Example 3

Preparation, Expression, Purification, and Kinetic Characterization of an FTase Mutant Mutagenesis of the human FTase sequence (Long et al., 2001) was performed using the QUIKCHANGE® site-directed mutagenesis system (Stratagene, La Jolla, Calif., United States of America), converting the W102β residue to a threonine (W102T mutant). Mutant and WT FTase were expressed in *E. coli* and purified as previously described for the WT FTase enzyme (Long et al., 2001). Prenylation reactions were conducted and processed essentially as previously described (Zhang et al., 1994b), with substrate concentrations of 500 nM $^3$H-FPP or $^3$H-GGPP and 1 μM Ras-CVLS (SEQ ID NO: 3) or Ras-CVLL (SEQ ID NO: 4), and 50 ng of either FTase (WT or W102T mutant) or GGTase-I.

Discussion of Examples 1-3

Based on the structures presented herein and previous structural, chemical, and biochemical observations, a general theory of protein prenyltransferase inhibitor specificity is disclosed. A comparison of the FTase and GGTase-I active sites reveals key differences that can be exploited to create more specific inhibitors. One key difference between FTase and GGTase-I are the residues that usually contact the $a_2$ residue of the substrate $Ca_1a_2X$ peptide, the "$a_2$ site" (see FIG. 5). The FTase $a_2$ site consists of residues Trp 102β, Trp 106β, and Tyr 361β, and their orientation provides an excellent fit for aromatic rings, permitting face-on-face and edge-on-face stacking interactions. The equivalent GGTase-I $a_2$ site presents a different surface and lacks aromatic character, consisting of residues Thr 49β, Phe 106β, and Leu 361β, respectively. A simple comparison of FTase and GGTase-I therefore reveals that FTase inhibitors can achieve specificity through aromatic stacking interactions with the FTase $a_2$ pocket.

The importance of the direct and end-on aromatic stacking between FTIs and the $a_2$ site is illustrated by all other available FTase:FTI structures. The FTase-specific inhibitors L,739-750, U66, the clinical candidate SCH 66336, the clinical candidate R115777, and the clinical candidate BMS-214662 all place naphthalene, phenyl, pyridinyl, chlorophenyl, and/or methylphenyl aromatic rings in the FTase $a_2$ pocket (Bell et al., 2002; Long et al., 2001; Strickland et al., 1999). The importance complementing the $a_2$ site is underscored by R115777 and BMS-214662, both of which achieve selectivity towards FTase through aromatic stacking interactions with the $a_2$ site alone. A superposition of FTase and GGTase-I shows no GGTase-I active-site residues that would clash sterically or electrostatically with R115777 or BMS-214662; the only differences in the residues that contact the drug are in the $a_2$ site. Furthermore, mutations that alter the aromatic properties of the $a_2$ site render FTase resistant to many FTase inhibitors (Del Villar et al., 1999). These results indicate that inhibitor specificity can be maximized by complementing the unique steric, electrostatic, and aromatic properties of the FTase or GGTase-I residues that coordinate the $a_2$ portion of the $Ca_1a_2X$ peptide. These findings thus have general application in the design of inhibitors specific to individual members of the protein prenyltransferase family including, but not limited to FTase and GGTase-1.

Example 4

Sample Preparation and Crystallization of Human PTases with L-778,123

Human FTase was expressed and purified as previously described (Long et al., 2001). FTase ternary Complex 5 (FIG. 10A) was obtained by co-crystallization of FTase with L-778, 123 using the following method: the protein was incubated first with FPP (Sigma Chemical Co., St. Louis, Mo., United States of America), followed by incubation with L-778,123 a clinical candidate non-peptide inhibitor designed to selectively compete with the $Ca_1a_2X$ peptide binding in FTase ($K_i$=0.9 nM; see Word et al., 1999a), for a final molar ratio of FTase/FPP/L-778,123 (1:3:1). FTase crystals, which belonged to space group P6$_1$, with 1 molecule per asymmetric unit, were then grown and cryo-protected as previously described (Long et al., 2001).

Rat GGTase-I was expressed, purified, and crystallized as described herein (see Example 1). The active-site composition of rat and human GGTase-I is identical. GGTase-I crystallized in the monoclinic space group C2 with 6 molecules per asymmetric unit. Unless otherwise noted, all GGTase-I solutions contained 5 μM ZnCl2, 10 mM tris(2-carboxyethyl) phosphine-HCl (TCEP), and 100 mM MES at pH 6.3.

Attempts to co-crystallize GGTase-I with L-778,123 under standard conditions did not yield usable crystals. To obtain the GGTase-I/SO4/L-778,123 Complex 6 (FIG. 10B), product crystals containing a geranylgeranyl-modified KKKSK-TKCVIL peptide (SEQ ID NO: 1) prepared as in Example 1 were soaked 4 days in a stabilization solution [1.5 M NH$_4$SO$_4$, 175 mM Na3-citrate, 0.1 mM GGPP (approximately 1000-fold molar excess), and 0.1 mM L-778,123], transferred stepwise into a cryo-solvent [30% (w/v) sucrose and 1.8 M NH$_4$SO$_4$] and flash-cooled in liquid nitrogen.

To obtain GGTase-I/GGPP/L-778,123 Complex 7, a ternary complex of GGTase-I, L-778,123, and GGPP, co-crystals containing a prenyl-peptide product were transferred stepwise from a stabilization solution to cryo-solvent [30% (w/v) sucrose, 90° mM Na$_3$-citrate, 0.1 mM GGPP, and 0.1 mM L-778,123] and soaked for 7 days before flash-cooling. FTase or GGTase co-crystals containing a prenyl-peptide product were soaked with an excess of isoprenoid diphosphate (FPP or GGPP, respectively), L-778,123, and pyrophosphate ions; this procedure resulted in the formation of Complex 5 in FTase and Complex 6 in GGTase-I, with no differences in ligand binding.

Example 5

Data Collection, Model Building, and Refinement

Figure 10:
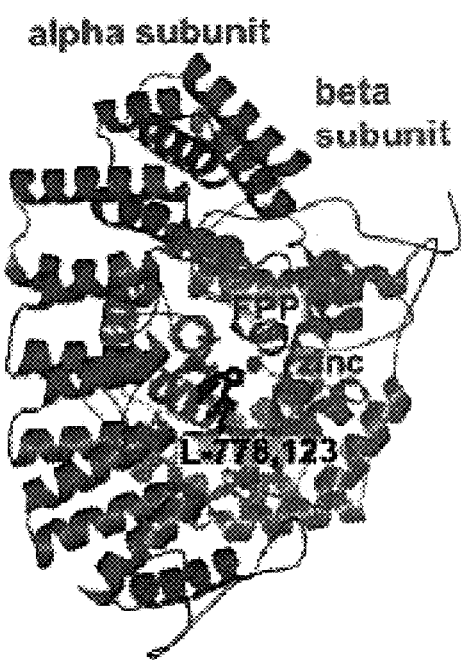
FIGS. 10A and 10B depict protein and inhibitor structures.
Figure 10:
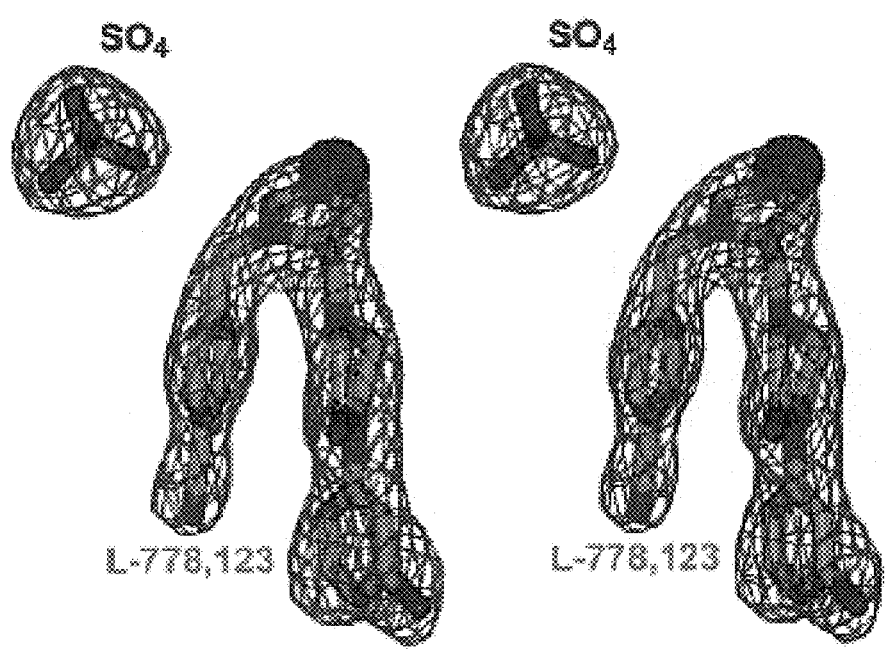

Diffraction data were collected at 100 K at the Brookhaven National Labs National Synchrotron Light Source (BNLNSLS) stations X12B and X25 and at the Argonne National Labs Advanced Photon Source (ANL-APS) station 14-BMC and 22-ID. The programs DENZO and SCALEPACK were utilized for data reduction and scaling (Otwinowski & Minor, 1997). Phases were determined using molecular replacement as implemented in CNS version 1.0 (Brünger et al., 1998). Structure refinement consisted of iterative cycles of model building in 0 (Jones & Kjeldgaard, 1993), followed by simulated annealing, minimization, and B-factor refinement (Brünger et al., 1998). Non-crystallographic symmetry (NCS) restraints were employed during GGTase-I refinement. Electron density for the ligands is continuous and well-defined in all structures and allowed the conformation of L-778,123 to be determined unambiguously (FIG. 10B). REDUCE and PROBE were used to highlight potential steric clashes (Wortd et al., 1999). All included waters had at least a 3σ peak in omit $F_o$-$F_c$ maps, with density recapitulated in 2$F_o$-$F_c$ maps, and satisfy the hydrogen-bonding criteria as implemented in the CNS programs WATERPICK and WATERDELETE. Swiss PDB Viewer was used for sequence-based superpositions (Guex & Peitsch, 1997). All six GGTase-I heterodimers within the crystallographic asymmetric unit are identical, except for a few side chains in crystal contacts, and so only 1 GGTase-I molecule is considered for discussion (protein chains K and L in the PDB coordinates). Data collection and refinement statistics are presented in Table 3. For the FTase/FPP/L-778 complex, collection of all diffraction data in the high-resolution shells was limited by the detector size.

2002; Long et al., 2002). The inhibitor adopts a U-shaped turn, stabilized by van der Waals stacking between rings 1 and 3. At the apex of the turn, the imidazole group (ring 2) coordinates the catalytic zinc ion at a nitrogen-zinc distance of 2.0 Å. Besides zinc coordination, L-778,123 forms only van der Waals interactions with the protein and surrounding ligands. These consist primarily of contacts between ring 1 and Tyr 166α, stacking between ring 1 and the FPP farnesyl moiety, and end-on stacking interactions between rings 3 and 4 of the inhibitor and residues Trp 102β, Trp 106β, and Tyr 361β. A comparison of Complex 5 with structures of FTase complexed with a substrate $Ca_1a_2X$ peptide illustrates that L-778,123 mimics the "$Ca_1a_2$" portion of the $Ca_1a_2X$

TABLE 3

Data Collection and Refinement Statistics
Data Collection (all data)

| | FTase/FPP/L-778,123 Complex 5 | GGTase-I/SO4/L-778,123 Complex 6 | GGTase-I/GGPP/L-778,123 Complex 7 |
|---|---|---|---|
| beam line | NSLS X12B | APS 14BMC | APS 14BMC |
| wavelength (Å) | 1.038 | 1.000 | 1.000 |
| resolution (Å) (outer shell) | 50-1.9 (1.97-1.9) | 30-2.55 (2.64-2.55) | 30-2.75 (2.85-2.75) |
| number of reflection (unique/total) | 88,408/581,302 | 300,151/902,912 | 241,177/682,598 |
| mean I/$\sigma_1$* | 31.1 (10.5) | 15.2 (3.1) | 11.2 (2.6) |
| completeness (%) | 96.3 (76.0) | 93.3 (85.6) | 95.2 (88.5) |
| $R_{sym}$ (%)[a] | 5.5 (12.7) | 5.0 (25.6) | 7.0 (29.5) |
| space group | P61 | C2 | C2 |
| cell dimensions a, b, c (Å) | 178.2, 178.2, 64.5 | 271.2, 268.6, 184.6 | 271.2, 267.9, 185.1 |
| cell angles α, β, γ (deg) | 90, 90, 120 | 90, 131.5, 90 | 90, 131.6, 90 |
| $R_{cryst}$ (%)[a] | 16.2 (19.7) | 19.3 (31.0) | 18.3 (31.3) |
| $R_{free}$ (%)[a] | 18.7 (21.2) | 21.4 (32.0) | 20.4 (31.8) |
| number of non-hydrogen atoms | 6547 | 33,734 | 33,708 |
| number of water molecules | 557 | 1375 | 1043 |
| Ramachandran plot favored (%) | 92.3 | 88.9 | 88.2 |
| Ramachandran plot allowed (%) | 7.7 | 11.1 | 11.8 |
| RMSD bond lengths (Å) | 0.009 | 0.007 | 0.007 |
| RMSD bond angles (deg) | 1.3 | 1.17 | 1.17 |
| average B factor (Å$^2$) (all) | 20.0 | 57.0 | 53.4 |
| (drug) | 16.5 | 41.8 | 54.2 |
| SigmaA coordinate error (Å$^2$) | 0.15 | 0.46 | 0.49 |
| PDB identification | 1S63 | 1S64 | |

[a]$R_{sym} = (\Sigma|(I - <I>)|)/(\Sigma I)$, where <I> is the average intensity of multiple measurements. $R_{cryst}$ and $R_{free} = \Sigma|F_{obs} - F_{calc}|)/(\Sigma|F_{obs}|)$. $R_{free}$ was calculated over 5% of the amplitudes not used in refinement. Parentheses indicate the outer resolution shell

Discussion of Examples 4 and 5

Structure of FTase and GGTase-I Complexes. Like previous FTase and GGTase-I structures determined with bound substrates, products, and inhibitors, L-778,123 does not alter the active-site structure of either enzyme (average RMSD for all $C_\alpha$ atoms is about 0.2 Å; see Strickland et al., 1998; Long et al., 2000; Long et al., 2001; Long et al., 2002). FTase and GGTase-I have similar structures ($C_\alpha$ RMSD=1.16 Å); the α subunit is composed of α-helical pairs, forming a crescent that wraps around the α-α barrel of the β subunit (FIG. 10A). In both FTase and GGTase-I, L-778,123 binds in the active site, a deep hydrophobic cleft formed at the interface of the α and β subunits. In both enzymes, L-778,123 coordinates the catalytic zinc ion, which is located at the rim of the active site and bound at full occupancy.

FTase/FPP/L-778,123 Complex 5. In FTase ternary complex 1, L-778,123 occupies the peptide-binding site, consistent with solution studies that indicate a peptide-competitive mechanism (FIG. 11A; Huber et al. 2001). FPP binds adjacently in the lipid-substrate-binding pocket, as previously seen in other substrate or inhibitor complexes (Long et al., 1998; Strickland et al., 1999; Long et al., 2001; Bell et al., 2002; Long et al., 2002). The inhibitor adopts a U-shaped peptide substrate (FIG. 11B; Strickland et al., 1998; Long et al., 2000. Side chains that form the $Ca_1a_2X$ peptide "X" residue-binding pocket do not interact with the inhibitor. Instead, 5 solvent molecules now occupy the "specificity pocket".

Figure 17:
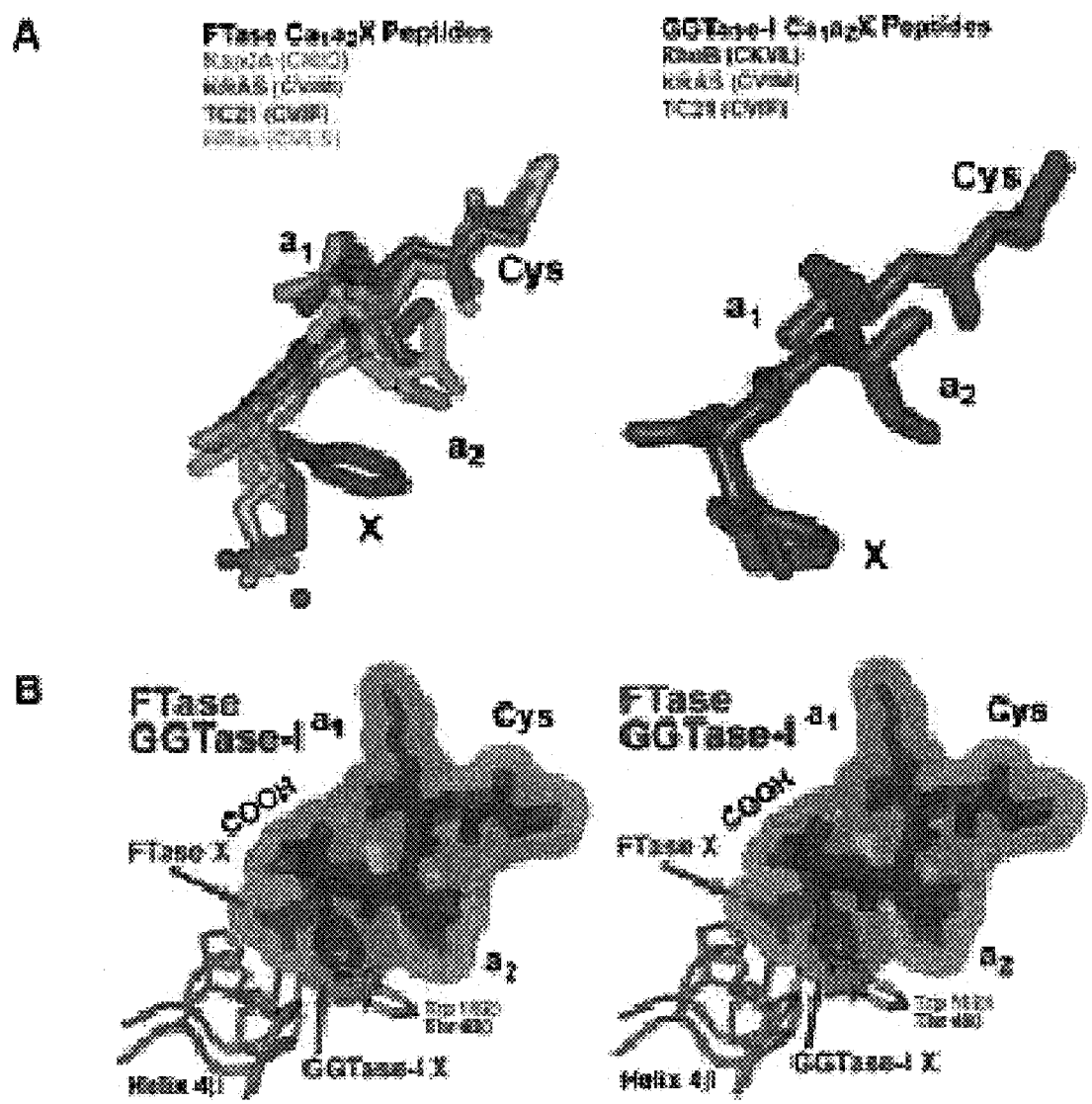
FIGS. 17A and 17B depict comparisons of $Ca_1a_2X$ substrate binding in FTase and GGTase-I.

GGTase-I/L-778,123 Anion Complex 6. The GGTase-I Complex 6 with L-778,123 is strikingly different from FTase Complex 5. Even in the presence of an approximately 1000-fold molar excess of GGPP, the inhibitor does not form a ternary complex with the lipid substrate. Instead, L-778,123 occupies the lipid-substrate-binding pocket and a portion of the peptide-substrate-binding pocket. Additionally, a well-ordered sulfate anion is bound in a positively charged pocket, where the diphosphate group of GGPP usually binds the "diphosphate binding site". Complex 6 is consistent with the observation that, in the presence of anions (such as sulfate), L-778,123 becomes a potent inhibitor of GGTase-I and is competitive with the GGPP lipid substrate (Huber et al., 2001). The sulfate anion forms only van der Waals contact with L-778,123 (closest inhibitor-anion contact is 3.6 Å). L-778,123 adopts the same U-shape seen in Complex 5, except that ring 4 is rotated 167° (all atom RMSD for L-778, 123 is 1.48 Å). Despite the shift in binding location, the imidazole nitrogen maintains zinc coordination as in Complex 5. The inhibitor makes both van der Waals contacts and hydrogen bonds with GGTase-I. The ring 1 nitrile group forms weak polar interactions with Gln 212β, and the ring 3 carbonyl oxygen forms a hydrogen bond with Arg 173β. A comparison of Complex 6 with structures of GGTase-I complexed with the GGPP lipid substrate and a substrate $Ca_1a_2X$ peptide illustrates that L-778,123 overlaps with the binding of GGPP isoprenes 1-3 and the "C" and "$a_2$" portion of the $Ca_1a_2X$ peptide and the sulfate anion overlaps with the GGPP β phosphate (FIG. 17D). The residues that contact the 4th GGPP isoprene and the residues that coordinate the "X" portion of the substrate $Ca_1a_2X$ peptide make no contacts with L-778,123. This space is occupied by 3 solvent molecules and what appears to be a poorly ordered MES buffer molecule from the crystallization buffer.

GGTase-I/GGPP/L-778,123 Low-Affinity Complex 7. In the absence of certain anions (sulfates, phosphates, or their derivatives), L-778,123 binds only weakly to GGTase-I and is competitive with the peptide substrate ($K_i$=10 μm; Huber et al., 2001). To investigate this mode of inhibitor binding, sulfate anions, which strongly synergize inhibition (Dinsmore et al., 2001), were replaced with citrate anions in the crystallization buffer. The resulting Complex 7 is consistent with a peptide-competitive mode of inhibitor binding (FIG. 17E). Here, L-778,123 is bound in the peptide-substrate-binding site, and GGPP is bound in the lipid-substrate-binding site, analogous to FTase Complex 5 (Taylor et al., 2003). Bound citrate is not observed. Additionally, a second partially ordered GGPP is bound (FIG. 17E). Isoprenes 3 and 4 of the second GGPP make van der Waals contacts with L-778,123, while isoprenes 1 and 2 and the diphosphate moiety extend into a solvent-accessible groove and are not well-ordered. In Complex 7, L-778,123 adopts a conformation similar to that seen in Complex 6 (all atom RMSD for L-778,123 is 0.52 Å). The inhibitor imidazole group (ring 2) coordinates the catalytic zinc ion, the ring 1 nitrile group forms a polar interaction with Arg 173β, and the ring 3 carbonyl forms a water-mediated hydrogen bond with His201α. The inhibitor forms stacking interactions with the geranylgeranyl moieties of the two GGPP molecules. As in FTase, L-778,123 occupies the space where the "$Ca_1a_2$" portion of the substrate $Ca_1a_2X$ peptide binds (FIG. 17F).

Structural Mechanism of GGTase-I and FTase Inhibition. Given the structural similarity of FTase and GGTase-I, it is notable that L-778,123 adopts a different high-affinity binding mode in each enzyme ($K_i$ values of 0.9 and 4 nM, respectively). A similar phenomenon has been observed with a low-affinity inhibitor ($IC_{50}$ values are in the range of 1 μm) that adopts different binding modes in homologous kinases (De Moliner et al., 2003). The results presented here indicate that alternate binding modes are possible in homologous enzymes even when $K_i$ values approach 4 nM.

Figure 18:
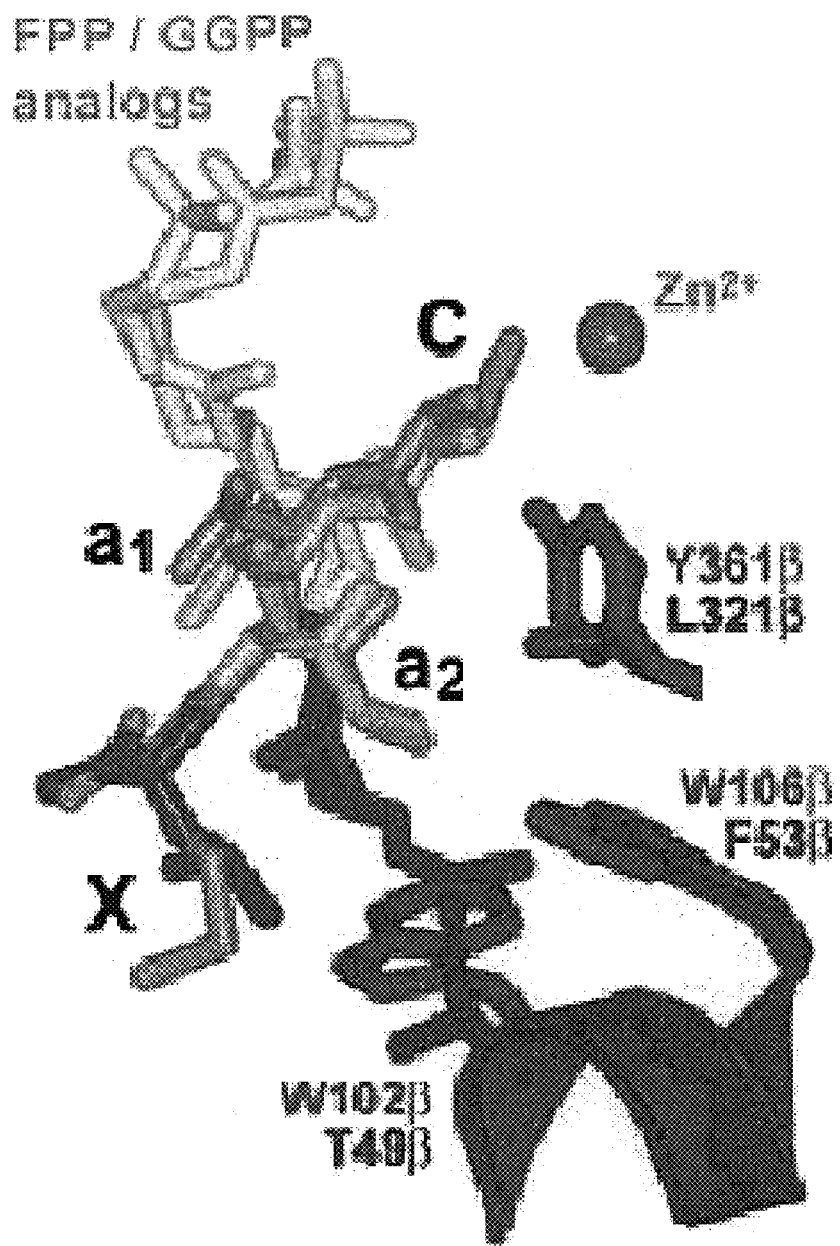
FIG. 18 depicts a comparison of the $a_2$ binding site in FTase and GGTase-I. Superposition of FTase and GGTase-I shows residues that interact with the $a_2$ residue of the $Ca_1a_2X$ motif. Regions of the FTase ternary complex forming the $a_2$ binding site (enzyme residues Trp 102β, Trp 106β and Tyr 361β and isoprene 3) are colored red. Corresponding regions of the GGTase-I ternary complex (enzyme residues Thr 49β, Phe 53β and Leu 321β, isoprenes 3 and 4, and substrate peptide X residue) are colored blue. Portions of the FPP and GGPP analogs (gray) and of the CVIM (SEQ ID NO: 24, pink) and CVIL (SEQ ID NO: 2, light blue) peptides not forming the $a_2$ site are also shown.

To delineate the structural features that contribute to the distinct high-affinity-binding modes in FTase and GGTase-I, Complexes 5 and 6 were superimposed ($C_\alpha$, RMSD of 1.17 Å). This comparison revealed no steric blocks that would prevent L-778,123 from adopting lipid-competitive binding in FTase (mode 6) or peptide-competitive binding in GGTase-I (mode 5). Indeed, a low-affinity Complex with L-778,123 bound in the GGTase-I peptide-binding site, albeit stabilized by an additional GGPP, was also captured. Nevertheless, Complex 5 forms preferentially in FTase, and Complex 6 forms preferentially in GGTase-I in the presence of certain anions (Huber et al., 2001). A comparison of the two active sites suggests that aromatic stacking interactions may govern the preferential formation of Complex 5 in FTase and Complex 6 in GGTase-I, respectively. The residues that coordinate the $a_2$ residue of the substrate $Ca_1a_2X$ peptide, the "$a_2$-binding site", consist of Trp 102β, Trp 106β, and Tyr 361β in FTase, and the orientation of these side chains provides an excellent fit for aromatic rings, permitting face-on-face and edge-on-face aromatic stacking interactions (FIG. 18A; Tatko, 2002). However, the equivalent GGTase-I $a_2$-binding site has less aromatic character, consisting of residues Thr 49β, Phe 53β, and Leu 361β, respectively (FIG. 17A). In FTase, L-778,123 adopts mode 5 because of favorable stacking interactions with the $a_2$-binding site, whereas in GGTase-I, L-778,123 adopts mode 6, permitting hydrogen-bond formation in lieu of aromatic stacking interactions. The absence of anions that synergize inhibition of GGTase-I, such as sulfate, encourages the binding of both L-778,123 and a second GGPP molecule in the GGTase-I peptide-binding site. In this low-affinity Complex 7, the geranylgeranyl moiety of the second GGPP ligand occupies the $a_2$-binding site and provides a complementary surface for stacking interactions with L-778,123 (FIG. 18B). These stacking interactions would not be possible in the absence of the second GGPP molecule. Differences in the GGTase-I and FTase $a_2$-binding site have been hypothesized also to play a subtle role in Ca1a2X peptide-substrate specificity (Long et al., 2000). The results of the experiments presented here indicate that the $a_2$-binding site plays an important role in $Ca_1a_2X$ prenyltransferase inhibitor specificity as well.

The alternate binding modes of L-778,123 in FTase and GGTase-I might have implications for the design of GTIs. The synthesis of GGTase-I antagonists has generally focused on utilizing existing peptide-competitive FTIs as a design scaffold (Sebti & Hamilton, 2000; Dinsmore & Bell, 2003). This design process generally assumes that these inhibitors will adopt a homologous binding mode in the GGTase-I $Ca_1a_2X$ peptide-binding site. The results presented here, however, indicate that in some instances the extrapolation of FTI-binding modes to GGTase-I might be misleading. Instead, in addition to other contributing factors, it might be more useful to consider the contributions of stacking interactions with the $a_2$-binding site when designing inhibitors that are selective toward one prenylation enzyme.

Implications for CaaX Prenyltransferase Inhibition. Inhibitor specificity is an important concern in the development of therapeutics based on $Ca_1a_2X$ prenyltransferase inhibitors. Selective FTIs are well-tolerated as cancer therapeutics (Caponigro et al., 2003) and in preclinical studies GTIs have demonstrated antitumor activity (Sebti & Hamilton, 2000). Although GTIs have been shown to halt the G1 to S phase transition of the cell cycle, inhibit tumor cell growth, and arrest tumor growth in nude mice, (Vogt et al., 1996; Stark et al., 1998; Walters et al., 2002; Sun et al., 2003), these inhibitors can be toxic at high dosages (Lobell et al., 2001). Furthermore, although low-level inhibition of all cellular protein prenylation is well-tolerated (Wong et al., 2002), complete inhibition of prenylation is toxic (Lobell et al., 2001; deSolms et al., 2003). Consequently, inhibitors should be highly selective toward one prenylation enzyme to avoid toxicity, and further therapeutic development efforts would therefore greatly benefit from a better understanding of inhibitor potency and specificity.

A comparison of the FTase and GGTase-I structures reveals that aromatic differences in the $a_2$-binding site may contribute to the different binding modes of L-778,123 in FTase and GGTase-I. This comparison also suggests that differences in the $a_2$-binding site could modulate the selectivity of other protein prenyltransferase inhibitors. Unlike peptide-substrate discrimination, which is determined primarily by complementarity between the $Ca_1a_2X$ motif "X" residue and the residues that constitute the "X" residue binding pocket, the "specificity pocket" (Strickland et al., 1998; Long et al., 2000; Taylor et al., 2003), inhibitor specificity can be determined by complementarity with both the specificity pocket and the $a_2$-binding site. The importance of the direct and end-on aromatic stacking between FTIs and the $a_2$-binding site is illustrated by other available FTase/FTI structures. In Complex 5, the L-778,123 chlorophenyl group (ring 4) is bound similarly to the naphthalene ring of the aminopyrrolidine FTIs U49 and U66 (a L-778,123 related inhibitor; Bell et al., 2002), the bromochlorophenyl ring of the clinical candidate SCH 66336 (Strickland et al., 1999), the chlorophenyl ring of R115777 (Reid & Beese, 2004), the methylphenyl ring of BMS-214662 (Reid & Beese, 2004), and the phenyl group of the tetrapeptide inhibitor CVFM and related peptidomimetic L,739-750 (FIG. 18C; Long et al., 2001). Furthermore, mutations that alter the aromatic properties of the $a_2$-binding site render FTase resistant to FTIs such as SCH 66336 (Del Villar et al., 1999).

Overall, the results presented herein indicate that inhibitor specificity can be modulated by complementing the unique steric, electrostatic, and aromatic properties of the FTase or GGTase-I residues that coordinate the $Ca_1a_2X$ peptide "$a_2$" residue. Indeed, recent structures of R115777 and BMS-214662 Complexed with FTase suggest that these two clinical candidates achieve selectivity toward FTase over GGTase-I through aromatic stacking interactions with the FTase a-binding site (Reid & Beese, 2004). Sequence alignments of all available CaaX prenyltransferase sequences reveal that the FTase $a_2$-binding site is strictly conserved from mammals to protists (Buckner et al., 2002), while the GGTase-I $a_2$-binding site shows less sequence conformation. Protein prenyltransferase inhibitors show promise for treating opportunistic fungal infections such as *Candida albicans* (Murthi et al., 2003) or parasitic infections such as *Plasmodium falciparum* (malaria; Chakrabarti et al., 1998), and it would be desirable to create inhibitors that are selective toward the parasitic rather than the endogenous host enzyme. On the basis of our observations, we therefore propose that differences in the $a_2$-binding site can be exploited to create species specific inhibitors.

Molecular Mechanism of Anion-Inhibitor Synergy and Implications for Drug Design. L-778,123 inhibits GGTase-I through concerted inhibition with anions such as sulfates, phosphates, or their derivatives. This pattern of inhibition can occur when two ligands bind in separate, non-overlapping sites in an active site and exhibit synergistic-binding interactions (Theorell & Yonetani, 1965; Segel, 1975). Complex 6 is consistent with such a mechanism; L-778,123 competes with GGPP lipid moiety binding, and anions compete with the GGPP diphosphate moiety binding. Therefore, anions that more closely approximate the GGPP diphosphate moiety, such as sulfate or pyrophosphate, should produce stronger inhibition than other anions such as acetate or chloride, which cannot form the same network of hydrogen bonds and salts with the diphosphate-binding pocket (Huber et al., 2001). This additionally provides an explanation for the formation of Complex 7, when citrate anions were substituted for sulfate anions in the crystallization solution. While the inventors do not wish to be limited to any particular theory of operation, it might be that anion binding induces a small conformational change that pre-forms the lipid-binding site of the apo enzyme for inhibitor binding. Evidence for such a structural change is seen in other prenyltransferase structures. In FTase and RabGGTase, the residue side chains that form the lipid-binding site move upon binding of the lipid substrate (Partk et al., 1997; Long et al., 1998; Zhang et al., 2000; Pylypenko et al., 2003). In GGTase-I, these residues adopt an analogous lipid-bound conformation upon binding of an anion in the diphosphate-binding pocket but in the absence of the lipid substrate (Taylor et al., 2003). This provides an explanation for a similar type of anion-inhibitor synergy observed in FTase, where phosphate anions modulate the binding of FPP-competitive FTIs (Scholten et al., 1997).

Potent inhibitors can be created by tethering low-affinity, low-molecular-weight ligands that bind in separate, non-overlapping sites in the target enzyme (Erlanson et al., 2000; Hajduk et al., 2000; Szczepankiewicz et al., 2003). Such a fragment-based approach has been previously used to produce adenosine kinase and tyrosine phosphatase 1B inhibitors. Inhibition of GGTase-I by L-778,123 and an anion illustrates that potent inhibition can also be achieved by two inhibitor fragments without the necessity of a covalent linkage, through concerted inhibition. Such cases can be taken advantage of to create new classes of inhibitors that bypass physiological barriers to drug uptake. Charged species do not readily cross cell membranes; consequently, amphiphatic inhibitors, such as isoprenoid diphosphate analogues, generally show poor bioavailability. Under the right circumstances, depending on the structural details of the target molecule, an amphiphatic substrate analogue could be broken into a hydrophobic moiety that can easily cross cell membranes and a polar/charged group already present in the cytoplasm, relying on synergistic binding at the target to effect inhibition. Concerted inhibition involving anions has been observed in phosphoenolpyruvate mutase, arginine kinase, creatine kinase, and fucosyltransferase (Milner-White & Watts, 1971; Seidel & Knowles, 1994; Scholten et al., 1997; Zhou et al., 1998), and it may be applicable to other enzymes that utilize diphosphate-coupled lipid substrates, such as the cholesterolbiosynthesis enzymes geranyl and farnesyl synthase. Concerted inhibition should therefore be taken into account in structure-based drug-design strategies or in inhibitor-screening protocols by adding phosphate anions to buffer systems.

Example 6

Protein Expression, Purification and Crystallization

Rat and human FTase (rFTase and hFTase) were expressed and purified as described herein. The sequences of rat and human FTase are 95% identical with complete sequence and structural conservation around the active site. Complexes with the H-Ras (GCVLS; SEQ ID NO: 6) and Rap2b (TKCVIL; SEQ ID NO: 7) peptides (Sigma-Genosys, >95% purity) were formed by incubating the rFTase with FPT-II (EMD Biosciences CALBIOCHEM®, San Diego, Calif., United States of America) followed by the appropriate $Ca_1a_2X$ peptide for a final rFTase:FPTII: $Ca_1a_2X$ molar ratio of 1:3:3 and crystallized. The rFTase:FPTII:TC21 complex was obtained by soaking a co-crystal of farnesylated-KKKSKTKCVIM product (SEQ ID NO: 8) bound to FTase in stabilization solution supplemented with FPT-II (50 µM) and TC21 peptide (200 µM; Sigma-Genosys, >95% purity) for a period of three days. The TC21 peptide (KKSKT-KCVIF; SEQ ID NO: 9) is a chimera of the TC21 $Ca_1a_2X$ motif and the polylysine sequence derived from K-Ras4B that improves peptide solubility. The hFTase:FPT-II:Rap2a complex was formed by incubating hFTase with FPT-II followed by Rap2a peptide (DDPTASACNIQ (SEQ ID NO: 10); Sigma-Genosys, >95% purity) for a final molar ratio of 1:3:3 and crystallized. The FTase:FPTII:Ca$_1$a$_2$X complexes were transferred to cryoprotection solutions and flash-cooled in liquid nitrogen.

Rat GGTase-I was expressed and purified as previously described herein (see also SAtrickland et al., 1999). All GGTase:3'azaGGPP:Ca$_1$a$_2$X ternary complexes were obtained by soaking co-crystals of a geranylgeranylated-KKKSKTKCVIL product (SEQ ID NO: 1) bound to GGTase-I, crystallized as described herein, in a stabilization solution supplemented with the appropriate ligands. GGTase-I product co-crystals were first transferred stepwise from their mother liquor (1.3 M NH$_4$SO$_4$, 175 mM Na$_3$-citrate, 100 mM MES pH 6.3, and 20 mM DTT) to cyrosolvent (30% (w:v) sucrose, 900 mM Na$_3$-citrate, 100 mM MES pH 6.3, 10 mM TCEP, and 1 μM ZnCl$_2$) supplemented with 0.2 mM 3'azaGGPP and 0.2 mM of the appropriate Ca$_1$a$_2$X peptide (Sigma-Genosys, >95% purity). All crystals were soaked for a week to allow for ternary complex formation and flash-cooled in liquid nitrogen. Ligand binding in the Ca$_1$a$_2$X prenyltransferases has been previously demonstrated to be independent of the means by which the ligand is introduced (i.e., co-crystallization vs. soaking; see Park et al., 1997; Strickland et al., 1999; Long et al., 2001; Reid & Beese, 2004).

Example 7

Data Collection, Model Building, and Refinement

Diffraction data were collected at 100 K with an R-Axis IV image plate system (Molecular Structure Corp., The Woodlands, Tex., United States of America) mounted on a Rigaku RU-H3R rotating anode generator with double mirror optics (Molecular Structure Corp.). Diffraction data were also collected at the BioCARS and SER-CAT beamlines at the Advanced Photon Source, Argonne National Labs and at the X25 beamline at the National Synchrotron Light Source, Brookhaven National Labs (BNLNSLS). Data were integrated and scaled using DENZO, SCALEPACK, and HKL200050.

Figure 13:
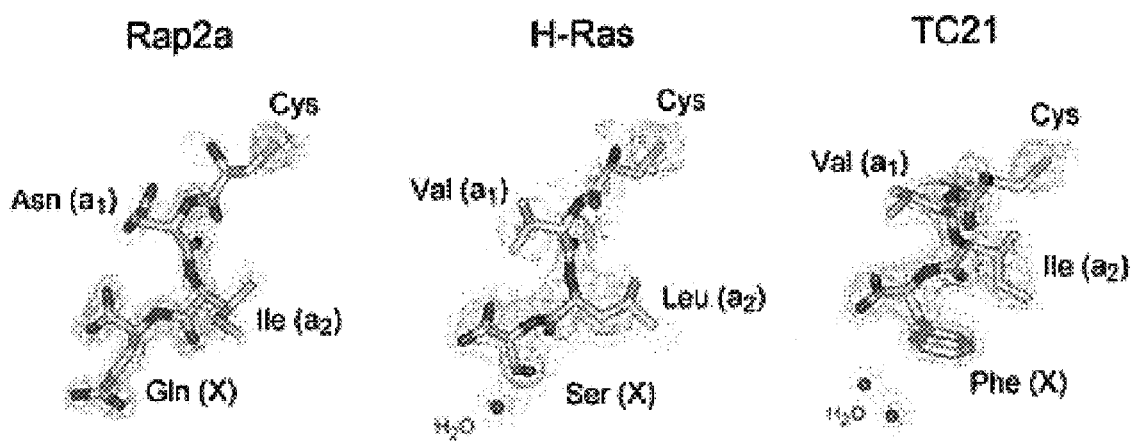
FIG. 13 depicts a omit electron density of peptide substrates complexed with FTase. Electron density maps were calculated using Fourier coefficients $(F_{obs}-F_{calc})\alpha_{calc}$ with the substrate peptide omitted from the final model. Electron density is shown at a +5σ contour level (dark blue) and a +3σ contour level (light blue).
Figure 14:
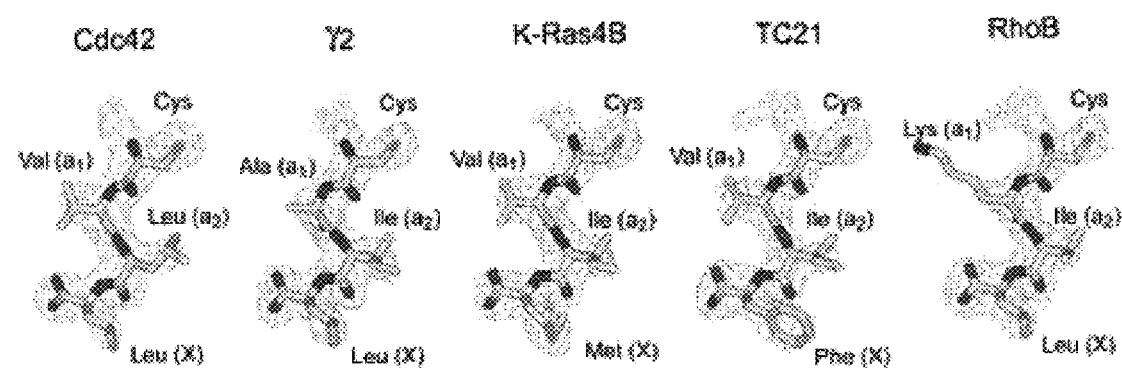
FIG. 14 depicts an omit electron density of peptide substrates complexed with GGTase-I. Electron density is shown at +5σ level (in blue) and was calculated using Fourier coefficients $(F_{obs}-F_{calc})\alpha_{calc}$ with the substrate peptide omitted from the final model.

Both rat and human FTase complexes crystallize in space group P6$_1$ with unit cell dimensions listed in Table 4 and one FTase heterodimer per asymmetric unit. The crystals are isomorphous to previously reported ternary complexes of rat FTase (Long et al., 2000) or human FTase (Long et al., 2001). The structures were determined by rigid body refinement using either rat FTase (Brookhaven Protein Data Bank code 1 D8D) or human FTase (Brookhaven Protein Data Bank code 1JCQ) as the initial model with ligands removed. Initial σ$_A$ weighted F$_o$-F$_c$ maps revealed 5σ peaks in the active site that clearly delineated the conformation of the FPT-II and the Ca$_1$a$_2$X substrate peptides (FIG. 13). After rigid body refinement, FPT-II and the Ca$_1$a$_2$X peptides were fit into σ$_A$ weighted F$_o$-F$_c$ maps and the complexes refined against all data with |F|≧0 by iterative cycles of simulated annealing, minimization, individual B-factor refinement, and model building. Refinements were carried out using CNS v1.0 (Brünger et al., 1998) and models built using O (Jones et al., 1991). Refinement statistics are shown in Table 4. Rat GGTase-I crystals belong to the space group C2 with cell dimensions of a=271 Å, b=268 Å, c=185 Å, β=132°. Crystals contain six GGTase-I heterodimers per asymmetric unit (546,000 MW) and have a high solvent content (about 75%). The crystals are isomorphous to the previously reported 2.4 Å resolution ternary complex of rat GGTase-I (Taylor et al., 2003). The structures were determined by rigid body refinement using this 2.4 Å GGTase-I structure (Brookhaven Protein Data Bank code 1N4Q) with ligands removed as an initial model. Each of the six GGTase-I molecules in the asymmetric unit was initially refined as a separate rigid group. Initial σ$_A$ weighted F$_o$-F$_c$ maps revealed 5σ peaks in the active site that clearly delineated the conformation of the 3'azaGGPP and the Ca$_1$a$_2$X substrate peptides (FIG. 14). Structures were refined against all data with |F|≧0 by iterative cycles of simulated annealing, minimization, and model building. The 3'azaGGPP and peptide ligands were included in the model after the first cycle of refinement. Non-crystallographic symmetry (NCS) restraints were employed during refinement as described herein. Refinements were carried out using CNS v1.0 and models built using O. Group B-factor refinement was applied to the protein, treating each of the six GGTase-I molecules in the asymmetric unit as a separate domain. Individual B-factor refinement was applied to all bound ligands. All water molecules included in the final model have at least a 3σ peak in σ$_A$ weighted omit F$_o$-F$_c$ maps, and conform to hydrogen bonding criteria as implemented in WATERPICK and WATERDELETE. Waters were inspected to ensure at least 1σ density in σ$_A$ weighted 2F$_o$-F$_c$ maps and proper hydrogen bonding environment after refinement. Waters that refined to a B-factor >65 Å$^2$ were deleted. Progress of the refinement was assessed by R$_{cryst}$ and minimizing divergence between R$_{cryst}$ and R$_{free}$.

TABLE 4

FTase Data Collection and Refinement Statistics

| Complex | Rap2a DDPTASACNIQ SEQ ID NO: 10 | TC21 KKSKTKCVIF SEQ ID NO: 9 | H-Ras GCVLS SEQ ID NO: 6 | Rap2b TKCVIL SEQ ID NO: 7 |
|---|---|---|---|---|
| Data Collection | ANL-APS 14BMC | ANL-APS 14BMD | Cu Kα[a] | Cu Kα[a] |
| wavelength (Å) | 1.0000 | 0.9000 | 1.5418 | 1.5418 |
| resolution (Å) | 50-1.8 | 30-2.3 | 50-2.25 | 50-2.10 |
| (outer shell) | (1.86-1.80) | (2.38-2.30) | (2.33-2.25) | (2.18-2.10) |
| number of unique reflection (unique/total) | 97,342/389,196 | 48,988/165,965 | 52,549/233,003 | 64,128/239,227 |
| mean I/σ$_1$* | 28.5 (5.6) | 14.3 (3.1) | 15.1 (3.3) | 19.9 (3.8) |
| completeness (%) | 89.1 (62.2) | 92.5 (84.0) | 95.3 (86.8) | 95.4 (89.0) |
| R$_{sym}$ (%)* | 4.2 (10.7) | 6.6 (23.4) | 8.5 (25.8) | 5.3 (20.7) |
| Unit Cell: | | | | |
| a = b (Å) | 178.5 | 171.0 | 171.2 | 170.4 |
| c (Å) | 64.7 | 69.6 | 69.3 | 69.4 |
| R$_{cryst}$ (%) | 17.9 (20.4) | 18.0 (23.9) | 19.3 (27.6) | 18.7 (23.4) |
| R$_{free}$ (%) | 19.9 (22.8) | 20.7 (26.9) | 21.8 (31.1) | 21.2 (26.4) |
| number of non-hydrogen atoms: Total/H$_2$O | 6,706/659 | 6,384/357 | 6,324/314 | 6,394/416 |

TABLE 4-continued

FTase Data Collection and Refinement Statistics

RMSD from ideal geometry

| | | | | |
|---|---|---|---|---|
| bond lengths (Å) | 0.005 | 0.006 | 0.006 | 0.006 |
| bond angles (deg) | 1.23 | 1.19 | 1.19 | 1.17 |

Average Isotropic B factor Å$^2$

| | | | | |
|---|---|---|---|---|
| Enzyme | 21.3 ± 7.2 | 34.0 ± 13.1 | 41.1 ± 14.3 | 28.8 ± 9.9 |
| Ca$_1$a$_2$X peptide | 27.9 ± 7.2 | 34.0 ± 5.5 | 64.0 ± 4.2 | |
| FPT-II | 27.1 ± 5.0 | 23.0 ± 5.2 | 32.4 ± 5.8 | 24.4 ± 3.5 |
| Solvent | 34.0 ± 9.8 | 36.7 ± 9.7 | 41.7 ± 9.1 | 36.2 ± 9.9 |
| SigmaA coordinate error (Å$^2$) | 0.10 | 0.25 | 0.29 | 0.19 |
| PDB identification | 1TN6 | 1TN7 | 1TN8 | |

$R_{sym} = (\Sigma |(I - <I>)|)/(\Sigma I)$, where <I> is the average intensity of multiple measurements.
$R_{cryst}$ and $R_{free} = \Sigma |F_{obs} - F_{calc}|/(\Sigma |F_{obs}|)$. $R_{free}$ was calculated over 5% of the amplitudes not used in refinement.
*Values in parentheses correspond to those in the outer resolution shell
[a]Rigaku RU-H3R rotating anode generator The structures of all six GGTase-I heterodimers were identical, except for a few side chains in crystal contacts; the average B-factor for each GGTase-I molecule varied by ±10 Å$^2$. For this reason, the most well-ordered GGTase-I molecule is considered for discussion (protein chains K, L, and R in the PDB coordinates). Refinement statistics are shown in Table 5. Ligands in all complexes were refined at full occupancy.

Swiss PDB Viewer (Guex & Peitsch, 1997) and O were used to build Ca$_1$a$_2$X peptide models, and REDUCE and PROBE (Word et al., 1999) used to identify and correct steric clashes within these models. Swiss PDB Viewer was used for structure-based sequence alignments. Superpositions utilized all homologous Ca atoms in FTase and GGTase-I; RMSD differences for the various Ca$_1$a$_2$X motifs were calculated using sequence-based superpositions of the entire protein. PYMOL was used to create all structural figures (Delano, 2002).

Example 8

Database Searches

To search for potential human FTase and GGTase-I substrates, the Swiss-Prot/TrEMBL Scan ProSite server (O'Donovan et al., 2002) was used to search for all proteins within the human genome that contain a C-terminal CXXX motif (where X is any amino acid, Prosite syntax CXXX>). From the resulting list, only those with a C-terminal X residue that can function as a substrate for FTase (Met, Gln, Ala, Ser, Cys or Thr) or GGTase-I (Leu, Val, Ile or Phe) were retained. Of the remaining proteins, only those with an a$_2$ residue that would be expected to function as an FTase or GGTase-I substrate (Val, Ile, Leu, Met, Phe, Tyr, Pro, or Thr) were retained. All Rab or Rab-related proteins, which are exclusively prenylated by Rab GGTase in vivo, were removed from the list (Wilson et al., 1998). The hepatitis delta virus large antigen, which is expressed and prenylated in human cells, was also included in the list (Otto & Casey, 1996).

TABLE 5

GGTase-1 Data Collection and Refinement Statistics

| Complex | TC21 KKSKTKCVIF SEQ ID NO: 9 | KRas-4B KKKSKTKCVIM SEQ ID NO: 8 | RhoB GCINCCKVL SEQ ID NO: 11 | RhoB KKSKTKCKVL SEQ ID NO: 12 | y2 FREKKFFCAIL SEQ ID NO: 13 | Cdc42-II RRCVLL SEQ ID NO: 14 |
|---|---|---|---|---|---|---|
| Data Collection | ANL-APS 14BMD | ANL-APS 22ID | ANL-APS 22ID | ANL-APS 14BMC | ANL-APS 22ID | BNLNLSL X25 |
| wavelength (Å) | 0.9000 | 1.0717 | 1.0717 | 0.9000 | 1.0060 | 1.1000 |
| resolution (Å) | 30-2.85 (2.96-2.85) | 30-2.7 (2.8-2.7) | 3.0-2.7 (2.8-2.7) | 30-2.65 (2.75-2.65) | 30-2.7 (2.8-2.7) | 30-2.9 (3.0-2.9) |
| number of reflection (unique/total) | 217,761/ 627,208 | 251,777/ 747,778 | 249,550/ 723,429 | 261,126/ 979,223 | 250,142/ 713,161 | 197,897/ 554,112 |
| mean I/σ$_1$* | 11.1 (2.7) | 12.3 (2.5) | 12.9 (2.5) | 12.0 (2.2) | 15.0 (2.5) | 11.9 (2.1) |
| completeness (%) | 95.6 (88.8) | 92.2 (81.8) | 94.5 (89.7) | 92.4 (78.1) | 94.1 (82.6) | 91.4 (81.9) |
| R$_{sym}$ (%)* | 7.7 (27.7) | 6.5 (19.3) | 8.0 (29.2) | 7.0 (28.1) | 5.8 (24.7) | 6.7 (29.5) |
| Unit Cell: | | | | | | |
| a, b, c (Å) | 271.1, 266.7, 185.1 | 272.5, 268.5, 185.9 | 270.4, 266.6, 184.8 | 270.9, 266.6, 184.3 | 270.9, 264.0, 185.0 | 271.3, 266.9, 185.8 |
| β (°) | 131.7 | 131.5 | 131.6 | 131.5 | 131.7 | 131.9 |
| R$_{cryst}$ (%) | 18.9 (31.6) | 19.4 (31.3) | 19.3 (31.7) | 19.5 (30.9) | 19.3 (32.9) | 19.9 (34.3) |
| R$_{free}$ (%) | 21.0 (35.1) | 21.1 (34.0) | 21.2 (34.2) | 21.3 (32.8) | 21.2 (34.1) | 21.8 (36.3) |

TABLE 5-continued

GGTase-1 Data Collection and Refinement Statistics

| Complex | TC21 KKSKTKCVIF SEQ ID NO: 9 | KRas-4B KKKSKTKCVIM SEQ ID NO: 8 | RhoB GCINCCKVL SEQ ID NO: 11 | RhoB KKSKTKCKVL SEQ ID NO: 12 | γ2 FREKKFFCAIL SEQ ID NO: 13 | Cdc42-II RRCVLL SEQ ID NO: 14 |
|---|---|---|---|---|---|---|
| non-hydrogen atoms: Total/H$_2$O | 33,505/ 881 | 33,291/ 677 | 33,465/ 824 | 33,665/ 1,102 | 33,566/ 1,005 | 32,873/ 256 |
| RMSD from ideal geometry | | | | | | |
| bond lengths (Å) | 0.007 | 0.007 | 0.007 | 0.007 | 0.007 | 0.007 |
| bond angles (deg) | 1.17 | 1.18 | 1.18 | 1.17 | 1.17 | 1.19 |
| Average Isotropic B Value, Å$^2$ | | | | | | |
| All non-solvent atoms | 47.0 ± 13.9 | 65.0 ± 14.8 | 61.4 ± 14.1 | 53.8 ± 13.8 | 54.5 ± 14.8 | 78.5 ± 14.2 |
| Solvent | 37.8 ± 8.8 | 54.7 ± 6.9 | 50.1 ± 7.8 | 50.8 ± 8.1 | 45 ± 8.5 | 59.2 ± 5.8 |
| GGTase-I Enzyme | 37.3 ± 11.2 | 56.0 ± 12.4 | 51.3 ± 11.3 | 45.2 ± 11.2 | 45.4 ± 12.3 | 68.8 ± 11.3 |
| Ca$_1$a$_2$X peptide | 35.5 ± 2.8 | 54.0 ± 6.7 | 54.0 ± 13.2 | 49.9 ± 7.2 | 36.8 ± 8.8 | 63.9 ± 6.6 |
| 3'azaGGPP | 32.1 ± 9.1 | 54.7 ± 8.3 | 50.8 ± 10.8 | 46.3 ± 7.6 | 42.4 ± 10.8 | 67.2 ± 8.9 |
| SigmaA coordinate error (Å$^2$) | 0.50 | 0.44 | 0.45 | 0.43 | 0.44 | 0.58 |
| PDB identification | 1TNB | 1TNO | 1TNU | | 1TNY | 1TNZ |

$R_{sym} = (\Sigma| (I - <I>)|)/(\Sigma I)$, where $<I>$ is the average intensity of multiple measurements.
$R_{cryst}$ and $R_{free} = \Sigma|F_{obs} - F_{calc}|/(\Sigma|F_{obs}|)$. $R_{free}$ was calculated over 5% of the amplitudes not used in refinement.
*Values in parentheses correspond to those in the outer resolution shell

Discussion of Examples 6-8

Figure 15:
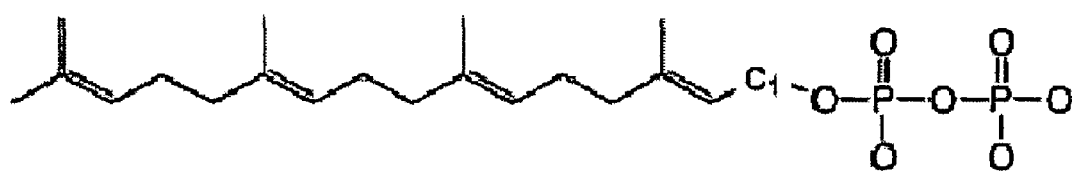
FIG. 15 depicts the chemical structures of isoprenoid diphosphates and non-hydrolyzable analogs.
Figure 15:
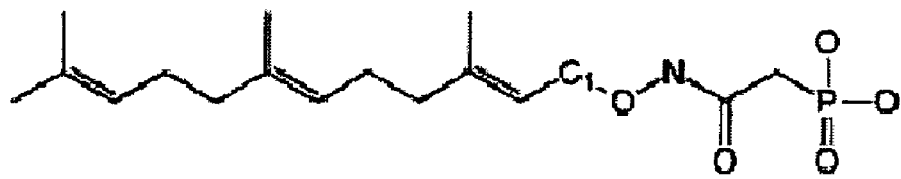
Figure 15:
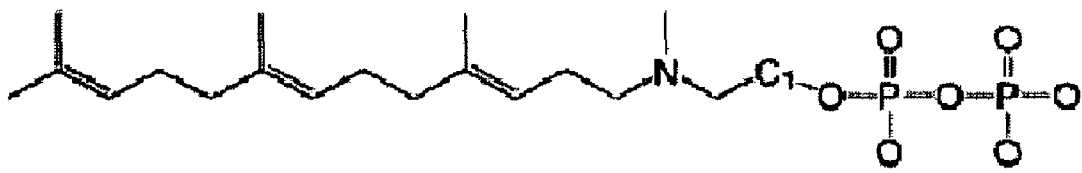
Figure 16:
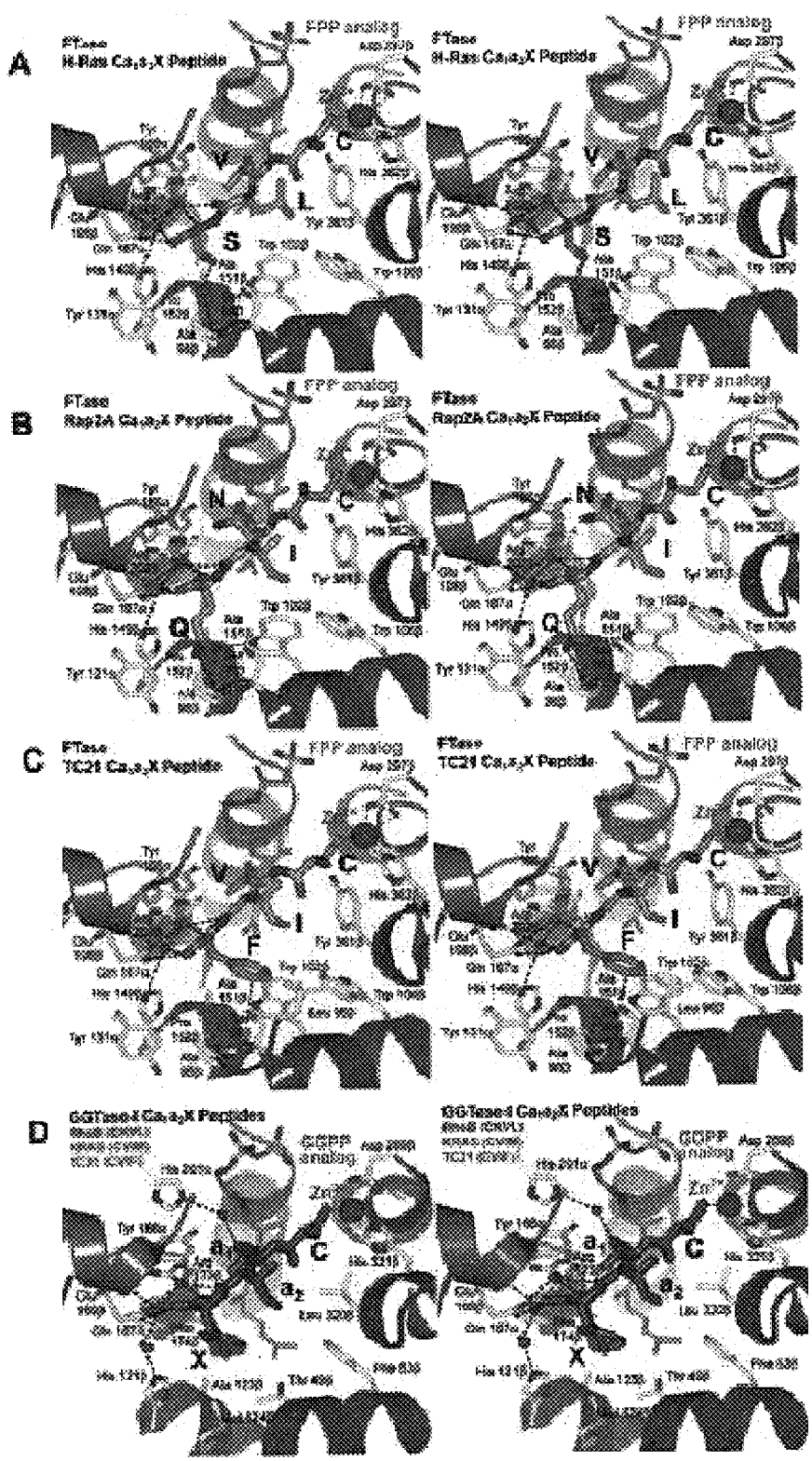
FIGS. 16A-16D depict $Ca_1a_2X$ peptide binding in FTase and GGTase-I. Stereo pairs of FTase and GGTase-I are all shown in the same orientation.

The structures of FTase in ternary complexes with an FPP analog (FPT-II, FIG. 15) and peptides derived from the cognate substrates H-Ras (GCVLS (SEQ ID NO: 6), FIG. 16A) and Rap2a (DDPTASACNIQ (SEQ ID NO: 10), FIG. 16B), the cross-reactive substrate TC21 (KKSKTKCVIF (SEQ ID NO: 9), FIG. 16C), and the non-substrate Rap2b (TKCVIL; SEQ ID NO: 7) were determined. The structures of GGTase-I in ternary complexes with a GGPP analog (3'azaGGPP, FIG. 15) and peptides derived from the cognate substrates Cdc42 splice isoform 2 (RRCVLL (SEQ ID NO: 14) Ca1a2X motif) and the heterotrimeric G protein γ2 subunit (FREKKFFCAIL; SEQ ID NO: 13), and the cross-reactive substrates RhoB (GCINCCKVL; SEQ ID NO: 11), K-Ras4B (KKKSKTKCVIM; SEQ ID NO: 8) and TC21 (FIG. 10D) were also determined. These nine structures were also compared to previously-determined structures of FTase in ternary complexes with K-Ras4B-derived peptides (Strickland et al., 1998; Long et al., 2000), and with GGTase-I in ternary complexes with a Rap2b chimera peptide (KKKSKTKCVIL; SEQ ID NO: 1; disclosed herein). The peptides were chosen because their Ca$_1$a$_2$X motifs are representative of the most common a$_2$ (Val, Leu and Ile) and X (Leu, Met, Phe, Glu, and Ser) residues, and for their importance in signal transduction and cancer biology. The four FTase and six GGTase-I peptide substrates are bound as a ternary complex with the non-hydrolyzable lipid analogs FPT-II (Manne et al., 1995) and 3'azaGGPP, respectively. The two lipid analogs bind as previously observed, adopting a conformation similar to that of the respective lipid substrate as disclosed herein (see also Long et al., 2000). The eight cognate and crossreactive peptide substrates presented herein bind with the Ca$_1$a$_2$X motif inserted into the peptide binding site, and bind without altering the enzyme or isoprenoid diphosphate structure, consistent with previous structures with bound substrates, products and inhibitors as disclosed herein (see also Park et al., 1997; Strickland et al., 1998; Long et al., 2000; Long et al., 2001; Long et al., 2002; deSolms et al., 2003). The Ca$_1$a$_2$X motif of the non-substrate Rap2b does not adopt an ordered conformation within the FTase active site, consistent with the observation that this peptide is a very poor FTase substrate.

Conformation of the Ca1a2X peptide backbone. The Ca$_1$a$_2$X motifs of the four FTase and six GGTase-I peptide substrates adopt the same "extended" conformation along one side of the funnel-shaped active site (FIG. 17A). The backbone of the Ca$_1$a$_2$X motif adopts a similar conformation in both FTase and GGTase; the only significant difference between FTase and GGTase-I peptide substrates is the positioning of the C-terminal X residue (FIG. 17B, discussed below). FTase appears to permit more flexibility within the Ca$_1$a$_2$X backbone: the four FTase and six GGTase-I substrates show an average backbone root mean square deviation (RMSD; as compared within each enzyme) of 0.93 Å and 0.29 Å, respectively. The Cys residue of the Ca$_1$a$_2$X motif, which is thought to bind as a thiolate, is located in the same position in all ten structures and coordinates the catalytic zinc ion (Hightower et al., 1998). Approximately 12 Å away from the Cys residue of the Ca$_1$a$_2$X motif, the C-termini of all substrate peptides are anchored by direct and water-mediated hydrogen bonds with conserved Gln, Glu, His, and Arg residues. A shift in GGTase-I helix 4β relative to FTase necessitates an additional water molecule to form hydrogen bonds between the C-terminus of GGTase-I peptide substrates and the conserved His residue.

Conformation of the a$_1$ and a$_2$ residues. The a$_1$ residues of the Ca$_1$a$_2$X motif (Val, Ala, Asn, and Lys) are mostly exposed to the solvent. At the a$_1$ position of Rap2a, an Asn side chain forms a hydrogen bond with FTase, and in RhoB a Lys side chain at the a$_1$ position is disordered in GGTase-I. In GGTase-I, but not in FTase, the a$_1$ residue is additionally stabilized by a water-mediated hydrogen bond between the carbonyl moiety of the a$_1$ residue and His 201α. Modeling studies using the Rap2a and γ2 peptide substrates presented here as a template indicate that both FTase and GGTase-I can accept any amino acid at the a$_1$ position without steric hindrance or altering the extended conformation of the Ca$_1$a$_2$X motif. These modeling studies also reveal that polar or charged $a_1$ residues could form direct or water-mediated hydrogen bonds with the enzyme.

Figure 12:
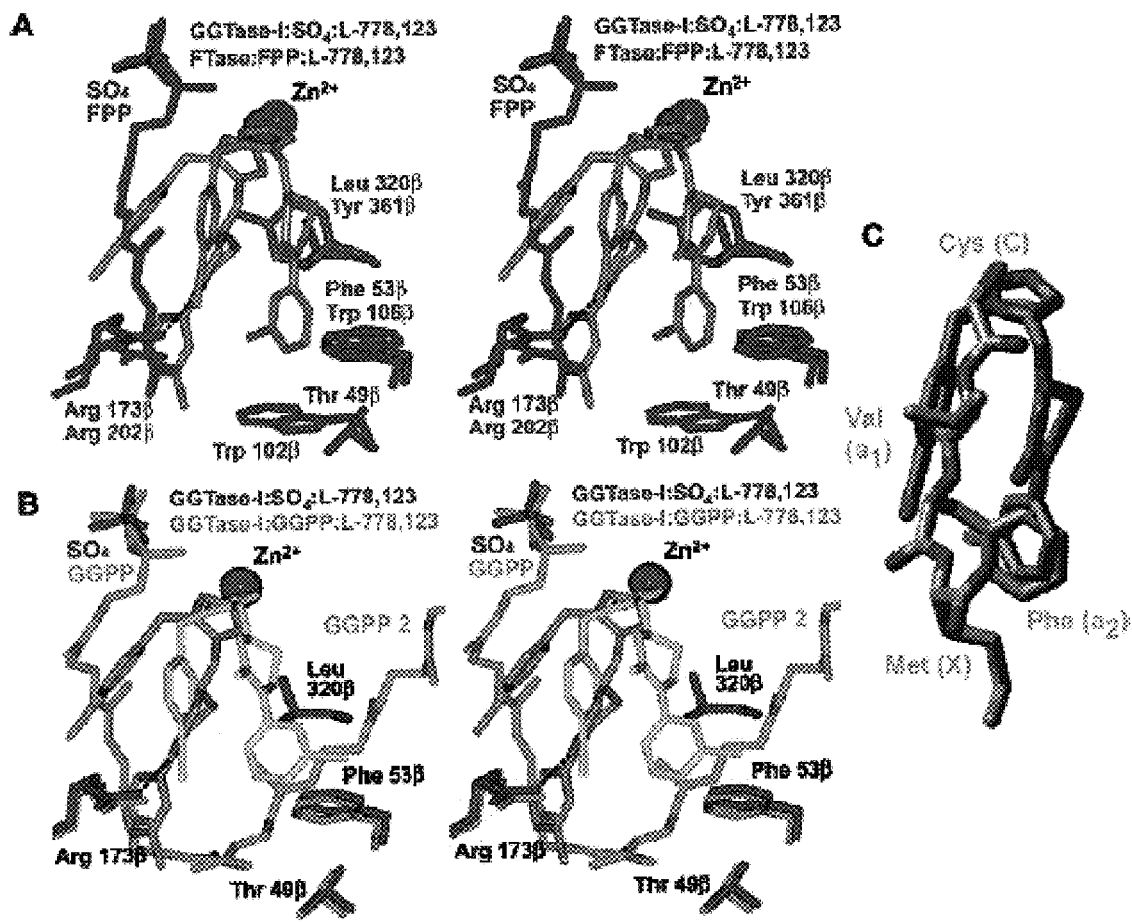
FIGS. 12A-12C depict superpositions of FTase and GGTase-I that suggest molecular mechanism for inhibitor selectivity.

For the peptide substrates presented here, all $a_2$ residues of the $Ca_1a_2X$ motif form a direct hydrogen bond with an Arg residue conserved in the β subunits of FTase (R202β) and GGTase-I (R173β). The side chains of the $a_2$ residues (Leu, Ile, and Val) bind isosterically in the hydrophobic "$a_2$ binding pocket," defined by regions of the protein and isoprenoid that contact the $a_2$ residue (FIG. 12, Table 6). Previous structural studies show that a Phe side chain can also bind in this space in FTase (Long et al., 2001). Additional modeling studies, again using the Rap2a and γ2 peptide substrates as a template, indicate that other similarly shaped amino acids such as Pro, Thr, Tyr, and Met can also be accommodated in the $a_2$ binding site of FTase and GGTase-I without steric clashes or significantly altering the conformation of the backbone of the $Ca_1a_2X$ peptide (Long et al., 2001. Large residues such as Arg or Trp cannot fit in the $a_2$ pocket without major disruptions to the $Ca_1a_2X$ motif backbone, and small amino acids such as Ala or Gly would leave unoccupied space. The hydrophobic nature of the a2 pocket makes it unlikely that it could accept charged or very polar residues such as Lys, Glu, Asp, His, Gln, Asn, Cys, or Ser. Peptide substrate recognition at the $a_2$ position of the $Ca_1a_2X$ motif is therefore dominated by steric and hydrophobic interactions between the $a_2$ residue and its binding site (see Table 6 for summary).

Figure 11:
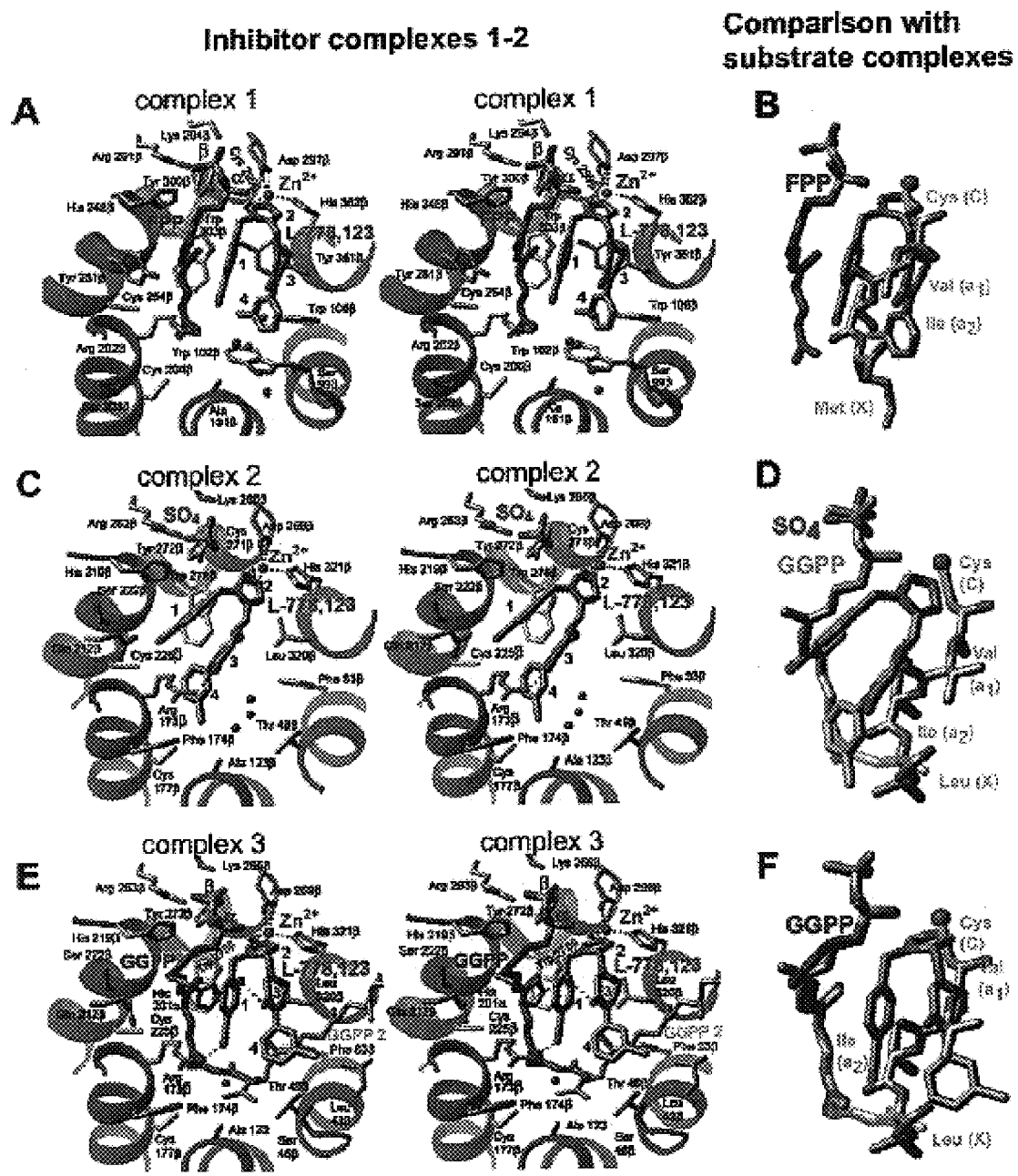
FIGS. 11A-11F depict different binding modes of L-778, 123 in FTase and GGTase-I. All structures are shown in approximately the same orientation.

Binding of the C-terminal X residue. In GGTase-I, the C-terminal Leu, Met, and Phe side-chains of the peptide substrates all bind isosterically in the hydrophobic "specificity pocket", defined by the residues and ligands that contact the X residue (FIG. 11B, Table 6). These three residues are stabilized entirely by hydrophobic interactions and van der Waals contact with the enzyme. Although the majority of GGTase-I substrates have Leu as the X residue, kinetic studies indicate that $Ca_1a_2X$ peptides with Ile or Val in the X position can also function as substrates for this enzyme (Moores et al., 1991; Roskoski & Ritchie, 1998). Examples of proteins with these C-terminal residues include 2'3'-cyclic nucleotide 3'phosphodiesterase (CTII; De Angelis & Braun, 1994), RhoJ/TCL (CSII) and the Cdc42 homolog Wrch-1 (CCFV; Tao et al., 2001). Using the RhoB peptide as a template, Ile or Val can be modeled in the specificity pocket without steric clashes or repositioning the $Ca_1a_2X$ motif backbone (Word et al., 1999). Larger amino acids such as Tyr, Trp and Arg, or Pro, which has restricted backbone flexibility, cannot be accommodated without disrupting the extended conformation of the $Ca_1a_2X$ motif. The hydrophobic nature of the GGTase-I specificity pocket is expected to discriminate against polar or charged residues.

Figure 19:
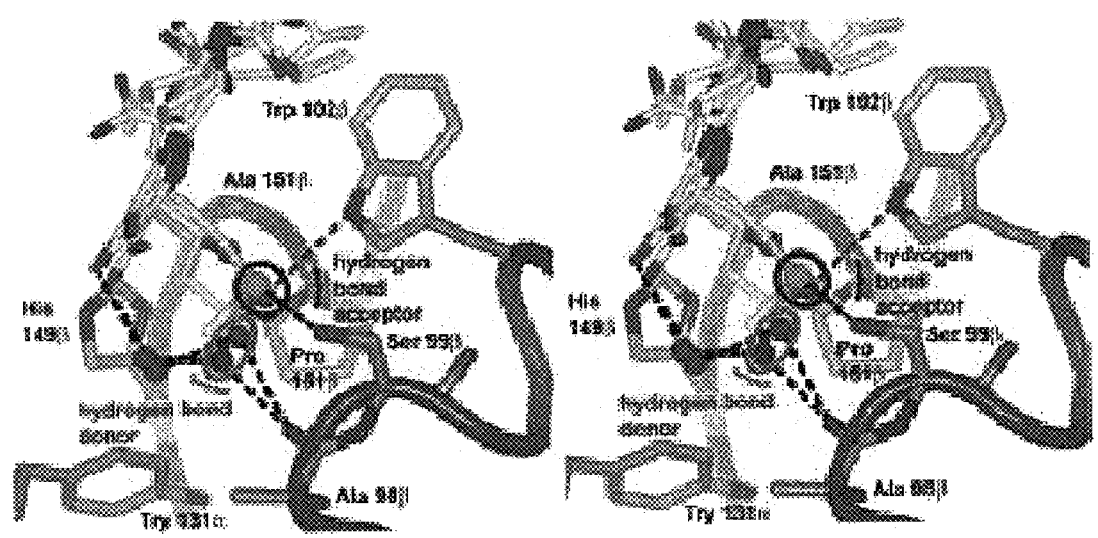
FIG. 19 depicts the FTase C-terminal X specificity pocket. Stereo pair shows a superposition of K-Ras4B (CVIM; SEQ ID NO: 24), Rap2a (CNIQ; SEQ ID NO: 26) and H-Ras (CVLS; SEQ ID NO: 3) peptides bound to FTase. Only the $Ca_1a_2X$ motif of substrate peptides and the residues in FTase that interact with the X-residue of the $Ca_1a_2X$ peptide, the "specificity pocket", are shown. A comparison of the binding of these three substrates reveals the FTase specificity pocket possesses two distinct subsites: one that can donate a hydrogen bond, and one that can accept a hydrogen bond. The $S_δ$ atom of Met (K-Ras4B; green sphere) and $O_{ε1}$ atom of Gln (Rap2a; red sphere) are hydrogen bond acceptors (circled in brown). The C-terminal $N_{ε2}$ atom of Gln (blue sphere), and the water molecule that accompanies the Ser of H-Ras (red sphere), are both hydrogen bond donors (circled in purple). The C-terminal residue of FTase substrates must not only complement the shape of the specificity pocket, but also place hydrogen bond donor or acceptor atoms in specific locations.

In FTase, the C-terminal Met, Gln, and Ser X residues of the peptide substrates all bind isosterically in the specificity pocket (FIG. 11B, Table 6). Unlike GGTase-I peptide substrates, these three X residues form both van der Waals and electrostatic interactions with the enzyme. The C-terminal Met (K-Ras4B) is oriented such that the thioether can accept a weak hydrogen bond from the Ser 99β hydroxyl group (sulfur-to-oxygen distance 3.2 Å; Desiraju & Steiner, 1999). The C-terminal Gln (Rap2a) donates a hydrogen bond to the 98β carbonyl oxygen and an adjacent buried water molecule and accepts a hydrogen bond from Trp 102β $N_{ε1}$. The smaller Ser (H-Ras) is accompanied by a water molecule hydrogen-bonded to the Ser hydroxyl and the adjacent Ala 98β carbonyl oxygen. A comparison of the binding of these three substrates reveals the FTase specificity pocket possesses two distinct subsites: one that can donate a hydrogen bond, and one that can accept a hydrogen bond (FIG. 19).

A surprising result was obtained when the binding of the TC21 peptide substrate in FTase was examined. Although the FTase specificity pocket is shaped incorrectly to accommodate the C-terminal Phe of the TC21 substrate, this peptide binds to FTase by placing the side chain of the X residue in an alternative hydrophobic binding site (FIG. 10C, Table 6), and two solvent molecules are now observed in the specificity pocket. The phenyl ring of the Phe is stabilized by face-on-face aromatic stacking interactions with Trp 102β (Jorgensen & Severance, 1990; Tatko, 2002), and a weak hydrogen bond with the Ser 99β hydroxyl (carbon-to-oxygen distance of 2.96 Å; Desiraju & Steiner, 1999). In addition to accommodating $Ca_1a_2X$ substrates terminating in a Phe residue, this secondary binding site could be utilized by atypical $Ca_1a_2X$ peptides.

Although the majority of known mammalian FTase substrates have Met, Ser, or Gln X residues (FIG. 20C), kinetic studies indicate that Thr, Cys, or Ala can also function as substrates (Moores et al., 1991; Roskoski & Ritchie, 1998). Examples of proteins with these C-terminal residues include the human proteins RhoQ (CLIT; SEQ ID NO: 15) (Murphy et al., 1996), the prostacyclin receptor, (CSLC; SEQ ID NO: 16; Hayes et al., 1999), and cerebral protein-5 (CVLA; SEQ ID NO: 17; Frattini et al., 1997). Using the H-Ras structure as a template, Cys, Ala, or Thr can be modeled in the specificity pocket without steric clashes or repositioning the $Ca_1a_2X$ motif backbone. As with Ser, these three X-residues would be

TABLE 6

Comparison of $Ca_1a_2X$ binding sites in FTase and GGTase-I

| Residue | | FTase | GGTase-1 |
|---|---|---|---|
| upstream residues | binding site | enzyme surface (variable) | enzyme surface (variable) |
| | accepts | no apparent restrictions | no apparent restrictions |
| C | binding site | coordinates catalytic zinc | coordinates catalytic zinc |
| | accepts | Cys only | Cys only |
| $a_1$ | binding site | solvent accessible H-bonding to enzyme possible | solvent accessible H-bonding to enzyme possible |
| | accepts | no apparent restrictions | no apparent restrictions |
| $a_2$ | binding site 1 "specificity pocket" | Trp 102β, Trp 106β, Tyr 361β, FPP isoprene 3 | Thr 49β, Phe 53β, Leu 320β, GGPP isoprene 3-4, X residue |
| | accepts | Val, Ile, Leu, Phe, Tyr, Thr, Met; preference for Ile, Val | Val, Ile, Leu, Phe, Tyr, Thr, Met; preference for Ile, Leu |
| X | binding site | Tyr 131α, Ala 98β, Ser 99β, Trp102β, His 149β, Ala 151β, Pro 152β | Thr 49β, His 121β, Ala 123β, Phe174β, 4th GGPP isoprene, $a_2$ residue |
| | accepts | Met, Gln-polar interactions Ser, Ala, Thr, Cys-with buried water | Leu, Ile, Val, Phe |
| | binding site 2 | Leu 96β, Ser 99β, Trp 102β, Trp 106β, Ala 151β, 3rd FPP isoprene, $a_2$ residue | not observed |
| | accepts | Phe, possibly Leu, Asn, or His | not observed | accompanied by a buried water molecule that fills unoccupied space in the specificity pocket. The FTase specificity pocket is incorrectly shaped to accommodate other residues with a van der Waals shape similar to that of Glu or Met, including His, Asn, Leu, Phe, and Ile. Larger residues such as Tyr, Trp and Arg, or Pro, which has restricted backbone flexibility, cannot be accommodated without disrupting the extended conformation of the $Ca_1a_2X$ motif. Although Leu or the polar residues Asn and His (at pH 7.5) cannot be modeled in the FTase specificity pocket without steric clashes, $Ca_1a_2X$ peptides with these residues in the X position (e.g. peptides derived from RhoB, with a C-terminal Leu) can function as FTase substrates (Moores et al., 1991; Adamson et al., 1992; Roskoski & Ritchie, 1998; Baron et al., 2000). Using the TC21 peptide as a template, a C-terminal Asn, His, or Leu can be placed in the secondary binding site where Phe binds without steric clashes or distorting the $Ca_1a_2X$ backbone. As with TC21, $Ca_1a_2X$ sequences terminating in these three residues would be predicted to bind with two water molecules occupying the specificity pocket. Furthermore, although the charged residues Glu or Asp could bind in a manner similar to Gln or Asn, respectively, there are no residues available to stabilize the negative charges of these two residues, so such binding would be expected to be of low affinity.

Figure 21:
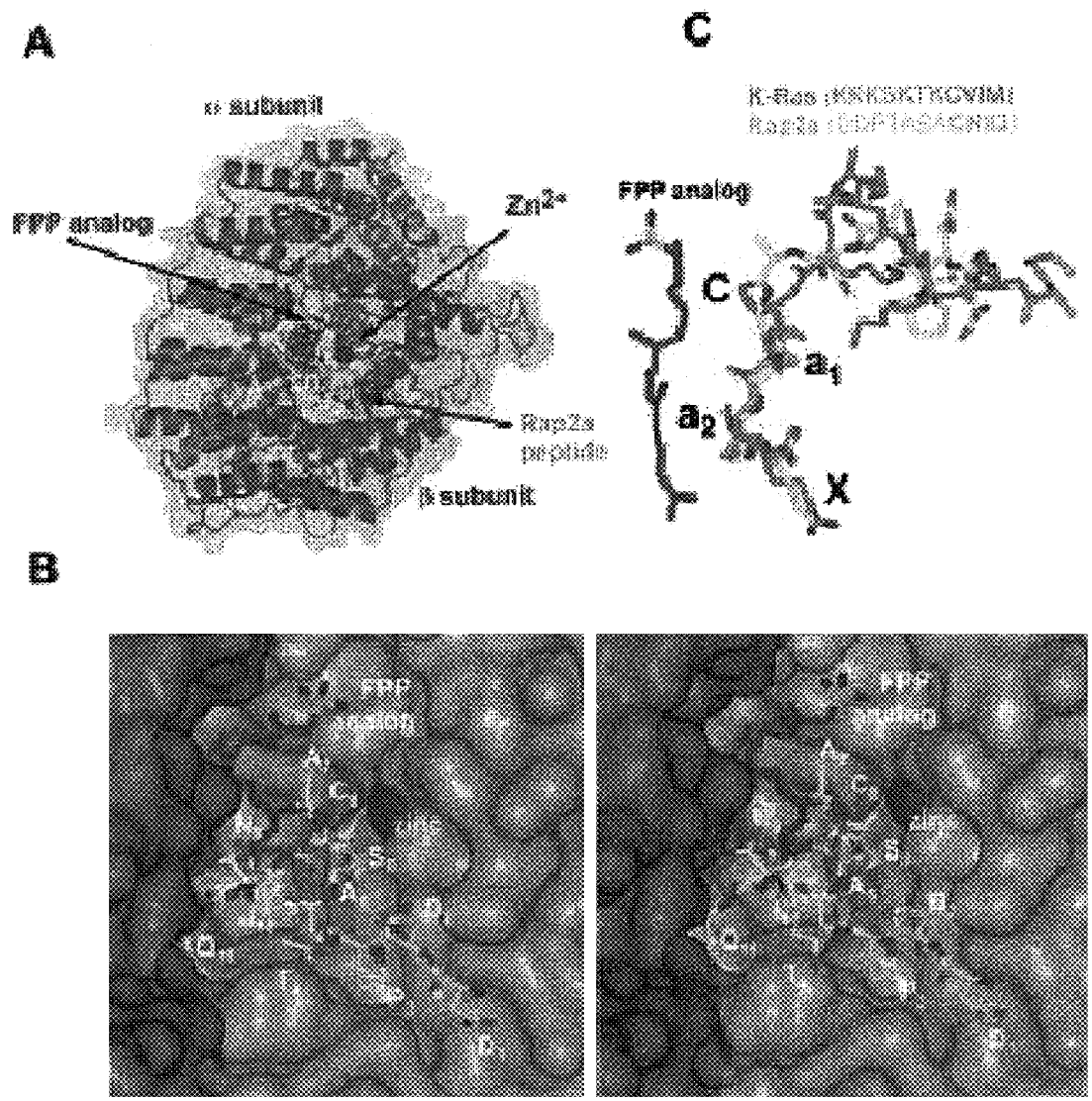
FIGS. 21A-21C depict peptide substrate binding upstream of the $Ca_1a_2X$ motif.

Effect of peptide sequence upstream of the $Ca_1a_2X$ motif on binding. In FTase, the upstream sequences of Rap2a (DDPTASA; SEQ ID NO: 18, FIGS. 21A and 21B) and K-Ras4B (KKKSKTK; SEQ ID NO: 19) bind along the rim of the peptide binding site, stabilized primarily by direct and water-mediated hydrogen bonds with the surface of the enzyme. Although these two upstream sequences each adopt significantly different conformations, the $Ca_1a_2X$ motifs of the two peptides adopt the same extended conformation discussed above (FIG. 21C). In all GGTase-I substrate complexes, the sequences upstream of the $Ca_1a_2X$ motif (KKKSKTK (SEQ ID NO: 19) for K-Ras4B, FREKKFF (SEQ ID NO: 20) for γ6 and GCINC (SEQ ID NO: 21) for RhoB) are partially disordered, with electron density disappearing two or three residues beyond the Cys residue of the $Ca_1a_2X$ motif. Regardless of the upstream sequence, all $Ca_1a_2X$ substrates adopt the same conformation in the GGTase-I active site. Indeed, the results presented herein show that the $Ca_1a_2X$ motif of RhoB (CKVL; SEQ ID NO: 22) binds identically to GGTase-I whether the upstream sequence is native (GCINC; SEQ ID NO: 21), or contains the polylysine sequence derived from K-Ras4B (KKSKTK; SEQ ID NO: 19).

Figure 20:
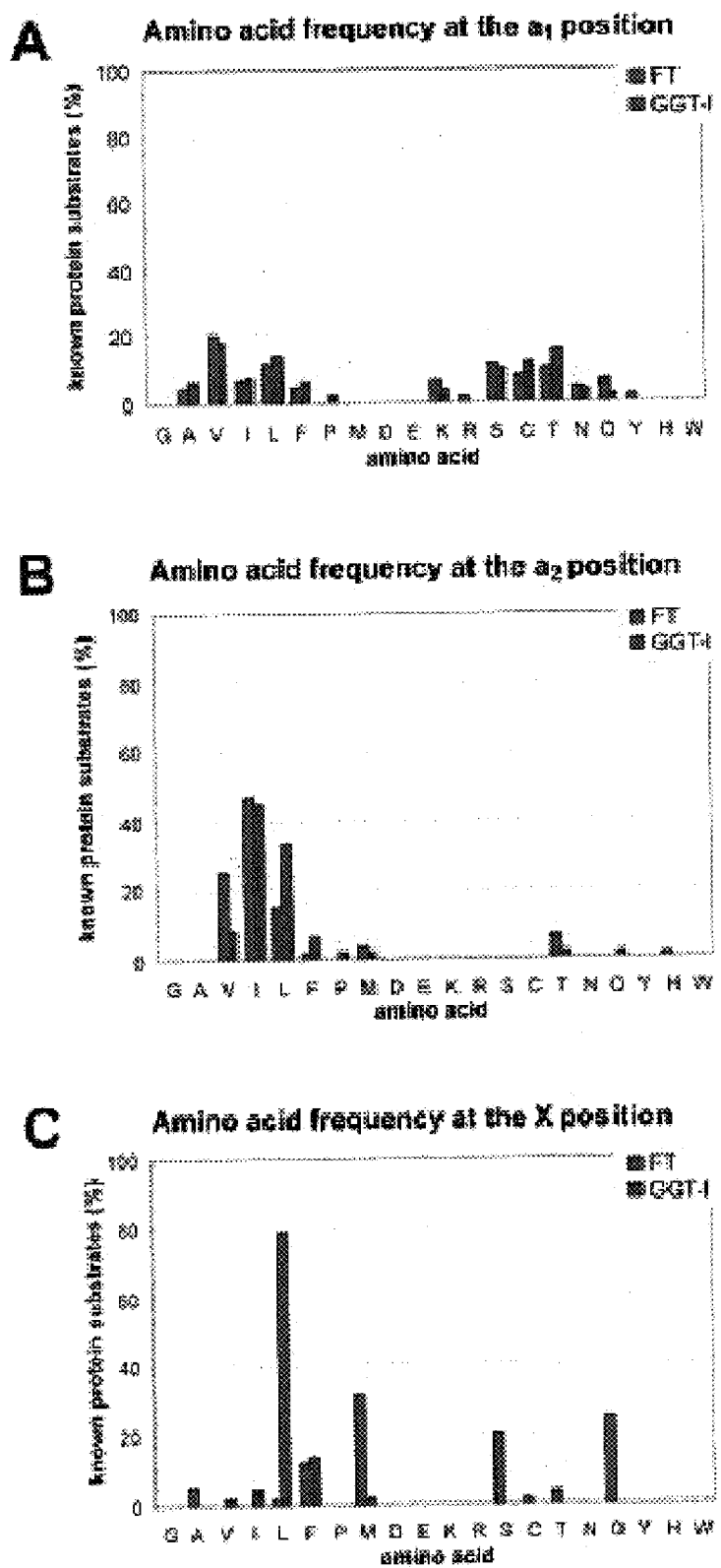
FIGS. 20A-20C depict amino acid sequence preferences within the $Ca_1a_2X$ motif.

A CaaX prenyltransferase peptide specificity model. A comparison of the eleven structures discussed herein suggests a series of rules that govern peptide substrate specificity for the CaaX prenyltransferases (Table 6). Substrate peptide binding clearly does not induce a change in the peptide binding site. The $Ca_1a_2X$ motif of substrate peptides bind in the rigid peptide binding site in an extended conformation, anchored at the Cys residue by zinc-coordination and at the C-terminal end by direct and water-mediated hydrogen bonds. These two fixed anchor points discriminate against peptides that are too long or too short or that lack a cysteine at the correct position. In this conformation, any amino acid can be accommodated at the $a_1$ position. An analysis of proteins shown to be prenylated illustrates that there is, in fact, little preference shown by either enzyme for specific amino acids in the $a_1$ position (FIG. 20A). Unexpectedly, however, it has been found that polar or charged amino acids at the $a_1$ position, such as Asn in Rap2a, can form direct or water-mediated hydrogen bonds with the enzyme and thereby enhance binding affinity. The $a_2X$ residues are buried in the active site, and substrate specificity for cognate and cross-reactive $Ca_1a_2X$ motif peptides is determined by steric and electrostatic complementarity between the $a_2$ residue and the $a_2$ binding pocket, and the X residue and the specificity pocket. Although sequence upstream of the $Ca_1a_2X$ motif can enhance peptide substrate affinity through electrostatic interactions with the protein surface, this sequence does not influence the conformation of the $Ca_1a_2X$ motif itself, and should not permit $Ca_1a_2X$ peptides that violate the general rules of specificity to function as proper substrates. There is no indication that either GGTase-I or FTase have specific sites that bind upstream sequences in a generalized conformation, in contrast to the binding site for the $Ca_1a_2X$ motif itself. Indeed, upstream sequences of $Ca_1a_2X$ proteins are highly variable, and in fact this region has been dubbed the hypervariable region in Ras superfamily members (Barbacid, 1987).

Sequence preference at the $a_2$ position. The $a_2$ binding sites of FTase and GGTase-I have unique steric and aromatic properties, suggesting that the $a_2$ residue can influence $Ca_1a_2X$ prenyltransferase peptide recognition. Overall, the structures presented herein suggest that accommodation of the $a_2$ residue is primarily restricted to Val, Ile, Leu, Phe, Tyr, Pro, Thr, and Met, consistent with the previous studies of FTase peptide selectivity in mammalian and yeast systems (Reiss et al., 1991; Dolence et al., 2000). The $a_2$ binding site in FTase is smaller and has more aromatic character than the corresponding binding site in GGTase-I (Table 6, FIG. 12). To investigate whether these differences influence peptide selectivity, an analysis of all proteins known to be prenylated for amino acid preferences at the $a_2$ position of the $Ca_1a_2X$ motif was undertaken (FIG. 20B). As expected, the small aliphatic amino acids Leu, Val and Ile predominate. There do, however, appear to be subtle preferences within this group: for FTase, Val is observed more often than Leu, whereas in GGTase-I Leu is seen more commonly than Val; Ile, however, appears equally in substrates for both enzymes. This is consistent with the differently sized binding sites for the $a_2$ residue in FTase and GGTase-I, and suggests that the $a_2$ residue can influence peptide substrate preferences. This comparison, however, does not reveal any a2 residue that absolutely determines whether a $Ca_1a_2X$ motif is a GGTase-I or FTase substrate (as is the case with the X residue within the $Ca_1a_2X$ motif).

Sequence preference at the C-terminal X position. The X residue of the $Ca_1a_2X$ motif is the primary determinant of whether a peptide is a substrate for FTase, GGTase-I, both or neither. Overall, the results of this study are consistent with previous kinetic analyses examining the effect of the X residue on peptide specificity (Casey et al., 1991; Moores et al., 1991; Reiss et al., 1991; Yokoyama et al., 1991; Roskoski & Ritchie, 1998). The structures presented herein demonstrate that recognition of the X residue is a function of steric and electrostatic complementarity between the X residue and the specificity pocket. The specificity pockets of both $Ca_1a_2X$ prenyltransferases discriminate against bulky amino acids such as Tyr, Trp, or Arg. The specificity pocket of FTase can accommodate similarly-shaped hydrophobic (Met) or polar residues (Gln), or small residues (Cys, Ser, Thr, or Ala) that are accompanied by a buried water molecule. These three residue types are stabilized by a specific network of electrostatic interactions (FIG. 19). While the FTase specificity pocket can accommodate polar residues, it cannot accommodate charged residues such as Lys, Asp, or Glu. Interestingly, the presently disclosed subject matter shows that while the FTase specificity pocket is too small to accommodate a Phe group, this residue can bind in an adjacent hydrophobic cavity. This alternate binding site could also accommodate other atypical X residues such as Leu, Asn, or His. In contrast, GGTase-I has only one binding site for X residues, and this specificity pocket is shaped to accommodate hydrophobic residues with a van der Waals shape similar to Leu, including Met, Phe, Ile and Val (FIG. 20C). The hydrophobic nature of the specificity pocket in GGTase-I discriminates against appropriately shaped polar or charged amino acids, including Glu, Gln and His, and also against small residues such as Gly, Ser, or Ala binding in conjunction with a buried solvent molecule, as observed in FTase. The GGTase-I specificity pocket thus discriminates against all X-residues of FTase substrates except Met and Phe, both of which can fit into the GGTase-I specificity pocket through a change in conformation in the X-residue side chain.

A model of peptide cross-specificity. The proteins TC21, K-Ras4B and RhoB have C-terminal $Ca_1a_2X$ motifs that permit them to function as both FTase and GGTase-I substrates. The structures presented herein suggest that cross-reactivity of substrate peptides is a function of their unique sequences rather than any special binding conformation, particularly in the X position, that permit binding in the active sites of both enzymes.

Peptides derived from RhoB bind in the same conformation to GGTase-I as other substrate peptides. While it was not possible to crystallize a complex of FTase with RhoB, the structures presented herein permit a hypothetical model of RhoB binding in FTase to be constructed. This model might explain why this Leu-terminal peptide functions as a FTase substrate while others do not. The $Ca_1a_2X$ peptide of RhoB was modeled bound to FTase using the CVIF (SEQ ID NO: 23) peptide from TC21 as a template and mutating the side chain identities of the latter to CKVL (SEQ ID NO: 22). The C-terminal Leu side chain of RhoB could be placed in the same location as the Phe side chain of TC21; i.e., the alternate hydrophobic site rather than the specificity pocket, without steric clashes with the surrounding protein and FPP ligand. The Val residue in the $a_2$ position of RhoB could be nicely modeled as binding as the Ile of TC21 does. The Lys side chain in the $a_1$ position of RhoB can adopt numerous conformations, several of which permit direct or water-mediated hydrogen bonds with the FTase, suggesting that the Lys group stabilizes binding via a hydrogen bond with the enzyme. Furthermore, the a2 Val residue, which better complements the a2 binding site in FTase than Leu or other larger residues, may also be crucial, as it is smaller and less likely to clash with the terminal Leu as modeled. The importance of these two particular a1 and a2 residues is further highlighted by a comparison with another GGTase-I substrate, Rap2b (CVIL; SEQ ID NO: 2), whose $Ca_1a_2X$ motif differs from that of RhoB only in the $a_1$ and $a_2$ residues. This peptide, unlike RhoB, cannot serve as a FTase substrate) Roskoski & Ritchie, 1998), indicating a gain-of-function associated with the Lys and Val residues in the $a_1$ and $a_2$ positions of RhoB. Together with studies of the ability of RhoB proteins containing altered $Ca_1a_2X$ sequences to be modified by FTase or GGTase-I, the presently disclosed subject matter indicates that it is the specific combination of the $a_1$, $a_2$, and X residues of the CKVL (SEQ ID NO: 22) sequence that allows RhoB to function as a FTase substrate.

A compilation of $Ca_1a_2X$ prenyltransferase substrates. Using the rules of protein substrate specificity delineated herein and summarized in Table 6, an extensive list of known and hypothetical prenylated proteins has been generated by database searching. The results of this search is presented in FIGS. 22 and 23. While it is certainly possible that some proteins included in the list incorporate their C-terminus into the protein fold and are therefore not prenylated, the search revealed some interesting potential substrates, including two B melanoma antigen (BAGE) proteins that are expressed in melanomas, bladder and lung carcinomas and other tumor types, but not most normal tissues (Ruault et al., 2002). In addition to highlighting the functional diversity of $Ca_1a_2X$ prenyltransferase substrates, this list might be useful for identifying novel prenylated proteins involved in oncogenesis and in understanding the biological effects of $Ca_1a_2X$ prenyltransferase inhibitors.

Implications for drug design. Understanding enzyme substrate specificity is a key component of designing drugs that are selective towards one particular enzyme over another. $Ca_1a_2X$ prenyltransferase inhibitors are under evaluation in phase II/III clinical trials for the treatment of cancer and, in preclinical studies, show indications for the treatment of hepatitis C and D and parasitic infections such as malaria and sleeping sickness. Because complete inhibition of prenylation can be toxic, the use of these inhibitors as human therapeutics will likely require that these inhibitors are selective towards a specific prenylation enzyme. Comparison of the structures presented herein highlight features unique to FTase and GGTase-I that can be exploited to achieve this selective inhibition. In GGTase-I and FTase, the residues that coordinate the $a_2X$ portion of substrate $Ca_1a_2X$ are significantly different. Specifically, differences in the hydrogen bonding within the FTase specificity pocket and the aromatic character of the $a_2$ pocket could be exploited to create more selective inhibitors.

REFERENCES

The references listed below as well as all references cited in the specification are incorporated herein by reference to the extent that they supplement, explain, provide a background for or teach methodology, techniques and/or compositions employed herein.

Adams P D, Pannu N S, Read R J & Brünger A T (1997) Cross-validated maximum likelihood enhances crystallographic simulated annealing refinement. *Proc Natl Acad Sci USA* 94:5018-23.

Adamson P, Marshall C J, Hall A & Tilbrook P A (1992). Post-translation modifications of p21 rho proteins, *J Biol Chem* 267:20033-20038.

Adjei A (2001) Blocking oncogenic Ras signaling for cancer therapy, *J Natl Cancer Inst* 93:1062-74.

Agrawal S (ed.) (1993) Protocols for oligonucleotides and analogs: synthesis and properties; Methods in Molecular Biology, volume 20, Humana Press, Totowa, N.J., United States of America.

Alexandrov K, Horiuchi H, Steele-Mortimer O, Seabra M C & Zerial M (1994) Rab escort protein-1 is a multifunctional protein that accompanies newly prenylated rab proteins to their target membranes, *EMBO J.* 13:5262-73.

Allen F H, Davies J E, Galloy J, Johnson 0, Kennard 0, Macrea C F, Mitchell E M, Mitchell G F, Smith J M & Watson D G (1991) The development of version 3 and version 4 of the Cambridge Structural Database system. *J Chem Inf Comput Sci* 31:187-195.

Altschul S F, Gish W, Miller W, Myers E W & Lipman D J (1990) Basic Local Alignment Search Tool, *J Mol Biol* 215:403-410.

Amemiya Y (1997) *Methods in Enzymology*, Vol. 276. Academic Press, San Diego, United States of America, at pp. 233-243.

Andres D A, Seabra M C, Brown M S, Armstrong S A, Smeland T E, Cremers F P & Goldstein J L (1993) cDNA cloning of component A of Rab geranylgeranyl transferase and demonstration of its role as a Rab escort protein. *Cell* 73:1091-9.

Appelt K (1993) Crystal structures of HIV-1 protease-inhibitor complexes. *Perspectives in Drug Discovery and Design* 1:23-48.

Armstrong S A, Hannah V C, Goldstein J L & Brown M S (1995) CaaX geranylgeranyl transferase transfers farnesyl as efficiently as geranylgeranyl to RhoB, *J Biol Chem* 270:7864-7868.

Ausubel F M, Brent R, Kingston R E, Moore D, Seidman J G, Smith J A & Struhl K, eds (1994) *Current Protocols in Molecular Biology*. Wiley, New York, United States of America.

Barbacid M (1987). ras Genes. *Annu Rev Biochem* 56:779-827.

Baron R, Fourcade E, Lajoie-Mazenc I, Allal C, Couderc B, Barbaras R, Favre G, Faye J C & Pradines A (2000). RhoB prenylation is driven by the three carboxylterminal amino acids of the protein: evidenced in vivo by an anti-farnesyl cysteine antibody, *Proc Natl Acad Sci USA* 97:11626-11631.

Bartlett et al. (1989) *Special Publ, Royal Chem Soc* 78: 182-96.

Bell I M, Gallicchio S N, Abrams M, Beese L S, Beshore D C, Bhimnathwala H, Bogusky M J, Buser C A, Culberson J C, Davide J, Ellis-Hutchings M, Fernandes C, Gibbs J B, Graham S L, Hamilton K A, Hartman G D, Heimbrook D C, Homnick C F, Huber H E, Huff J R, Kassahun K, Koblan K S, Kohl N E, Lobell R B, Lynch J, Jr, Robinson R, Rodrigues A D, Taylor J S, Walsh E S, Williams T M & Zartman C B (2002) 3-Aminopyrrolidinone farnesyltransferase inhibitors: design of macrocyclic compounds with improved pharmacokinetics and excellent cell potency. *J Med Chem* 45: 2388-2409.

Bergo M O, Leung G K, Ambroziak P, Otto J C, Casey P J & Young S G (2000) Targeted inactivation of the isoprenylcysteine carboxyl methyltransferase gene causes mislocalization of K-Ras in mammalian cells, *J Biol Chem* 275: 17605-10.

Blundell T L & Johnson L N (1976) *Protein Crystallography*, Academic Press, New York, N.Y., United States of America.

Blundell T L & Johnson L N (1985) *Method. Enzymol.* 114A & 115B, (Wyckoff et al., eds.), Academic Press.

Bohm H J (1992) LUDI: Rule-Based Automatic Design of New Substituents for Enzyme Inhibitor Leads *J Comput Aid Mol Des* 6:593-606.

Boobbyer D N, Goodford P J, McWhinnie P M & Wade R C (1989) New hydrogen-bond potentials for use in determining energetically favorable binding sites on molecules of known structure. *J Med Chem* 32:1083-1094.

Bowie J U, Luthy R & Eisenberg D (1991) A method to identify protein sequences that fold into a known three-dimensional structure. *Science* 253:164-70.

Brint A T & Willett P (1987) Pharmacophoric pattern matching in files of 3D chemical structures: comparison of geometric searching algorithms. *J Mol Graph* 5:49-56.

Brooks B R, Bruccoleri R E, Olafson B D, States D J, Swaminathan S & Karplus M (1983) CHARMM: A program for macromolecular energy minimization and dynamics calculations. *J Comp Chem* 4:187-217.

Brünger A T (1992) *X-PLOR, Version 3.1. A System for X-ray Crystallography and NMR*, Yale University Press, New Haven, Conn., United States of America.

Brünger A T, Adams P D, Clore G M, DeLano W L, Gros P, Grosse-Kunstleve R W, Jiang J-S, Kuszewski J, Nilges M, Pannu N S, Read R J, Rice L M, Simonson T & Warren G L (1998) Crystallography & NMR System: A New Software Suite for Macromolecular Structure Determination, *Acta Crystallogr D* 54:905-921.

Buckner F S, Eastman R T, Nepomuceno-Silva J L, Speelmon E C, Myler P J et al. (2002) Cloning, heterologous expression, and substrate specificities of protein farnesyltransferases from *Trypanosoma cruzi* and *Leishmania major, Mol Biochem Parasitol* 122:181-188.

Bugg C E, Carson W M & Montgomery J A (1993) Drugs by Design. *Scientific American* 269:92-98.

Bundell et al. (1988) *Eur J Biochem* 172:513.

Caponigro F, Casale M & Bryce J (2003) Farnesyl transferase inhibitors in clinical development, *Expert Opin Invest Drugs* 12:943-954.

Case D A, Pearlman F A, Caldwell J W, Cheatham T E III, Ross W S, Simmerling C L, Darden T A, Mertz K M, Stanton R V, Cheng A L, Vincent J, Crowley M, Ferguson D M, Radmer R J, Seibel G L, Singh UC, Weiner P K & Kollmann P A (1997) AMBER 5, University of California, San Francisco.

Casey P J & Seabra M C (1996) Protein prenyltransferases. *J Biol Chem* 271:5289-5292.

Casey P J, Thissen J A & Moomaw J F (1991) Enzymatic modification of proteins with a geranylgeranyl isoprenoid, *Proc Natl Acad Sci USA* 88:8631-8635.

Chakrabarti D, Azam T, DelVecchio C, Qiu L, Park Y I & Allen C M (1998) Protein prenyl transferase activities of *Plasmodium falciparum, Mol Biochem Parasitol* 94:175-84.

Choy E, Chiu V K, Silletti J, Feoktistov M, Morimoto T, Michaelson D, Ivanov I E & Philips M R (1999) Endomembrane trafficking of ras: the CAAX motif targets proteins to the ER and Golgi. *Cell,* 98, 69-80.

Clausen V A, Edelstein R L & Distefano M D (2001) Stereochemical analysis of the reaction catalyzed by human protein geranylgeranyl transferase. *Biochem* 40, 3920-3930.

Cohen N C, Blaney J M, Humblet C, Gund P & Barry D C (1990) Molecular Modeling Software and Methods for Medicinal Chemistry. *J Med Chem* 33:883-894.

Collaborative Computational Project, Number 4. 1994. *Acta Cryst D*50:760-763.

Cox A D (2001) Farnesyltransferase inhibitors: potential role in the treatment of cancer, *Drugs* 61:723-32.

Creighton T E (1983) *Proteins: Structures and Molecular Principles*, W.H. Freeman & Co., New York, N.Y., United States of America.

Cwirla S E, Peters E A, Barrett R W & Dower W J (1990) Peptides on phage: a vast library of peptides for identifying ligands. *Proc Natl Acad Sci USA* 87:6378-6382. De Angelis D A & Braun P E (1994). Isoprenylation of brain 2',3'-cyclic nucleotide 3'-phosphodiesterase modulates cell morphology. *J Neurosci Res* 39:386-397.

Delano W L (2002). *The PYMOL molecular graphics system*. DeLano Scientific, San Carlos, Calif.

Del Villar K, Urano J, Guo L & Tamanoi F (1999) A mutant form of human protein farnesyltransferase exhibits increased resistance to farnesyltransferase inhibitors. *J Biol Chem* 274:27010-27017.

De Moliner E, Brown N R & Johnson, L N (2003) Alternative binding modes of an inhibitor to two different kinases, *Eur J Biochem* 270:3174-3181.

DesJarlais R L, Sheridan R P, Dixon J S, Kuntz I D & Venkataraghavan R (1986) Docking flexible ligands to macromolecular receptors by molecular shape. *J Med Chem* 29:2149-2153.

DesJarlais R L, Sheridan R P, Seibel G L, Dixon J S, Kuntz I D & Venkataraghavan R (1988) Using shape complementarity as an initial screen in designing ligands for a receptor binding site of known three-dimensional structure. *J Med Chem* 31:722-729.

Desiraju G R & Steiner T (1999). *The weak hydrogen bond in structural chemistry and biology*. Monographs on Crystallography, 9, Oxford University Press/International Union of Crystallography, Oxford, England.

Desnoyers L & Seabra M C (1998) Single prenyl-binding site on protein prenyltransferases, *Proc Natl Acad Sci USA* 95:12266-70.

deSolms S J, Ciccarone T M, MacTough S C, Shaw A W, Buser C A, Ellis-Hutchings M, Fernandes C, Hamilton K A, Huber H E, Kohl N E, Lobell R B, Robinson R G, Tsou N, Walsh E S, Graham S L, Beese L S & Taylor J S (2003) Dual protein farnesyltransferase—geranylgeranyltransferase-1 inhibitors as potential cancer chemotherapeutic agents. *J Med Chem* 46:2973-2984.

Devlin J, Panganiban L C & Devlin P E (1990) Random peptide libraries: a source of specific protein binding molecules. *Science* 249:404-406.

Dinsmore C J & Bell I M (2003) Inhibitors of farnesyltransferase and geranylgeranyltransferase-1 for antitumor therapy: Substrate-based design, conformational constraint, and biological activity, *Curr Top Med Chem* 3:1075-1093.

Dinsmore C J, Bogusky M J, Culberson J C, Bergman J M, Homnick C F, et al. (2001) Conformational restriction of flexible ligands guided by the transferred NOE experiment: Potent macrocyclic inhibitors of farnesyltransferase, *J Am Chem Soc* 123:2107-2108.

Dolence J M, Cassidy P B, Mathis J R & Poulter C D (1995) Yeast protein farnesyltransferase: steady-state kinetic studies of substrate binding, *Biochemistry* 34:16687-16694.

Dolence J M, Steward L E, Dolence E K, Wong D H & Poulter C D (2000). Studies with recombinant *Saccharomyces cerevisiae* CaaX prenyl protease Rce1p, *Biochemistry* 39:4096-4104.

Ducruix A & Geige G (1992) *Crystallization of Nucleic Acids and Proteins: A Practical Approach*, IRL Press, Oxford, England.

Dunbrack R L Jr, Gerloff D L, Bower M, Chen X, Lichtarge 0 & Cohen F E (1997) Meeting review: the Second meeting on the Critical Assessment of Techniques for Protein Structure Prediction (CASP2), Asilomar, Calif., December 13-16,1996. *Folding & Design* 2:R27-42.

Dunten P, Kammlott U, Crowther R, Weber D, Palermo R & Birktoft J (1998) Protein Farnesyltransferase: Structure and Implications for Substrate Binding, *Biochemistry* 37:7907-7912.

Ebel S, Lane A N & Brown T (1992) Very stable mismatch duplexes: structural and thermodynamic studies on tandem G.A mismatches in DNA. *Biochem* 31:12083-6.

Eisen M B, Wiley D C, Karplus M & Hubbard R E (1994). HOOK: a program for finding novel molecular architectures that satisfy the chemical and steric requirements of a macromolecule binding site. *Proteins* 19:199-221.

Erickson (1993) *Perspectives in Drug Discovery and Design* 1:109-128.

Erlanson D A, Braisted A C, Raphael D R, Randal M, Stroud R M et al., (2000) Site-directed ligand discovery, *Proc Natl Acad Sci USA* 97:9367-9372.

Farnsworth C, Seabra M C, Ericsson L H, Gelb M H & Glomset J A (1994) Rab geranylgeranyl transferase catalyzes the geranylgeranylation of adjacent cysteines in the small GTPases, Rab1A, Rab3A and Rab5A, *Proc Natl Acad Sci USA* 91:11963-11967.

Fitzgerald P MD (1988) *J Appl Cryst* 21:273-278.

Frattini A, Faranda S, Zucchi I & Vezzoni P (1997) A low-copy repeat in Xq26 represents a novel putatively prenylated protein gene (CXX1) and its pseudogenes (DXS9914, DXS9915, and DXS9916), *Genomics* 46:167-169.

Goeddel; Gene Expression Technology, in *Methods in Enzmmology*, volume 185, Academic Press, San Diego, Calif., United States of America.

Goodford P J (1985) A Computational Procedure for Determining Energetically Favorable Binding Sites on Biologically Important Macromolecules. *J Med Chem* 28:849-857.

Goodsell D S & Olson A J (1990) Automated Docking of Substrates to Proteins by Simulated Annealing. *Proteins* 8:195-202.

Greer J (1985) Model structure for the inflammatory protein C5a. *Science* 228:1055-60.

Gribskov M & Burgess R (1986) Sigma Factors from *E. coli, B. Subtilis*, Phage Sp01, and Phage T4 Are Homologous Proteins. *Nucleic Acids Res* 14:6745-6763.

Guex N & Peitsch M C (1997) SWISS-MODEL and the Swiss-PdbViewer: An environment for comparative protein modeling, *Electrophoresis* 18:2714-2723.

Gutberlet T, Heinemann U & Steiner M (2001) *Acta Crystallogr D Biol Crystallogr* 57:349-54.

Hahn M (1997) Three-dimensional shape-based searching of conformationally flexible compounds. *Chem. Inf. Comp. Sci.* 37: 80-86.

Hajduk P J, Gomtsyan A, Didomenico S, Cowart M, Bayburt E K et al. (2000) Design of adenosine kinase inhibitors from the NMR-based screening of fragments, *J Med Chem* 43:4781-4786.

Hauptman H (1997) Phasing Methods for Protein Crystallography. *Curr Opin Struct Biol* 7:672-680.

Hayes J S, Lawler O A, Walsh M T & Kinsella B T (1999). The prostacyclin receptor is isoprenylated. Isoprenylation is required for efficient receptor-effector coupling, *J Biol Chem* 274:23707-23718.

Hendrickson W A (2000) Synchrotron crystallography. *Trends Biochem Sci* 25:637-43.

Hendrickson W A & Ogata C M (1997) *Meth Enzymol* 276: 494-523.

Hightower K E, Huang C-C, Casey P J & Fierke C A (1998) H-ras peptide and protein substrates bind protein farnesyltransferase as an ionized thiolate, *Biochemistry* 37:15555-15562.

Hoffman G R, Nassar N & Cerione R A (2000) Structure of the Rho family GTP binding protein Cdc42 in complex with the multifunctional regulator RhoGDI, *Cell* 100:345-56.

Holton J M & Alber T (2004) Automated protein crystal structure determination using ELVES, *Proc Natl Acad Sci USA* 101:1537-1542.

Horiuchi H, Kawata M, Katayama M, Yoshida Y, Musha T, Ando S & Takai Y (1991) A novel prenyltransferase for a small GTP-binding protein having a C terminal Cys-Ala-Cys structure, *J Biol Chem* 266:16981-4.

Huber H E, Robinson R G, Watkins A, Nahas D, Abrams M T, et al. (2001) Anions modulate the potency of geranylgeranyl-protein transferase-1 inhibitors, *J Biol Chem* 276: 24457-24465.

Jakes S E & Willett P (1986) Pharmacophoric pattern matching in files of 3-D chemical structures: selection of interatomic distance screens. *J Mol Graph* 4:12-20.

Jakes S E, Watts N, Willett P, Bawden D & Fisher J D (1987) Pharmacophoric pattern matching in files of 3D chemical structures: evaluation of search performance. *J Mol Graph* 5:41-48.

James G L, Goldstein J L & Brown M S (1995) Polylysine and CVIM sequences of K-RasB dictate specificity of prenylation and confer resistance to benzodiazepine peptidomimetic in vitro, *J Biol Chem* 270:6221-6226.

Jancarik J & Kim S H (1991) *J Appl Cryst* 24:409-411.

Johnston S R D (2001). Farnesyl transferase inhibitors: a novel targeted therapy for cancer, *The Lancet Oncology* 2:18-26.

Jones T A & Kjeldgaard M (1993) *O Version 5.9, The manual*, Uppsala University, Uppsala, Sweden.

Jones G, Willett P & Glen R C (1995) Molecular recognition of receptor sites using a genetic algorithm with a description of desolvation. *J Mol Biol* 245:43-53.

Jones G, Willett P, Glen R C, Leach A R & Taylor R (1997) Development and validation of a genetic algorithm for flexible docking. *J Mol Biol* 267:727-748.

Jones G, Willett P, Glen R C, Leach A R, & Taylor R (1999) Further development of a genetic algorithm for ligand docking and its application to screening combinatorial libraries. *ACS Symp. Ser.* 719: 271-291.

Jones T A, Zou J Y, Cowan S W & Kjeldgaard M (1991) Improved methods for binding protein models in electron density maps and the location of errors in these models, *Acta CrystallogrA* 47:110-119.

Jorgensen W L & Severance D L (1990). Aromatic-Aromatic Interactions: Free Energy Profiles for the Benzene Dimer in Water, Chloroform, and Liquid Benzene, *J Am Chem Soc* 112:4768-4774.

Kahn R & Fourme R (1997) *Meth Enzymol* 276:268-286.

Kato K, Cox A D, Hisaka M, Graham S M, Buss J E & Der C J (1992) Isoprenoid addition to Ras protein is the critical modification for its membrane association and transforming activity, *Proc Natl Acad Sci USA* 89:6403-7.

Kim E, Ambroziak P, Otto J C, Taylor B, Ashby M, Shannon K, Casey P J & Young S G (1999) Disruption of the mouse Rce1 gene results in defective Ras processing and mislocalization of Ras within cells, *J Biol Chem* 274:8383-90.

Kleywegt G J & Brünger A T (1996) *Structure* 4:897-904.

Knighton D R, Pearson R B, Sowadski J M, Means A R, Ten Eyck L F, Taylor S & Kemp B E (1992) Structural basis of the intrasteric regulation of myosin light chain kinases. *Science* 258:130-135.

Kohl N E, Omer C A, Conner M W, Anthony N J, Davide J P, deSolms S J, Giuliani E A, Gomez R P, Graham S L, Hamilton K, Handt L K, Hartman G D, Koblan K S, Kral A M, Miller P J, Mosser S D, O'Neill T J, Rands E, Schaber M D, Gibbs J B & Oliff A (1995) Inhibition of farnesyltransferase induces regression of mammary and salivary carcinomas in ras transgenic mice, *Nature Med* 1:792-797.

Kuntz I D, Blaney J M, Oatley S J, Langridge R & Ferrin T E (1982) A Geometric Approach to Macromolecule-Ligand Interactions. *J Mol Biol* 161:269-288.

Kyte J & Doolittle R F (1982) A Simple Method for Displaying the Hydropathic Character of a Protein. *J Mol Biol* 157:105-132.

Lam P Y S, Jadhav P K, Eyermann C J, Hodge C N, Ru Y, Bacheler L T, Meek J L, Otto M J, Rayner M, Wong Y N, Chang C-H, Weber P C, Jackson D A, Sharpe T R & Erickson-Viitanen S (1994) Rational design of potent, bioavailable, nonpeptide cyclic ureas as HIV protease inhibitors. *Science* 263:380-384.

Lambert (1997) in *Practical Application of Computer-Aided Drug Design*, (Charifson, ed.) pp. 243-303, Marcel-Dekker, New York, N.Y., United States of America.

Laskowski et al. (1993) *J Appl Cryst* 26:283-291.

Lattman E (1985) Diffraction Methods for Biological Macromolecules. Use of the Rotation and Translation Functions. *Methods Enzymol* 115:55-77.

Lattman E (1996) *Proteins* 25:i-ii.

Lawrence M C & Davis P C (1992) CLIX: a search algorithm for finding novel ligands capable of binding proteins of known three-dimensional structure. *Proteins* 12:31-41.

Levitt D G (2001) A new software routine that automates the fitting of protein X-ray crystallographic electron-density maps. *Acta Crystallogr D Biol Crystallogr D* 57:1013-9.

Li X, Liu L, Tupper J C, Bannerman D, Winn R K, Sebti S M, Hamilton A D & Harlan J M (2002) Inhibition of protein geranylgeranylation and RhoA/RhoA kinase pathway induces apoptosis in human endothelial cells, *J Biol Chem* 277:15309-16.

Lobell R B, Omer C A, Abrams M T, Bhimnathwala H G, Brucker M J, Buser C A, Davide J P, deSolms S J, Dinsmore C J, Ellis-Hutchings M S, Kral A M, Liu D, Lumma W C, Machotka S V, Rands E, Williams T M, Graham S L, Hartman G D, Oliff A I, Heimbrook D C & Kohl N E (2001) Evaluation of farnesyl:protein transferase and geranylgeranyl:protein transferase inhibitor combinations in preclinical models. *Cancer Res* 61:8758-8768.

Loew A, Ho Y K, Blundell T & Bax B (1998) Phosducin induces a structural change in transducin beta gamma, *Structure* 6:1007-19.

Long S B, Casey P J & Beese L S (1998) Co-Crystal Structure of Protein Farnesyltransferase with a Farnesyl Diphosphate Substrate, *Biochemistry* 37:9612-9618.

Long S B, Casey P J & Beese L S (2000) The basis for K-Ras4B binding specificity to protein farnesyltransferase revealed by 2A resolution ternary complex structures, *Structure Fold Des* 8:209-22.

Long S B, Casey P J & Beese L S (2002) Reaction path of protein farnesyltransferase at atomic resolution. *Nature*, 419:645-650.

Long S B, Hancock P J, Kral A M, Hellinga H W & Beese L S (2001) The crystal structure of human protein farnesyltransferase reveals the basis for inhibition by CaaX tetrapeptides and their mimetics, *Proc Natl Acad Sci USA* 98:12948-53.

Luthy R, Bowie J U & Eisenberg D (1992) Assessment of protein models with three-dimensional profiles. *Nature* 356:83-85.

Manne V, Ricca C S, Brown J G, Tuomari A V, Yan N, Patel D, Schmidt R, Lynch M J, Ciosek Jr C P, Carboni J M, Robinson S, Gordon E M, Barbacid M, Seizinger B R & Biller S A (1995). Ras farnesylation as a target for novel antitumor agents: poteint and selective farnesyl diphosphate analog inhibitors of farnesyltransferase. *Drug Dev. Res.* 34:121-137.

Martin Y C (1992) 3d Database Searching in Drug Design. *J Med Chem* 35:2145-2154.

McPherson A (1982) *Preparation and Analysis of Protein Crystals*, John Wiley, New York, N.Y., United States of America.

McPherson A (1990) Current approaches to macromolecular crystallization. *Eur J Biochem* 189:1-23.

McRee D E (1992) XtalView: A Visual Protein Crystallographic Software System for XII/Xview. *J Mol Graphics* 10: 44-47.

Milner-White E J & Watts D C (1971) Inhibition of adenosine 5'-triphosphate-creatine phosphotransferase by substrate-anion complexes. Evidence for the transition-state organization of the catalytic site, *Biochem J* 122:727-740.

Miranker A & Karplus M (1991) Functionality Maps of Binding Sites: A Multiple Copy Simultaneous Search Method. *Proteins* 11:29-34.

Moores S L, Schaber M D, Mosser S D, Rands E, O'Hara M B, Garsky V M, Marshall M S, Pompliano D L & Gibbs J B (1991) Sequence dependence of protein isoprenylation, *J Biol Chem* 266:14603-14610.

Murphy C, Saffrich R, Grummt M, Gournier H, Rybin V, Rubino M, Auvinen P, Lutcke A, Parton R G & Zerial M (1996). Endosome dynamics regulated by a Rho protein, *Nature* 384:427-432.

Murshudov G N, Vagin M & Dodson E J (1997) *Acta Crystallogr D Biol Crystallogr* D 53:240-255.

Murthi K, Smith S E, Kluge A F, Bergnes G, Bureau P et al. (2003) Antifungal activity of a *Candida albicans* GGTase I inhibitor-alanine conjugate Inhibition of Flp prenylation in *C. albicans*, *Bioorg Med Chem Lett* 13:1935-1937.

Myung C S, Yasuda H, Liu W, Harden T K & Garrison J C (1999) Role of isoprenoid lipids on the heterotrimeric G protein gamma subunit in determining effector activation, *J Biol Chem* 274:16595-603.

Navaza (1994) *Acta Crystallogr* A50:157-163.

Navaza J & Saludjian P (1997) AMoRe: an automated molecular replacement program package. *Meth Enzymol.* 276A:581-94.

Navia M A & Murcko M A (1992) Use of structural information in drug design *Curr Opin Struct Biol* 2:202-210.

Needleman S B & Wunsch C D (1970) A General Method Applicable to the Search for Similarities in the Amino Acid Sequence of Two Proteins. *J Mol Biol* 48:443-453.

Nicholls A, Sharp K A & Honig B (1991) Protein folding and association: insights from the interfacial and thermodynamic properties of hydrocarbons. *Proteins* 11:281-96.

Nishibata Y & Itai A (1991) Automatic creation of drug candidate structures based on receptor structure. Starting point for lead generation. *Tetrahedron* 47: 8985-8990.

O'Donovan C, Martin M J, Gattiker A, Gasteiger E, Bairoch A & Apweiler R (2002). High-quality protein knowledge resource: SWISS-PROT and TrEMBL. *Brief Bioinform* 3:275-284.

Otto J C & Casey P J (1996). The hepatitis delta virus large antigen is farnesylated both in vitro and in animal cells. *J Biol Chem* 271:4569-4572.

Otwinowski Z (1991) in *Isomorphous Replacement and Anomalous Scattering*, (Evans & Leslie, eds.), pages 80-86, Daresbury Laboratory, Daresbury, United Kingdom.

Otwinowski Z & Minor W (1997) Processing of X-ray Diffraction Data Collected in Oscillation Mode. *Meth Enzymol* 276A: 307-326.

Overmeyer J H, Wilson A L & Maltese W A (2001) Membrane targeting of a Rab GTPase that fails to associate with Rab escort protein (REP) or guanine nucleotide dissociation inhibitor (GDI), *J Biol Chem* 276:20379-86.

Park H-W, Boduluri S R, Moomaw J F, Casey P J & Beese L S (1997) Crystal structure of protein farnesyltransferase at 2.25 Å resolution, *Science* 275:1800-1804.

PCT International Patent Publication WO 84/03564

Pearlman D A, Case D A, Caldwell J W, Ross W S, Cheatham T A, DeBolt S, Ferguson D M, Seibel G & Kollman P (1995) AMBER, a package of computer programs for applying molecular mechanics, a normal mode analysis, molecular dynamics and free energy calculations to simulate the structural and energetic properties of molecules. *Comput Phys Commun* 91:1-41.

Perrakis A, Morris R & Lamzin V S (1999) Automated protein model building combined with iterative structure refinement. *Nat Struct Biol* 6:458-463.

Petsko G A (1985) *Meth Enzymol* 114:147-156.

Pylypenko O, Rak A, Reents R, Niculae A, Sidorovitch V et al. (2003) Structure of Rab escort protein-1 in complex with Rab geranylgeranyltransferase, *Mol Cell* 11:483-494.

Rarey M, Wefing S & Lengauer T (1996) Placement of medium-sized molecular fragment into active sites of protein. *J Comput Aid Mol Des* 10:41-54.

Reid T S & Beese L S (2004) Crystal structures of the anticancer clinical candidates R115777 (Tipifarnib) and BMS-214662 complexed with protein farnesyltransferase suggest a mechanism of FTI selectivity, *Biochemistry* 43:6877-6884.

Reiss Y, Goldstein J L, Seabra M C, Casey P J & Brown M S (1990) Inhibition of purified p21 ras farnesyl:protein transferase by Cys-AAX tetrapeptides, *Cell* 62:81-88.

Reiss Y, Stradley S J, Gierasch L M, Brown M S & Goldstein J L (1991). Sequence requirements for peptide recognition by rat brain p21ras farnesyl:protein transferase. *Proc Natl Acad Sci USA* 88:732-736.

Roskoski R Jr & Ritchie P (1998). Role of the carboxyterminal residue in peptide binding to protein farnesyltransferase and protein geranylgeranyltransferase. *Arch Biochem Biophys* 356:167-176.

Rossmann M G (ed.) (1972) *The Molecular Replacement Method*, Gordon & Breach, New York, N.Y., United States of America.

Ruault M, van der Bruggen P, Brun M E, Boyle S, Roizes G & De Sario A (2002) New BAGE (B melanoma antigen) genes mapping to the juxtacentromeric regions of human chromosomes 13 and 21 have a cancer/testis expression profile, *Eur J Hum Genet* 10:833-840.

Sambrook J & Russell D W (2001) *Molecular Cloning: A Laboratory Manual*, Third Edition, Cold Spring Harbor Laboratory, Cold Spring Harbor, N.Y., United States of America.

Scholten J D, Zimmerman K, Oxender M G, Leonard D, Sebolt-Leopold J et al. (1997) Synergy between anions and farnesyldiphosphate competitive inhibitors of farnesyl:protein transferase, *J Biol Chem* 272:18077-18081.

Schulz G E & Schirmer R H (1979) *Principles of Protein Structure*, Springer-Verlag, New York, N.Y., United States of America.

Schwartz R M & Dayhoff M O (1979) in *Atlas of Protein Sequence and Structure*, Dayhoff M O (ed), pp. 357-358, National Biomedical Research Foundation, Silver Spring, Md., United States of America.

Scott J K & Smith G P (1990) for Peptide Ligands with an Epitope Library. *Science* 249:386-390.

Seabra M C (1998) Membrane association and targeting of prenylated Ras-like GTPases, *Cell Signal* 10:167-72.

Seabra M C, Goldstein J L, Sudhof T C & Brown M S (1992) Rab geranylgeranyltransferase: A multisubunit enzyme that prenylates GTP-binding proteins terminating in Cys-Cys or Cys-X-Cys, *J Biol Chem* 267:14497-14503.

Sebti S M & Hamilton A D (2000) Farnesyltransferase and geranylgeranyltransferase I inhibitors and cancer therapy: lessons from mechanism and bench-to-bedside translational studies, *Oncogene* 19:6584-93.

Segel I H (1975) *Enzyme Kinetics: Behaviour and Analysis of Rapid Equilibrium and Steady-State Systems*, pp 465-504, Wiley, New York, N.Y.

Seidel H M & Knowles J R (1994) Interaction of inhibitors with phosphoenolpyruvate mutase: Implications for the reaction mechanism and the nature of the active site, *Biochemistry* 33:5641-5646.

Sheldrick G M (1990) Phase annealing in SHELX-90: direct methods for larger structures *Acta Cryst. A* 46:467.

Smith T F & Waterman M (1981) Comparison of Biosequences. *Adv Appl Math* 2:482-489.

Stark W Jr, Blaskovich M A, Johnson B A, Qian Y, Vasudevan A, Pitt B, Hamilton A D, Sebti S M & Davies P (1998) Inhibiting geranylgeranylation blocks growth and promotes apoptosis in pulmonary vascular smooth muscle cells, *Am J Physiol* 275:L55-63.

Steiger A, Pyun H-J & Coates R M (1992) Synthesis and characterization of aza analogue inhibitors of squalene and geranylgeranyl diphosphate synthases, *J Org Chem* 57:3444-3449.

Stirtan W G & Poulter C D (1997) Yeast protein geranylgeranyltransferase Type-1: steady-state kinetics and substrate binding, *Biochemistry* 36:4452-4557.

Stoddard B L (1998) New results using Laue diffraction and time-resolved crystallography. *Curr Opin Struct Biol* 8:612-8.

Strickland C L, Weber P C, Windsor W T, Wu Z, Le H V, Albanese M, Alvarez C S, Cesarz D, del Rosario J, Deskus J, Mallams A K, Njoroge F G, Piwinski J, Remiszewski S, Rossman R, Taveras A G, Vibulbhan B, Doll R J, Girijavallabhan V M & Ganguly A K (1999) Tricyclic farnesyl protein transferase inhibitors: crystallographic and calorimetric studies of structure-activity relationships. *J Med Chem* 42:2125-2135.

Strickland C L, Windsor W T, Syto R, Wang L, Bond R, Wu Z, Schwartz J, Le H V, Beese L S & Weber P C (1998) Crystal Structure of Farnesyl Protein Transferase Complexed with a CaaX Peptide and Farnesyl Diphosphate Analogue, *Biochemistry* 37:16601-16611.

Sun J, Ohkanda J, Coppola D, Yin H, Kothare M et al. (2003) eranylgeranyltransferase I inhibitor GGTI-2154 induces breast carcinoma apoptosis and tumor regression in H-Ras transgenic mice, *Cancer Res* 63:8922-8929.

Sun J, Qian Y, Hamilton A D & Sebti S M (1998) Both farnesyltransferase and geranylgeranyltransferase-1 inhibitors are required for inhibition of oncogenic K-Ras prenylation but each alone is sufficient to suppress human tumor growth in nude mouse xenografts. *Oncogene* 16:1467-1473.

Szczepankiewicz B G, Liu G, Hajduk P J, Abad-Zapatero C, Pei Z et al. (2003) Discovery of a potent, selective protein tyrosine phosphatase 1B inhibitor using a linked-fragment strategy, *J Am Chem Soc* 125:4087-4096.

Tamanoi F & Sigman D S (eds.) (2001) *Protein Lipidation, Third Edition*, Academic Press, San Diego, Calif., United States of America.

Tao W, Pennica D, Xu L, Kalejta R F & Levine A J (2001). Wrch-1, a novel member of the Rho gene family that is regulated by Wnt-1, *Genes Dev.* 15:1796-1807.

Tatko C D (2002) *Aromatic Interactions in Biological Systems*, pp 4, American Chemical Society, Division of Organic Chemistry, Washington, D.C.

Terwilliger T C (1999) Reciprocal-space solvent flattening, *Acta Crystallogr D Biol Crystallogr* 55:1863-71.

Terwilliger T C (2000) Maximum-likelihood density modification, *Acta Crystallogr D Biol Crystallogr* 56:965-72.

Terwilliger T C & Berendzen J (1999) Automated MAD and MIR structure solution, *Acta Crystallogr D Biol Crystallogr* 55:849-61.

Theorell H & Yonetani T (1965) Optical rotatory dispersion of liver alcohol dehydrogenase, and its complexes with coenzymes and inhibitors, *Arch Biochem Biophys* 110:413-421.

Thoma N H, Niculae A, Goody R S & Alexandrov K (2001) Double prenylation by RabGGTase can proceed without dissociation of the mono-prenylated intermediate, *J Biol Chem* 276:48631-6.

Tibanyenda N et al., (1984) *Eur J Biochem* 139:19.

Tijssen (1993) *Laboratory Techniques in biochemistry and molecular biology*, Elsevier, New York, N.Y., United States of America.

Tschantz W R, Furfine E S & Casey P J (1997) Substrate binding is required for release of product from mammalian protein farnesyltransferase, *J Biol Chem* 272:9989-9993.

U.S. Pat. No. 4,554,101
U.S. Pat. No. 5,463,564
U.S. Pat. No. 5,834,228
U.S. Pat. No. 5,872,011
U.S. Pat. No. 6,008,033

Vasudevan A, Qian Y, Vogt A, Blaskovich M A, Ohkanda J, Sebti S M & Hamilton A D (1999) Potent, highly selective, and non-thiol inhibitors of protein geranylgeranyltransferase-1, *J Med Chem* 42:1333-40.

Villieux F MD & Read R J (1997) *Meth Enzymol* 277:18-52.

Vogt A, Qian Y, McGuire TF, Hamilton A D & Sebti S M (1996) Protein geranylgeranylation, not farnesylation, is required for the Gi to S phase transition in mouse fibroblasts, *Oncogene* 13:1991-1999.

Walters C E, Pryce G, Hankey D J, Sebti S M, Hamilton A D, Baker D, Greenwood J & Adamson P (2002) Inhibition of Rho GTPases with protein prenyltransferase inhibitors prevents leukocyte recruitment to the central nervous system and attenuates clinical signs of disease in an animal model of multiple sclerosis, *J Immunol* 168:4087-94.

Weber P C (1991) Physical Principles of Protein Crystallization. *Adv Protein Chem* 41:1-36.

Weeks C M, DeTitta G T, Hauptman H A, Thuman P & Miller R (1994) Structure solution by minimal-function phase refinement and Fourier filtering. II. Implementation and applications. *Acta Crystallogr A* 50:210-20.

Wellner (1971) *Anal Chem* 43:597.

West M L & Fairlie D P (1995) Targeting HIV-1 protease: a test of drug-design methodologies. *Trends Pharmaceutical Sci* 16:67-75.

Westbrook E M & Naday I (1997) *Meth Enzymol* 276:244-268.

Wetmur J G & Davidson N (1968) Kinetics of renaturation of DNA. *J Mol Biol* 31:349-70.

Wilson A L, Erdman R A, Castellano F & Maltese W A (1998). Prenylation of Rab8 GTPase by type I and type II geranylgeranyl transferases. *Biochem J* 333(Pt 3):497-504.

Wlodawer A & Erickson J W (1993) Structure-based inhibitors of HIV-1 protease. *Ann Rev Biochem* 62:543-585.

Wong W, Dimitroulakos J, Minden M D & Penn L Z (2002) HMG-CoA reductase inhibitors and the malignant cell: the statin family of drugs as triggers of tumor-specific apoptosis. *Leukemia* 16:508-519.

Word J M, Lovell S C, LaBean TH, Taylor H C, Zalis M E, Presley B K, Richardson J S & Richardson D C (1999a) Visualizing and quantifying molecular goodness-of-fit: small-probe contact dots with explicit hydrogen atoms, *J Mol Biol* 285:1711-33.

Word J M, Lovell S C, Richardson J S & Richardson D C (1999b) Asparagine and glutamine: using hydrogen atom contacts in the choice of side-chain amide orientation, *J Mol Biol* 285:1735-47.

Yokoyama K, Goodwin G W, Ghomashchi F, Glomset J A & Gelb M H (1991) A protein geranylgeranyltransferase from bovine brain: Implications for protein prenylation specificity, *Proc Natl Acad Sci USA* 88:5302-5306.

Yokoyama K, McGeady P & Gelb M H (1995) Mammalian protein geranylgeranyltransferase-1: substrate specificity, kinetic mechanism, metal requirements, and affinity labeling, *Biochemistry* 34:1344-1354.

Yokoyama K, Zimmerman K, Scholten J & Gelb M H (1997) Differential prenyl pyrophosphate binding to mammalian protein geranylgeranyltransferase-1 and protein farnesyltransferase and its consequences on the specificity of protein prenylation, *J Biol Chem* 272:3944-3952.

Zhang F L & Casey P J (1996) Influence of metal ions on substrate binding and catalytic activity of mammalian protein geranylgeranyltransferase type-1. *Biochem J* 320:925-32.

Zhang F L, Diehl R E, Kohl N E, Gibbs J B, Giros B, Casey P J & Omer C A (1994a) cDNA cloning and expression of rat and human protein geranylgeranyltransferase Type-I, *J Biol Chem* 269:3175-3180.

Zhang F L, Kirschmeier, P, Carr D, James L, Bond R W, Wang L, Patton R, Windsor W T, Syto R, Zhang R & Bishop W R (1997) Characterization of Ha-Ras, N-Ras, Ki-Ras4A, and Ki-Ras4B as in vitro substrates for farnesyl protein transferase and geranylgeranyl protein transferase type I, *J Biol Chem* 272:10232-10239.

Zhang F L, Moomaw J F & Casey P J (1994b) Properties and kinetic mechanism of recombinant mammalian protein geranylgeranyltransferase type I, *J Biol Chem* 269:23465-23470.

Zhang H, Seabra M C & Deisenhofer J (2000) Crystal structure of Rab geranylgeranyltransferase at 2.0 Å resolution, *Structure Fold Des* 8:241-51.

Zhang K Y J, Cowtan, K. & Main, P (1997) *Meth Enzymol* 277:53-64.

Zhou G, Somasundaram T, Blanc E, Parthasarathy G, Ellington W R et al. (1998) Transition state structure of arginine kinase: Implications for catalysis of bimolecular reactions, *Proc Natl Acad Sci USA* 95:8449-8454.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for designing a ligand for a farnesyl transferase (ETase), the method comprising:
   (a) providing a molecule that binds to a geranylgeranyl transferase type I (GGTase-1) $a_2$ site;
   (b) determining a moiety of the molecule that interacts with the GGTase-I $a_2$ site;
   (c) modifying the moiety to produce a modified molecule; wherein the modifying comprises modifying a moiety that interacts with one or more of residues Thr491β, Phe 106β, and Leu 361β of a human GGTase-I polypeptide;
   (d) modeling a first interaction between the modified molecule and the GGTase-I $a_2$ sites
   (e) modeling a second interaction between the modified molecule with an FTase $a_2$ site;
   (f) identifying in a modified molecule that is predicted to be unable to bind to the GGTase-I $a_2$ site but able to bind to the FTase $a_2$ site; and
   (g) displaying a structure of the modified molecule identified in step (f),
   whereby a ligand for a FTase is designed.

2. The method of claim 1, wherein the ligand comprises an inhibitor.

3. The method of claim 1, wherein the determining comprises identifying a moiety of the molecule that interacts with residues Thr 49β, Phe 106β, and Leu 361β of a human GGTase-I polypeptide.

4. The method of claim 1, wherein the modifying comprises substituting the moiety with a group comprising an aromatic ring.

5. The method of claim 1, wherein the molecule is a peptide or a small molecule.

6. The method of claim 5, wherein the modified molecule comprises a change in an amino acid that interacts with the $a^2$ site of the GGTase from an amino acid with a non-aromatic side chain to an amino acid comprising an aromatic side chain.

7. The method of claim 1, wherein the modeling a first interaction between the modified molecule and the GGTase-1 $a_2$ site comprises evaluating the first interaction between the modified molecule and the GGTase-1 $a^2$ site with respect to a three-dimensional structure of a crystal comprising the GGTase-1 $a^2$ site. aromatic side chain.

* * * * *